United States Patent
Jiang et al.

(10) Patent No.: US 10,682,352 B2
(45) Date of Patent: Jun. 16, 2020

(54) COMPOUND HAVING MUTANT IDH INHIBITORY ACTIVITY, PREPARATION METHOD AND USE THEREOF

(71) Applicants: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

(72) Inventors: Lei Jiang, Shanghai (CN); Meiyu Geng, Shanghai (CN); Qiangang Zheng, Shanghai (CN); Min Huang, Shanghai (CN); Huixin Wan, Shanghai (CN); Shuai Tang, Shanghai (CN); Xianlei Fu, Shanghai (CN); Xiaojing Lan, Shanghai (CN); Jianhua Cao, Shanghai (CN); Feifei Liu, Shanghai (CN); Jian Ding, Shanghai (CN)

(73) Assignees: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/087,556

(22) PCT Filed: Mar. 21, 2017

(86) PCT No.: PCT/CN2017/077467
§ 371 (c)(1),
(2) Date: Sep. 21, 2018

(87) PCT Pub. No.: WO2017/162133
PCT Pub. Date: Sep. 28, 2017

(65) Prior Publication Data
US 2019/0111056 A1   Apr. 18, 2019

(30) Foreign Application Priority Data

Mar. 22, 2016 (CN) .......................... 2016 1 0165095

(51) Int. Cl.
| | | |
|---|---|---|
| A61K 31/506 | (2006.01) | |
| A61P 35/00 | (2006.01) | |
| A61P 35/02 | (2006.01) | |
| C07D 403/04 | (2006.01) | |
| C07D 403/14 | (2006.01) | |
| C07D 413/04 | (2006.01) | |
| C07D 413/14 | (2006.01) | |
| C07D 401/14 | (2006.01) | |
| C07D 405/14 | (2006.01) | |

(52) U.S. Cl.
CPC ............ *A61K 31/506* (2013.01); *A61P 35/00* (2018.01); *C07D 401/14* (2013.01); *C07D 403/04* (2013.01); *C07D 403/14* (2013.01); *C07D 405/14* (2013.01); *C07D 413/04* (2013.01); *C07D 413/14* (2013.01)

(58) Field of Classification Search
CPC .. A61K 31/506; C07D 403/04; C07D 403/14; C07D 413/04; C07D 413/14
USPC ......................................... 514/275; 544/330
See application file for complete search history.

(56) References Cited

U.S. PATENT DOCUMENTS

| | | |
|---|---|---|
| 2014/0235620 A1 | 8/2014 | Caferro et al. |
| 2015/0152093 A1 | 6/2015 | Caferro et al. |
| 2016/0039802 A1 | 2/2016 | Cho et al. |
| 2016/0318915 A1 | 11/2016 | Caferro et al. |

FOREIGN PATENT DOCUMENTS

| | | |
|---|---|---|
| CN | 103958506 A | 7/2014 |
| CN | 105209460 A | 12/2015 |
| CN | 105263929 A | 1/2016 |
| WO | 2012/020787 A1 | 2/2012 |
| WO | 2014/147586 A1 | 9/2014 |
| WO | 2016/044781 A1 | 3/2016 |

OTHER PUBLICATIONS

English Translation of the International Search Report dated Jun. 2, 2017 corresponding to PCT/CN2017/077467 filed Mar. 21, 2017; 4 pages.

*Primary Examiner* — Brenda L Coleman
(74) *Attorney, Agent, or Firm* — Mintz Levin Cohn Ferris Glovsky and Popeo PC

(57) ABSTRACT

Provided in the present invention are a compound having the effects of preventing and treating diseases related to IDH mutation, and a preparation method and use thereof. In particular, provided in the present invention are the compound as shown in formula (I), a stereoisomer, a racemic body or a pharmaceutically acceptable salt thereof, and the use thereof in preparing drugs for preventing and treating diseases related to IDH mutation

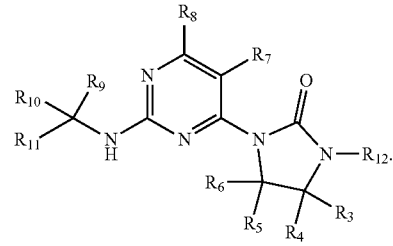

15 Claims, No Drawings

COMPOUND HAVING MUTANT IDH INHIBITORY ACTIVITY, PREPARATION METHOD AND USE THEREOF

TECHNICAL FIELD

The present invention belongs to the field of chemical synthesis, and in particular, the present invention relates to a compound having mutant IDH inhibitory activity, preparation method and use thereof.

BACKGROUND ART

Isocitrate dehydrogenase (IDH) catalyzes oxidative decarboxylation of isocitrate to 2-oxoglutarate (alpha-ketoglutarate) while producing carbon dioxide and NADPH/NADH. This process plays an important role in the metabolism of cells. Depending on electron acceptors, these enzymes can be divided into two distinct subclasses, one using NAD(+) and the other using NADP(+). In five reported isocitrate dehydrogenases, three of them are NAD(+)-dependent isocitrate dehydrogenases, and mainly present in mitochondrial matrix; the other two are NADP(+)-dependent, i.e. isocitrate dehydrogenase 1 and isocitrate dehydrogenase 2. Isocitrate dehydrogenase 1 is mainly present in the cytoplasm, while isocitrate dehydrogenase 2 is mainly present in the mitochondria. Mutations of isocitrate dehydrogenase occur in a wide variety of cancer types including (but not limited to) glioma, glioblastoma, paraganglion cell tumors, acute leukemia, prostate cancer, thyroid cancer, colon cancer, chondrosarcoma, cholangiocarcinoma, peripheral T cell leukemia, melanoma, etc. (see L. Deng, et al., Trends Mol. Med., 2010, 16,387; T. shibata et al., Am. J. Pathol., 2011, 178(3), 1395; Gaal et al., J. Clin. Endocrinol. Metab. 2010; Hayden et al., Cell cycle, 2009; Balss et al., Acta Neuropathol., 2008).

Non-mutated IDH1 catalyzes oxidative decarboxylation of isocitrate to alpha-ketoglutarate, thereby reducing NAD+ (NADP+) to NADP (NADPH) in the following forward reactions:

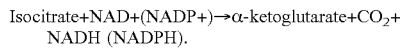

The mutant isocitrate dehydrogenase loses the above normal function, but instead catalyzes NAPH-dependent reduction of α-ketoglutarate to R(−)-2-hydroxyglutarate (2HG). The concentration level of 2HG in normal cells is very low. The production of high concentration of 2HG contributes to the formation and development of cancer (Dang, L et al, Nature 2009, 462: 739-44). For example, a high concentration of 2-HG was detected in patients of acute leukemia with IDH mutation. (S. Gross et al., J. Exp. Med., 2010, 207(2), 339). High concentration of 2HG is highly correlated with oncogenes. Therefore, there is an urgent need in the art to develop mutant IDH inhibitors.

SUMMARY OF THE INVENTION

The object of the present invention is to provide a compound of formula I or a pharmaceutically acceptable salt thereof, a pharmaceutical composition comprising the compound or the pharmaceutically acceptable salt thereof, and use of the compound or the composition for preventing and treating IDH mutation-related diseases.

In the first aspect of the invention, a compound of formula I, a stereoisomer, a racemate or a pharmaceutically acceptable salt thereof is provided:

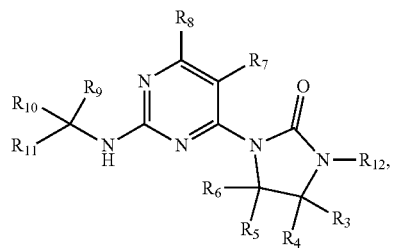

(I)

wherein $R_3$ and $R_4$ are each independently selected from: H, D, a substituted or unsubstituted $C_{1-4}$ alkyl;

or $R_3$ and $R_4$ together with a carbon atom connecting to them form a substituted or unsubstituted $C_{3-6}$ cycloalkyl, or $R_3$ and $R_4$ together with a carbon atom connecting to them form a substituted or unsubstituted $C_{3-6}$ epoxyalkyl;

$R_5$ and $R_6$ are each independently selected from: H, a substituted or unsubstituted $C_{1-4}$ alkyl, a substituted or unsubstituted $C_{6-10}$ aryl, a substituted or unsubstituted $C_{3-6}$ cycloalkyl;

or $R_5$ and $R_6$ together with a carbon atom connecting to them form a substituted or unsubstituted $C_{3-6}$ cycloalkyl;

$R_7$ and $R_8$ are each independently selected from: H, halogen, a substituted or unsubstituted $C_{1-4}$ alkyl;

$R_9$ is selected from: H, a substituted or unsubstituted $C_{1-4}$ alkyl;

$R_{10}$ is a substituted or unsubstituted $C_{1-4}$ alkyl;

or $R_9$ and $R_{10}$ together with a carbon atom connecting to them form a substituted or unsubstituted $C_{3-6}$ cycloalkyl;

$R_{11}$ is selected from: a substituted or unsubstituted $C_{6-10}$ aryl, a substituted or unsubstituted $C_{5-10}$ heteroaryl; wherein the $C_{5-10}$ heteroaryl contains 1-4 heteroatoms selected from N, O or S; and the term "substituted" means having one or more (e.g., 1, 2, 3 or 4) substituents selected from Group A:

the substituents of Group A are selected from the group consisting of H, D, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, —C(O)NHRa';

wherein Ra' is selected from: a substituted or unsubstituted $C_{1-6}$ alkyl, a substituted or unsubstituted $C_{3-8}$ cycloalkyl;

$R_{12}$ is selected from: H, D, a substituted or unsubstituted $C_{1-4}$ alkyl, a substituted or unsubstituted 3-6 membered ring;

for $R_3$-$R_{12}$, the term "substituted" means having one or more substituents selected from Group B;

the substituents of Group B are selected from the group consisting of H, D, halogen, a substituted or unsubstituted $C_{1-6}$ alkyl, —OH, a substituted or unsubstituted $C_{1-4}$ alkoxy, 3-8 membered cycloalkyl, amino, nitro;

and, in the substituents of Group A and Group B, the term "substituted" means having one or more (e.g., 1, 2, 3, 4 or 5) substituents selected from the group consisting of D, halogen, $C_{1-4}$ alkyl, trifluoromethyl, amino, nitro, —OH.

In another preferred embodiment, $R_3$ and $R_4$ together with a carbon atom connecting to them form a substituted or unsubstituted $C_{3-6}$ cycloalkyl.

In another preferred embodiment, $R_3$ and $R_4$ together with a carbon atom connecting to them form a substituted or unsubstituted $C_{3-6}$ epoxyalkyl.

In another preferred embodiment, $R_3$ is selected from the group consisting of H, D, and methyl.

In another preferred embodiment, $R_4$ is H, D or methyl.

In another preferred embodiment, $R_5$ is H or methyl.

In another preferred embodiment, $R_6$ is H, a substituted or unsubstituted $C_{1-4}$ alkyl group, a substituted or unsubstituted $C_{6-10}$ aryl, a substituted or unsubstituted $C_{3-6}$ cycloalkyl.

In another preferred embodiment, $R_6$ is methyl, 1-hydroxyethyl, haloethyl, isopropyl, phenyl or cyclopropyl.

In another preferred embodiment, $R_5$ and $R_6$ together with a carbon atom connecting to them form a substituted or unsubstituted five-membered cycloalkyl.

In another preferred embodiment, $R_9$ is H or methyl.

In another preferred embodiment, $R_{10}$ is methyl.

In another preferred embodiment, $R_9$ and $R_{10}$ together with a carbon atom connecting to them form a substituted or unsubstituted 3-8 membered cycloalkyl or heterocyclyl, preferably a 3-6 membered cycloalkyl, more preferably 3 membered ring.

In another preferred embodiment, $R_{11}$ has the following structure:

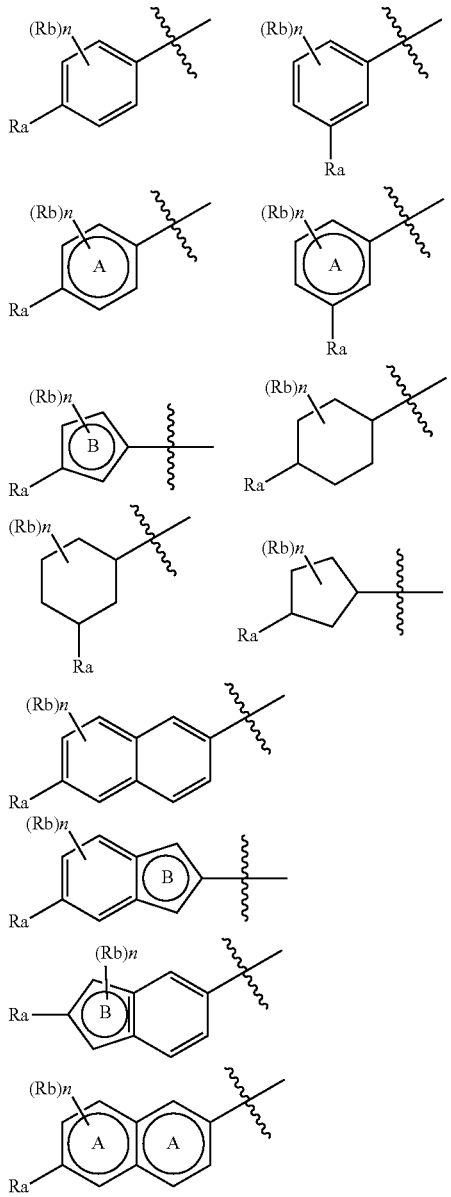

wherein ring A is a substituted or unsubstituted $C_{5-10}$ heteroaryl containing 1 to 3 heteroatoms, and ring B is a substituted or unsubstituted $C_{5-10}$ heteroaryl having 1 to 4 heteroatoms, wherein the heteroatom is selected from the group consisting of N, O and S;

$R_a$ is selected from: H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{1-3}$ alkyl $C_{5-8}$ cycloalkyl, a substituted or unsubstituted $C_{6-10}$ aryloxy, —C(O)NHRa',

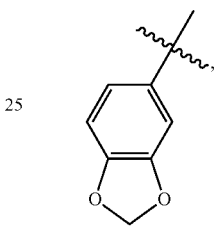

wherein Ra' is selected from: a substituted or unsubstituted $C_{1-6}$ alkyl, a substituted or unsubstituted $C_{3-8}$ cycloalkyl;

$R_b$ is selected from H, halogen, —CN, a substituted or unsubstituted $C_{1-4}$ alkyl;

n is 0, 1, 2 or 3.

In another preferred embodiment, the ring A is a six-membered heteroaryl having 1 to 3 heteroatoms.

In another preferred embodiment, the ring B is a five-membered heterocyclyl containing 1 to 4 heteroatoms.

In another preferred embodiment, $R_{11}$ is selected from the group consisting of a substituted or unsubstituted $C_{6-10}$ aryl, a substituted or unsubstituted $C_{5-10}$ heteroaryl.

In another preferred embodiment, $R_{11}$ is a 5-6 membered heterocyclyl having 1-3 heteroatoms.

In another preferred embodiment, the 5-6 membered heterocyclyl is unsaturated.

In another preferred embodiment, the 5-6 membered heterocyclyl is an aromatic heterocyclyl.

In another preferred embodiment, the substituted or unsubstituted $C_{6-10}$ aryl and the substituted or unsubstituted $C_{5-10}$ heteroaryl are each independently monocyclic, bicyclic or tricyclic.

In another preferred embodiment, $R_{11}$ is

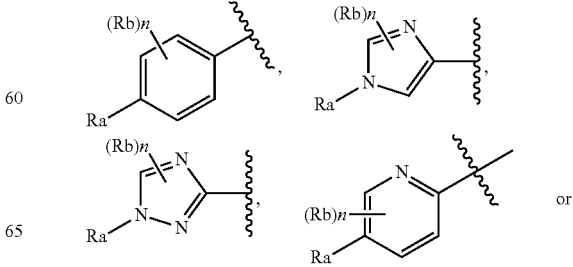

-continued

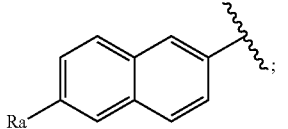

wherein, Ra and Rb are as defined above, and n is 1, 2 or 3.

In another preferred embodiment, R₁₁ is selected from the group consisting of a substituted imidazolyl, substituted phenyl, substituted triazolyl, substituted pyridyl.

In another preferred embodiment, R₁₁ is

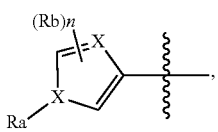

wherein X is N, and Ra, Rb and n are as defined above.

In another preferred embodiment, R₁₁ is

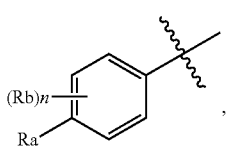

wherein Ra, Rb and n are as defined above.

In another preferred embodiment, R₁₁ is

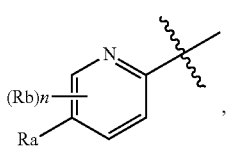

wherein Ra, Rb and n are as defined above.

In another preferred embodiment, the substituents of Group B means having one or more (e.g., 1-3) substituents selected from the group consisting of H, halogen, $C_{1-3}$ alkyl, —OH, $C_{1-3}$ alkoxy, 3-8 membered cycloalkyl, amino, nitro.

In another preferred embodiment, $C_{6-10}$ aryl is selected from the group consisting of a phenyl, pyridyl, pyrazolyl, thiazolyl, imidazolyl, isoxazolyl or oxazolyl.

In another preferred embodiment, the compound is selected from the group consisting of:

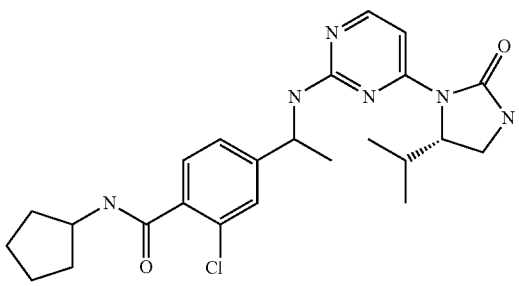

-continued

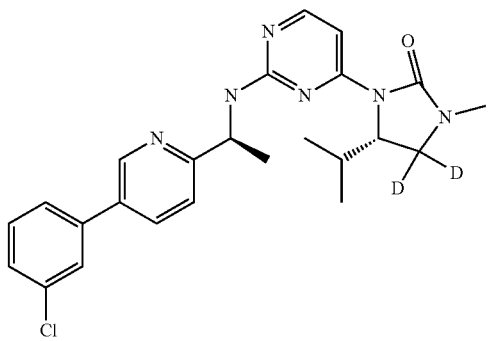

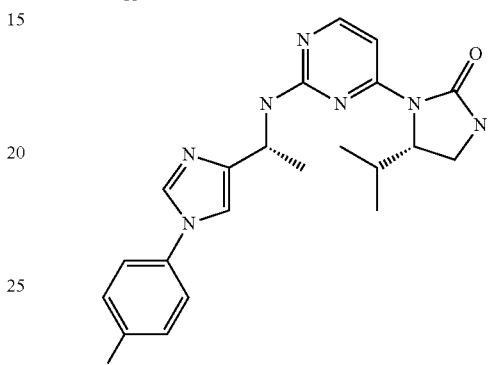

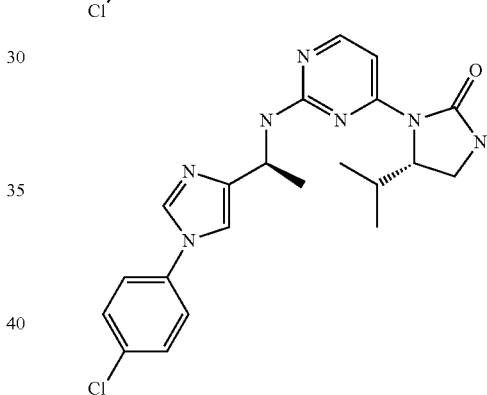

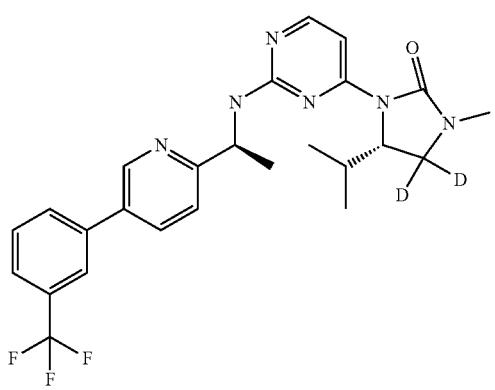

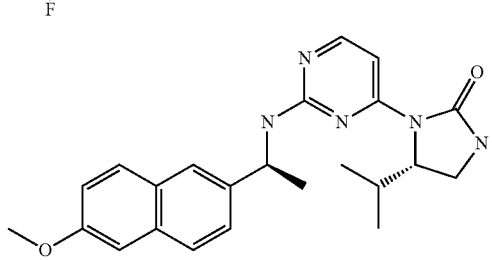

7
-continued
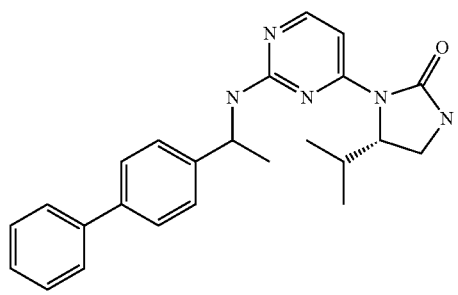
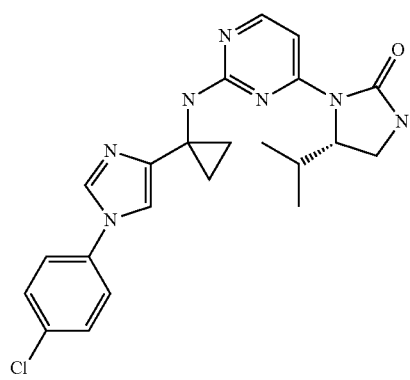
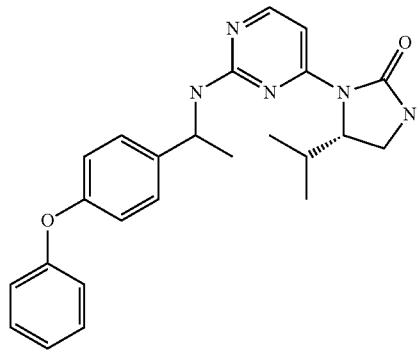
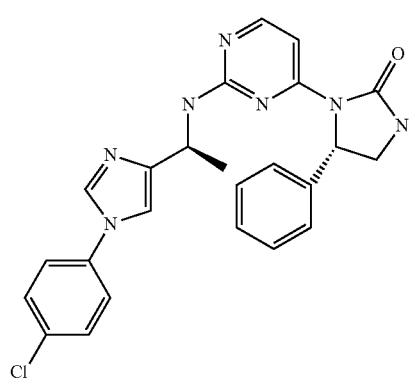
8
-continued
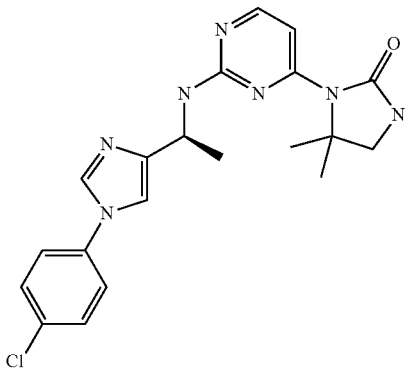
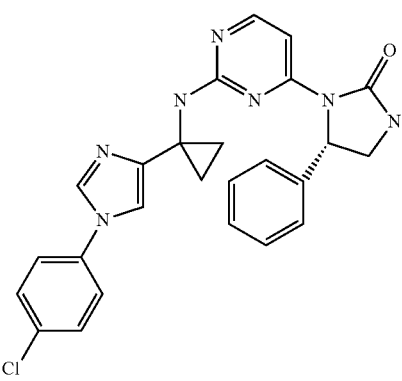
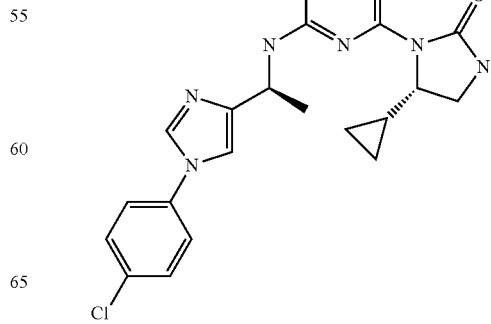

-continued
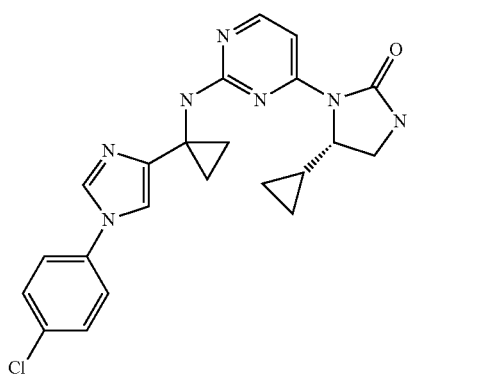
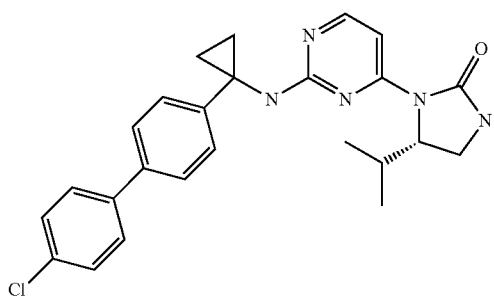
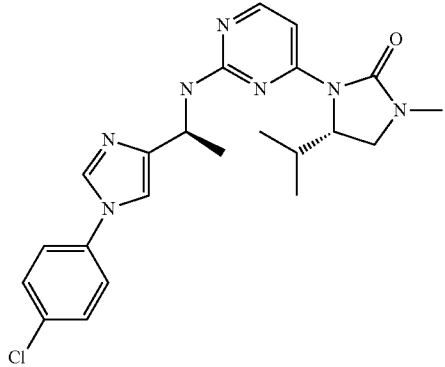
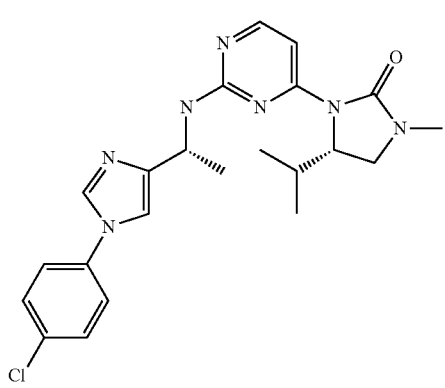
-continued
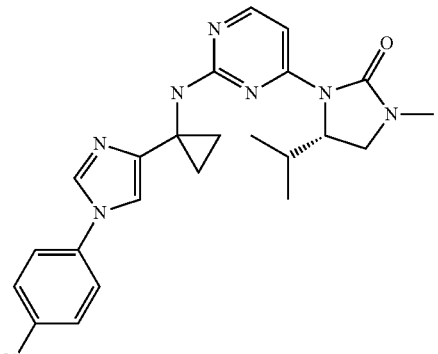
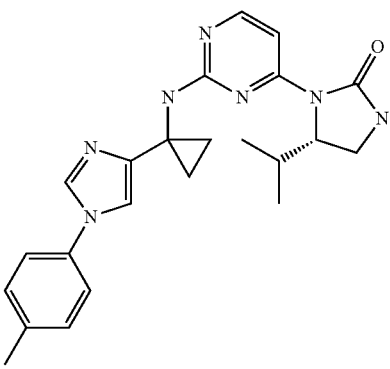
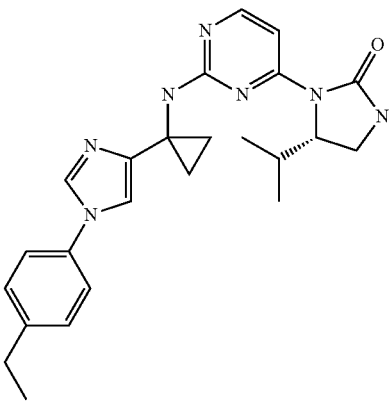
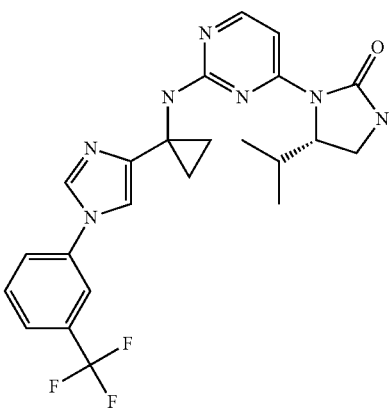

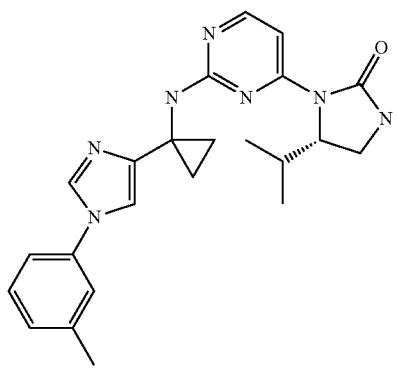
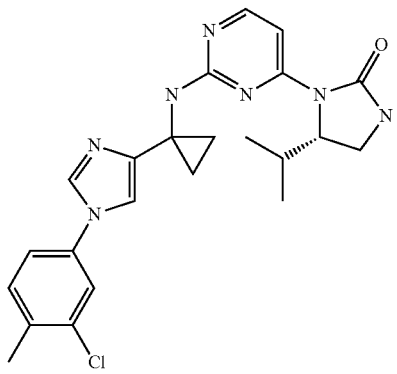
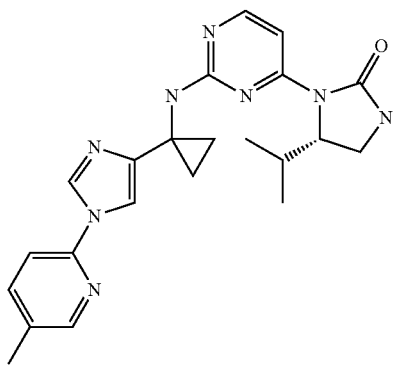
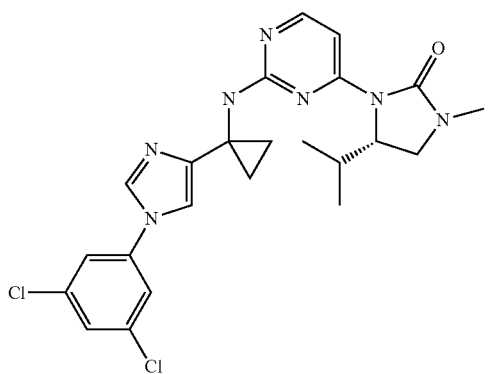
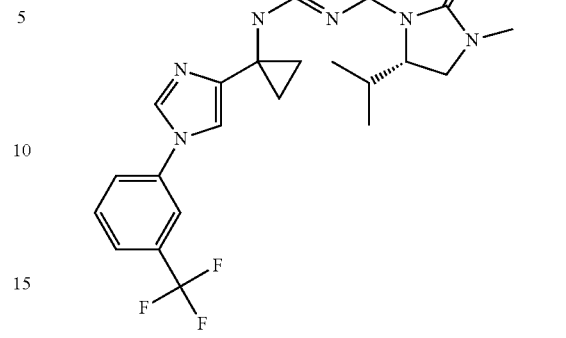
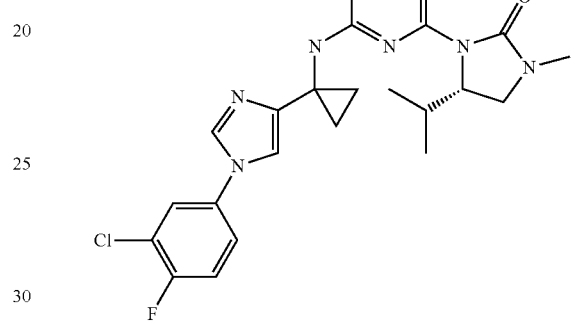
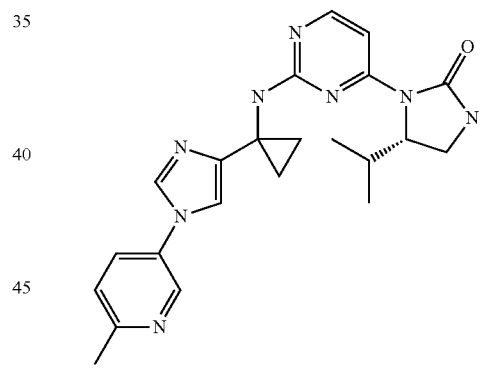
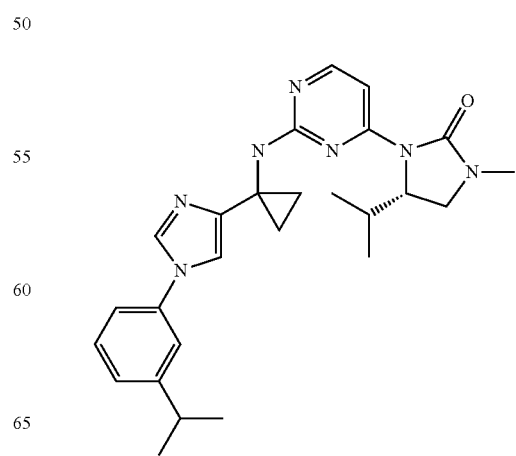

-continued
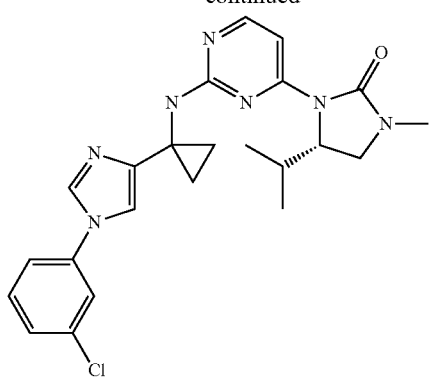
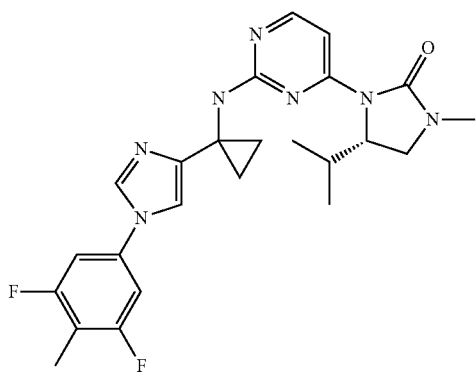
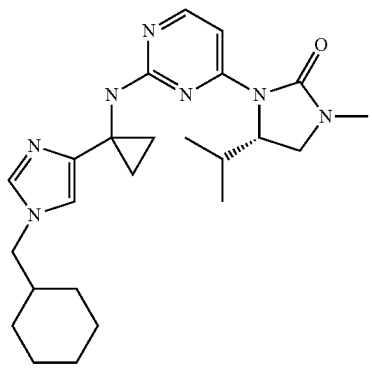
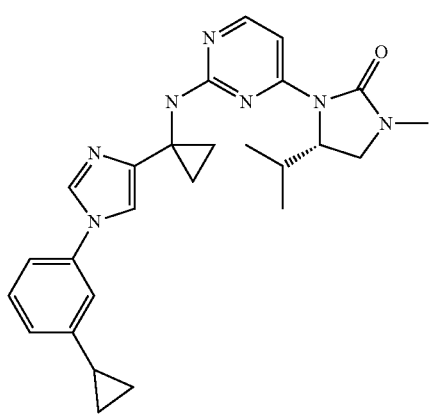
-continued
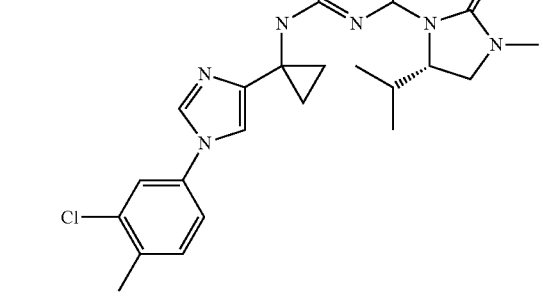
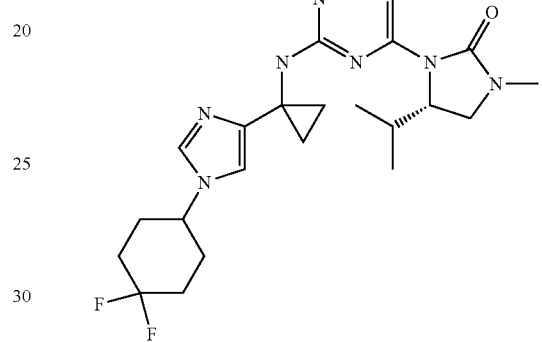
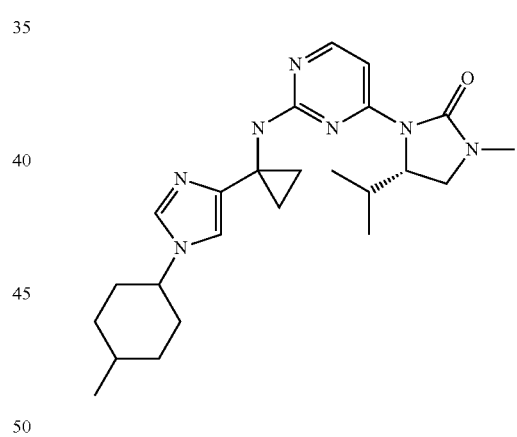
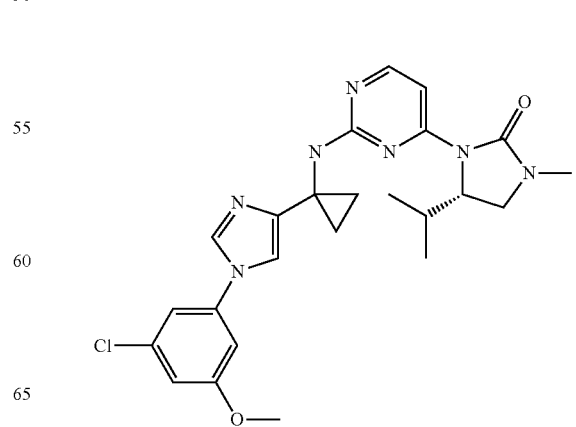

-continued
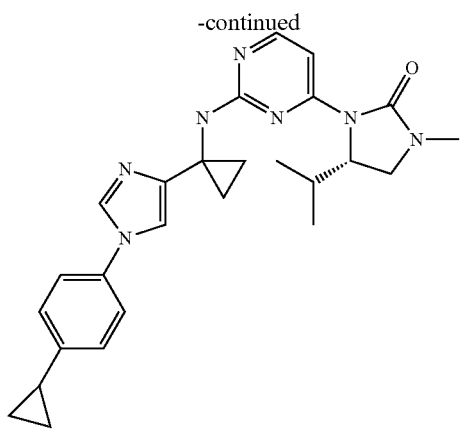
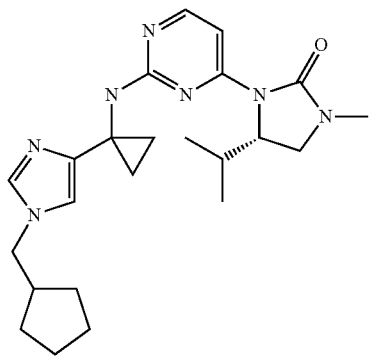 [SMILES: CC(C)[C@H]1CN(C)C(=O)N1c1ccnc(NC2(c3cn(CC4CCCC4)cn3)CC2)n1]
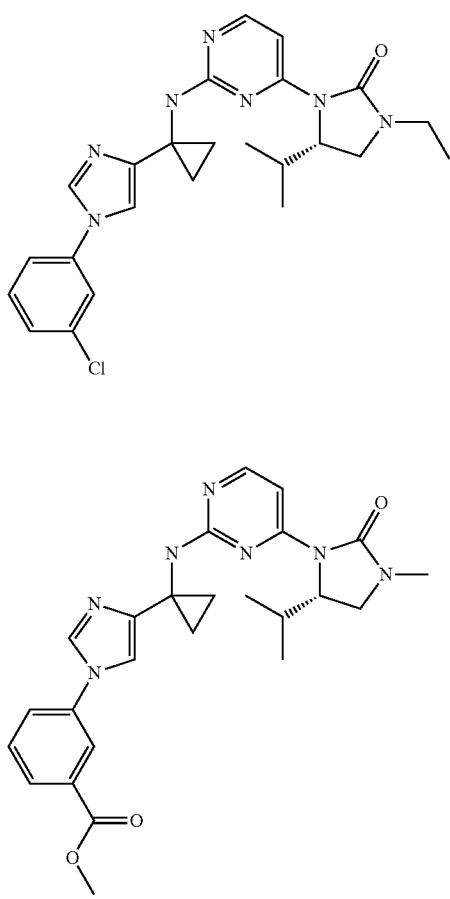
-continued
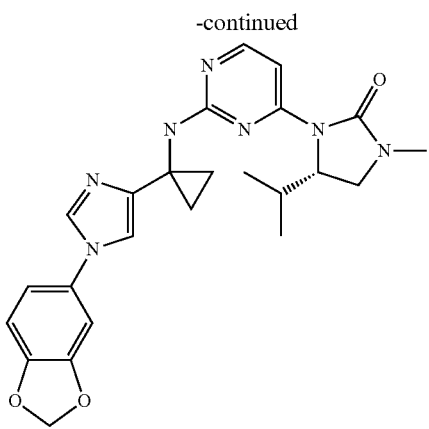
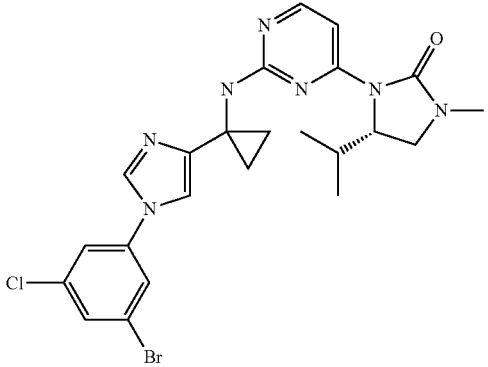
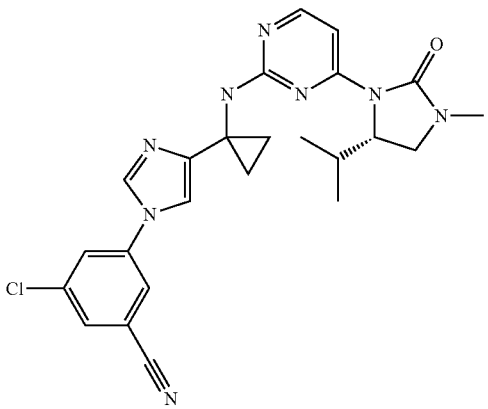
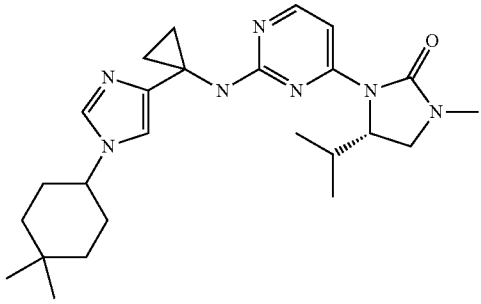

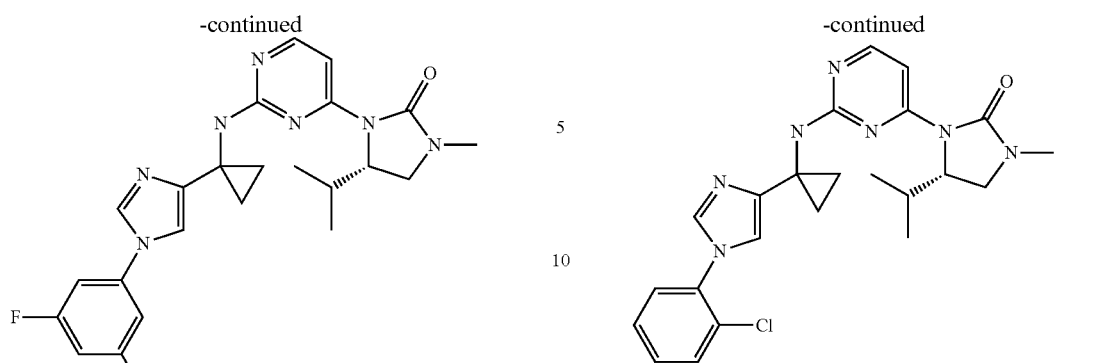
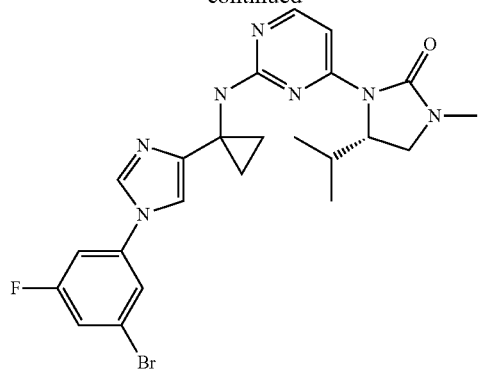
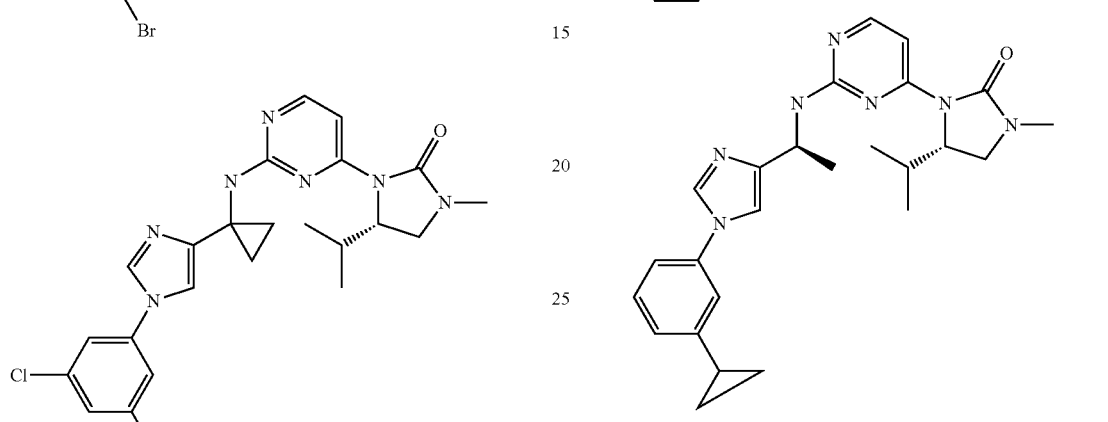
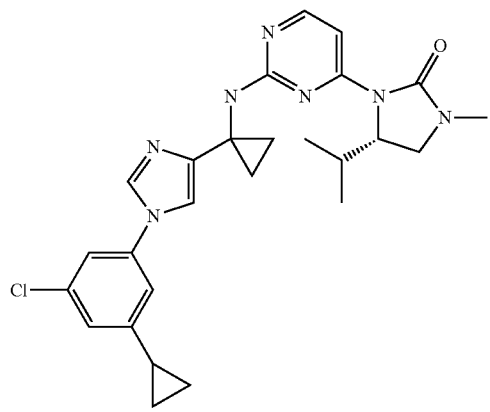
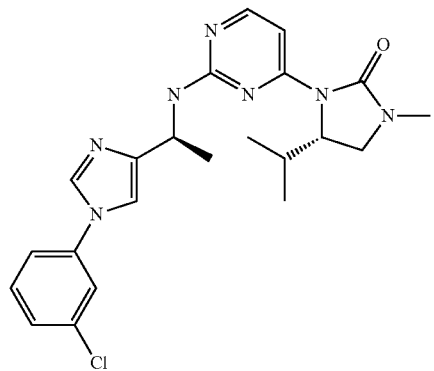
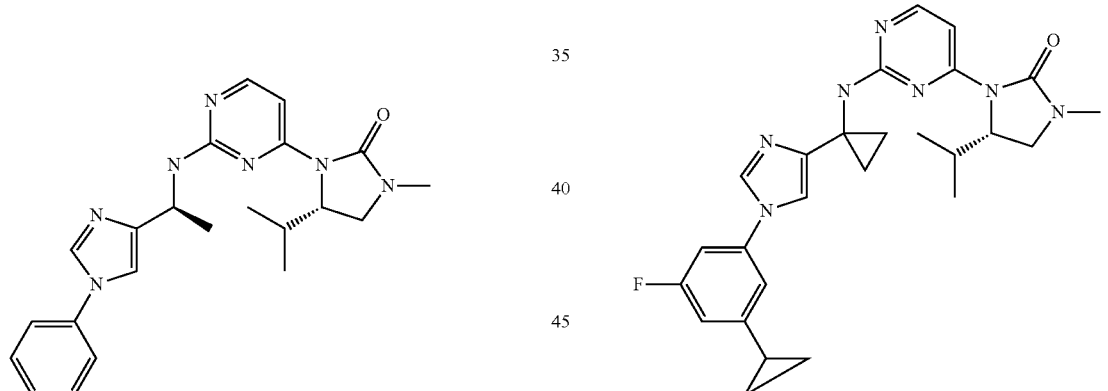
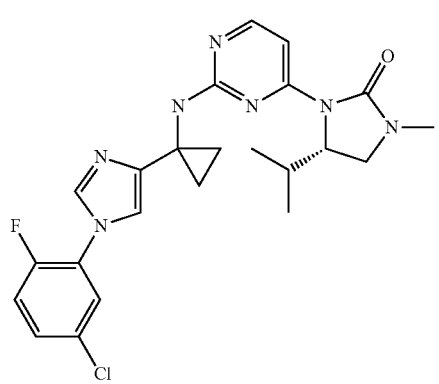
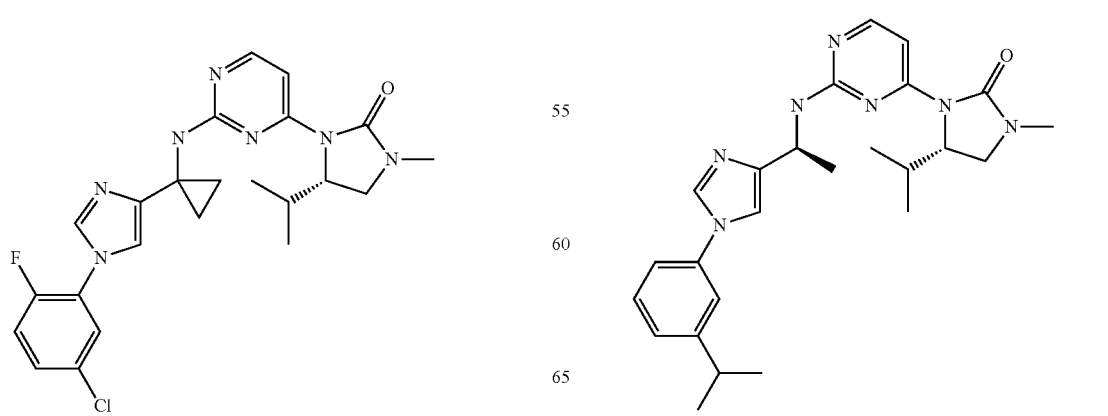

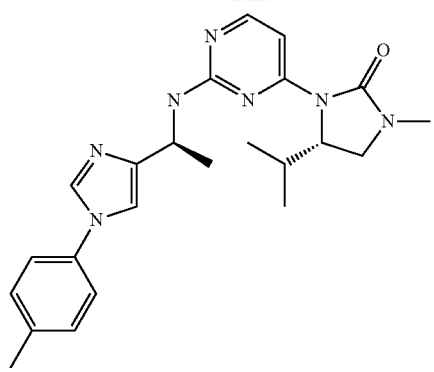
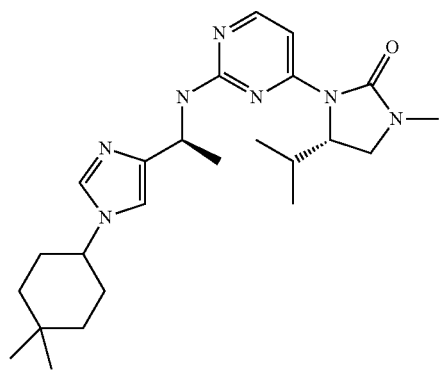
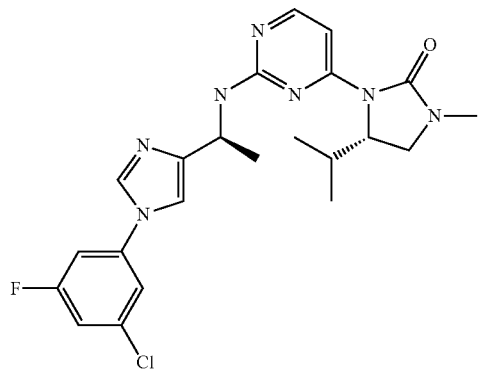
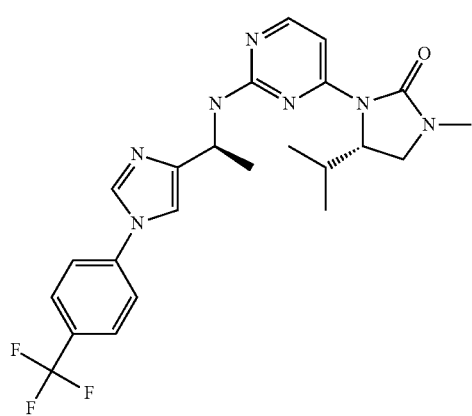
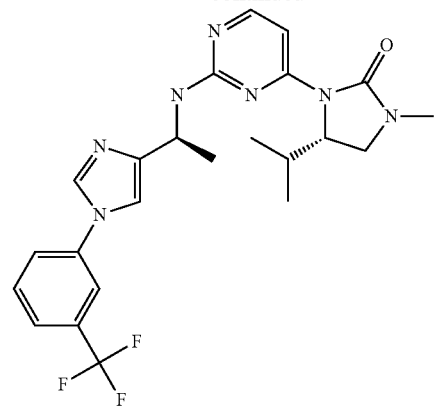
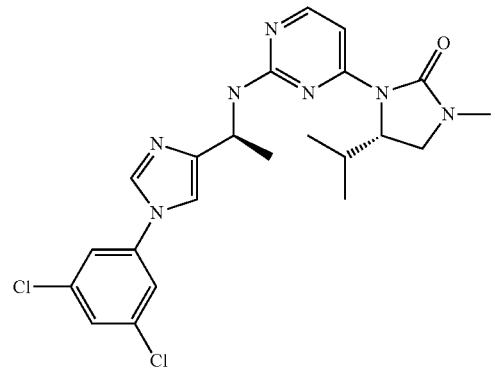
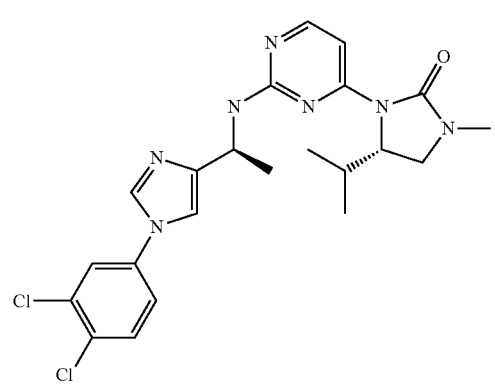
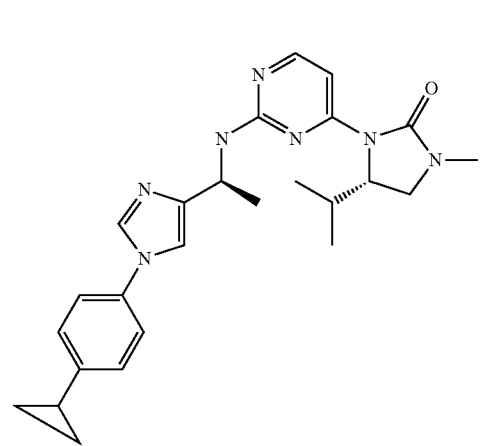

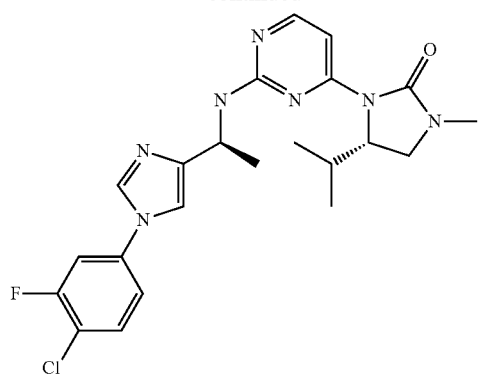
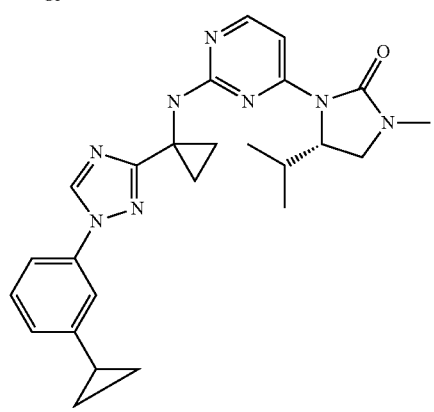
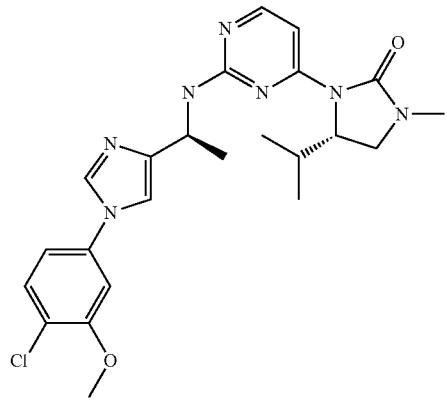
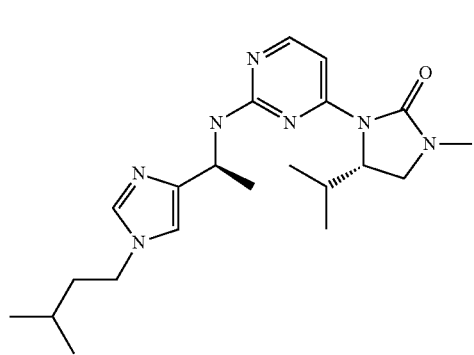
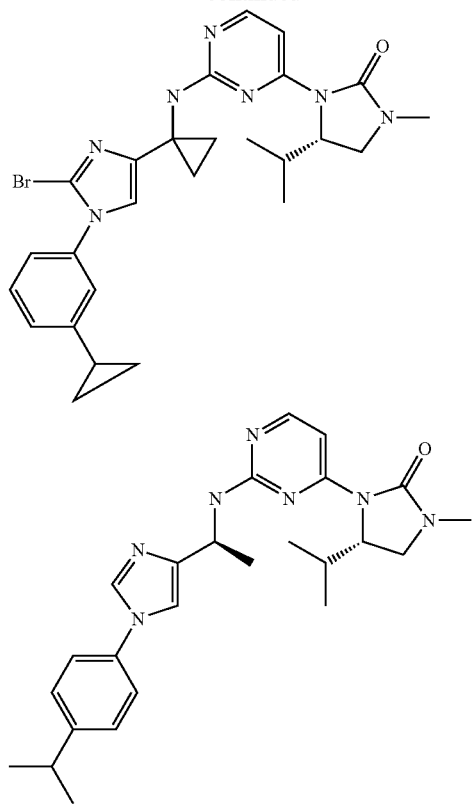
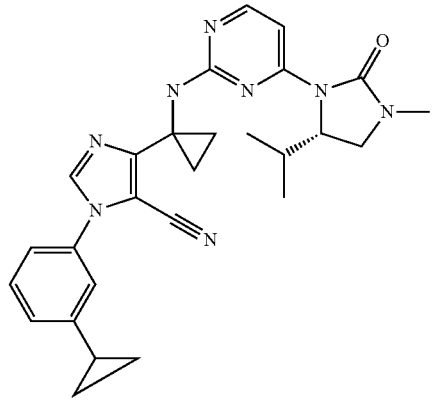
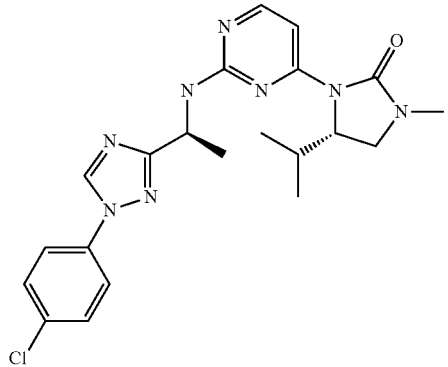

-continued
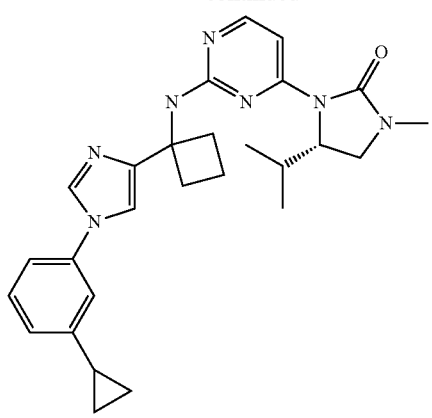
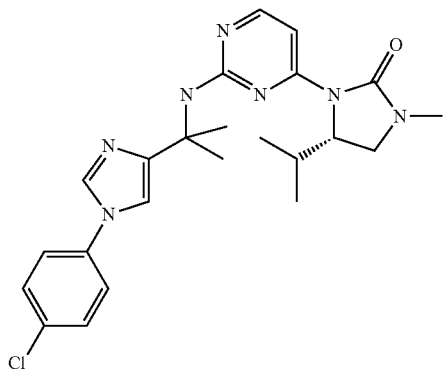
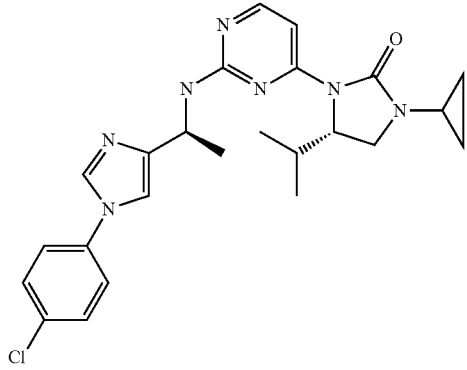
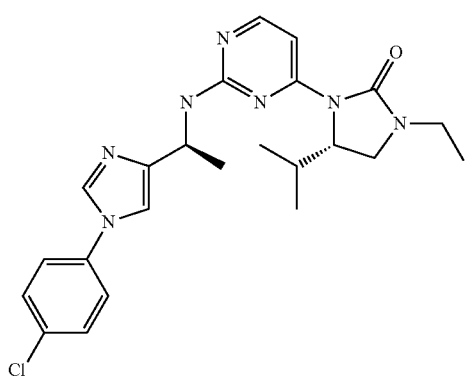
-continued
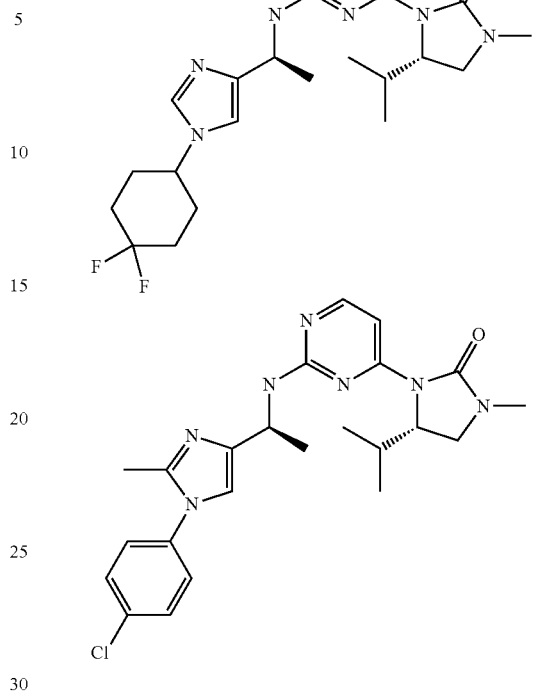
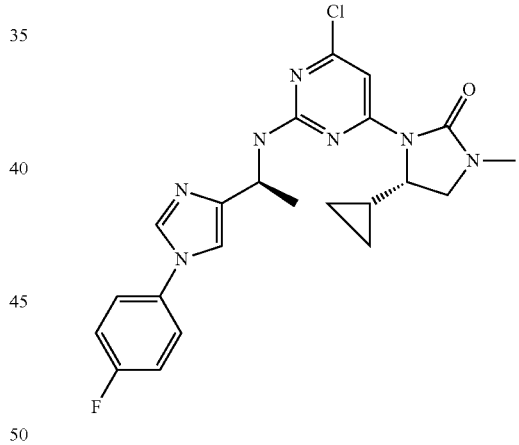
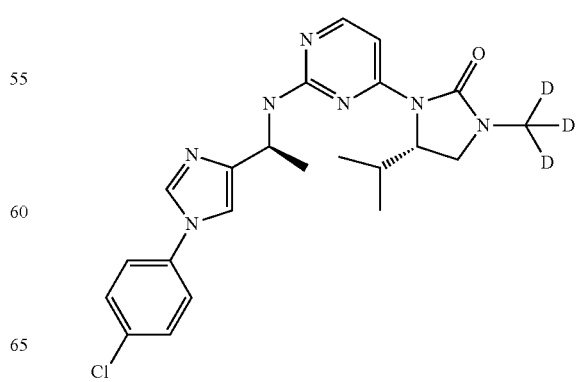

25
-continued
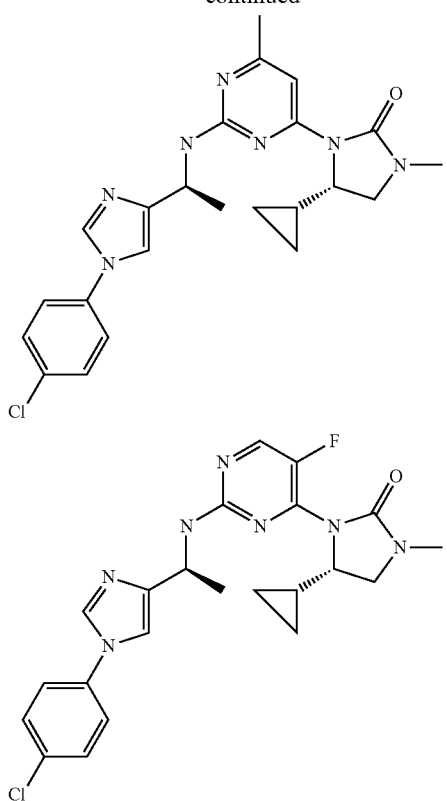
26
-continued
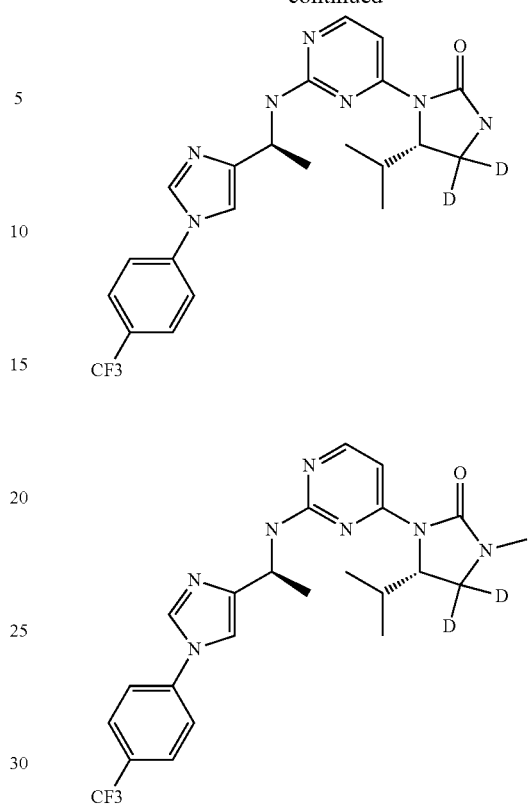
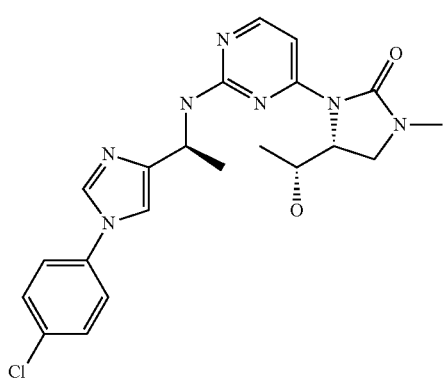
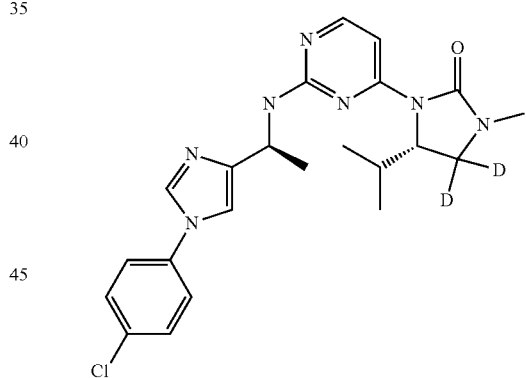
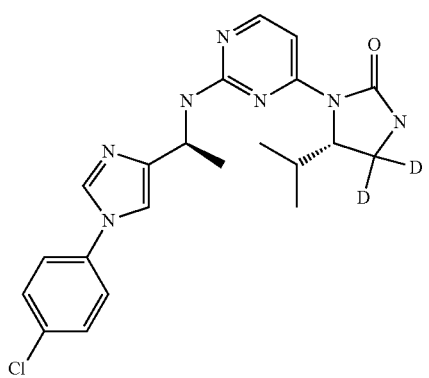
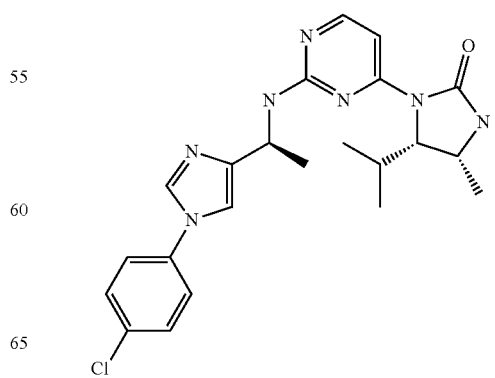

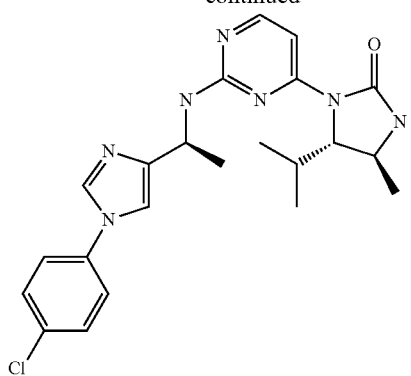
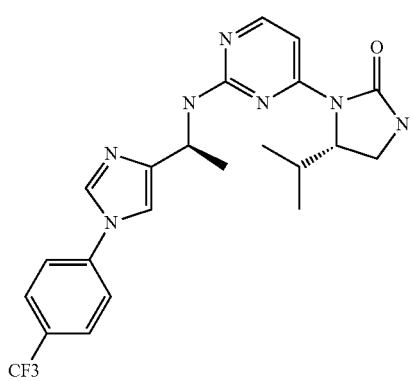
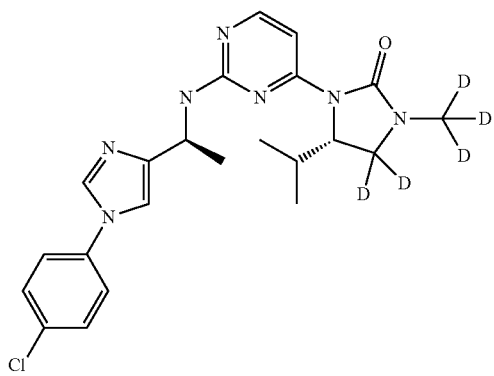
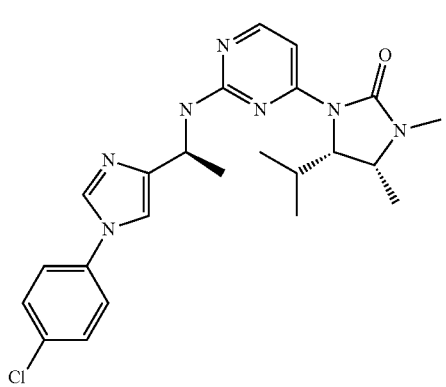
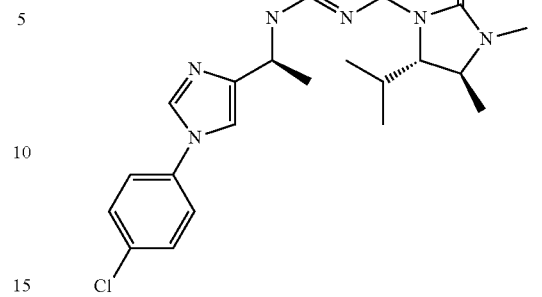
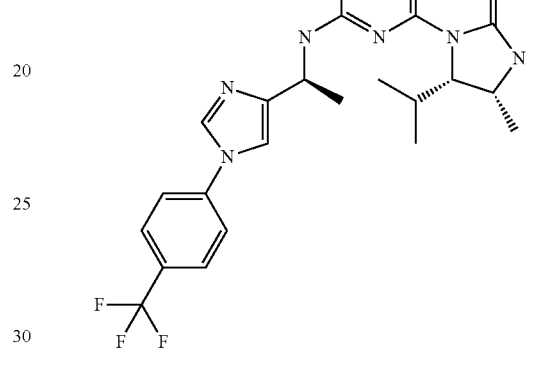
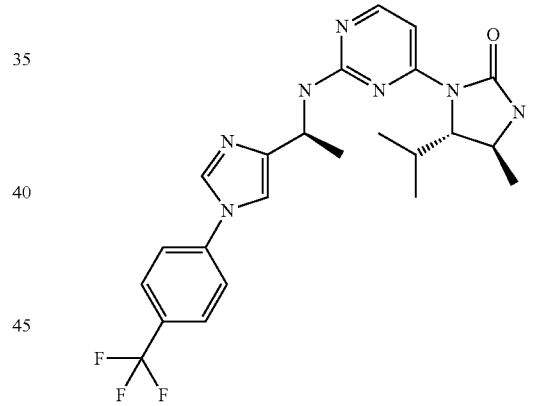
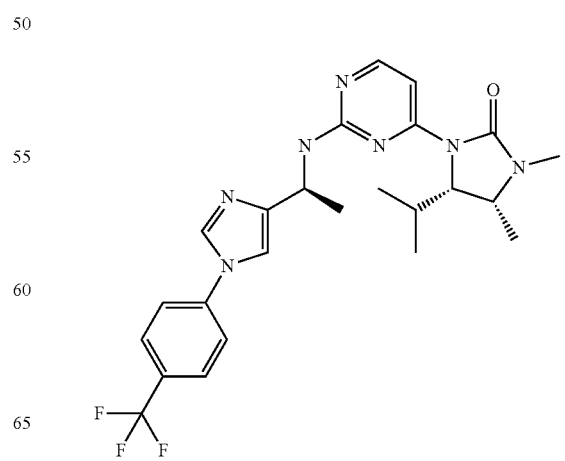

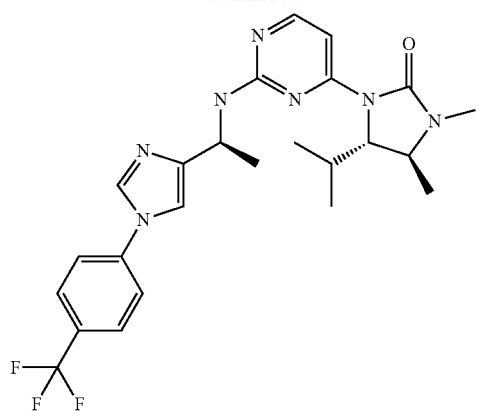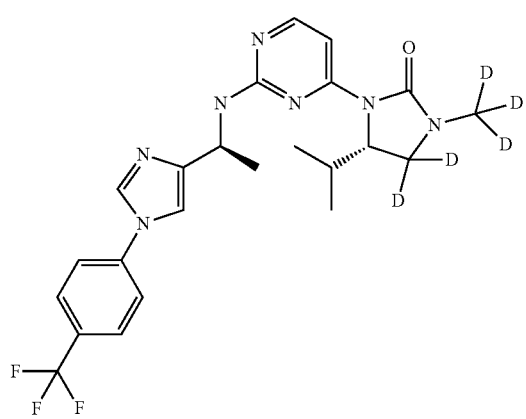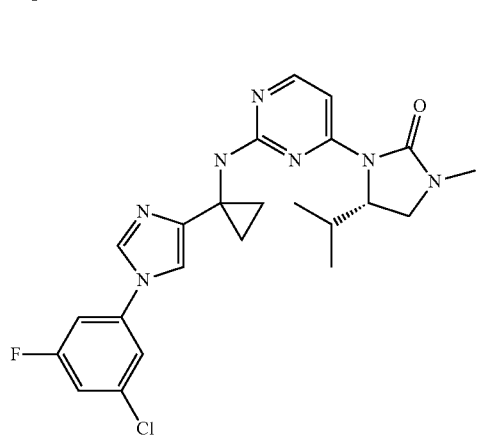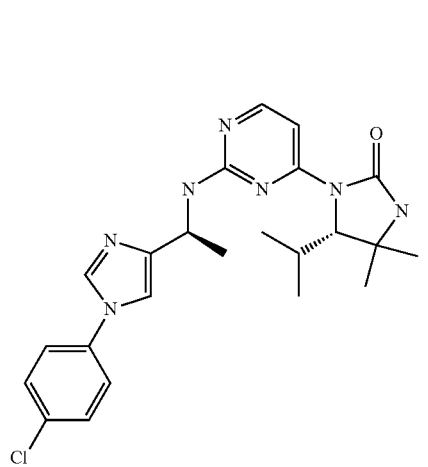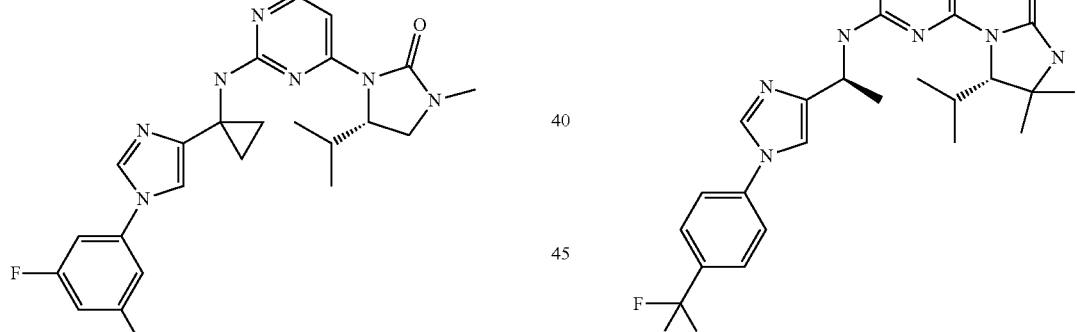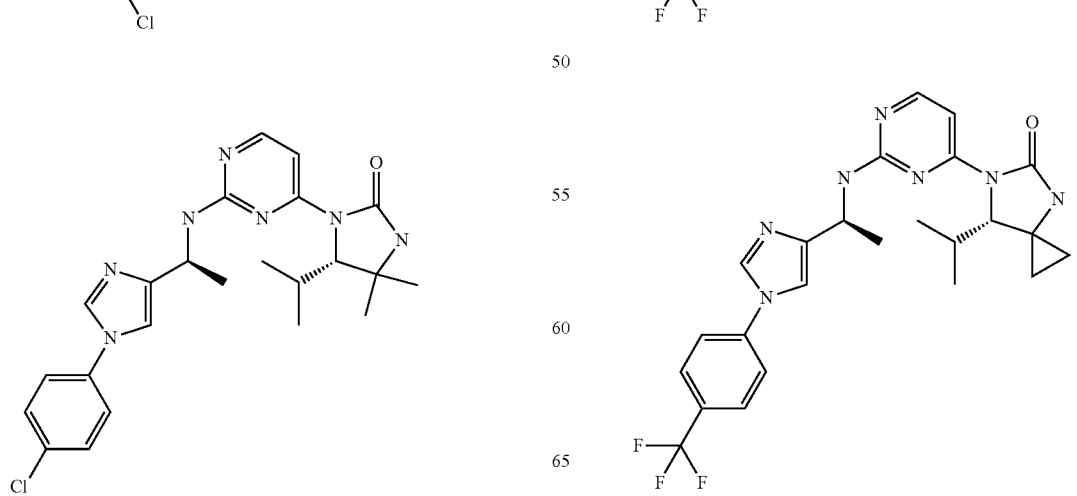

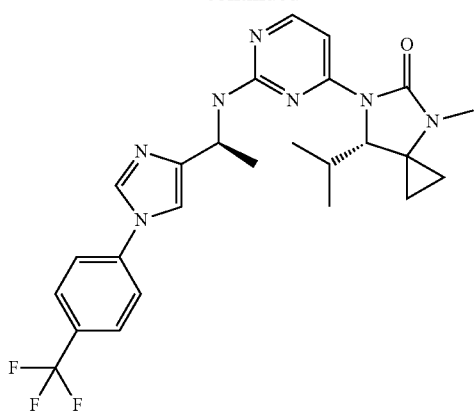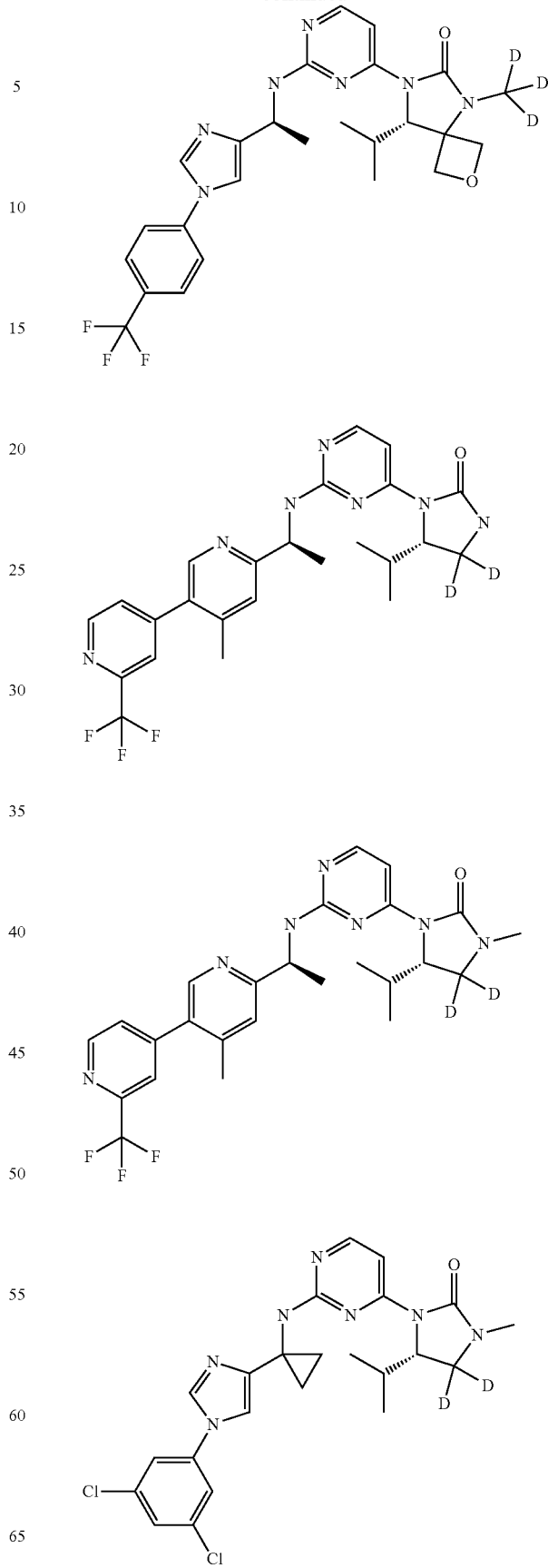

-continued

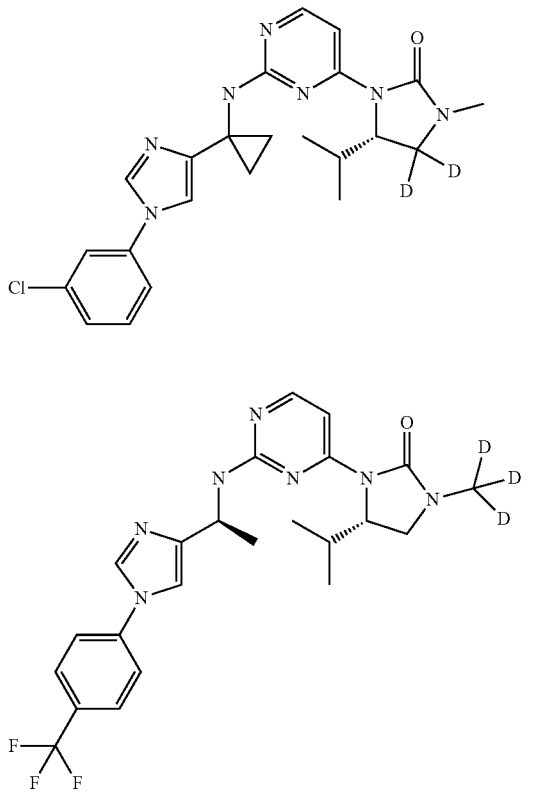

-continued

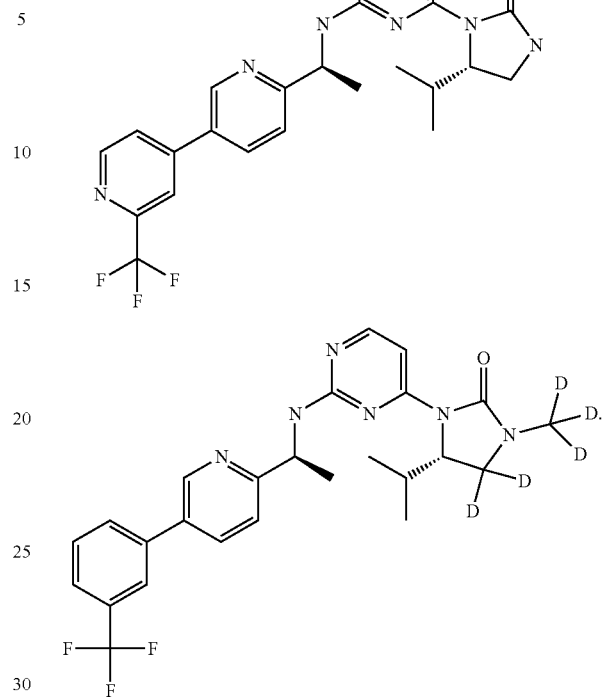

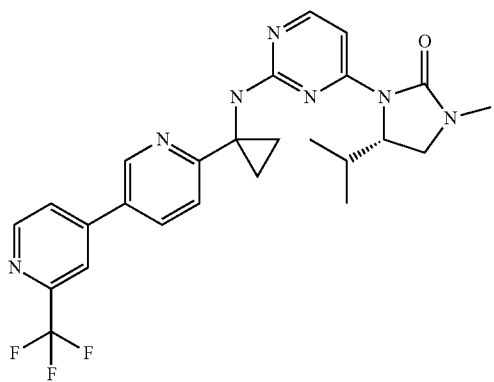

In the second aspect of the invention, a pharmaceutical composition is provided, comprising a therapeutically effective amount of the compound according to the first aspect of the invention, a stereoisomer, a racemate or a pharmaceutically acceptable salt thereof and a pharmaceutically acceptable excipient.

In the third aspect of the invention, a method of preparing the compound according to the first aspect of the invention is provided, comprising the steps of:

(i) in the absence of a solvent, intermediate C and intermediate D are subjected to a substitution reaction by heating to give compound I, and $R_3$-$R_{12}$ are as defined above, and X is a halogen,

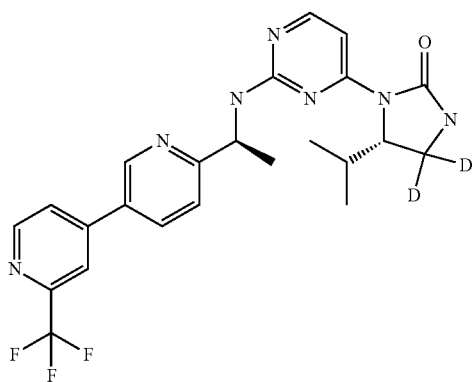

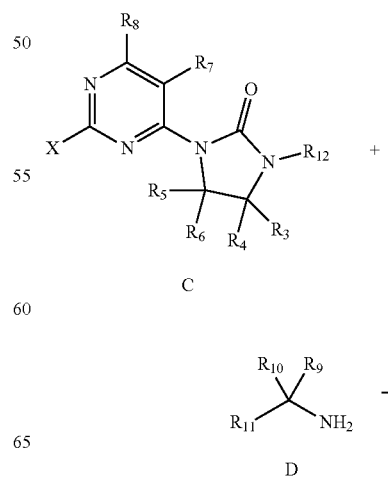

-continued

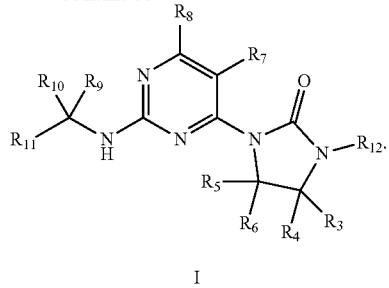

I

In another preferred embodiment, before step (i), the method further comprises step (i-1): in an inert solvent, intermediate A and intermediate B are subjected to a substitution reaction in the presence of a basic substance to form intermediate C,

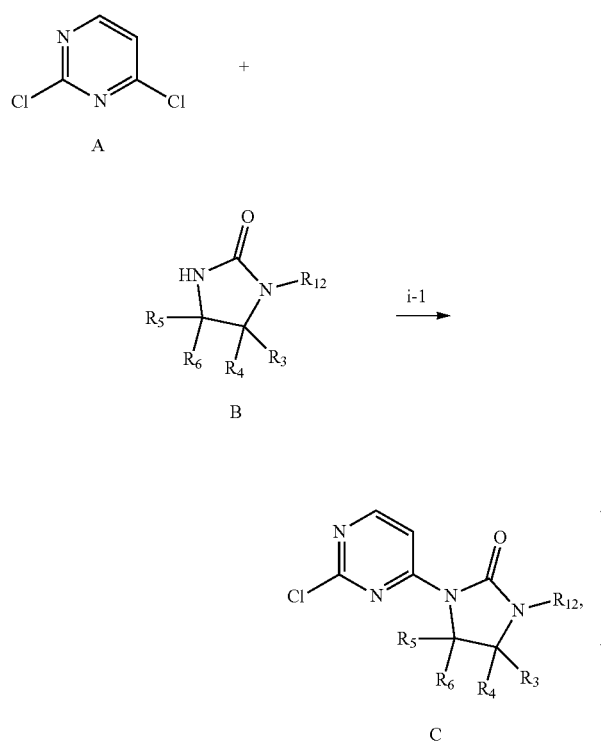

wherein, $R_3$-$R_6$ and $R_{12}$ are as defined above.

In another preferred embodiment, the inert solvent is selected from the group consisting of dichloromethane, chloroform, 1,2-dichloroethane, dioxane, DMF, acetonitrile, DMSO, NMP, THF or a combination thereof.

In another preferred embodiment, the basic substance includes an organic base and an inorganic base.

In another preferred embodiment, the organic base is selected from the group consisting of TEA, DIPEA or a combination thereof.

In another preferred embodiment, the inorganic base is selected from the group consisting of sodium hydride, potassium carbonate, sodium carbonate, cesium carbonate, potassium t-butoxide, sodium t-butoxide, LiHMDS, LDA, butyl lithium or a combination thereof.

In another preferred embodiment, the compound of formula I is a compound of formula J

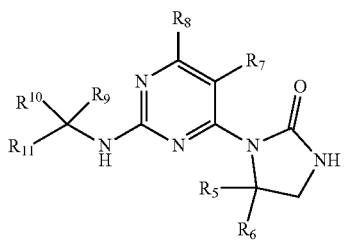

wherein $R_5$-$R_{11}$ are as defined above.

In another preferred embodiment, in step (i), intermediate L and intermediate D are subjected to a substitution reaction by heating in the absence of a solvent to form a compound of formula J:

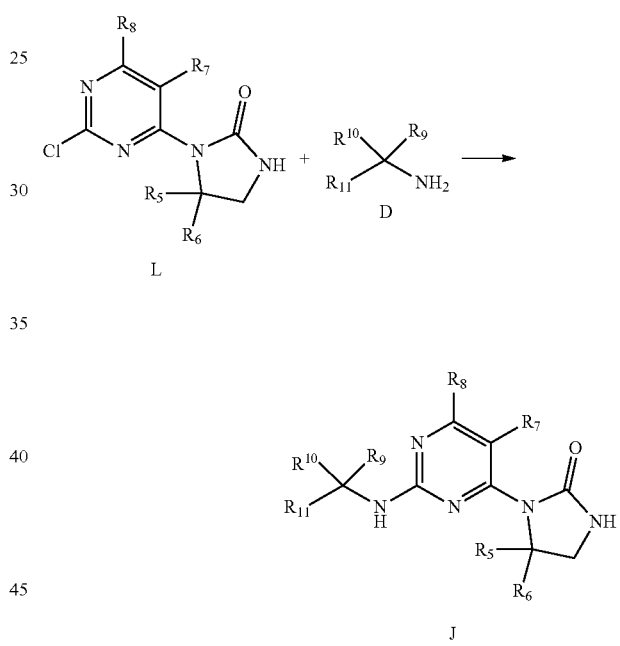

wherein each group is as defined above.

In another preferred embodiment, before step (i), the method further comprises the steps of:

(i-1a) reacting a compound of formula Q with a dehydrating agent (preferably triphosgene, trifluoroacetic anhydride, acetic anhydride) in an inert solvent to form a compound of formula P, and (i-1b) reacting the compound of formula P with a reductant N (preferably lithium aluminium hydride, lithium aluminium deuteride, sodium borohydride, borane, hydrogen/palladium carbon, deuterium/palladium carbon) in an inert solvent to form a compound of formula M, and (i-1c) reacting the compound of formula M with triphosgene or carbonyldiimidazole in the presence of a basic substance in an inert solvent to form the compound of formula L:

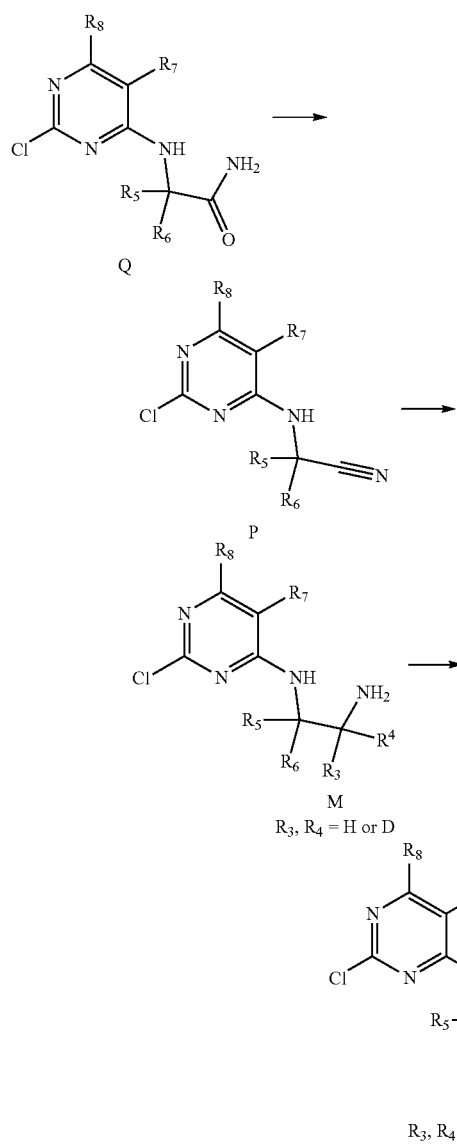

wherein each group is as defined above.

In the fourth aspect of the invention, a use of the compound according to the first aspect of the invention, a stereoisomer or a pharmaceutically acceptable salt thereof or the composition according to the second aspect of the invention is provided, for the preparation of a medicament for preventing and treating an IDH mutation-related disease, the use includes:

(a) preparation of a medicament for treating a disease related to a mutant IDH enzyme activity or expression level;

(b) preparation of a mutant IDH enzyme-targeted inhibitor;

(c) non-therapeutic inhibition of the activity of a mutant IDH enzyme in vitro;

(d) non-therapeutic inhibition of tumor cell proliferation in vitro; and/or (e) treatment of a disease related to mutant IDH enzyme activity or expression level.

In another preferred embodiment, the disease is an IDH mutation related tumor.

In another preferred embodiment, the tumor is selected from the group consisting of glioma, acute myeloid leukemia, sarcoma, prostate cancer, melanoma, non-small cell lung cancer, articular chondrosarcoma and cholangioma.

In the fifth aspect of the invention, a method for preventing and/or treating an IDH mutation-related disease in a mammal is provided, comprising administering to a mammal in need thereof a therapeutically effective amount of the compound according to the first aspect of the invention, a stereoisomer or a pharmaceutically acceptable salt thereof, or a therapeutically effective amount of the pharmaceutical composition according to the second aspect of the invention.

In another preferred embodiment, the disease is an IDH mutation-related tumor.

In another preferred embodiment, the tumor is selected from the group consisting of glioma, acute myeloid leukemia, sarcoma, prostate cancer, melanoma, non-small cell lung cancer, articular chondrosarcoma and cholangioma.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Through extensive and intensive long research, the inventors have made unexpected discoveries for the first time, on which the present invention has been completed.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all values between 99 and 101 (eg, 99.1, 99.2, 99.3, 99.4, etc.).

As used herein, the terms "contains" or "includes (comprises)" may be open-ended, semi-close-ended and close-ended. In other words, the terms also include "consisting essentially of" or "consisting of".

Definitions

The definition of standard chemical terms can be found in references (including Carey and Sundberg "ADVANCED ORGANIC CHEMISTRY 4TH ED." Vols. A (2000) and B (2001), Plenum Press, New York). Conventional methods within the scope of the art, such as mass spectrometry, NMR, IR and UV/VIS spectroscopy and pharmacological methods, are employed unless otherwise indicated. Unless specifically defined, the terms used herein in relation to analytical chemistry, organic synthetic chemistry and pharmaceutical and pharmaceutical chemistry are known in the art. Standard techniques can be used in chemical synthesis, chemical analysis, pharmaceutical preparation, preparation and delivery as well as treatment in patients. For example, the reaction can be carried out and purified by using the manufacturer's instructions for use of the kit, or by methods well known in the art or as described in the present invention. The above techniques and methods can generally be carried out according to conventional methods well known in the art and the description in various summary and more specific references cited and discussed in this specification.

In the present specification, the group and its substituents can be selected by those skilled in the art to provide stable structural moieties and compounds.

When a substituent is described by a conventional chemical formula written from left to right, the substituent also includes a chemically equivalent obtained substituent when the structural formula is written from right to left. For example, —CH$_2$O— is equivalent to —OCH$_2$—.

The section headings used herein are for the purpose of organizing articles only and are not to be construed as limiting the subject matter. All literatures or parts of the literatures cited in this application, including but not limited to patents, patent applications, articles, books, operating manuals and papers, are hereby incorporated by reference in their entirety.

Certain chemical groups defined herein are preceded by a simplified symbol to indicate the total number of carbon atoms present in the group. For example, C1-C6 alkyl refers to an alkyl having 1 to 6 carbon atoms in total as defined below. The total number of carbon atoms in the simplified symbol does not include carbon that may be present in the substituents of the group.

In addition to the foregoing, when used in the specification and claims of the present application, the following terms have the meanings indicated below unless otherwise specifically indicated.

In the present application, the term "halogen" means fluoro, chloro, bromo or iodo.

"Hydroxy" means an —OH group.

"Hydroxyalkyl" means an alkyl group as defined below which is substituted by a hydroxy (—OH).

"Carbonyl" means a —C(=O)— group.

"Nitro" means —NO$_2$.

"Cyano" means —CN.

"Amino" means —NH$_2$.

"Substituted amino" means an amino substituted by one or two alkyls, alkylcarbonyls, aralkyls, heteroaralkyls as defined below, for example, monoalkylamino, dialkylamino, alkylamido, aralkylamino, heteroarylalkylamino.

"Carboxyl" means —COOH.

In the present application, as a group or part of another group (for example, in a group such as a halogen-substituted alkyl), the term "alkyl" means a fully saturated straight or branched hydrocarbon chain group, which consists only of carbon atoms and hydrogen atoms, and for example, has 1 to 12 (preferably 1 to 8, more preferably 1 to 6) carbon atoms, and is bonded to the rest of the molecule by a single bond, for example, including (but not limited to) methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl and decyl etc. For the present invention, the term "alkyl" refers to an alkyl containing 1 to 6 carbon atoms.

In the present application, as a group or part of another group, the term "alkenyl" means a straight or branched hydrocarbon chain group consisting only of carbon atoms and hydrogen atoms, containing at least one double bond, having for example 2 to 14 (preferably 2 to 10, and more preferably 2 to 6) carbon atoms and attached to the remainder of the molecule by a single bond, such as (but not limited to) vinyl, propenyl, allyl, but-1-enyl, but-2-enyl, pent-1-enyl, pent-1,4-dienyl and the like.

In the present application, as a group or part of another group, the term "cyclic hydrocarbon group" means a stable non-aromatic monocyclic or polycyclic hydrocarbon group consisting only of carbon atoms and hydrogen atoms, which may include a fused ring system, a bridged ring system or a spiro ring system, and it has 3 to 15 carbon atoms, preferably 3 to 10 carbon atoms, more preferably 3 to 8 carbon atoms, and it is saturated or unsaturated and may be attached to the rest of the molecule via any suitable carbon atom by a single bond. Unless otherwise specifically indicated in the specification, a carbon atom in a cyclic hydrocarbon group may be optionally oxidized. Examples of cyclic hydrocarbon group include (but are not limited to) cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-indanyl, 1,2,3,4-tetrahydro-naphthyl, 5,6,7,8-tetrahydro-naphthyl, 8,9-dihydro-7H-benzocycloheptene-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-cyclopentadienyl and the like.

In the present application, as a group or part of another group, the term "heterocyclyl" means a stable 3- to 20-membered non-aromatic cyclic group consisting of 2 to 14 carbon atoms and 1 to 6 heteroatoms selected from the group consisting of nitrogen, phosphorus, oxygen and sulfur. Unless otherwise specifically indicated in the specification, a heterocyclyl may be a monocyclic, bicyclic, tricyclic or more cyclic ring system, which may include a fused ring system, a bridged ring system or a spiro ring system. In the heterocyclyl, the nitrogen, carbon or sulfur atom may optionally be oxidized and the nitrogen atom may optionally be quaternized. The heterocyclyl may be partially or fully saturated. The heterocyclyl may be bonded to the remainder of the molecule via a carbon atom or a heteroatom by a single bond. In the heterocyclyl containing a fused ring, one or more of the rings may be an aryl or heteroaryl group as defined hereinafter, provided that the connection point to the rest of the molecule is a non-aromatic ring atom. For the present invention, the heterocyclyl is preferably a stable 4 to 11 membered non-aromatic monocyclic, bicyclic, bridged or spiro group containing 1 to 3 heteroatoms selected from nitrogen, oxygen and sulfur, more preferably, a stable 4- to 8-membered non-aromatic monocyclic, bicyclic, bridged or spiro group containing 1 to 3 heteroatoms selected from nitrogen, oxygen and sulfur. Examples of heterocyclyl include (but are not limited to) pyrrolidinyl, morpholinyl, piperazinyl, homopiperazinyl, piperidinyl, thiomorpholinyl, 2,7-diaza-spiro[3.5]nonane-7-yl, 2-oxa-6-aza-spiro[3.3]heptane-6-yl, 2,5-diaza-bicyclo[2.2.1]heptan-2-yl, azacyclobutanyl, pyranyl, tetrahydropyranyl, thiopyranyl, tetrahydrofuranyl, oxazinyl, dioxolanyl, tetrahydroisoquinolinyl, decahydroisoquinolinyl, imidazolinyl, imidazolidinyl, quinoxalinyl, thiazolidinyl, isothiazolidinyl, isoxazolidinyl, indolinyl, octahydroindolyl, octahydroisoindolyl, pyrrolidinyl, pyrazolidinyl, phthalimido and the like.

In the present application, as a group or part of another group, the term "aryl" means a conjugated hydrocarbon ring system group having 6 to 18 carbon atoms (preferably 6 to 10 carbon atoms). For the present invention, an aryl may be a monocyclic, bicyclic, tricyclic or more cyclic ring system, and may also be fused to a cycloalkyl or heterocyclyl as defined above, provided that the aryl is connected to the rest of the molecule via atoms on the aromatic ring by a single bond. Examples of aryl include (but are not limited to) phenyl, naphthyl, anthracenyl, phenanthryl, fluorenyl, 2,3-dihydro-1H-isoindolyl, 2-benzoxazolinone, 2H-1, 4-benzoxazine-3(4H)-keto-7-yl and the like.

In the present application, the term "arylalkyl" refers to an alkyl as defined above substituted with an aryl as defined above.

In the present application, as a group or part of another group, the term "heteroaryl" means a 5- to 16-membered conjugated ring system group having 1 to 15 carbon atoms (preferably 1 to 10 carbon atoms) and 1 to 6 heteroatoms selected from nitrogen, oxygen and sulfur in the ring. Unless otherwise specifically indicated in the specification, a heteroaryl may be a monocyclic, bicyclic, tricyclic or more cyclic ring system, and may also be fused to a cycloalkyl or heterocyclyl as defined above, provided that the heteroaryl is connected to the remainder of the molecule via an atom on the aromatic ring by a single bond. In the heteroaryl, the nitrogen, carbon or sulfur atom can be optionally oxidized and the nitrogen atom can optionally be quaternized. For the present invention, the heteroaryl is preferably a stable 5- to 12-membered aromatic group containing 1 to 5 heteroatoms selected from nitrogen, oxygen and sulfur, more preferably a stable 5- to 10-membered aromatic group containing 1 to 4 heteroatoms selected from nitrogen, oxygen and sulfur or a 5- to 6-membered aromatic group containing 1 to 3 heteroatoms selected from nitrogen, oxygen and sulfur. Examples of heteroaryl include (but are not limited to) thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolyl, isoquinolyl, diaza naphthyl, naphthyridinyl, quinoxalinyl, pteridyl, carbazolyl, carbolinyl, phenanthridinyl, phenanthrolinyl, acridinyl, phenazinyl, isothiazolyl, benzothiazolyl, benzothienyl, oxtriazolyl, cinnolinyl, quinazolinyl, phenylthio, indolizinyl, o-phenanthrolinyl, isoxazolyl, phenoxazinyl, phenothiazinyl, 4,5,6,7-tetrahydrobenzo[b]thienyl, naphthopyridyl, [1,2,4]triazolo[4, 3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine and the like.

In the present application, the term "heteroarylalkyl" refers to an alkyl as defined above substituted with a heteroaryl as defined above.

In the present application, "optional" or "optionally" means that the subsequently described event or condition may or may not occur, and the description includes both the occurrence and non-occurrence of the event or condition. For example, "optionally substituted aryl" means that the aryl is substituted or unsubstituted, and the description includes both the substituted aryl and the unsubstituted aryl. The "optionally" substituents described in the claims and the specification of the present invention are selected from the group consisting of alkyl, alkenyl, alkynyl, halogen, haloalkyl, haloalkenyl, haloalkynyl, cyano, nitro an optionally substituted aryl, an optionally substituted heteroaryl, an optionally substituted cycloalkyl, an optionally substituted heterocyclic hydrocarbon group.

The terms "moiety", "structural moiety", "chemical moiety", "group" and "chemical group" as used herein refer to a particular fragment or functional group in a molecule. A chemical moiety is generally considered to be a chemical entity that is embedded or attached to a molecule.

"Stereoisomer" refers to a compound composed of same atoms, bonded by same bonds, but having a different three-dimensional structure. The invention will cover various stereoisomers and mixtures thereof.

When the compound of the present invention contains an olefinic double bond, the compounds of the present invention are intended to include E- and Z-geometric isomers unless otherwise stated.

"Tautomer" refers to an isomer formed by the transfer of a proton from one atom of a molecule to another atom of the same molecule. All tautomeric forms of the compounds of the invention will also fall within the scope of the invention.

The compounds or pharmaceutically acceptable salts thereof of the invention may contain one or more chiral carbon atoms, thereby forming enantiomers, diastereomers, and other stereoisomeric forms. Each chiral carbon atom can be defined as (R)- or (S)-based on stereochemistry. The invention is intended to include all possible isomers, as well as racemate and optically pure forms thereof. Racemates, diastereomers or enantiomers may be used as starting materials or intermediates for the preparation of the compounds of the invention. Optically active isomers can be prepared using chiral synthons or chiral reagents, or resolved using conventional techniques, such as by crystallization and chiral chromatography.

Conventional techniques for the preparation/isolation of individual isomers include chiral synthesis from a suitable optically pure precursor, or resolution of the racemate (or racemic form of a salt or derivative) using, for example, chiral high performance liquid chromatography, for example, see Gerald Githitz and Martin G. Schmid (Eds.), Chiral Separations, Methods and Protocols, Methods in Molecular Biology, Vol. 243, 2004; A. M. Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" means a salt formed with an inorganic acid or organic acid which retains the bioavailability of the free base without other side effects. Inorganic acid salts include, but are not limited to, hydrochlorides, hydrobromides, sulfates, nitrates, phosphates, and the like; organic acid salts include, but are not limited to, formate, acetate, 2,2-dichloroacetate, trifluoroacetate, propionate, hexanoate, octoate, decanoate, undecylenate, glycolate, gluconate, lactate, sebacate, adipate, glutarate, malonates, oxalates, maleates, succinates, fumarates, tartrates, citrates, palmitates, stearates, oleates, cinnamate, laurate, malate, glutamate, pyroglutamate, aspartate, benzoate, methanesulfonate, besylate, p-toluenesulfonate, alginate, ascorbate, salicylate, 4-aminosalicylate, naphthalene disulfonate, and the like. These salts can be prepared by methods known in the art.

"Pharmaceutically acceptable base addition salt" means a salt formed with an inorganic base or organic base capable of maintaining the bioavailability of the free acid without other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium, sodium, potassium, calcium and magnesium salts. Salts derived from organic bases include, but are not limited to, the following salts: primary amines, secondary amines and tertiary amines, substituted amines, including naturally substituted amines, cyclic amines, and basic ion exchange resins, For example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline and caffeine. These salts can be prepared by methods known in the art.

In the present application, "pharmaceutical composition" refers to a preparation of the compound of the invention and a medium generally accepted in the art for delivering a bioactive compound to a mammal (such as a human). The medium includes a pharmaceutically acceptable carrier. The purpose of the pharmaceutical composition is to promote the administration of the organism, thereby facilitating the absorption of the active ingredient and thereby exerting biological activity.

The term "pharmaceutically acceptable" as used herein refers to a substance (such as a carrier or diluent) that does not affect the biological activity or properties of the compound of the invention, and is relatively non-toxic, i.e, the substance can be administered to an individual without causing undesirable biological reaction or interacting with any of the components contained in the composition in an undesirable manner.

In the present application, "pharmaceutically acceptable excipients" include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant government authorities for acceptable use by humans or domestic animals.

The term "tumor" of the present invention includes, but is not limited to, glioma, sarcoma, melanoma, articular chondroma, cholangiocarcinoma, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanin tumor, kidney cancer, oral cancer and the like.

The terms "preventive", "preventing" and "prevent" as used herein include reducing the possibility of the occurrence or deterioration of a disease or condition in a patient.

The term "treatment" and other similar synonyms as used herein include the following meanings:

(i) preventing a disease or condition from occurring in a mammal, particularly when such a mammal is susceptible to the disease or condition, but has not been diagnosed as having the disease or condition;

(ii) inhibiting a disease or condition, i.e. curbing its development;

(iii) alleviating the disease or condition, i.e. causing the state of the disease or condition to subside; or (iv) alleviating the symptoms caused by the disease or condition.

The term "effective amount", "therapeutically effective amount" or "pharmaceutically effective amount" as used herein refers to a amount of at least one agent or compound, after its administration, it is sufficient to alleviate one or more symptoms of the disease or condition being treated to some extent. The result can be a reduction and/or alleviation of signs, symptoms or causes, or any other desired change in the biological system. For example, an "effective amount" for treatment is an amount of the composition comprising the compound disclosed herein that is required to provide a significant clinical condition relief effect. An effective amount suitable for any individual case can be determined using techniques such as dose escalation testing.

As used herein, the terms "administration", "administered", "administering" and the like refers to a method capable of delivering a compound or composition to a desired site for biological action. These methods include, but are not limited to, oral route, duodenal route, parenteral injection (including intravenous, subcutaneous, intraperitoneal, intramuscular, intraarterial injection or infusion), topical administration and rectal administration. The techniques of administration of the compounds and methods described herein are well known to those skilled in the art, for example, those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

As used herein, the terms "pharmaceutical combination", "drug combination", "combined medication", "applying other treatments", "administering other therapeutic agents" and the like mean a pharmaceutical treatment obtained by mixing or combining more than one active ingredient, it includes both fixed and unfixed combinations of active ingredients. The term "fixed combination" refers to the simultaneous administration of at least one compound described herein and at least one synergistic agent to a patient in the form of a single entity or a single dosage form. The term "unfixed combination" refers to the simultaneous administration, combination or sequential administration in variable intervals of at least one of the compounds described herein and at least one synergistic agent to the patient in the form of separate entities. These are also applied to cocktail therapy, for example the administration of three or more active ingredients.

It will also be understood by those skilled in the art that, in the methods described below, functional groups of the intermediate compound may need to be protected by a suitable protecting group. Such functional groups include a hydroxyl group, an amino group, a thiol group and a carboxylic acid. Suitable hydroxy protecting groups include trialkylsilyl or diarylalkylsilyl (e.g., tert-butyldimethylsilyl, tert-butyldiphenylsilyl or trimethylsilyl) tetrahydropyranyl, benzyl and the like. Suitable protecting groups for amino, guanyl and guanidyl include t-butoxycarbonyl, benzyloxycarbonyl and the like. Suitable thiol protecting groups include —C(O)—R" (wherein R" is alkyl, aryl or aralkyl), p-methoxybenzyl, trityl and the like. Suitable carboxy protecting groups include alkyl, aryl or aralkyl esters.

Protecting groups can be introduced and removed according to standard techniques known to those skilled in the art and as described herein. The use of protecting groups is described in detail in Greene, T. W. and P. G. M. Wuts, Protective Groups in Organi Synthesis, (1999), 4th Ed., Wiley. The protecting group can also be a polymeric resin.

Compound of Formula I

A compound of formula I, a stereoisomer, a racemate or a pharmaceutically acceptable salt thereof is provided in the present invention:

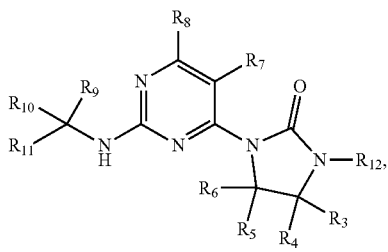

(I)

wherein, $R_3$ and $R_4$ are each independently selected from: H, D, substituted or unsubstituted $C_{1-4}$ alkyl;

or $R_3$ and $R_4$ together with a carbon atom connecting to them form a substituted or unsubstituted $C_{3-6}$ cycloalkyl, or $R_3$ and $R_4$ together with a carbon atom connecting to them form a substituted or unsubstituted $C_{3-6}$ epoxyalkyl;

$R_5$ and $R_6$ are each independently selected from: H, a substituted or unsubstituted $C_{1-4}$ alkyl, a substituted or unsubstituted $C_{6-10}$ aryl, a substituted or unsubstituted $C_{3-6}$ cycloalkyl;

or $R_5$ and $R_6$ together with a carbon atom connecting to them form a substituted or unsubstituted $C_{3-6}$ cycloalkyl;

$R_7$ and $R_8$ are each independently selected from H, halogen, a substituted or unsubstituted $C_{1-4}$ alkyl;

$R_9$ is selected from: H, a substituted or unsubstituted $C_{1-4}$ alkyl;

$R_{10}$ is a substituted or unsubstituted $C_{1-4}$ alkyl;

or $R_9$ and $R_{10}$ together with a carbon atom connecting to them form a substituted or unsubstituted $C_{3-6}$ cycloalkyl;

$R_{11}$ is selected from: a substituted or unsubstituted $C_{6-10}$ aryl, a substituted or unsubstituted $C_{5-10}$ heteroaryl; wherein the $C_{5-10}$ heteroaryl contains 1-4 heteroatoms selected from N, O or S; and the term "substituted" means having one or more (eg 1, 2, 3 or 4) substituents selected from Group A:

the substituents of Group A are selected from the group consisting of H, D, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, —C(O)NHRa', wherein Ra' is selected from: a substituted or unsubstituted $C_{1-6}$ alkyl, a substituted or unsubstituted $C_{3-8}$ cycloalkyl;

for $R_3$-$R_{12}$, the term "substituted" means having one or more (e.g., 1, 2, 3 or 4) substituents selected from Group B;

the substituents of Group B are selected from the group consisting of H, D, halogen, a substituted or unsubstituted $C_{1-6}$ alkyl, —OH, a substituted or unsubstituted $C_{1-4}$ alkoxy, 3-8 membered cyclic hydrocarbon group, amino, nitro;

and, in the substituents of Group A and Group B, the "substituted" means having one or more (eg 1, 2, 3, 4 or 5) substituents selected from the group consisting of D, halogen, $C_{1-4}$ alkyl, trifluoromethyl, amino, nitro, —OH.

In another preferred embodiment, $R_3$ and $R_4$ together with a carbon atom connecting to them form a substituted or unsubstituted $C_{3-6}$ cycloalkyl.

In another preferred embodiment, $R_3$ is selected from the group consisting of H, D, and methyl.

In another preferred embodiment, $R_4$ is H, D or methyl.

In another preferred embodiment, $R_5$ is H or methyl.

In another preferred embodiment, $R_6$ is H, a substituted or unsubstituted $C_{1-4}$ alkyl group, a substituted or unsubstituted $C_{6-10}$ aryl, a substituted or unsubstituted $C_{3-6}$ cycloalkyl.

In another preferred embodiment, $R_6$ is methyl, 1-hydroxyethyl, haloethyl, isopropyl, phenyl or cyclopropyl.

In another preferred embodiment, $R_5$ and $R_6$ together with a carbon atom connecting to them form a substituted or unsubstituted five-membered cycloalkyl.

In another preferred embodiment, $R_9$ is H or methyl.

In another preferred embodiment, $R_{10}$ is methyl.

In another preferred embodiment, $R_9$ and $R_{10}$ together with a carbon atom connecting to them form a substituted or unsubstituted 3-8 membered cycloalkyl or heterocyclyl, preferably a 3-6 membered cycloalkyl, more preferably 3 membered ring.

In another preferred embodiment, $R_{11}$ has the following structure:

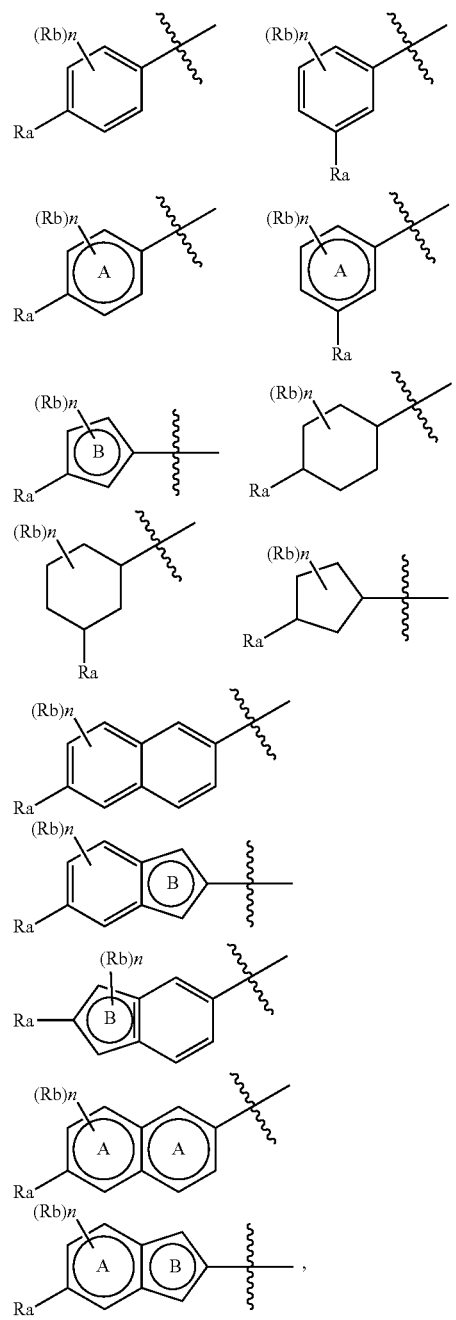

wherein ring A is a substituted or unsubstituted $C_{5-10}$ heteroaryl containing 1 to 3 heteroatoms, ring B is a substituted or unsubstituted $C_{5-10}$ heteroaryl containing 1 to 4 heteroatoms, wherein the heteroatoms are selected from N, O and S;

Ra is selected from: H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{1-3}$ alkyl $C_{5-8}$ cycloalkyl, a substituted or unsubstituted $C_{6-10}$ aryloxy, —C(O)NHRa',

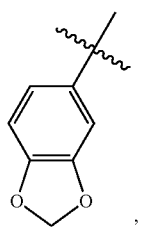

wherein Ra' is selected from: a substituted or unsubstituted $C_{1-6}$ alkyl, a substituted or unsubstituted $C_{3-8}$ cycloalkyl;

$R_b$ is selected from H, halogen, —CN, a substituted or unsubstituted $C_{1-4}$ alkyl; n is 0, 1, 2 or 3.

In another preferred embodiment, the ring A is a six-membered heteroaryl having 1 to 3 heteroatoms.

In another preferred embodiment, the ring B is a five-membered heterocyclyl containing 1 to 4 heteroatoms.

In another preferred embodiment, $R_{11}$ is selected from the group consisting of a substituted or unsubstituted $C_{6-10}$ aryl, a substituted or unsubstituted $C_{5-10}$ heteroaryl.

In another preferred embodiment, $R_{11}$ is a 5-6 membered heterocyclyl having 1-3 heteroatoms.

In another preferred embodiment, the 5-6 membered heterocyclyl is unsaturated.

In another preferred embodiment, the 5-6 membered heterocyclyl is an aromatic heterocyclyl.

In another preferred embodiment, the substituted or unsubstituted $C_{6-10}$ aryl and the substituted or unsubstituted $C_{5-10}$ heteroaryl are each independently monocyclic, bicyclic or tricyclic.

In another preferred embodiment, $R_{11}$ is

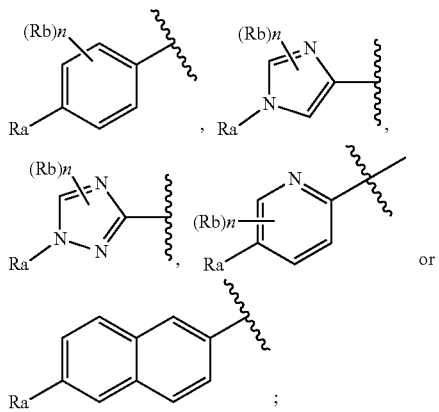

wherein Ra and Rb are as defined above, and n is 1, 2 or 3.

In another preferred embodiment, $R_{11}$ is selected from the group consisting of substituted imidazolyl, substituted phenyl, substituted triazolyl, substituted pyridyl.

In another preferred embodiment, $R_{11}$ is

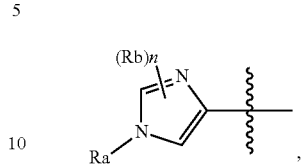

wherein X is N, and Ra, Rb and n are as defined above.

In another preferred embodiment, $R_{11}$ is

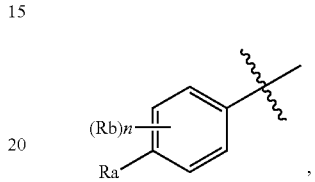

wherein Ra, Rb and n are as defined above.

In another preferred embodiment, $R_{11}$ is

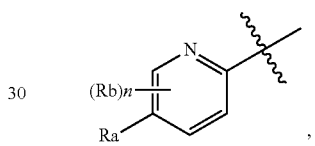

wherein Ra, Rb and n are as defined above.

In another preferred embodiment, the substituents of Group B means having one or more (e.g., 1-3) substituents selected from the group consisting of H, halogen, $C_{1-3}$ alkyl, —OH, $C_{1-3}$ alkoxy, 3-8 membered cyclic hydrocarbon group, amino, nitro.

In another preferred embodiment, $C_{6-10}$ aryl is selected from the group consisting of phenyl, pyridyl, pyrazolyl, thiazolyl, imidazolyl, isoxazolyl or oxazolyl.

Preparation of Compounds of Formula I

The following reaction schemes exemplify a process for the preparation of a compound of formula I, a stereoisomer or a mixture, or a pharmaceutically acceptable salt thereof, wherein each group is as described in the above embodiment section of the compound of formula I. It will be understood that in the following reaction schemes, combinations of substituents and/or variables in the formula are permissible only if such combinations result in stable compounds. It should also be understood that other general formulas, such as general formula (Ia), (Ia-1), (Ia-2), (Ia-3), (Ia-4), (Ib), (Ib-1), (Ib-2), (Ib-3), (Ib-4) and other compounds of Formula I specifically disclosed herein can be prepared by those skilled in the art of organic chemistry by the methods disclosed herein (modify synthetic parameters as needed by applying suitably substituted starting materials and utilizing methods well known to those skilled in the art) or known methods.

A method for preparing the compound of the present invention is provided in the present invention, comprising the steps of:

(i) in the absence of a solvent, intermediate C and intermediate D are subjected to a substitution reaction by heating to give compound I, and $R_3$-$R_{12}$ are as defined above, and X is halogen,

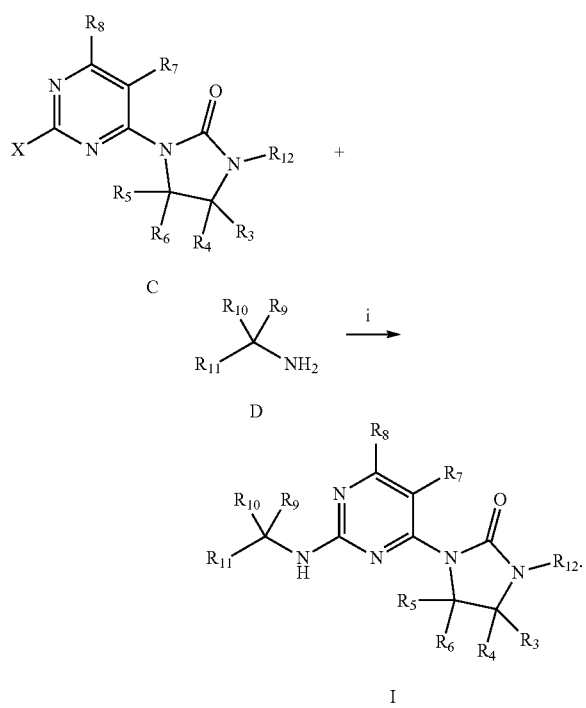

In another preferred embodiment, before the step (i), the method further comprises step (i-1): in an inert solvent, intermediate A and intermediate B are subjected to a substitution reaction in the presence of a basic substance to form intermediate C,

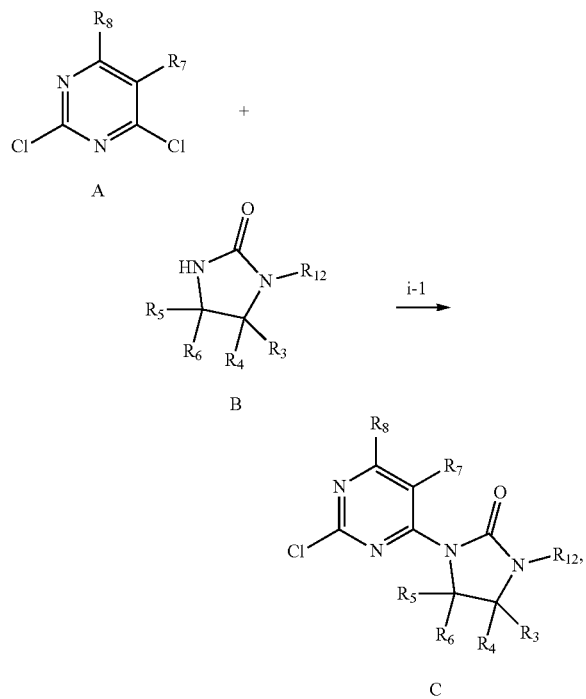

wherein $R_3$-$R_{12}$ are as defined above.

In another preferred embodiment, the inert solvent is selected from the group consisting of dichloromethane, chloroform, 1,2-dichloroethane, dioxane, DMF, acetonitrile, DMSO, NMP, THF or a combination thereof.

In another preferred embodiment, the basic substance includes an organic base and an inorganic base.

In another preferred embodiment, the organic base is selected from the group consisting of TEA, DIPEA or a combination thereof.

In another preferred embodiment, the inorganic base is selected from the group consisting of sodium hydride, potassium carbonate, sodium carbonate, cesium carbonate, potassium t-butoxide, sodium t-butoxide, LiHMDS, LDA, butyl lithium or a combination thereof.

In another preferred embodiment, the compound of formula I is a compound of formula J

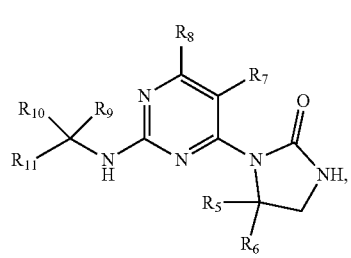

wherein $R_5$-$R_{11}$ are as defined above.

In another preferred embodiment, in step (i), intermediate L is reacted with intermediate D to form a compound of formula J:

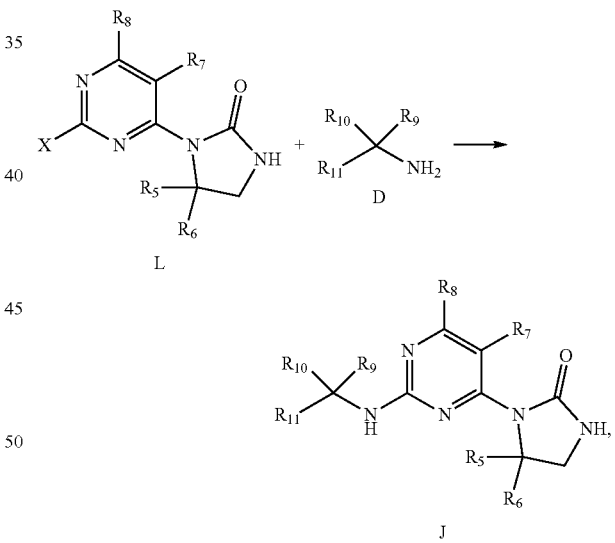

wherein each group is as defined above.

In another preferred embodiment, before step (i), the method further comprises the steps of:

(i-1a) reacting a compound of formula Q with a dehydrating agent (preferably triphosgene, trifluoroacetic anhydride, acetic anhydride) in an inert solvent to form a compound of formula P, and (i-1b) reacting the compound of formula P with a reductant N (preferably lithium aluminium hydride, lithium aluminium deuteride, sodium borohydride, borane, hydrogen/palladium carbon, deuterium/palladium carbon) in an inert solvent to form a compound of formula M, and (i-1c) reacting the compound of formula M with triphosgene or carbonyldiimidazole in the presence of a basic substance in an inert solvent to form the compound of formula L;

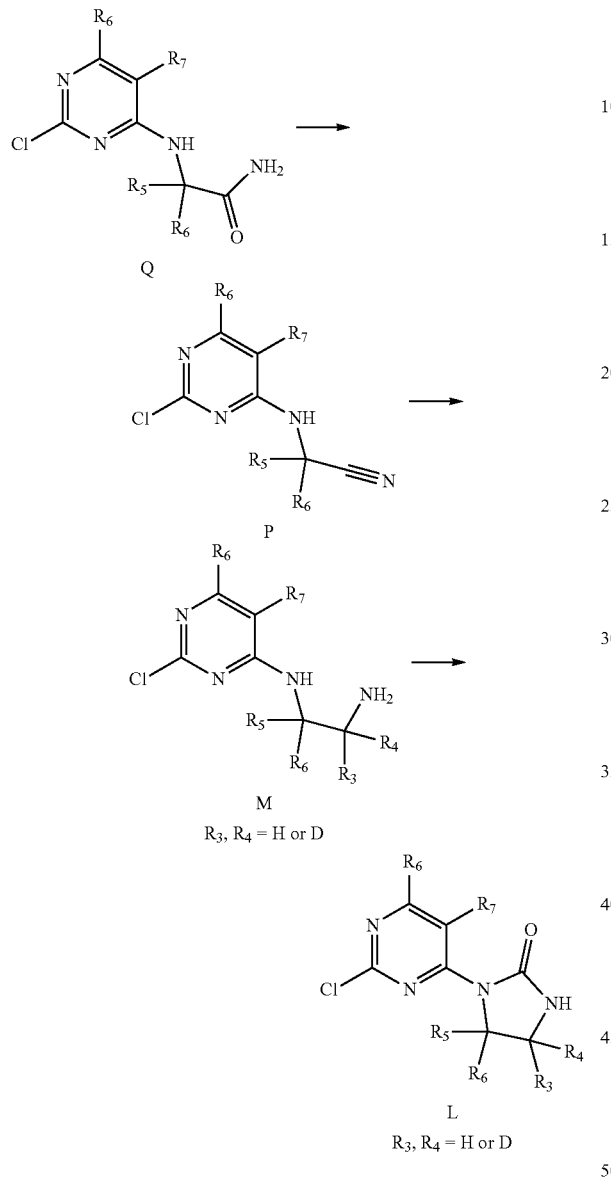

wherein each group is as defined above.

The Main Advantages of the Invention are:
1. a compound of formula I is provided.
2. a pharmaceutical composition having novel structure for preventing and treating IDH mutation-related diseases is provided.
3. a simple and efficient method for preparing a compound of formula I is provided.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

In each example:
LCMS instrument: Pump Agilent 1100 UV Detector: Agilent 1100 DAD
Mass Spectrometer API 3000
Chromatography column: Waters sunfire C18, 4.6×50 mm, 5 um
Mobile phase: A-acetonitrile B—H$_2$O (0.1% FA)

Synthesis of Intermediate A1:
4-(1-aminoethyl)-2-chloro-N-cyclopentylbenzamide

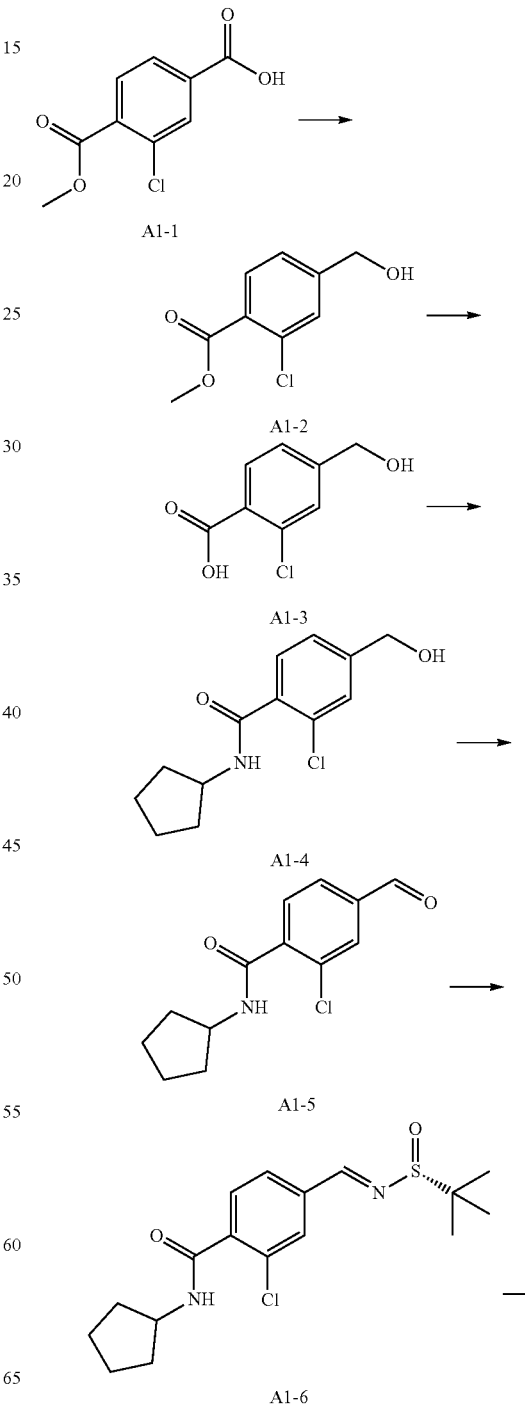

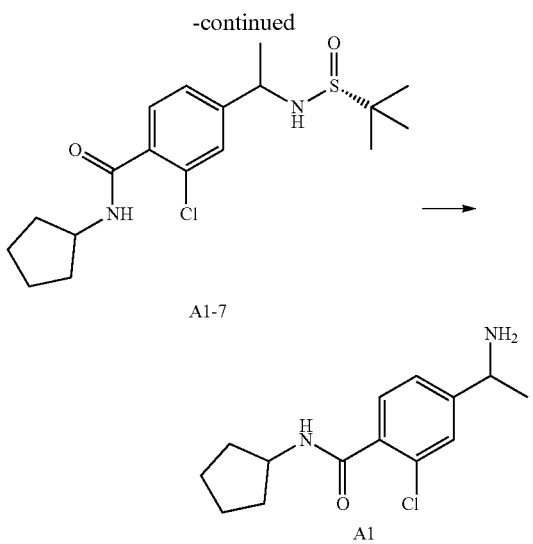

A1-7

A1

Step 1: Synthesis of methyl 2-chloro-4-(hydroxymethyl)benzoate (A1-2)

Under an atmosphere of dry nitrogen, Compound A1-1 (1.00 g, 4.67 mmol) and 20 mL of dry tetrahydrofuran were added sequentially into a 50 mL one-neck flask, and 10 mL borane tetrahydrofuran (9.34 mL, 9.34 mmol) was added. The reaction was stirred at room temperature for 6 hours. The reaction system was cooled to 0° C., and 5 ml water was added slowly to quench the reaction, and the reaction was extracted with EtOAc (3×20 m) and dried over anhydrous sodium sulfate, filtered, and, after concentration, purified through a silica gel column to yield colorless oily compound (A1-2) (756 mg, yield: 81.0%).

$^1$H-NMR (CDCl$_3$, 400 MHz): δ7.72 (d, J=8.0 Hz, 1H), 7.37 (s, 1H), 7.19 (d, J=8.0 Hz, 1H), 4.63 (s, 2H), 3.84 9 s, 3H).

Step 2: Synthesis of 2-chloro-4-(hydroxymethyl)benzoic acid (A1-3)

Compound A1-2 (400 mg, 2.0 mmol) and sodium hydroxide (240 mg, 6 mmol) and 10 mL of methanol were successively added to a 25 mL one-neck flask, and heated to 80° C. for 3 hours. After the reaction was completed, the solvent was evaporated, and 30 mL of 2N HCl was added, and ethyl acetate (30 mL×2) was used for extraction, and organic phases were combined. The obtained was dried over anhydrous sodium sulfate and filtered, and the filtrate was concentrated under reduced pressure to give a pale-yellow solid (A1-3) (350 mg, yield: 94.1%).

$^1$H-NMR (DMSO, 400 MHz): δ7.76 (d, J=8.0 Hz, 1H), 7.46 (s, 1H), 7.36 (d, J=8.0 Hz, 1H), 6.53 (brs, 1H), 5.44 (brs, 1H), 4.55 (s, 2H).

Step 3: Synthesis of 2-chloro-N-cyclopentyl-4-(hydroxymethyl)benzamide (A1-4)

Compound A1-3 (350 mg, 1.88 mmol), cyclopentylamine (80 mg, 1.88 mmol), HATU (859 mg, 2.26 mmol), triethylamine (380 mg, 3.76) and 10 mL of N,N-dimethylformamide were added sequentially to a dry 50 mL one-neck flask, stirred at room temperature for 6 hours. After the reaction was completed, the reaction mixture was added to 10 mL of water, and extracted with ethyl acetate (30 mL×2), and organic phases were combined, and the obtained was dried over anhydrous sodium sulfate and filtered, and the filtrate was concentrated under reduced pressure, purified by column chromatography to give a yellow oily product. (A1-4) (390 mg, yield: 82.0%).

LCMS: m/z 254.3 [M+H]$^+$; RT=1.1 min.

Step 4: Synthesis of 2-chloro-N-cyclopentyl-4-formaldehyde-benzamide (A1-5)

Compound (A1-4) (390 mg, 1.54 mmol) and 10 mL of dichloromethane and Dess-Martin (784 mg, 1.85 mmol) were sequentially added to a dry 50 mL one-neck flask, and the mixture was stirred at room temperature for 4 hours, and filtered to remove resulting solids, the filtrate was concentrated and purified by column chromatography to give pale yellow solid (A1-5) (300 mg, yield: 77.7%).

LCMS: m/z 252.2 [M+H]$^+$; RT=1.0 min.

Step 5: Synthesis of (R,E)-4-((tert-butyl sulfonimide)methyl)-2-chloro-N cyclopentyl-benzamide (A1-6)

Compound A1-5 (300 mg, 1.2 mmol), (R)-tert-butyl sulfenamide (145 mg, 1.2 mmol), cesium carbonate (780 mg, 2.4 mmol) and 15 mL 1,2-dichloroethane were sequentially added to a dry 50 mL three-neck flask, and heated to reflux for four hours. After the reaction was cooled to room temperature, 5 mL of water was added, organic phase was separated, dried over anhydrous sodium sulfate, filtered, and the filtrate was concentrated under reduced pressure and purified by column chromatography to afford white solid (A1-6) (339 mg, yield: 80.0%).

LCMS: m/z 355.2 [M+H]$^+$; RT=1.5 min.

Step 6: Synthesis of 2-chloro-N-cyclopentyl-4-(1-((R)-1,1-dimethylethylsulfonamide)ethyl)benzamide (A1-7)

Under an atmosphere of dry nitrogen, Compound A1-6 (339 mg, 0.95 mmol) and 5 mL of dry tetrahydrofuran were sequentially added into a 20 mL three-neck flask, cooled to −70° C. in dryice acetone bath, and methyl lithium (0.7 mL, 1.14 mmol) was added dropwise. After reaction at low temperature for 1 hour, the reaction was quenched with 5 mL of saturated ammonium chloride solution and extracted with ethyl acetate (30 mL×2), and organic phases were combined, which was dried over anhydrous sodium sulfate, and filtered. The filtrate was concentrated under reduced pressure and purified by column chromatography to afford yellow oily product A1-7 (246 mg, yield: 69.9%).

LCMS: m/z 370.2 [M+H]$^+$; RT=1.7 min.

Step 7: Synthesis of 4-(1-aminoethyl)-2-chloro-N-cyclopentylbenzamide (intermediate A1)

Compound A1-7 (246 mg, 0.66 mmol) and 5 mL of methanol and 2 mL of concentrated hydrochloric acid were successively added to a 50 mL one-neck flask, and the reaction was stirred at room temperature for 2 hours. After concentration, 15 mL of dichloromethane and 10 mL of 2N sodium hydroxide aqueous solution were added. The organic phase was dried over anhydrous sodium sulfate and filtered.

The filtrate was concentrated under reduced pressure to afford pale yellow liquid (130 mg, yield: 74.2%).
LCMS: m/z 267.3 [M+H]⁺; RT=0.3 min.

Synthesis of Intermediate A2: (S)-1-(1-(4-chlorophenyl)-1H-imidazol-4-yl)ethylamine

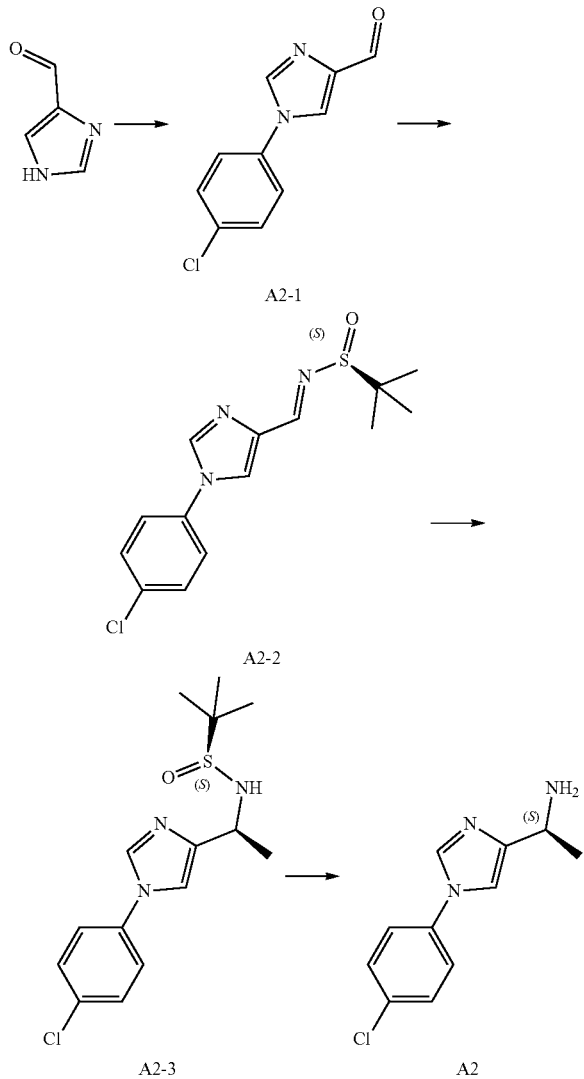

Step 1: Synthesis of 1-(4-chlorophenyl)-1H-imidazole-4-formaldehyde (A2-1)

1H-imidazole-4-formaldehyde (5.0 g, 52.03 mmol, 1.0 eq), 1-chloro-4-iodobenzene (18.6 g, 78.05 mmol, 1.5 eq), cesium carbonate (34.0 g, 104.06 mmol, 2.0 eq), cuprous iodide (500 mg, 2.60 mmol, 0.05 eq), trans-(1R,2R)—N,N'-dimethyl 1,2-cyclohexane diamine (1.5 g, 10.04 mmol, 0.2 q) and N,N-dimethylformamide (100 mL) were sequentially added to a dry 250 mL three-neck flask at room temperature, the air in the system were replaced with nitrogen for three times, and stirred at 110° C. for 18 hours under nitrogen. After the reaction was completed, the reaction mixture was cooled to 0° C., a saturated aqueous solution of ammonium chloride (500 mL) was added, and ethyl acetate (1200 mL) was used for extraction, the organic phase was dried over sodium sulfate and concentrated under reduced pressure to give a crude product. The crude product was purified through a silica gel column (petroleum ether: ethyl acetate=2:1) to give product 1-(4-chlorophenyl)-1H-imidazole-4-formaldehyde (6.0 g, yellow solid), yield 56%.
LCMS: m/z 207.2 [M+H]⁺; RT=1.327 min;

Step 2: Synthesis of Intermediate: (S)—N-((1-(4-chlorophenyl)-1H-imidazol-4-yl)methylene)-2-methylpropane-2-sulfenamide (A2-2)

intermediate (A1-2) (1.0 g, 4.83 mmol, 1.0 eq), (S)-(+)-tert-butylsulfinamide (880.0 mg, 7.26 mmol, 1.5 eq), cesium carbonate (3.67 g, 9.66 mmol, 3.0 eq) and 1,2-dichloroethane (30 mL) were sequentially added to a dry 100 mL one-neck flask at room temperature, stirred at 80° C. for 18 hours under nitrogen atmosphere. After the reaction was completed, the reaction solution was cooled to 0° C., and a saturated aqueous solution of ammonium chloride (200 mL) was added, and the reaction mixture was extracted with dichloromethane (300 mL). The organic phase was dried over sodium sulfate and concentrated under reduced pressure to give a crude product. The crude product was purified through a silica gel column (petroleum ether: ethyl acetate=2:1) to give product (R,Z)—N-((1-(4-chlorophenyl)-1H-imidazol-4-yl) methylene)-2-methylpropane-2-sulfinamide (1.20 g, yellow solid), yield 81%.
LCMS: m/z 310.1[M−43]⁺; RT=1.61 min;
¹H NMR (D6-DMSO, 400 MHz): δ 8.55 (s, 1H), 8.48 (s, 1H), 8.40 (s, 1H), 7.80 (d, J=8.8 Hz, 2H), 7.63 (d, J=8.8 Hz, 2H), 1.17 (s, 9H).

Step 3: Synthesis of (S)—N—((S)-1-(1-(4-chlorophenyl)-1H-imidazol-4-yl)ethyl)-2-methylpropane-2-sulfinamide (A2-3)

Intermediate (A1-3) (1.20 g, 3.29 mmol, 1.0 eq) and dichloromethane (50 mL) were added to a dry 250 mL three-neck flask at room temperature, and air of the system was replaced with nitrogen for three times, and the reaction mixture was cooled to −78° C. in a dry ice acetone bath, and methylmagnesium bromide (1.4 M, 11 mL, 16.45 mmol, 5.0 eq) was slowly added, and stirred at −78° C. for 1.5 hours. After the reaction was completed, a saturated aqueous solution of ammonium chloride (100 mL) was added, and the obtained was extracted with dichloromethane (200 mL). The organic phase was dried over sodium sulfate, concentrated under reduced pressure to give a crude product (S)—N—((S)-1-(1-(4-chlorophenyl)-1H-imidazol-4-yl) ethyl)-2-methylpropane-2-sulfinamide (1.5 g, yellow oily liquid), yield 100%.
LCMS: m/z 326.2[M−43]⁺; RT=1.10 min.

Step 4: Synthesis of (S)-1-(1-(4-chlorophenyl)-1H-imidazol-4-yl)ethylamine (Intermediate A2)

The intermediate (A1-4) (15 g, 4.6 mmol, 1.0 eq), methanol (10 mL) and concentrated hydrochloric acid (5 mL) were sequentially added to a 100 mL one-neck flask at room temperature, and stirred at room temperature for 2 hours. After the reaction was completed, the reaction liquid was concentrated under reduced pressure to remove methanol, the residue was diluted with water (30 mL), pH value was adjusted to 10 with 3M sodium hydroxide aqueous solution, the obtained mixture was extracted with dichloromethane (200 mL), and organic phase was dried over anhydrous sodium sulfate, and concentrated under reduced pressure to obtain a product (S)-1-(1-(4-chlorophenyl)-1H-imidazol-4-yl)ethylamine (900 mg, yellow oily liquid), yield 88%.

LCMS: m/z 205.2 [M–NH$_2$]$^+$; RT=0.86 min.

Intermediates A38, A41, A42, A43, A45, A46, A47, A48, A49, A50, A51, A52, A54, A57, A58 were obtained using similar starting materials using the process described above.

| Intermediate number | Name | Structural formula | analysis data |
|---|---|---|---|
| Intermediate A38 | (S)-1-(1-(3-chloro phenyl)-1H-imidazol-4-yl)ethylamine | 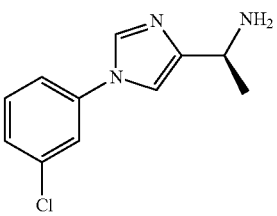 | LCMS: m/z 205.2 [M – NH$_2$]$^+$, RT = 0.79 min |
| Intermediate A41 | (S)-1-(1-(3-cyclopropylphenyl)-1 hydro-imidazol-4-yl)ethylamine | 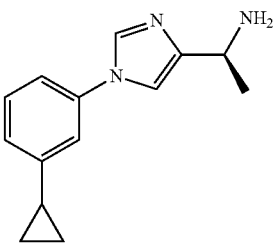 | LCMS: m/z 211.2 [M – NH$_2$]$^+$, RT = 0.85 min. |
| Intermediate A42 | (S)-1-(1-(3-isopropylphenyl)-1 hydro-imidazol-4-yl)ethylamine | 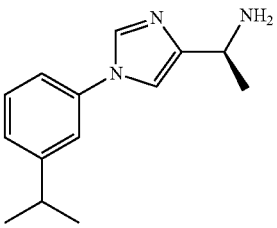 | LCMS: m/z 213.2 [M – NH$_2$]$^+$, RT = 0.76 min. |
| Intermediate A43 | (S)-1-(1-(4-methylphenyl)-1 hydro-imidazol-4-yl)ethylamine | 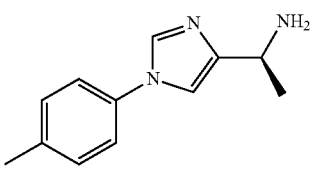 | LCMS: m/z 185.1 [M – NH$_2$]$^+$, RT = 0.84 min. |
| Intermediate A45 | (S)-1-(1-(3-chloro-5-fluorophenyl)-1 H-imidazol-4-yl) ethylamine | 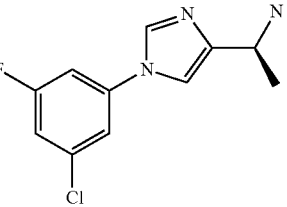 | LCMS: m/z 223.2 [M – NH$_2$]$^+$, RT = 1.03 min. |
| Intermediate A46 | (S)-1-(1-(4-trifluoromethylphenyl)-1 hydro-imidazol-4-yl)ethylamine | 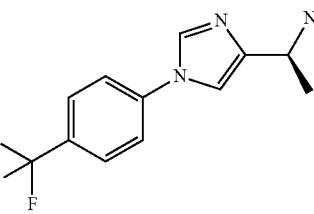 | LCMS: m/z 239.1 [M – NH$_2$]$^+$, RT = 1.15 min. |

-continued

| Intermediate number | Name | Structural formula | analysis data |
|---|---|---|---|
| Intermediate A47 | (S)-1-(1-(3-trifluoro-methylphenyl)-1 hydro-imidazol-4-yl)ethylamine | | LCMS: m/z 239.1 [M − NH$_2$]$^+$, RT = 0.82 min. |
| Intermediate A48 | (S)-1-(1-(3,5-di-chlorophenyl)-1 hydro-imidazol-4-yl)ethylamine | | LCMS: m/z 239.0 [M − NH$_2$]$^+$, RT = 1.10 min. |
| Intermediate A49 | (S)-1-(1-(3,4-di-chlorophenyl)-1 hydro-imidazol-4-yl)ethylamine | | LCMS: m/z 239.0 [M − NH$_2$]$^+$, RT = 1.05 min. |
| Intermediate A50 | (S)-1-(1-(4-cyclo-propylphenyl)-1 hydro-imidazol-4-yl)ethylamine | | LCMS: m/z 228.4 [M + H]$^+$, RT = 1.05 min. |
| Intermediate A51 | (S)-1-(1-(3-fluoro-4-chlorophenyl)-1 hydro-imidazol-4-yl)ethylamine | | LCMS: m/z 223.2 [M − NH$_2$]$^+$, RT = 0.84 min. |
| Intermediate A52 | (S)-1-(1-(3-methoxy-4-chlorophenyl)-1 hydro-imidazol-4-yl)ethylamine | | LCMS: m/z 235.2 [M − NH$_2$]$^+$, RT = 0.71 min. |
| Intermediate A54 | (S)-1-(1-(4-iso-propylphenyl)-1 hydro-imidazol-4-yl)ethylamine | | LCMS: m/z 213.2 [M − NH$_2$]$^+$, RT = 0.78 min. |

| Intermediate number | Name | Structural formula | analysis data |
|---|---|---|---|
| Intermediate A57 | (S)-1-(1-(4-chloro phenyl)-2-methyl-1H-imidazol-4-yl)ethylamine | | LCMS: m/z 218.9 [M − NH$_2$]$^+$, RT = 0.66 min. |
| Intermediate A58 | (S)-1-(1-(4-fluoro phenyl)-1H-imidazol-4-yl)ethylamine | | LCMS: m/z 189.1 [M − NH$_2$]$^+$, RT = 0.89 min. |

Synthesis of Intermediate A3: (R)-1-(1-(4-chlorophenyl)-1H-imidazol-4-yl)ethylamine Referring to the synthesis method of the intermediate A2, A3-2 can be obtained by using (R)-(+)-tert-butylsulfinamide in the first step. The same procedure can be used to obtain intermediate A3.

LCMS: m/z 205.2 [M−NH$_2$]$^+$; RT=0.86 min.

Synthesis of Intermediate A4: 1-(6-methoxynaphthalen-2-yl)ethylamine

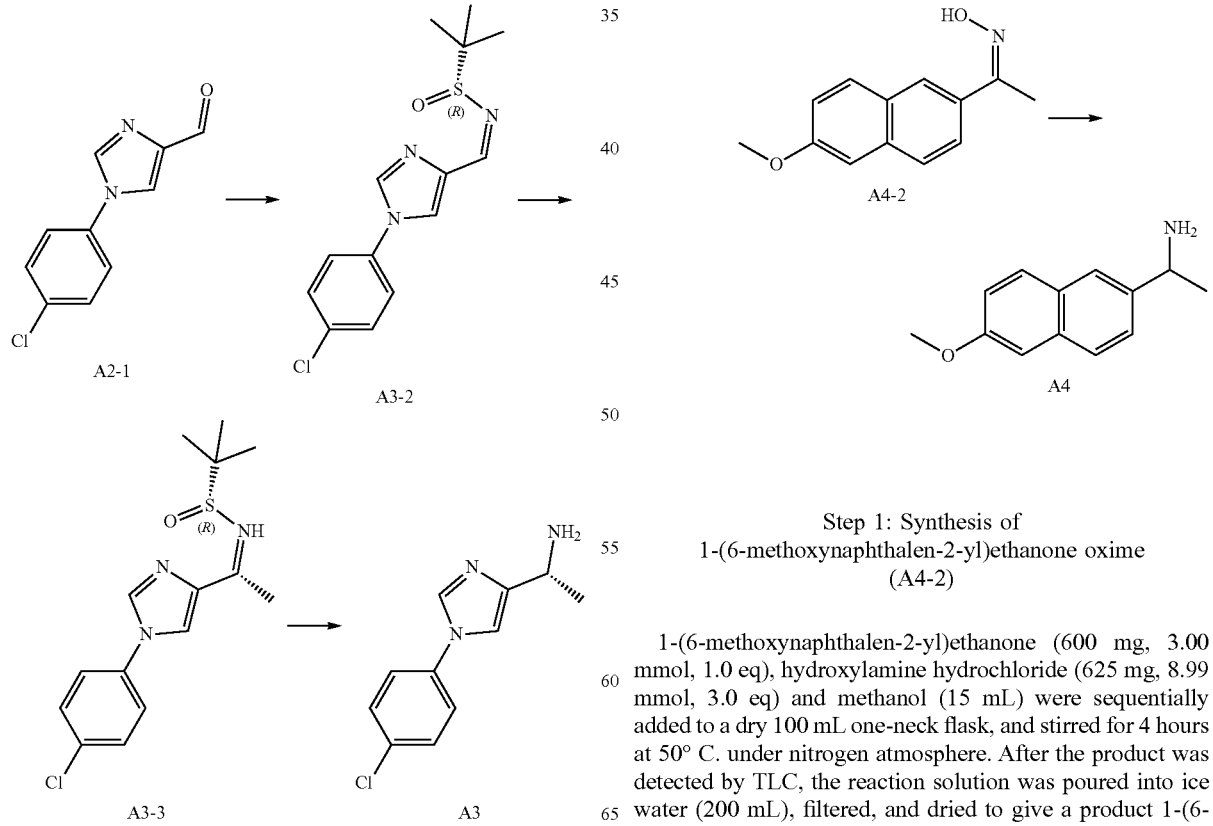

Step 1: Synthesis of 1-(6-methoxynaphthalen-2-yl)ethanone oxime (A4-2)

1-(6-methoxynaphthalen-2-yl)ethanone (600 mg, 3.00 mmol, 1.0 eq), hydroxylamine hydrochloride (625 mg, 8.99 mmol, 3.0 eq) and methanol (15 mL) were sequentially added to a dry 100 mL one-neck flask, and stirred for 4 hours at 50° C. under nitrogen atmosphere. After the product was detected by TLC, the reaction solution was poured into ice water (200 mL), filtered, and dried to give a product 1-(6-methoxynaphthalen-2-yl)ethanone oxime (600 mg, white solid), yield 93%.

Step 2: Synthesis of 1-(6-methoxynaphthalen-2-yl)ethylamine (Intermediate A4)

1-(6-methoxynaphthalen-2-yl)ethanone oxime (600 mg, 2.79 mmol, 1.0 eq), Raney nickel (2.0 g) and methanol (15 mL) were sequentially added to a dry 100 mL one-necked flask, and stirred for 16 hours at 80° C. under nitrogen atmosphere. After the product was detected by LCMS, the reaction mixture was filtered, and the filtrate was poured into water (200 mL), extracted with dichloromethane (200 mL), dried, filtered and concentrated under reduced pressure to obtain a product 1-(6-methoxynaphthalen-2-yl)ethylamine (500 mg, white solid), yield 89%.

LCMS: m/z 185.3 [M–NH$_2$]$^+$; RT=0.825 min.

Intermediates A5, A7 were obtained using different ketones as starting material using the above procedures.

Step 1: Synthesis of (4-chlorophenyl)-1H-imidazole-4-carbonitrile (A6-1)

Compound A2-1 (1.236 g, 6 mmoL) was dissolved in pyridine (30 mL), and hydroxylamine hydrochloride (626 mg, 9 mmoL) was added at room temperature for 1 hour, then acetic anhydride (1.224 g, 12 mmoL) was added, and the reaction system was refluxed overnight. After the reaction was completed, 30 mL of ethyl acetate was added. The organic phase was washed successively with water (50 mL×1) and saturated brine (60 mL×2). The organic phase was collected, dried over anhydrous sodium sulfate, filtered, and the filtrate was concentrated under reduced pressure, and purified through column chromatography (ethyl acetate:petroleum ether=1:8) to give a product 1-(4-chlorophenyl)-1H-imidazole-4-carbonitrile (1.1 g, white solid). yield 90.1%.

LCMS: m/z 204.1[M+H]$^+$; RT=0.63 min.

| Intermediate number | Name | Structural formula | analysis data |
|---|---|---|---|
| Intermediate A5 | 1-(1,1'-biphenyl-4-yl) ethylamine | | LCMS: m/z 182.1 [M – NH$_2$]$^+$; RT = 0.672 min. |
| Intermediate A7 | 1-(4-phenoxyphenyl) ethylamine | | LCMS: m/z 214 [M + H]$^+$, RT = 1.035 min. |

Intermediate A6: Synthesis of (1-(4-chlorophenyl)-1H-imidazol-4-yl)cyclopropylamine

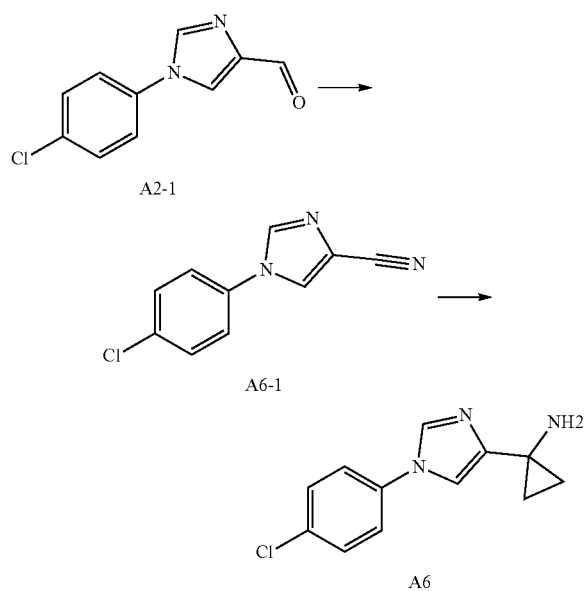

Step 2: Synthesis of (1-(4-chlorophenyl)-1H-imidazol-4-yl)cyclopropylamine (intermediate A6)

Compound A6-1 (1.34 g, 6.6 mmoL) was dissolved in dry tetrahydrofuran (30 mL), tetraisopropyl titanate (3.75 g, 13.2 mmol) was added at room temperature, then ethyl magnesium bromide (13.2 mL, 39.6 mmoL) was slowly added dropwise, reacted at room temperature for 1 hour. Boron trifluoride etherate (1.6 mL, 13.2 mmol) was added. The reaction was carried out for 1.5 hours at room temperature. 1N sodium hydroxide aqueous solution was added to pH=8 in an ice bath. After the reaction was completed, 50 mL of ethyl acetate was added for extraction. The organic phase was washed successively with water (50 mL×1) and saturated brine (60 mL×2). The organic phase was collected, dried over anhydrous sodium sulfate, filtered, and the filtrate was concentrated under reduced pressure, and purified by column chromatography (methanol:dichloromethane=1: 40) gave a product 1-(1-(4-chlorophenyl)-1H-imidazol-4-yl)cyclopropylamine (700 mg, yellow liquid), yield 45%.

LCMS: m/z 234.1 [M+H]$^+$; RT=1.07 min.

Synthesis of Intermediate A8: (S)-1-(4-methyl-2'-(trifluoromethyl)-[3,4'-bipyridyl]-6-yl)ethylamine

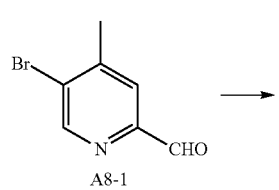
A8-1

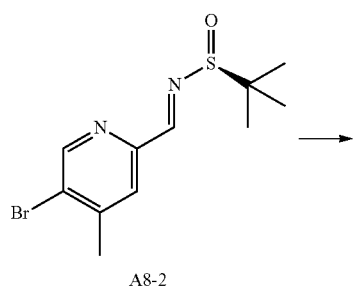
A8-2

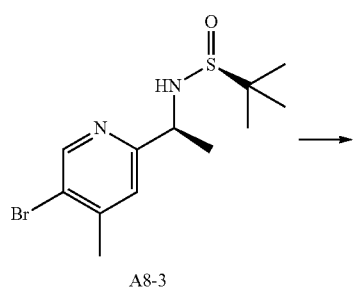
A8-3

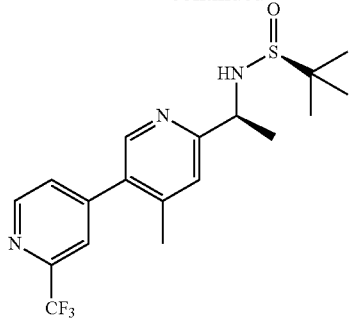
A8-4

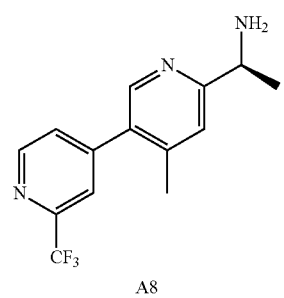
A8

Steps 1 and 2, A8-3 was obtained according to the second and third steps for intermediate A2. LCMS: m/z 318.2/321.2 [M+H]$^+$; RT=1.42 min.

Step 3: A8-3 (779 mg, 2.44 mmol), (4,4,5,5-tetramethyl-1,3,2-dioxaborolane-2-yl)-2-(trifluoromethyl)pyridine (1 g, 3.66 mmol), sodium carbonate (517 mg, 4.88 mmol) and Pd(dppf)Cl$_2$ (89 mg, 0.12 mmol) were added to a dry 100 ml three-neck flask, 15 ml of 1,4-dioxane was added, replaced with nitrogen for three times, reacted at 90° C. overnight, and a proper amount of water was added, extracted with ethyl acetate for three times, and organic phase was dried over anhydrous sodium sulfate, and concentrated under reduced pressure. The residue was purified by silica gel column chromatography and eluted with petroleum ether and ethyl acetate at a ratio of 5:1. Product A8-4 (600 mg, yellow oil) was obtained, yield 64%.

LCMS: m/z 386.3 [M+H]$^+$; RT=1.14 min.

Step 4: A8 was obtained according to the fourth step for intermediate A2. LCMS: m/z 282.3[M+H]$^+$; RT=0.72 min.

Intermediate A10 was obtained using a similar starting material using the procedure above.

| Intermediate number | Name | Structural formula | analysis data |
|---|---|---|---|
| Intermediate A11 | (S)-1-(2'-(trifluoromethyl)-[3,4'-bipyridyl]-6-yl)ethylamine | | LCMS: m/z 268.1 [M + H]$^+$, RT = 0.71 min. |

| Intermediate number | Name | Structural formula | analysis data |
|---|---|---|---|
| Intermediate A64 | (S)-1-(5-(3-chlorophenyl)pyridin-2-yl)ethylamine | 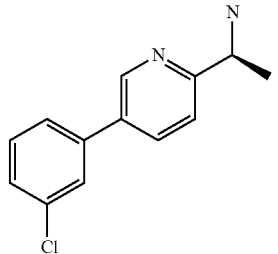 [SMILES: C[C@H](N)c1ccc(-c2cccc(Cl)c2)cn1] | LCMS: m/z 232.1 [M + H]$^+$, RT = 0.79 min. |
| Intermediate A65 | (S)-1-(5-(3-trifluoromethylphenyl)pyridin-2-yl)ethylamine | 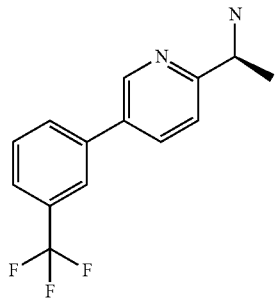 [SMILES: C[C@H](N)c1ccc(-c2cccc(C(F)(F)F)c2)cn1] | LCMS: m/z 266.1 [M + H]$^+$, RT = 0.85 min. |

Intermediate A9: Synthesis of 4'-chloro-(1,1'-biphenyl)-4-cyclopropylamine

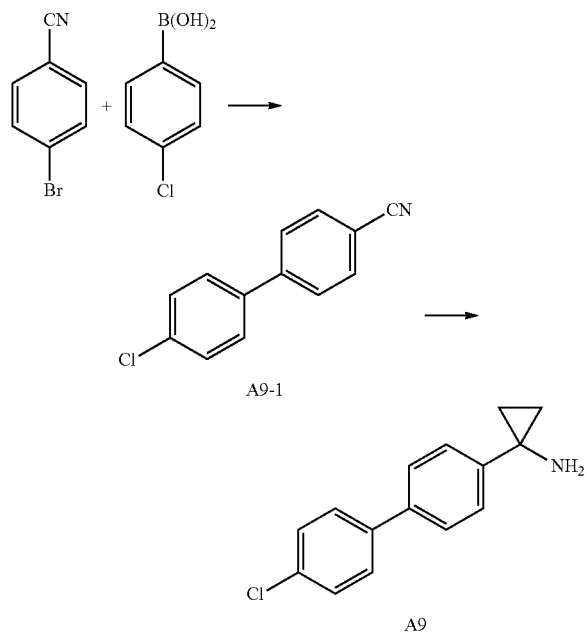

Step 1: Synthesis of 4'-chloro-(1,1'-biphenyl)-4-carbonitrile (A9-1)

P-bromobenzyl cyanide (2.18 g, 12 mmol), p-chlorophenylboronic acid (2.8 g, 18 mmol), [1,1'-bis(diphenylphosphino)ferrocene]palladium dichloride (0.88 g, 1.2 mmol), potassium carbonate (3.32 g, 24 mmol), 1,4-dioxane (40 ml) and water (10 ml) were sequentially added to a dry 100 ml round bottom flask at room temperature. Nitrogen was pumped and ventilated for 3 times. The reaction system was heated to 90° C. for 2 hours. After the reaction was completed, the reaction mixture was poured into 100 ml of water and extracted with ethyl acetate (50 ml×2). The organic phase was collected, dried over anhydrous sodium sulfate, filtered, and the filtrate was concentrated under reduced pressure. The crude product was purified using a chromatography column (petroleum ether: ethyl acetate=10:1) to afford a product 4'-chloro-(1,1'-biphenyl)-4-carbonitrile (2 g, white solid), yield 80%.

$^1$H-NMR (CDCl3, 400 MHz): 7.74 (d, J=8.4 Hz, 2H), 7.65 (d, J=8.4 Hz, 2H), 7.52 (d, J=8.4 Hz, 2H), 7.46 (d, J=8.4 Hz, 2H).

Step 2: Synthesis of 4'-chloro-(1,1'-biphenyl)-4-cyclopropylamine (A9)

Compound A9-1 (400 mg, 1.88 mmol), diethyl ether (10 ml), titanium tetraisopropoxide (568 mg, 2 mmol) and ethyl magnesium bromide (500 mg, 3.76 mmol) were sequentially added to a dry 100 ml three-neck flask at 0° C. The reaction was stirred at 0° C. for 15 minutes. The temperature was raised to room temperature for 1 hour. Boron trifluoride etherate (534 mg, 3.76 mmol) was added at room temperature for 1.5 hours. 1 mol/L sodium hydroxide aqueous solution was added to adjust pH to 8 in an ice bath, and the reaction mixture was extracted with diethyl ether (50 ml). The organic phase was collected, washed with saturated brine (20 ml×1), dried over anhydrous sodium sulfate, filtered, and the filtrate was concentrated under reduced pressure. The crude product was purified using a chromatography column (dichloromethane:methanol=10:1) to give a product 4'-chloro-(1,1'-biphenyl)-4-cyclopropylamine (100 mg, yellow solid), yield 22%.

LCMS: m/z 227.0 [M–NH$_2$]$^+$; RT=0.837 min.

Intermediate A11 was obtained using a similar starting material using the procedure above.

| Intermediate number | Name | Structural formula | analysis data |
|---|---|---|---|
| Intermediate A11 | 1-(5-(4-chlorophenyl) pyridin-2-yl) cyclopropylamine | | LCMS: m/z 245.1 [M + H]$^+$, RT = 0.89 min. |
| Intermediate A30 | 1-(2'-(Trifluoro- methyl)-[3,4'- bipyridyl]-6-yl) cyclopropylamine | | LCMS: m/z 280.2 [M + H]$^+$, RT = 0.753 min. (2.00 min) |

1-(2'-(trifluoromethyl)-[3,4'-bipyridin]-6-yl)cyclopropan-1-amine

Synthesis of Intermediate A12: 1-(1-(p-tolyl)-1H-imidazol-4-yl)cyclopropylamine

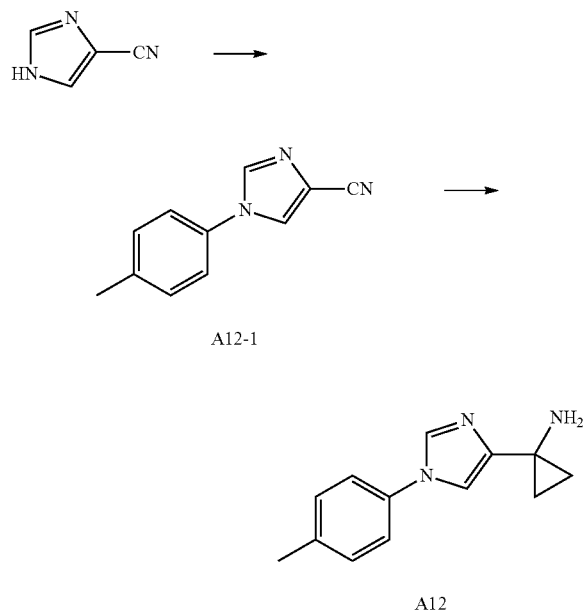

Step 1: Synthesis of 1-(p-tolyl)-1H-imidazole-4-carbonitrile (A12-1)

Cyanimidazole (2.50 g, 26.86 mmol), dry N,N-dimethylformamide (40 mL), 1-iodo-4-methylbenzene (8.78 g, 40.29 mmol), (1R,2R)—N1,N2-dimethylcyclohexane-1,2-diamine (0.38 g, 2.69 mmol), cuprous iodide (0.51 g, 2.69 mmol) and cesium carbonate (17.50 grams, 53.72 mmol) were sequentially added to a dry 250 mL one-neck flask at room temperature. Nitrogen was pumped and ventilated for 3 times. The reaction system was heated to 100° C. for 2 hours. After completion of the reaction, the reaction mixture was cooled to room temperature, poured into 200 ml of water and extracted with ethyl acetate (150 ml×2). The organic phase was collected, washed with saturated brine (150 ml×1), dried over anhydrous sodium sulfate, filtered, and the filtrate was concentrated under reduced pressure. The crude product was purified using a chromatography column (petroleum ether: ethyl acetate=2:1) to afford a product 1-(p-tolyl)-1H-imidazole-4-carbonitrile (2.20 g, almost white solid), yield 44.7%.

$^1$H-NMR (CDCl3, 400 MHz): 8.71 (s, 1H), 8.47 (s, 1H), 7.59-7.58 (d, J=6.8 Hz, 2H), 7.44 (d, J=6.4 Hz, 2H).

Step 2: Synthesis of 1-(1-(p-tolyl)-1H-imidazol-4-yl)cyclopropylamine (A12)

Compound A12-1 (500 mg, 2.73 mmol), toluene (10 ml), diethyl ether (10 ml), titanium tetraisopropoxy (0.97 ml, 3.28 mmol) and ethyl magnesium bromide (2.28 ml, 6.83 mmol)) were sequentially added to a dry 100 ml three-neck flask at −70° C., and stirred at −70° C. for 15 minutes. The temperature was raised to 20° C. at room temperature for 1 hour. Boron trifluoride etherate (0.67 ml, 5.46 mmol) was added and the mixture was reacted at room temperature for 1.5 hours. 1N sodium hydroxide aqueous solution was added to adjust pH to 8 in an ice bath. The reaction mixture was extracted with ethyl acetate (50 mL×2). The organic phase was collected, dried over anhydrous sodium sulfate, filtered, and the filtrate was concentrated under reduced pressure. The crude product was purified using a chromatography column (dichloromethane:methanol=10:1) to give a product 1-(1-(p-tolyl)-1H-imidazol-4-yl)cyclopropylamine 4 (290 mg, yellow oil), yield 49.8%.

LCMS: m/z 214.3 [M+H]$^+$; RT=0.28 min (2.00 min).

Intermediates A13, A14, A15, A16, A17, A18, A19, A20, A21, A22, A23, A26, A29, A31, A33, A34, A35, A37, A39, A40, A62 were obtained using similar starting materials using the above procedure.

| Intermediate number | Name | Structural formula | analysis data |
|---|---|---|---|
| Intermediate A13 | 1-(1-(4-ethylphenyl)-1H-imidazol-4-yl)cyclopropylamine | 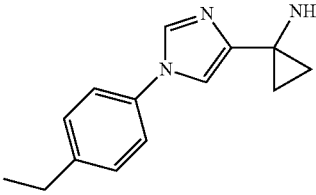 | LCMS: m/z 228.2 [M + H]⁺; RT = 0.78 min |
| Intermediate A14 | 1-(1-(3-(trifluoromethyl)phenyl)-1H-imidazol-4-yl)cyclopropylamine | 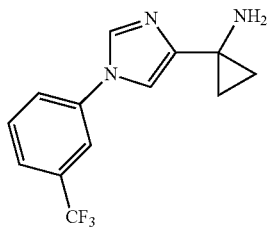 [SMILES: NC1(c2cn(-c3cccc(C(F)(F)F)c3)cn2)CC1] | LCMS: m/z 268.2 [M + H]⁺, RT = 0.98 min. |
| Intermediate A15 | 1-(1-(m-tolyl)-1H-imidazol-4-yl)cyclopropylamine | 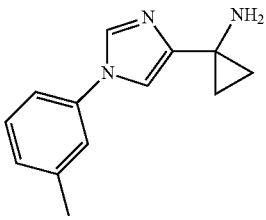 [SMILES: Cc1cccc(-n2cnc(C3(N)CC3)c2)c1] | LCMS: m/z 214.2 [M + H]⁺, RT = 0.71 min. |
| Intermediate A16 | 1-(1-(3-chloro-4-methylphenyl)-1H-imidazol-4-yl)cyclopropylamine | 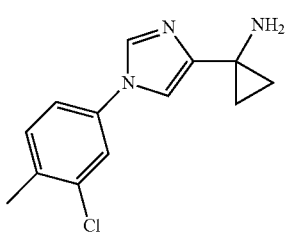 [SMILES: Cc1ccc(-n2cnc(C3(N)CC3)c2)cc1Cl] | LCMS: m/z 248.1 [M + H]⁺, RT = 0.85 min. |
| Intermediate A17 | 1-(1-(6-methylpyridin-3-yl)-1H-imidazol-4-yl)cyclopropan-1-amine | 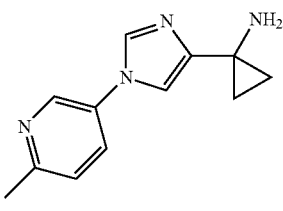 [SMILES: Cc1ccc(-n2cnc(C3(N)CC3)c2)cn1] | LCMS: m/z 215.2 [M + H]⁺, RT = 0.33 min. |
| Intermediate A18 | 1-(1-(3,5-dichlorophenyl)-1H-imidazol-4-yl)-cyclopropylamine | 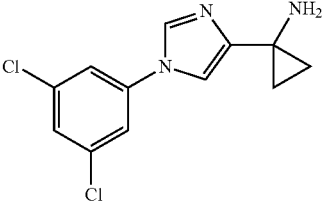 [SMILES: NC1(c2cn(-c3cc(Cl)cc(Cl)c3)cn2)CC1] | LCMS: m/z 268.0 [M + H]⁺, RT = 0.86 min. |
| Intermediate A19 | 1-(1-(3-chloro-4-fluorophenyl)-1H-imidazol-4-yl)-cyclopropylamine | 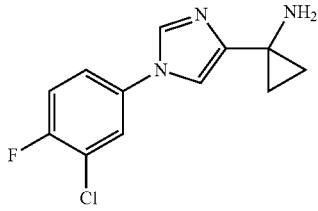 [SMILES: NC1(c2cn(-c3ccc(F)c(Cl)c3)cn2)CC1] | LCMS: m/z 251.9 [M + H]⁺, RT = 0.68 min. |

-continued

| Intermediate number | Name | Structural formula | analysis data |
|---|---|---|---|
| Intermediate A20 | 1-(1-(6-methylpyridin-3-yl)-1H-imidazol-4-yl)cyclopropan-1-amine | | LCMS: m/z 215.2 [M + H]+, RT = 0.33 min. |
| Intermediate A21 | 1-(1-(3-isopropylphenyl)-1H-imidazol-4-yl)-cyclopropylamine | | LCMS: m/z 242.1 [M + H]+, RT = 0.89 min. |
| Intermediate A22 | 1-(1-(3-chlorophenyl)-1H-imidazol-4-yl)cyclopropylamine | | LCMS: m/z 234.1 [M + H]+, RT = 0.72 min. |
| Intermediate A23 | 1-(1-(3,5-difluoro-4-methylphenyl)-1H-imidazol-4-yl)cyclopropylamine | | LCMS: m/z 250.2 [M + H]+, RT = 0.83 min. |
| Intermediate A26 | 1-(1-(3-cyclopropyl-phenyl)-1H-imidazol-4-yl)-cyclopropylamine | | LCMS: m/z 240.3 [M + H]+, RT = 0.83 min. |
| Intermediate A29 | 1-(1-(3-chloro-4-methylphenyl)-1H-imidazol-4-yl)cyclopropylamine | | LCMS: m/z 264.1 [M + H]+, RT = 0.99 min. |

-continued

| Intermediate number | Name | Structural formula | analysis data |
|---|---|---|---|
| Intermediate A31 | 1-(1-(4-cyclopropyl-phenyl)-1H-imidazol-4-yl)-cyclopropylamine | 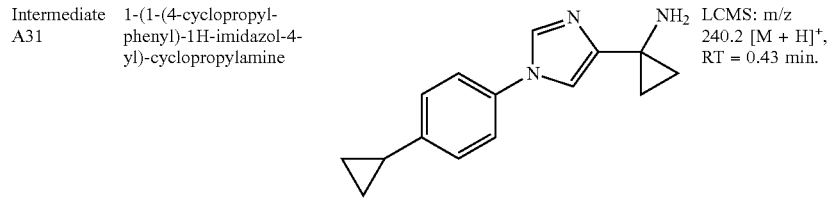 | LCMS: m/z 240.2 [M + H]+, RT = 0.43 min. |
| Intermediate A33 | 1-(1-(3-chloro-5-fluoro-phenyl)-1H-imidazol-4-yl)cyclopropylamine | 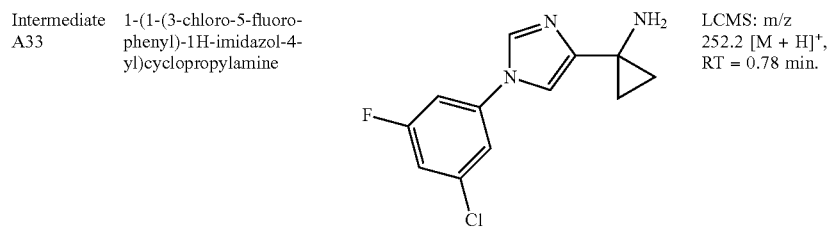 | LCMS: m/z 252.2 [M + H]+, RT = 0.78 min. |
| Intermediate A34 | 1-(1-(benzo[d][1,3]dioxol-5-yl)-1H-imidazol-4-yl)cyclopropylamine | 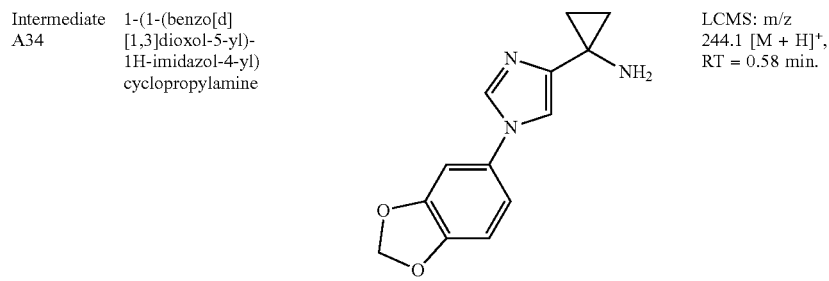 | LCMS: m/z 244.1 [M + H]+, RT = 0.58 min. |
| Intermediate A35 | 1-(1-(3-bromo-5-chloro-phenyl)-1H-imidazol-4-yl)-cyclopropylamine | 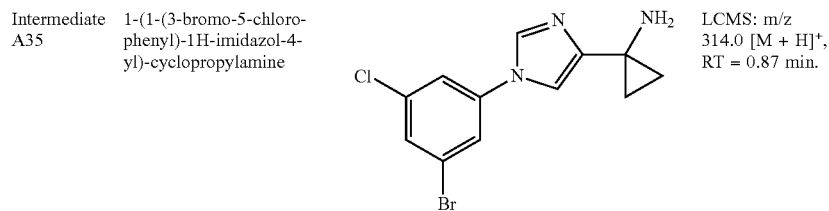 | LCMS: m/z 314.0 [M + H]+, RT = 0.87 min. |
| Intermediate A37 | 1-(1-(3-bromo-5-fluoro-phenyl)-1H-imidazol-4-yl)-cyclopropylamine | 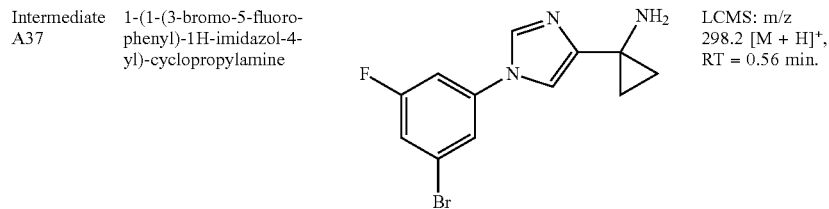 | LCMS: m/z 298.2 [M + H]+, RT = 0.56 min. |
| Intermediate A39 | 1-(1-(5-chloro-2-fluoro-phenyl)-1H-imidazol-4-yl)cyclopropylamine | 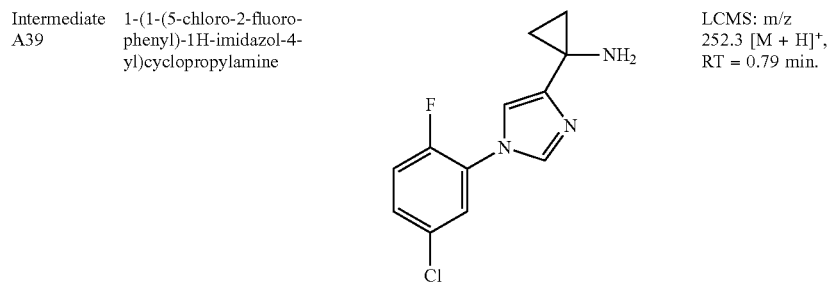 | LCMS: m/z 252.3 [M + H]+, RT = 0.79 min. |

-continued

| Intermediate number | Name | Structural formula | analysis data |
|---|---|---|---|
| Intermediate A40 | 1-(1-(2-chlorophenyl)-1H-imidazol-4-yl)cyclopropylamine | | LCMS: m/z 234.1 [M + H]$^+$, RT = 0.76 min. |
| Intermediate A62 | 1-(1-(3-bromophenyl)-1H-imidazol-4-yl)cyclopropylamine | | LCMS: m/z 278.0 [M + H]$^+$, RT = 0.77 min. |

Synthesis of Intermediate A24

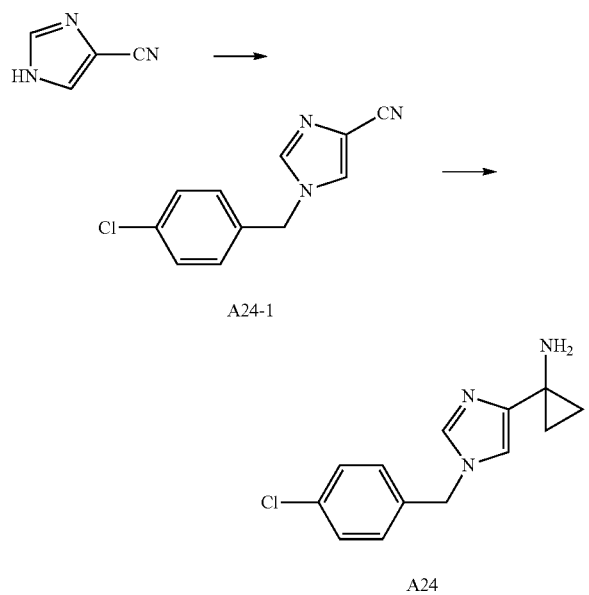

Step One: Synthesis of 1-(4-chlorobenzyl)-1H-imidazole-4-carbonitrile (A24-1)

Compound cyanoimidazole (1.00 g, 10.74 mmol), N,N-dimethylformamide (20 ml), 1-(bromomethyl)-4-chlorobenzene (2.65 g, 12.89 mmol) and cesium carbonate (7.00 g, 21.48 mmol) was sequentially added to a dry 100 ml one-neck flask at room temperature, and heated to 100° C. for 16 hours. After completion of the reaction, the reaction mixture was cooled to room temperature, poured into 200 ml of water and extracted with ethyl acetate (80 ml×2). The organic phase was collected, dried over anhydrous sodium sulfate, filtered, and the filtrate was concentrated under reduced pressure. The crude product was purified through a chromatography column (petroleum ether: ethyl acetate=1:1) give a product 1-(4-chlorobenzyl)-1H-imidazole-4-carbonitrile (0.80 g, yellow oil), yield 34.2%.

$^1$H-NMR (CDCl$_3$, 400 MHz): 8.22 (s, 1H), 8.04 (s, 1H), 7.46-7.44 (d, J=8.4 Hz, 2H), 7.35-7.33 (d, J=8.0 Hz, 2H), 5.29 (s, 2H).

Step two: 1-(1-(4-chlorobenzyl)-1H-imidazol-4-yl)cyclopropan-1-amine was synthesized by the same procedure as in step 2 of intermediate A12.

LCMS: m/z248.2[M+H]$^+$; RT=0.658 min.

Intermediates A25, A27, A28, A32, A36 were obtained using similar starting materials using the above procedure.

| Intermediate number | Name | Structural formula | analysis data |
|---|---|---|---|
| Intermediate A25 | 1-(1-(cyclohexylmethyl)-1H-imidazol-4-yl)cyclopropylamine | | LCMS: m/z 220.3 [M + H]$^+$; RT = 0.57 min |

| Intermediate number | Name | Structural formula | analysis data |
|---|---|---|---|
| Intermediate A27 | 1-(1-(4,4-difluoro-cyclohexyl)-1H-imidazol-4-yl)cyclopropylamine | | LCMS: m/z 242.3 [M + H]+, RT = 0.49 min. |
| Intermediate A28 | 1-(1-(4-methylcyclo-hexyl)-1H-imidazol-4-yl)cyclopropylamine | | LCMS: m/z 220.3 [M + H]+, RT = 0.47 min. |
| Intermediate A32 | (1-(1-(cyclopentyl-methyl)-1H-imidazol-4-yl)cyclopropylamine | | LCMS: m/z 206.1 [M + H]+, RT = 0.47 min. |
| Intermediate A36 | 1-(1-(4,4-dimethyl-cyclohexyl)-1H-imidazol-4-yl)cyclopropylamine | | LCMS: m/z 234.3 [M + H]+, RT = 0.76 min. |

Intermediate A53: Synthesis of (S)-1-(1-isopentyl-1H-imidazol-4-yl)ethylamine

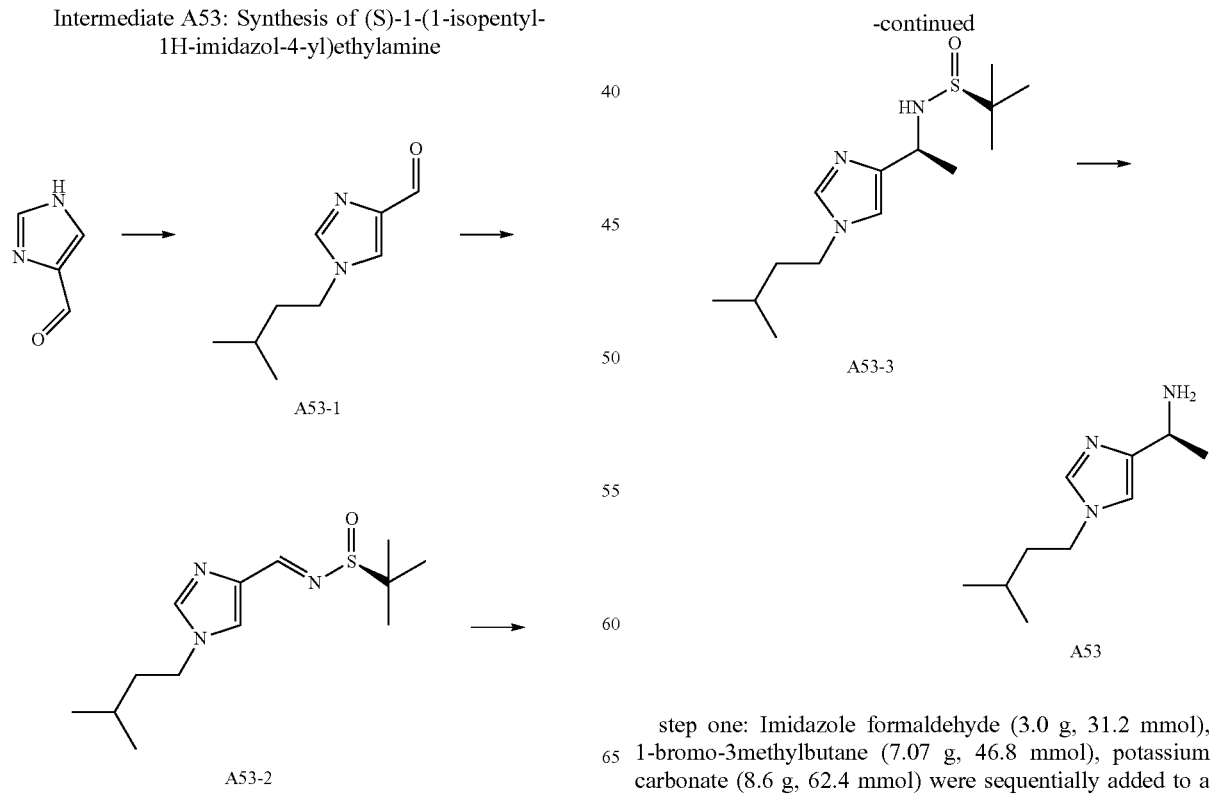

step one: Imidazole formaldehyde (3.0 g, 31.2 mmol), 1-bromo-3methylbutane (7.07 g, 46.8 mmol), potassium carbonate (8.6 g, 62.4 mmol) were sequentially added to a 250 ml round bottom flask containing 100 ml N,N-dimethylformamide at room temperature. The reaction solution was heated to 60° C. for 18 hours. After the reaction was completed, the reaction mixture was poured into water (300 mL) and extracted with ethyl acetate (100 mL) for three times. The organic phase was washed once with saturated sodium chloride aqueous solution (300 mL) and dried over sodium sulfate and filtered. The filtrate was concentrated under reduced pressure and purified through a silica gel column (petroleum ether: ethyl acetate=3:1) to afford a product (yellow oily liquid) A53-1 (2.402 g, yield 46%).

LCMS: m/z 167.3 [M+H]$^+$, t=1.02 min.

Step 2: A53-1 (2.4 g, 14.4 mmol, 1.0 eq), (S)-tert-butylsulfinamide (2.1 mg, 17.3 mmol, 1.2 eq), cesium carbonated (9.4 g, 28.9 mmol, 2.0 eq) and 1,2-dichloroethane (40 mL) were sequentially added to a 100 mL round bottom flask at room temperature. The reaction solution was heated to 75° C. and stirred for 18 hours. After the reaction was completed, the reaction solution was concentrated under reduced pressure and purified through a silica gel column (petroleum ether: ethyl acetate=2:1) to afford a product (yellow oily liquid) A53-2 (2.80 g, yield 72%).

LCMS: m/z 270.3 [M+H]$^+$, t=1.19 min.

Step 3: A53-2 (1.505 g, 5.59 mmol, 1.0 eq) and tetrahydrofuran (50 mL) were added to a dry 250 mL three-neck flask at room temperature. The system air was replaced with nitrogen for three times and cooled to below −60° C. in a dry ice-acetone bath. Methyl magnesium bromide (3 M, 9.3 mL) was slowly added under a nitrogen atmosphere at −60° C., and stirred at −60° C. for 2 hours. After the reaction was completed, water (10 mL) was added at −60° C., and the reaction solution was extracted with ethyl acetate (100 mL) for three times. The organic phase was washed once with a saturated sodium chloride aqueous solution (300 mL), and the organic phase was dried over sodium sulfate, filtered and distillated under reduced pressure to afford a crude product, which was purified through a silica gel column (dichloromethane:methanol=20:1) to afford a product (yellow oily liquid) A53-3 (1.048 g, yield 66%).

LCMS: m/z 286.3 [M+H]$^+$, t=0.9 min.

Step 4: A53-3 (1.048 g, 3.67 mmol, 1.0 eq), methanol (10 mL) and concentrated hydrochloric acid (2.5 mL) were sequentially added to a 100 mL one-neck flask at room temperature, and stirred at room temperature for 1.5 hours. After the reaction was completed, the reaction liquid was distilled under reduced pressure to remove methanol. The residue was diluted with water (20 mL) and ammonia water was used to adjust pH value to 10. The reaction solution was extracted with ethyl acetate (40 mL×3). The organic phase was washed once with a saturated sodium chloride aqueous solution (100 mL), and the organic phase was dried over sodium sulfate, filtered and distillated under reduced pressure to afford the crude product A53 (206 mg, yellow oily liquid).

LCMS: m/z 165.4 [M−NH$_2$]$^+$, t=0.53 min.

Using the procedure as above, intermediates A44, A56 were obtained using similar starting materials:

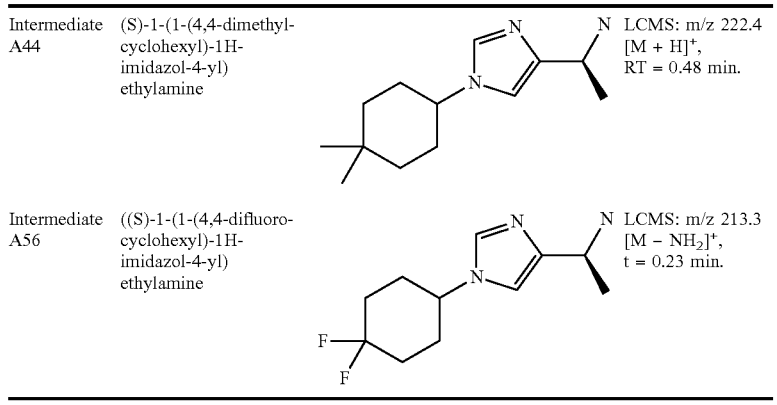

| Intermediate A44 | (S)-1-(1-(4,4-dimethyl-cyclohexyl)-1H-imidazol-4-yl)ethylamine | | LCMS: m/z 222.4 [M + H]$^+$, RT = 0.48 min. |
| --- | --- | --- | --- |
| Intermediate A56 | ((S)-1-(1-(4,4-difluoro-cyclohexyl)-1H-imidazol-4-yl)ethylamine | | LCMS: m/z 213.3 [M − NH$_2$]$^+$, t = 0.23 min. |

Intermediate A55: Synthesis of 2-(1-(4-chlorophenyl)-1H-imidazol-4-yl)propan-2-amine

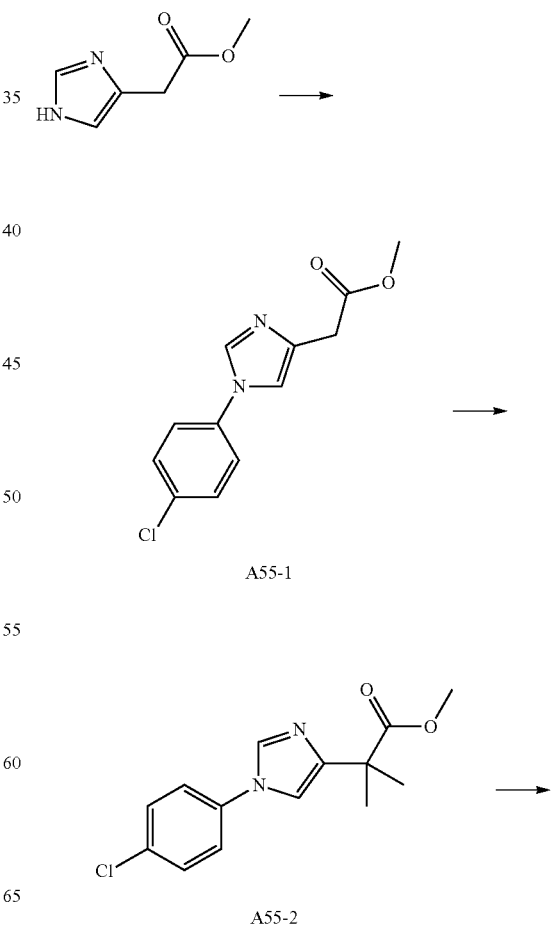

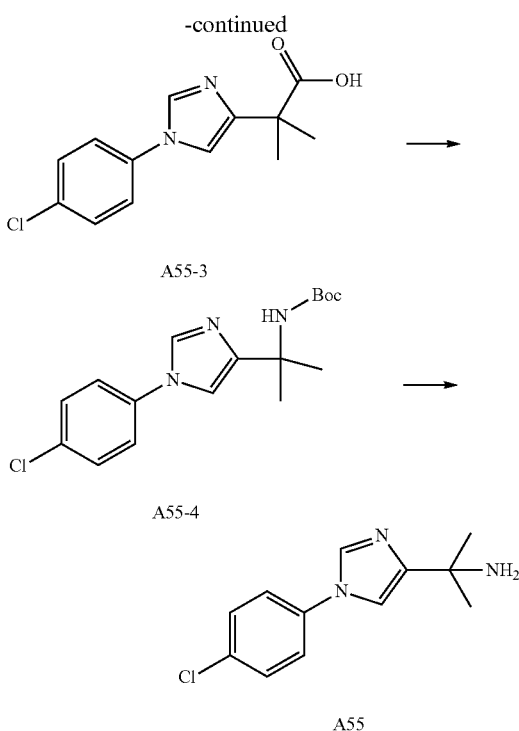

Step 1: Compound imidazole-4-acetic acid methyl ester (1.00 g, 7.14 mmol), dry N,N-dimethylformamide (12 ml), 1-chloro-4-iodobenzene (2.55 g, 10.71 mmol), (1R, 2R)—N1, N2-dimethylcyclohexane-1,2-diamine (0.10 g, 0.71 mmol), cuprous iodide (0.14 g, 0.71 mmol) and potassium carbonate (0.99 g, 7.14 mmol) were sequentially added to a dry 100 ml one-neck flask at room temperature. Nitrogen was pumped and ventilated for 3 times. The reaction mixture was heat to 100° C. for 16 hours. After completion of the reaction, the reaction solution was cooled to room temperature, poured into 120 ml water and extracted with ethyl acetate (45 ml×2). The organic phase was collected, dried over anhydrous sodium sulfate, filtered, and the filtrate was concentrated under reduced pressure. The crude product was purified using a chromatography column (petroleum ether: ethyl acetate=1:1) to afford a product methyl 2-(1-(4-chlorophenyl)-1H-imidazol-4-yl)acetate A55-1 (1.00 g, yellow solid), yield 55.9%.

LCMS: m/z 251.1 [M+H]$^+$; RT=1.335 min.

Step 2: Compound A55-1 (1.50 g, 5.98 mmol) and tetrahydrofuran (40 ml) were sequentially added to a dry 100 ml three-neck flask at −70° C., and sodium bis(trimethylsilyl)amide (17.94 ml, 17.94 mmol) was slowly added dropwise under nitrogen. The reaction mixture was stirred at −70° C. for 1 hour. Iodomethane (2.98 ml, 47.84 mmol) was added to the above reaction system at −70° C., and stirred at room temperature for 16 hours. After completion of the reaction, the reaction system was slowly poured into 50 ml of water, and extracted with ethyl acetate (40 mL×2). The organic phase was collected, dried over anhydrous sodium sulfate, filtered, and the filtrate was concentrated under reduced pressure. The crude product was purified using a chromatography column (petroleum ether: ethyl acetate=1:1) to give a product 2-(1-(4-chlorophenyl)-1H-imidazol-4-yl)-2-methylpropanoic acid-methyl ester (A55-2) (1.07 g, white solid), yield 64.1%.

LCMS: m/z 279.1 [M+H]$^+$; RT=1.219 min.

Step 3: Compound A55-2 (1.07 g, 3.84 mmol), tetrahydrofuran (10 ml), water (2 ml) and lithium hydroxide monohydrate (0.48 g, 11.52 mmol) were sequentially added to a dry 25 ml one-neck flask at room temperature, and heated to 50° C. for 16 hours. After completion of the reaction, 2 mol/ml hydrochloric acid aqueous solution was used to adjust the pH to 6. The reaction mixture was extracted with ethyl acetate (20 mL×2). The organic phase was collected, dried over anhydrous sodium sulfate, filtered, and the filtrate was concentrated under reduced pressure. The crude product was purified using a chromatography column (pure ethyl acetate) to give a product 2-(1-(4-chlorophenyl)-1H-imidazol-4-yl)-2-methylpropanoic acid (A55-3) (0.70 g, white solid), yield 68.6%.

$^1$H-NMR(DMSO-d$_6$, 400 MHz): 12.12-12.10 (m, 1H), 8.18 (s, 1H), 7.72-7.68 (m, 2H), 7.60-7.55 (m, 3H), 1.47 (s, 6H).

Step 4: Compound A55-3 (700 mg, 2.64 mmol) and tert-butanol (15 ml), triethylamine (1.10 mL, 7.92 mmol) and azide diphenyl phosphate (0.74 mL, 3.43 mmol) were sequentially added to a dry 50 ml one-neck flask at room temperature, and heat to 100° C. for 16 hours. After completion of the reaction, the reaction solution was concentrated under reduced pressure. The crude product was purified using a chromatography column (petroleum ether: ethyl acetate=1:1) to afford a product t-butyl (2-(1-(4-chlorophenyl)-1H-imidazol-4-yl)propane-2-yl)formate A55-4 (840 mg, white solid), yield 94.6%.

LCMS: m/z 336.1 [M+H]$^+$; RT=1.155 min.

Step 5: Compound A55-4 (840 mg, 2.50 mmol), dichloromethane (4 mL) and trifluoroacetic acid (2 mL) were sequentially added to a dry 50 ml one-neck flask at room temperature. The mixture was stirred at room temperature for 2 hours. After completion of the reaction, the reaction solution was concentrated under reduced pressure. 10 ml of water was added, and the reaction solution was extracted with diethyl ether (10 ml×2). The aqueous phase was adjusted to pH=8 with 6 moles/milliliter of sodium hydroxide aqueous solution, and extracted with ethyl acetate (20 mL×2). The organic phase was collected, dried over anhydrous sodium sulfate, filtered, and the filtrate was concentrated under reduced pressure to afford a product 2-(1-(4-chlorophenyl)-1H-imidazol-4-yl)propan-2-amine (A55) (500 mg, yellow solid), yield 84.7%.

LCMS: m/z 219.3 [M−NH$_2$]$^+$; RT=1.046 min.

Intermediate A59: Synthesis of (S)-1-(1-(4-chlorophenyl)-1H-1,2,4-triazol-3-yl)ethylamine

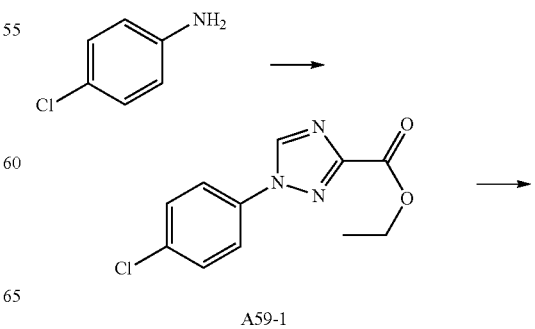

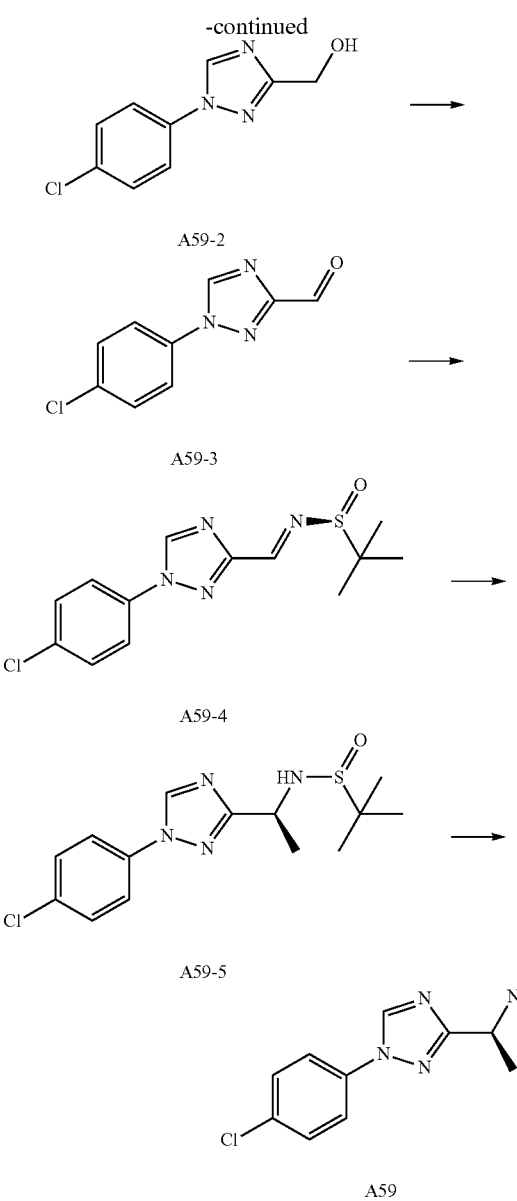

Step 2: Compound A59-1 (8.87 g, 35.24 mmol) and tetrahydrofuran (100 mL) were sequentially added to a dry 100 mL one-neck flask at room temperature, and stirred at 0° C. Lithium tetrahydroaluminum (2.67 g, 70.48 mmol) was added in batches, and stirred at room temperature for 1 hours. After completion of the reaction, 100 ml of water was slowly added at 0° C. The reaction mixture was extracted with ethyl acetate (80 mL×2). The organic phase was collected, dried over anhydrous sodium sulfate, filtered, and the filtrate was concentrated under reduced pressure. The crude product was purified through a chromatography column (petroleum ether: ethyl acetate=1:1) to afford a product (1-(4-chlorophenyl)-1H-1,2,4-triazol-3-yl)methanol (A59-2) (6.10 g, yellow solid), yield 82.5%.

LCMS: m/z 210.1[M+H]$^+$; RT=1.009 min.

Step 3: Compound A59-2 (3.00 g, 14.31 mmol), dichloromethane (50 mL) and Dess-Martin oxidizer (9.11 g, 21.47 mmol) were sequentially added to a dry 50 mL one-neck flask at room temperature, and stirred at room temperature for 16 hours. After completion of the reaction, the reaction solution was filtered, and the filtrate was poured into 50 ml of saturated sodium bicarbonate aqueous solution. The reaction solution was extracted with dichloromethane (50 mL×2). The organic phase was collected, dried over anhydrous sodium sulfate, filtered, and the filtrate was concentrated under reduced pressure. The crude product was purified through a chromatography column (petroleum ether: ethyl acetate=1:1) to afford a product 1-(4-chlorophenyl)-1H-1,2,4-triazole-3-formaldehyde (A59-3) (2.10 g, yellow solid), yield 70.7%.

LCMS: m/z 208.2 [M+H]$^+$; RT=1.099/1.319 min.

Step 4, Step 5 and Step 6: similar to the operation of intermediate A2. Intermediate A59: (S)-1-(1-(4-chlorophenyl)-1H-1,2,4-triazol-3-yl)ethylamine was obtained.

LCMS: m/z 233.3 [M−NH$_2$]$^+$; RT=1.025 min.

Synthesis of Intermediate A60: 1-(1-(3-cyclopropylphenyl)-1H-[1,2,4]-triazol-3-yl)cyclopropylamine

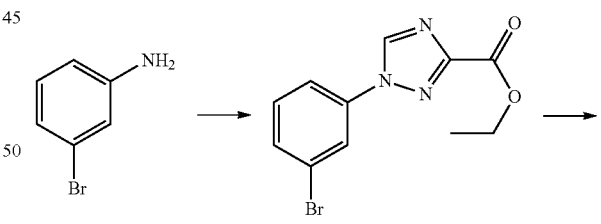

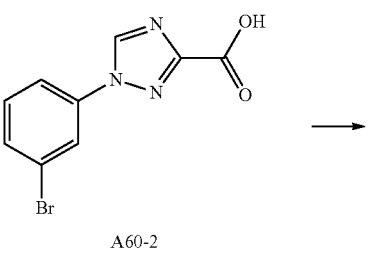

Step 1: Compound p-chloroaniline (6.00 g, 47.03 mmol), 3 mol/ml hydrochloric acid aqueous solution (40 ml) were added sequentially to a dry 100 ml one-neck flask at room temperature, and sodium nitrite (3.25 g, 47.03 mmol) in water (20 mL) solution was slowly added at 0° C., and stirred at 0° C. for 5 minutes. Then sodium bicarbonate (51.36 g, 611.39 mmol) solution in water (500 ml) was slowly added at 0° C. and stirred at 0° C. for 8 minutes. Ethyl 2-isocyanoacetate (5.85 g, 51.73 mmol) solution in methanol (40 mL) was slowly added at 0° C. and stirred at room temperature for 5 hours. After completion of the reaction, the reaction solution was extracted with chloroform: methanol (9:1, 150 ml×2). The organic phase was collected, dried over anhydrous sodium sulfate, filtered, and the filtrate was concentrated under reduced pressure. The crude product was purified using a chromatography column (petroleum ether: ethyl acetate=1:1) to afford a product ethyl 1-(4-chlorophenyl)-1H-1,2,4-triazole-3-carboxylate (A59-1) (8.87 g, yellow solid), yield 79.4%.

LCMS: m/z 252.2 [M+H]$^+$; RT=1.410 min.

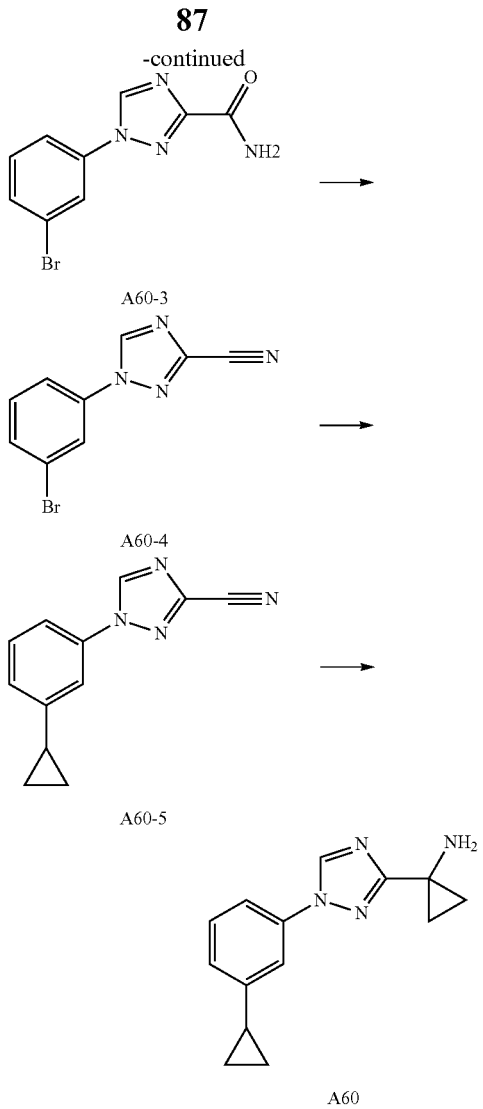

Step 1: A60-1 was obtained from m-bromoaniline as a starting material by the method of Step 1 for A59.

LCMS: m/z 298.1 [M+H]$^+$; RT=1.322 min.

Step 2: Compound A60-1 (3.61 g, 12.19 mmol), tetrahydrofuran (50 ml), water (25 ml) and sodium hydroxide (1.46 g, 36.57 mmol) were sequentially added to a dry 100 ml one-neck flask at room temperature, and stirred at room temperature for 16 hours. After completion of the reaction, the pH value was adjusted to pH=6 with a 6 mol/ml hydrochloric acid aqueous solution. The reaction solution was extracted with ethyl acetate (50 mL×2). The organic phase was collected, dried over anhydrous sodium sulfate, filtered, and the filtrate was concentrated under reduced pressure. The crude product was purified through a chromatography column (dichloromethane:methanol=10:1) to give a product 1-(3-bromophenyl)-1H-1,2,4-triazole-3-carboxylic acid (A60-2) (3.21 g, yellow solid), yield 98.2%.

LCMS: m/z 270.1 [M+H]$^+$; RT=1.296 min.

Step 3: Compound A60-2 (3.21 g, 11.97 mmol), dichloromethane (60 mL) and thionyl chloride (4.34 mL, 59.85 mmol) were sequentially added to a dry 100 mL round bottom flask at 0° C. The reaction solution was heated to 50° C. for 2 hours. The reaction solution was concentrated under reduced pressure, dissolved in tetrahydrofuran (60 ml), and ammonia water (0.46 ml, 11.97 mmol) and triethylamine (3.33 mL, 23.94 mmol) solution in tetrahydrofuran (60 mL) were slowly added, and stirred at room temperature for 1 hours. After completion of the reaction, the reaction solution was poured into 100 ml of water. The reaction solution was extracted with ethyl acetate (50 mL×2). The organic phase was collected, dried over anhydrous sodium sulfate, filtered, and the filtrate was concentrated under reduced pressure. The crude product was purified using a chromatography column (dichloromethane:methanol=10:1) to give a product 1-(3-bromophenyl)-1H-1,2,4-triazole-3-carboxamide (A60-3) (1.00 g, yellow solid), yield 31.3%.

LCMS: m/z 269.2 [M+H]$^+$; RT=1.204 min.

Step 4: Compound (A60-3) (1.00 g, 3.74 mmol), tetrahydrofuran (10 ml), triethylamine (1.56 ml, 11.22 mmol) and trifluoroacetic anhydride (0.74 mL, 5.61 mmol) were sequentially added to a dry 100 ml three-neck flask at room temperature, and stirred at room temperature for 16 hours. After completion of the reaction, 30 ml of water was slowly added, and the reaction solution was extracted with ethyl acetate (30 ml×2). The organic phase was collected, dried over anhydrous sodium sulfate, filtered, and the filtrate was concentrated under reduced pressure. The crude product was purified through a chromatography column (petroleum ether: ethyl acetate=1:1) to give a product 1-(3-bromophenyl)-1H-1,2,4-triazole-3-carbonitrile (A60-4) (0.93 mg, yellow solid), yield 99.7%.

LCMS: m/z 249.2 [M+H]$^+$; RT=1.59 min.

Step 5: Compound A60-4 (970 mg, 3.89 mmol), toluene (20 mL), cyclopropylboronic acid (502 mg, 5.84 mmol), [1,1'-bis(diphenylphosphino)ferrocene]palladium dichloride (285 mg, 0.39 mmol) and cesium carbonate (2535 mg, 7.78 mmol)] were sequentially added to a dry 100 mL round bottom flask at room temperature, and heated to 100° C. for 16 hours. After completion of the reaction, the reaction solution was concentrated under reduced pressure. The crude product was purified using a chromatography column (petroleum ether: ethyl acetate=1:1) to give a product 1-(3-cyclopropylphenyl)-1H-1,2,4-triazole-3-carbonitrile (A60-5) (610 g, yellow solid), yield 74.5%.

LCMS: m/z 211.2 [M+H]$^+$; RT=1.63 min.

Step 6: Compound A60-5 (610 mg, 2.90 mmol), toluene (12 ml) and diethyl ether (12 ml) were sequentially added to a dry 100 ml three-neck flask at room temperature. Titanium tetraisopropoxide (1.72 ml, 5.80 mmol) and ethyl magnesium bromide (2.90 ml, 8.70 mmol) were slowly sequentially added at −70° C., stirred at −70° C. for 15 minutes, and warmed to room temperature for 1 hour. Boron trifluoride diethyl ether solution (1.06 ml, 8.70 mmol) was added, and the mixture was reacted at room temperature for 1.5 hours. After completion of the reaction, 1 mol/ml hydrochloric acid aqueous solution (12 ml), diethyl ether (25 ml) and 1 mol/ml sodium hydroxide aqueous solution (25 ml) were successively added. The reaction solution was extracted with ethyl acetate (50 mL×2). The organic phase was collected, dried over anhydrous sodium sulfate, filtered, and the filtrate was concentrated under reduced pressure. The crude product was purified using a chromatography column (dichloromethane:methanol=10:1) to give a product 1-(1-(3-cyclopropylphenyl)-1H-[1,2,4]-triazole-3-yl)cyclopropylamine (A60) (400 mg, yellow oil), yield 57.4%.

LCMS: m/z 241.3 [M−NH$_2$]$^+$; RT=0.90 min.

Synthesis of Intermediate A61:1-(2-bromo-1-(3-cyclopropylphenyl)-1H-imidazol-4-yl)cyclopropylamine

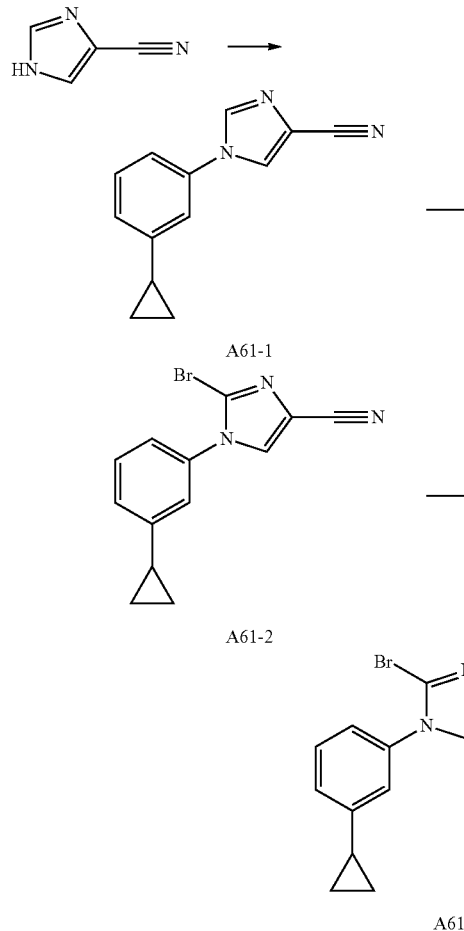

Step 1: Using the method in Step 1 for intermediate A12, A61-1 was obtained.

Step 2: Compound A61-1 (1.0 g, 5.0 mmol), N-bromosuccinimide (0.89 g, 5.0 mmol) and azobisisobutyronitrile (0.246 g, 1.5 mmol) were sequentially added to a 100 ml round bottom flask containing 40 ml of carbon tetrachloride at room temperature. The gas was ventilated for 3 times under the protection of nitrogen, and then heated to reflux for 8 hours. The system was cooled to room temperature and then washed with water. The organic phase was washed with saturated brine, dried over anhydrous sodium sulfate, and filtered, and the filtrate was concentrated and separated through a column to afford compound A61-2 (500 mg, yield: 34.7%), the product is a yellow solid.

$^1$H NMR (CDCl$_3$-d4, 400 MHz): δ7.64 (s, 1H), 7.41 (t, J=8.0 Hz, 1H), 7.25 (t, J=6.4 Hz, 1H), 7.09 (d, J=8.0 Hz, 1H), 7.01 (s, 1H), 2.87-2.97 (m, 1H), 1.05-1.10 (m, 2H), 0.73-0.77 (m, 2H);

Step 3: A61-2 (500 mg, 1.74 mmol, 1.0 eq), dry toluene and diethyl ether (15 mL+15 mL) were sequentially added to a dry 50 mL three-neck flask at room temperature. Under nitrogen atmosphere, the reaction solution was cooled to −70° C., tetraisopropyl titanate (988 mg, 3.48 mmol, 2.0 eq) was added, then ethyl magnesium bromide in diethyl ether (3M, 1.74 mL, 4.8 mmol, 3.0 eq) was slowly added. After stirring at low temperature for 20 minutes, the mixture was warmed to room temperature and stirred for 2 hours. Boron trifluoride. diethyl ether (495 mg, 3.48 mmol) was added to the reaction system. After stirring for 1 hour, 10 mL 1N HCl was added, and stirred for 10 minutes, and then 2N NaOH was used to adjust pH to basic. After filtration, the filtrate was extracted for three times with ethyl acetate (30 mL). The organic phase was dried, concentrated under reduced pressure and purified by silica gel column to afford a product 1-(2-bromo-1-(3-cyclopropylphenyl)-1H-imidazol-4-yl)cyclopropylamine (A61) (300 mg, yellow solid), yield 54.2%. LCMS: m/z 319.1 [M+H]$^+$; RT=1.07 min.

Synthesis of Intermediate A63: 1-(5-bromo-1-(3-cyclopropylphenyl)-1H-imidazol-4-yl)cyclopropylamine

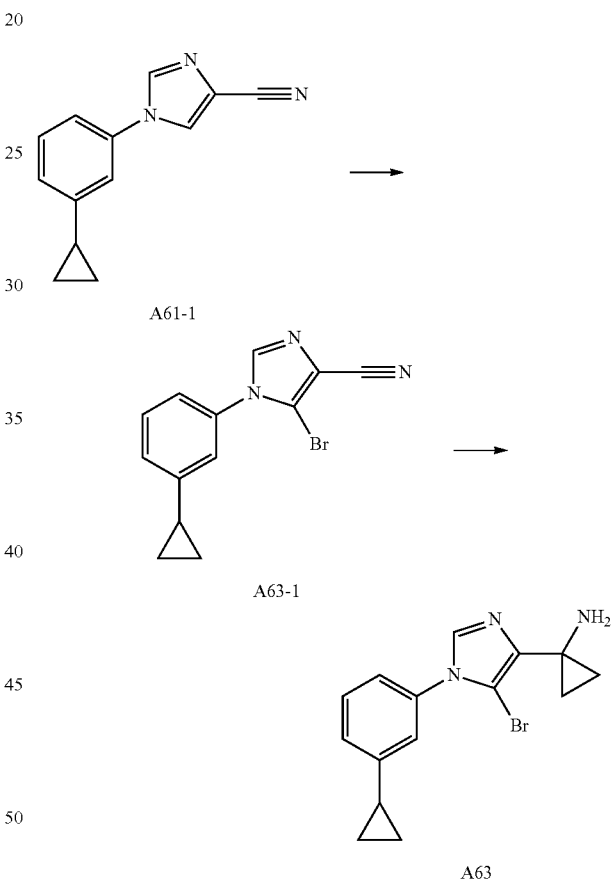

Step 1: Intermediate A61-1 (440 mg, 2.10 mmol), NBS (1.5 g, 8.4 mmol) were sequentially added to a 100 ml round bottom flask containing 20 ml of acetic acid at room temperature, and then heated to 70° C. for 3 hours. TLC test showed the reaction was almost complete. After the system was cooled to room temperature, the solvent was evaporated, and the residual was eluted with ethyl acetate. Saturated sodium bicarbonate was used to adjust pH to 8, the resulting mixture was washed with water, and the organic phase was washed with saturated brine, dried over anhydrous sodium sulfate and filtered, and then the filtrate was concentrated and separated by column to give compound A63-1 (300 mg, yield 50%) as white solids.

¹H-NMR (CDCl₃, 400 MHz): 7.79 (s, 1H), 7.73-7.69 (m, 2H), 7.07-7.05 (m, 1H), 6.93 (s, 1H).

Step 2: using step 3 of A61, A63 was obtained from A63-1.

LCMS: m/z 319.1 [M+H]⁺; RT=1.07 min.

Synthesis of Intermediate A64: 1-(1-(3-bromophenyl)-1H-imidazol-4-yl)cyclobutylamine

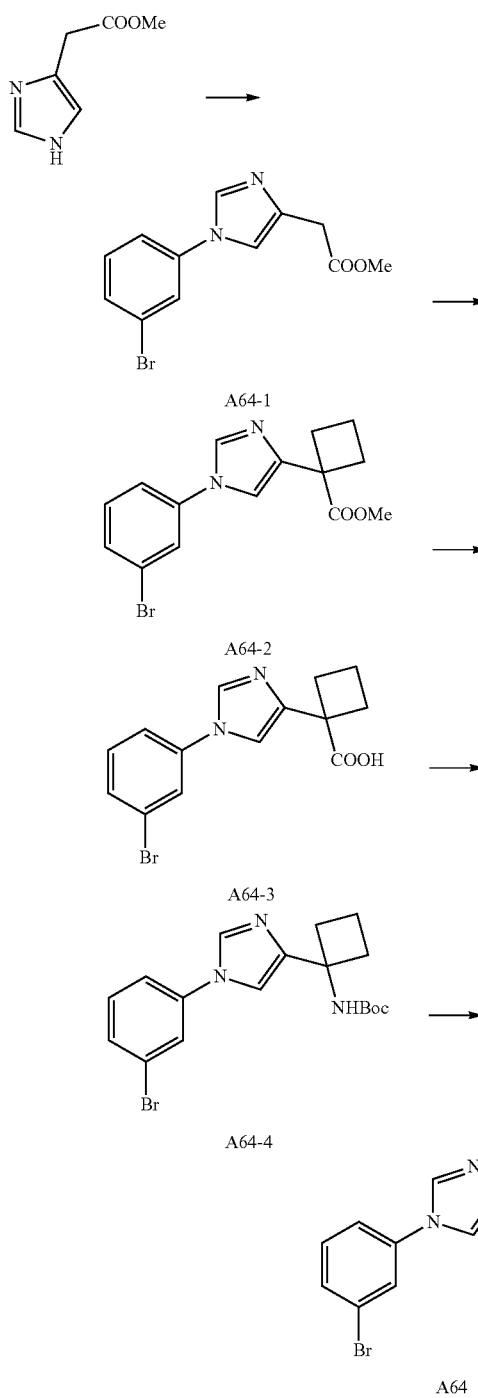

Step 1: Intermediate A64-1 was obtained by reacting methyl imidazole-4-acetate with m-bromoiodobenzene using the method in Step 1 for Intermediate A55.

¹H-NMR (CDCl₃, 400 MHz): 7.78 (s, 1H), 7.55 (s, 1H), 7.50-7.47 (m, 1H), 7.34-7.33 (m, 2H), 7.26 (s, 1H), 3.75-3.63 (m, 5H).

Step 2: Sodium hydride (398 mg, 9.96 mmol) was added to a 100 ml three-neck round bottom flask containing 20 ml of N,N-dimethylformamide at room temperature, cooled to 0° C., a mixture of A64-1 (1.4 g, 4.74 mmol) and 1,3-dibromopropane in N,N-dimethylformamide was slowly added, the obtained mixture was reacted for 40 minutes and TLC detection showed that the reaction was basically completed. The reaction was quenched by saturated ammonium chloride, diluted with water and extracted with ethyl acetate. The organic phase was washed with saturated brine, dried over anhydrous sodium sulfate and filtered, and the filtrate was concentrated and separated through a column to give intermediate A64-2 (650 mg, yield 43%) as a yellow oil.

¹H-NMR (CDCl₃, 400 MHz): 7.80 (s, 1H), 7.56 (s, 1H), 7.50-7.48 (m, 1H), 7.34 (d, J=4.8 Hz, 2H), 7.17 (s, 1H), 3.75 (s, 3H), 2.81-2.74 (m, 2H), 2.58-2.52 (m, 2H), 2.05-2.00 (m, 2H).

Step 3: A64-3 was obtained from A64-2 using the method in Step 3 for Intermediate A55.

¹H-NMR (CDCl₃, 400 MHz): 7.87-7.84 (m, 1H), 7.59-7.54 (m, 2H), 7.39-7.34 (m, 2H), 7.26-7.23 (m, 1H), 2.90-2.87 (m, 2H), 2.32 (s, 2H), 2.11-2.04 (m, 2H).

Step 4: A64-4 was obtained from A64-3 using the method in Step 4 for Intermediate A55.

¹H-NMR (CDCl₃, 400 MHz): 7.78 (s, 1H), 7.56 (s, 1H), 7.48-7.47 (m, 1H), 7.36-7.33 (m, 2H), 7.18 (s, 1H), 2.64-2.62 (m, 4H), 2.04-1.90 (m, 2H), 1.42 (s, 9H).

Step 5: A64 was obtained from A64-4 using the method in Step 5 for Intermediate A55.

LCMS: m/z 275.1 [M+H]⁺; RT=0.83 min.

Intermediate B1: (S)-1-(2-chloropyrimidin-4-yl)-5-isopropylimidazolidine-2-one

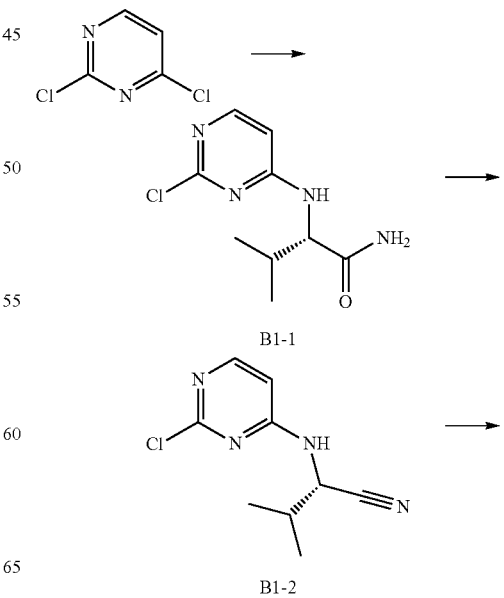

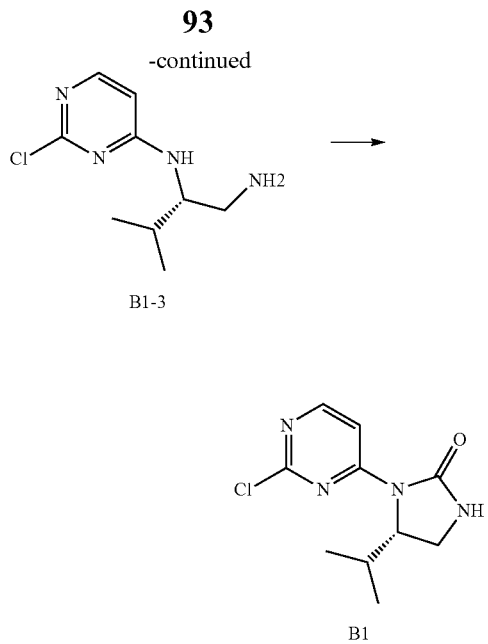

Step 1: Compound 2,4-dichloropyrimidine (1.49 g, 10 mmoL), L-valinamide hydrochloride (1.68 g, 11 mmoL) and tetrahydrofuran (25 mL) were sequentially added to a dry 100 mL three-neck flask, and stirred at room temperature for 5 minutes. Triethylamine (2.2 g, 22 mmoL) was added and allowed to react at room temperature overnight. After the reaction was completed, 100 mL of ethyl acetate was added. The organic phase was washed successively with water (20 mL×1) and saturated brine (20 mL×2). The organic phase was collected, dried over anhydrous sodium sulfate, filtered, and the filtrate was concentrated under reduced pressure, and purified through column chromatography (ethyl acetate: petroleum ether=1:5) to afford product (S)-2-((2-chloropyrimidin-4-yl)amino)-3-methylbutanamide (B1-1) (1.1 g, white solid), yield 48.2%.

Step 2: Compound B1-1 (456 mg, 2.0 mmoL) and dichloromethane (10 mL) were sequentially added to a dry 25 mL one-neck flask and stirred at 0° C. for 15 minutes. Then triethylamine (606 mg, 6.0 mmoL) and triphosgene (297 mg, 1.0 mmoL) were added in sequence and stirred at room temperature for 3 hours. After the reaction was completed, 20 mL of dichloromethane was added. The organic phase was washed successively with water (20 mL×1) and saturated brine (20 mL×1). The organic phase was collected, dried over anhydrous sodium sulfate, filtered, and the filtrate was concentrated under reduced pressure, and purified through column chromatography (ethyl acetate: petroleum ether=1:6) to afford product (S)-1-((2-chloropyrimidin-4-yl)amine-3-methylbutyl cyanide (B1-2) (410 mg, white solid), yield 80.7%.

LCMS: m/z 211.2 [M+H]$^+$; RT=0.89 min.
$^1$H NMR (d6-DMSO, 400 MHz) δ 8.1 (d, 1H), 7.3 (d, 1H), 5.4 (d, 1H), 4.9 (s, 1H), 2.2 (m, 1H), 1.21 (m, 6H).

Step 3: Intermediate B1-2 (560 mg, 2.2 mmoL) was dissolved in tetrahydrofuran (15 mL) in a dry 100 mL one-neck flask and lithium aluminum hydride (251 mg, 6.6 mmoL) was added in batch at 0° C., then reacted at room temperature for 1 hour. After the reaction was completed, 15 mL of ethyl acetate was added. The organic phase was washed successively with water (30 mL×2) and saturated brine (20 mL×1). The organic phase was collected, dried over anhydrous sodium sulfate, filtered and the filtrate was concentrated under reduced pressure to give a crude product. The crude product was purified through column chromatography (dichloromethane:methanol=10:1) to give product B1-3, yield 33.9%.

LCMS: m/z 215.2 [M+H]$^+$; RT=1.04 min.

Step 4: B1-3 (214 mg, 1.0 mmoL) and dichloromethane (5 mL) were sequentially added to a dry 50 mL one-neck flask and stirred at 0° C. for 15 minutes. Then triethylamine (303 mg, 3.0 mmoL) and triphosgene (148 mg, 0.5 mmoL) were added in sequence and stirred at room temperature overnight. After the reaction was completed, 20 mL of dichloromethane was added. The organic phase was washed successively with water (20 mL×1) and saturated brine (20 mL×1). The organic phase was collected, dried over anhydrous sodium sulfate, filtered, and the filtrate was concentrated under reduced pressure and purified through column chromatography (ethyl acetate: petroleum ether=1:10) to afford product (S)-1-(2-chloropyrimidin-4-yl)-5-isopropylimidazolidine-2-one (B1) (160 mg, white solid), yield 66.67%.

LCMS: m/z 241.2 [M+H]$^+$; RT=1.22 min.

Intermediates B4, B5, B6, B7, B26 were obtained using similar starting materials using the method above.

| Intermediate number | Name | Structural formula | analysis data |
|---|---|---|---|
| Intermediate B4 | (S)-1-(2-chloro-pyrimidin-4-yl)-5-phenylimidazol-idine-2-one | | LCMS: m/z 275.1 [M + H]$^+$; RT = 1.34 min |

-continued

| Intermediate number | Name | Structural formula | analysis data |
|---|---|---|---|
| Intermediate B5 | 1-(2-chloro-pyrimidin-4-ylamino)-1,3-diazaspiro[4.4]nonan-2-one | | LCMS: m/z 253.2 [M + H]+, RT = 1.4 min. |
| Intermediate B6 | 1-(2-chloro-pyrimidin-4-yl)-5,5-dimethyl-imidazolidine-2-one | | LCMS: m/z 227.1 [M + H]+; RT = 0.47 min. |
| Intermediate B7 | (S)-1-(2-chloro-pyrimidin-4-yl)-5-cyclopropyl-imidazolidine-2-one | | LCMS: m/z 248.2 [M + H]+, RT = 0.64 min. |
| Intermediate B26 | (S)-5-cyclopropyl-1-(2,6-dichloro-pyrimidin-4-yl)imidazolidine-2-one | | LCMS: m/z 273.2 [M + H]+, RT = 1.52 min. |

Synthesis of Intermediate B8: (S)-3-(2-chloropyrimidin-4-yl)-4-isopropyl-1-methylimidazolidine-2-one

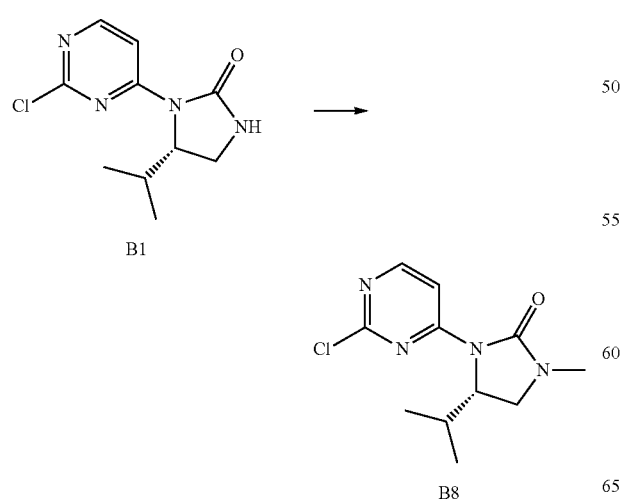

Experimental procedure: Intermediate B1 (48 mg, 0.2 mmol) and N,N-dimethylformamide (5 ml) were sequentially added to a dry 25 ml one-neck flask and stirred at room temperature for 5 min. Potassium carbonate (41 mg, 0.3 mmol) and methyl iodide (34 mg, 0.24 mmol) were sequentially added and stirred at room temperature overnight. After the reaction was completed, 10 ml of ethyl acetate was added. The organic phase was washed with water (20 ml×1) and saturated brine (20 ml×1) in sequence. The organic phase was collected, dried over anhydrous sodium sulfate, filtered, and the filtrate was concentrated under reduced pressure and purified through column chromatography (ethyl acetate: petroleum ether=1:6) to afford product (S)-3-(2-chloropyrimidin-4-yl)-4-isopropyl-1-methylimidazolidine-2-one (B8) (35 mg, white solid), yield 68.9%.

LCMS: m/z 255.2[M+H]+; RT=1.37 min.

Intermediates B9, B10, B12, B13, B14, B17, B20, B21, B23, B25 were obtained using similar starting materials using the above method.

| Intermediate number | Name | Structural formula | analysis data |
|---|---|---|---|
| Intermediate B9 | (S)-3-(2-chloro-pyrimidin-4-yl)-4-isopropyl-1-ethyl-imidazolidine-2-one | | LCMS: m/z 269.3 [M + H]$^+$; RT = 1.58 min |
| Intermediate B10 | Synthesis of (S)-3-(2,6-dichloro-pyrimidin-4-yl)-4-cyclopropyl-1-methylimidazolidine-2-one | | LCMS: m/z 287.2 [M + H]$^+$; RT = 1.7 min |
| Intermediate B12 | (S)-3-(2-chloro-pyrimidin-4-yl)-4-isopropyl-1-trideutero-methylimidazole-2-one | | LCMS: m/z 258.2 [M + H]$^+$, RT = 1.37 min. |
| Intermediate B13 | Synthesis of (S)-3-(2-chloro-6-methylpyrimidin-4-yl)-4-cyclopropyl-1-methylimidazolidine-2-one | | $^1$H-NMR(CDCl$_3$, 400 MHz): 8.05 (s, 1H), 4.27-4.22 (m, 1H), 3.59-3.54 (m, 1H), 3.27-3.24 (m, 1H), 2.92 (s, 3H), 2.44 (s, 3H), 1.17-1.12 (m, 1H), 0.90-0.85 (m, 1H), 0.63-0.58 (m, 1H), 0.52-0.45 (m, 1H), 0.30-0.25 (m, 1H). |
| Intermediate B14 | Synthesis of (S)-1-(2-chloro-5-fluoropyrimidin-4-yl)-5-isopropylimidazolidine-2-one | | LCMS: m/z 273.2 [M + H]$^+$, RT = 1.41 min. |
| Intermediate B17 | (S)-3-(2-chloro-pyrimidin-4-yl)-5,5-dideutero-4-isopropyl-1-methyl-imidazolidine-2-one | | LCMS: m/z 257.3 [M + H]$^+$, RT = 1.47 min. |

| Intermediate number | Name | Structural formula | analysis data |
| --- | --- | --- | --- |
| Intermediate B20 (obtained from intermediate 18 by methylation, absolute configuration not confirmed) | (5S)-1-(2-chloro-pyrimidin-4-yl)-5-isopropyl-3,4-dimethyl-imidazolidine-2-one | | $^1$H-NMR(CDCl$_3$, 400 MHz): 8.29 (d, J = 6.0 Hz, 1H), 8.24 (d, J = 6.4 Hz, 1H), 4.18-4.16 (m, 1H), 3.43-3.41 (m, 1H), 2.89 (s, 3H), 2.57-2.54 (m, 1H), 1.27 (t, d = 6.4 Hz, 3H), 0.98 (d, J = 7.2 Hz, 3H), 0.76 (d, J = 6.8 Hz, 3H) |
| Intermediate B21 (obtained from intermediate 19 by methylation, absolute configuration not confirmed) | (5S)-1-(2-chloro-pyrimidin-4-yl)-5-isopropyl-3,4-dimethyl-imidazolidine-2-one | | LCMS: m/z 269.3 [M + H]$^+$; RT = 1.58 min. |
| Intermediate B23 | (S)-3-(2-chloro-pyrimidin-4-yl)-5,5-dideutero-4-isopropyl-1-trideutero methylimidazolidine-2-one | | LCMS: m/z 260.3 [M + H]$^+$; RT = 2.5 min. |
| Intermediate B25 | (S)-6-(2-chloro-pyrimidin-4-yl)-7-isopropyl-4-methyl-4,6-diazaspiro[2.4]hept-5-one | | $^1$H-NMR(CDCl3, 400 MHz): 8.30 (d, J = 6.0 Hz, 1H), 8.23 (d, J = 6.0 Hz, 1H), 4.53 (s, 1H), 2.60 (s, 3H), 2.17-2.13 (m, 1H), 1.18-1.13 (m, 2H), 0.99-0.87 (m, 7H), 0.61-0.55 (m, 1H). |
| Intermediate B31 | (S)-7-(2-chloro-pyrimidin-4-yl)-8-isopropyl-5-methyl-2-oxa-5,7-diazaspiro[3.4]oct-6-one | | $^1$H-NMR(CDCl$_3$, 400 MHz): 8.32 (d, J = 6.0 Hz, 1H), 8.15 (d, J = 6.0 Hz, 1H), 5.20 (d, J = 8.0 Hz, 1H), 5.05 (d, J = 2.4 Hz, 1H), 4.92 (d, J = 8.4 Hz, 1H), 4.79-4.73 (m, 2H), 3.18 (s, 3H), 2.36-2.32 (m, 1H), 0.92-0.89 (m, 6H). |
| Intermediate B32 | (S)-7-(2-chloro-pyrimidin-4-yl)-8-isopropyl-5-trideuteromethyl-2-oxa-5,7-diazaspiro[3.4]oct-6-one | | 1H-NMR(CDCl3, 400 MHz): 8.32 (d, J = 6.0 Hz, 1H), 8.15 (d, J = 6.0 Hz, 1H), 5.20 (d, J = 8.0 Hz, 1H), 5.05 (d, J = 2.4 Hz, 1H), 4.92 (d, J = 8.4 Hz, 1H), 4.79-4.73 (m, 2H), 2.36-2.32 (m, 1H), 0.92-0.89 (m, 6H). |

Synthesis of Intermediate B11: (S)-3-(2-chloropyrimidin-4-yl)-1-cyclopropyl-4-isopropylimidazolidine-2-one

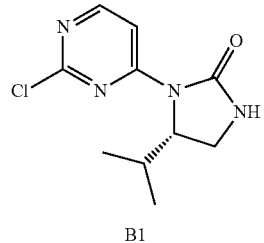

B1

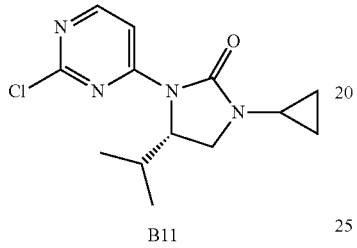

B11

Intermediate B1 (400 mg, 1.66 mmol), cyclopropylboronic acid (285.2 mg, 3.35 mmol), copper acetate (603.2 mg, 3.32 mmol) and triethylamine (420 mg, 4.15 mmol)) were sequentially added to a 100 ml round bottom flask containing 20 ml dichloromethane at room temperature, and open-stirred at room temperature for 24 hours. After the reaction was completed, 100 mL of water was added to the system, and the mixture was extracted with dichloromethane (20 mL×3). The organic phase was washed with saturated brine, dried over anhydrous sodium sulfate and filtered, and the filtrate was concentrated and purified through a silica gel column (petroleum ether: acetic acid=3:1) to give a product as white solid (S)-3-(2-chloropyrimidin-4-yl)-1-cyclopropyl-4-isopropylimidazolidine-2-one (B11) (163 mg, yield 35%).

LCMS: m/z 281.3 [M+H]$^+$; RT=1.6 min.

Synthesis of Intermediate B15: (R)-3-(2-chloropyrimidin-4-yl)-4-((R)-1-hydroxyethyl)-1-methylimidazolidine-2-one

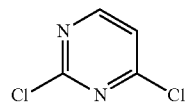

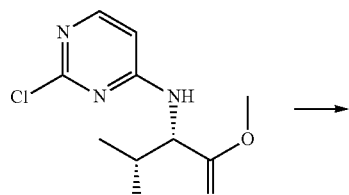

B15-1

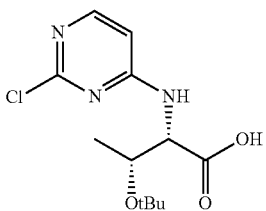

B15-2

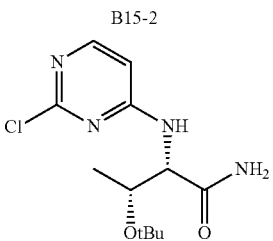

B15-3

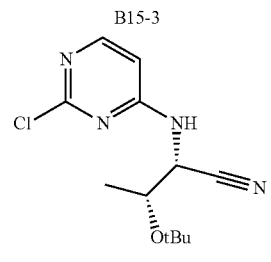

B15-4

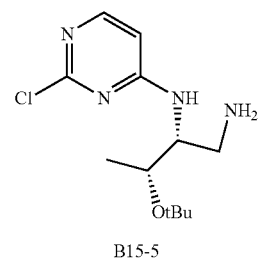

B15-5

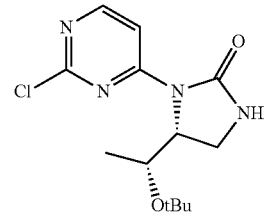

B15-6

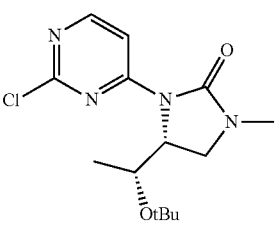

B15-7

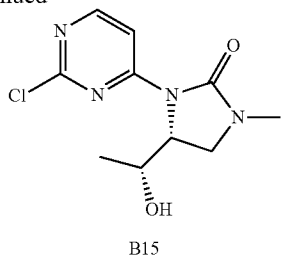

B15

Step 1: In a 100 ml round bottom flask containing 40 ml of tetrahydrofuran/water (5/1) mixed solvent, 2,4-dichloropyrimidine (2.3 g, 15.64 mmol), methyl (2S, 3R)-2-amino-3-(tert-butoxy)butanoate (3.2 g, 14.2 mmol) and triethylamine (4 mL, 28.4 mmol) were sequentially added at room temperature, and stirred at 60° C. overnight. TLC detection showed that the reaction was completed, and then the system was diluted with water, extracted with ethyl acetate. The organic phase was washed with water and saturated sodium chloride in sequence, dried over anhydrous sodium sulfate, filtered, concentrated, and purified through a column (petroleum ether/ethyl acetate=3/1) to give a product as white solid (2.4 g, yield 57%).

$^1$H-NMR (DMSO-d, 400 MHz): 8.70 (s, 2H), 4.23-4.00 (m, 1H), 3.76 (s, 3H), 1.13-1.11 (m, 1H), 0.67-0.53 (m, 4H).

Step 2: B15-1 (2.2 g, 7.66 mmol), triethylamine (3.2 mL, 22.9 mmol), ammonium chloride solid (811 mg, 15.32 mmol) and HATU (4.3 g, 11.5 mmol) were added to a 100 mL round bottom flask containing 30 mL of N,N-dimethylformamide at room temperature. The reaction was performed at room temperature overnight and TLC detection showed that the reaction was essentially completed. The mixture was diluted with water and extracted with ethyl acetate. The organic layer was washed with saturated brine, dried over anhydrous sodium sulfate, filtered and the filtrate was concentrated to give compound B15-2 as white solid (1.0 g, yield 48%).

$^1$H-NMR (DMSO-d, 400 MHz): 12.63-12.58 (m, 1H), 8.17 (d, J=5.6 Hz, 1H), 6.41 (s, 1H), 3.75 (s, 1H), 2.19 (s, 3H), 1.23-1.12 (m, 1H), 0.59-0.45 (m, 4H).

Step 3: In a 100 ml three-neck round bottom flask containing 10 ml of dry dichloromethane solution, B15-2 (200 mg, 0.69 mmol) and triethylamine (0.3 mL, 2.09 mmol) were sequentially added, and after cooling to 0° C. under nitrogen, a solution of triphosgene (103 mg, 0.34 mmol) in dichloromethane was added dropwise. After reacting for 3 hours, TLC detection showed that the reaction was completed, and then the reaction mixture was diluted with dichloromethane, washed with water. The organic phase was washed with a saturated sodium chloride aqueous solution, dried over anhydrous sodium sulfate, and filtered, and the filtrate was concentrated and purified through a column to afford B15-3 (170 mg, yield 80%) as white solid.

$^1$H-NMR (CDCl$_3$, 400 MHz): 7.96 (d, J=6.0 Hz, 1H), 7.47 (s, 1H), 7.05 (s, 1H), 6.43 (s, 1H), 3.92-3.88 (m, 1H), 2.17 (s, 3H), 1.08-1.03 (m, 1H), 0.52-0.33 (m, 4H).

Step 4: LiAlH4 (61 mg, 1.6 mmol) was added to a 50 ml three-neck round bottom flask containing 10 ml of dry tetrahydrofuran solution. After cooling to 0° C. under nitrogen atmosphere, B15-3 (200 mg, 0.64 mmol) in tetrahydrofuran solution was added dropwise and stirred for 30 minutes. After LCMS detection showed that the reaction was completed, the reaction mixture was quenched with 0.1 ml of water, 0.1 ml of 1N sodium hydroxide aqueous solution and 0.3 ml of water in sequence, dried over anhydrous magnesium sulfate. After filtration, the filtrate was concentrated to give B15-4 (230 mg, crude) as oil.

LCMS: m/z 227.3 [M+H]$^+$; RT=0.56 min.

Step 5: In a 50 ml round bottom flask containing 10 ml of N,N-dimethylformamide, B15-4 (230 mg, 0.84 mmol), DIEA (327 mg, 2.53 mmol) and CDI (202 mg, 1.26 mmol) were sequentially added. After the reaction was carried out for 2 hours at room temperature, LCMS detection showed that the reaction was completed, and then the reaction mixture was diluted with water and extracted with ethyl acetate. The organic phase was washed with saturated sodium chloride and dried over anhydrous sodium sulfate, filtered, and the filtrate was concentrated and prep-TLC separated to give B15-5 (140 mg, yield 56%) as white solid.

LCMS: m/z 298.1 [M+H]$^+$; RT=1.4 min.

Step 6: NaH (38 mg, 0.94 mmol) was added to a 50 ml three-neck round bottom flask containing 8 ml of N,N-dimethylformamide. After cooling to 0° C., B15-5 (140 mg, 0.47 mmol) in N,N-dimethylformamide solution was slowly added, stirred at room temperature for 30 min under nitrogen atmosphere, then MeI (99 mg, 0.70 mmol) was added, and reacted at room temperature for 1 hour. After TLC detection showed that the reaction was completed, the reaction solution was diluted with water and extracted with ethyl acetate. The organic phase was washed with saturated sodium chloride, dried over anhydrous sodium sulfate, filtered, and the filtrate was concentrated and prep-TLC separated to give B15-6 (130 mg, yield 89%) as white solid.

$^1$H-NMR (CDCl$_3$, 400 MHz): 8.03 (s, 1H), 4.97 (s, 1H), 4.39-4.34 (m, 1H), 3.69-3.65 (m, 1H), 3.36-3.33 (m, 1H), 2.46 (s, 3H), 1.25-1.20 (m, 1H), 0.91-0.87 (m, 1H), 0.65-0.61 (m, 1H), 0.52-0.48 (m, 1H), 0.30-0.25 (m, 1H).

Step 7: B15-6 (100 mg, 0.32 mmol) was added to a 50 ml round bottom flask containing 3 ml of dichloromethane. After cooling to 0° C., TFA (3 mL) was slowly added and stirred for 3 hours at room temperature. After TLC detection showed that the reaction was completed, the system was concentrated, diluted with ethyl acetate, and the pH value was adjusted to 8 with saturated sodium bicarbonate solution, extracted with ethyl acetate, and the organic phase was washed with saturated sodium chloride and dried over anhydrous sodium sulfate, filtered, and the filtrate was concentrated and prep-TLC separated to give B15 (80 mg, yield 98%) as white solid.

$^1$H-NMR (CDCl$_3$, 400 MHz): 8.05 (s, 1H), 4.27-4.22 (m, 1H), 3.59-3.54 (m, 1H), 3.27-3.24 (m, 1H), 2.92 (s, 3H), 2.44 (s, 3H), 1.17-1.12 (m, 1H), 0.90-0.85 (m, 1H), 0.63-0.58 (m, 1H), 0.52-0.45 (m, 1H), 0.30-0.25 (m, 1H).

Synthesis of Intermediate B16: (S)-1-(2-chloropyrimidin-4-yl)-4,4-dideutero-5-isopropylimidazolidine-2-one

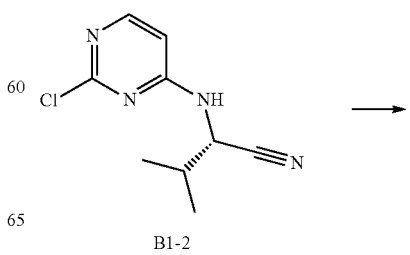

B1-2

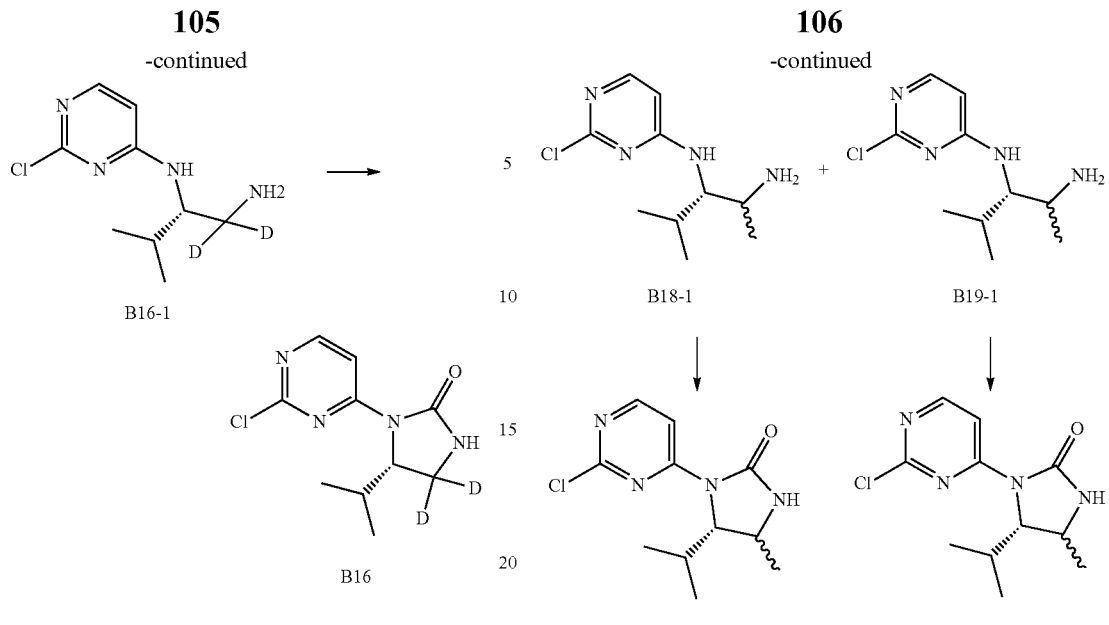

Step 1: Lithium aluminum deuteride (500 mg, 12 mmol) was added to a dry 250 ml three-neck flask, nitrogen was used for replacement for three times, and 5 ml of anhydrous tetrahydrofuran was added at 0° C. 10 ml of an intermediate B1-2 (1.25 g, 6 mmol) in anhydrous tetrahydrofuran was added at 0° C. The reaction was carried out at 0° C. for 0.5 hour, 0.5 ml of water was added, 0.5 ml of 15% sodium hydroxide solution was added, and 1.5 ml of water was added thereto, and an appropriate amount of anhydrous magnesium sulfate was added thereto, filtered, and the filtrate was concentrated under reduced pressure. Intermediate B16-1 (1.2 g, yellow solid) was obtained, yield 93%.

LCMS: m/z 217.3 [M+H]$^+$; RT=0.57 min.

Step 2: Intermediate B16-1 (4.1 g, 19 mmol) was added to a 25 ml round bottom flask, 100 ml of N,N-dimethylformamide was added, and N,N-diisopropylethylamine (7.3 g, 57 mmol) and N,N'-carbonyldiimidazole (4.6 g, 28 mmol) were added and stirred for 3 hours at room temperature. The mixture was quenched with water, extracted with ethyl acetate, washed with saturated brine, dried over anhydrous sodium sulfate and concentrated under reduced pressure. The crude product was purified through silica gel column chromatography and eluted with petroleum ether and ethyl acetate at a ratio of 3:1. Intermediate B16: (S)-1-(2-chloropyrimidin-4-yl)-4,4-dideutero-5-isopropylimidazolidine-2-one (3 g, yellow solid) was obtained, yield 65%.

LCMS: m/z 243.3[M+H]$^+$; RT=1.321 min (2.5 min).

Intermediate B18 and intermediate B19: (single material, absolute configuration not confirmed)

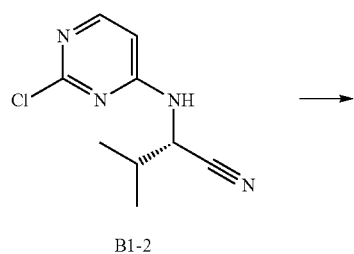

Step 1: Compound B1-2 (10.00 g, 47.47 mmol) and ethyl ether (100 ml) were sequentially added to a dry 500 ml three-neck flask at room temperature. Methyllithium (1.6 M, 119 mL, 189.88 mmol) was slowly added to the above system at 0° C. under nitrogen. The mixture was stirred at room temperature for 16 hours. After the reaction was completed, the reaction was quenched by adding 100 mL of methanol and concentrated under reduced pressure. 100 ml of methanol was added, sodium borohydride (3.59 g, 94.94 mmol) was added in batch at 0° C. and stirred at room temperature for 4 hours. The reaction solution was concentrated under reduced pressure. The crude product was purified using a reverse phase preparative column to afford two diastereomers.

B18-1: (3S)—N$^3$-(2-chloropyrimidin-4-yl)-4-methylpentane-2,3-diamine, yield 14.7%. LCMS: 229.3 [M+H]$^+$; RT=0.66 min.

B19-1: (3S)—N$^3$-(2-chloropyrimidin-4-yl)-4-methylpentane-2,3-diamine, yield: 18.5%. LCMS: 229.3 [M+H]$^+$; RT=0.69 min.

Step 2: Compound B18-1 or B19-1 (550 mg, 2.40 mmol), N,N-dimethylformamide (40 ml), N,N-diisopropylethylamine (0.79 ml, 4.80 mmol) and N,N'-carbonyldiimidazole (584 mg, 3.60 mmol) were sequentially added to a dry 100 ml one-neck flask at 0° C. The mixture was stirred at room temperature for 60 hours. After the reaction was completed, 400 ml of water was added. The resulting was extracted with ethyl acetate (150 mL×2). The organic phase was collected, dried over anhydrous sodium sulfate, filtered and the filtrate was concentrated under reduced pressure. The crude product was purified by a reverse phase preparative column to give the product.

B18: (5 S)-1-(2-chloropyrimidin-4-yl)-5-isopropyl-4-methylimidazolidine-2-one, yield 71.8%, LCMS: m/z 255.3 [M+H]$^+$; RT=1.407 min.

B19: (5 S)-1-(2-chloropyrimidin-4-yl)-5-isopropyl-4-methylimidazolidine-2-one $^1$H-NMR (CDCl$_3$, 400 MHz): 8.33 (d, J=6.0 Hz, 1H), 8.23 (d, J=6.0 Hz, 1H), 5.05 (s, 1H), 4.27 (s, 1H), 3.65 (d, J=6.4 Hz, 1H), 2.58-2.56 (m, 1H), 1.30 (d, J=6.4 Hz, 3H), 0.99 (d, J=7.2 Hz, 3H), 0.84 (d, J=6.8 Hz, 3H).

107

Synthesis of Intermediate B22: (S)-1-(2-chloropyrimidin-4-yl)-5-isopropyl-4,4-dimethylimidazolidine-2-one

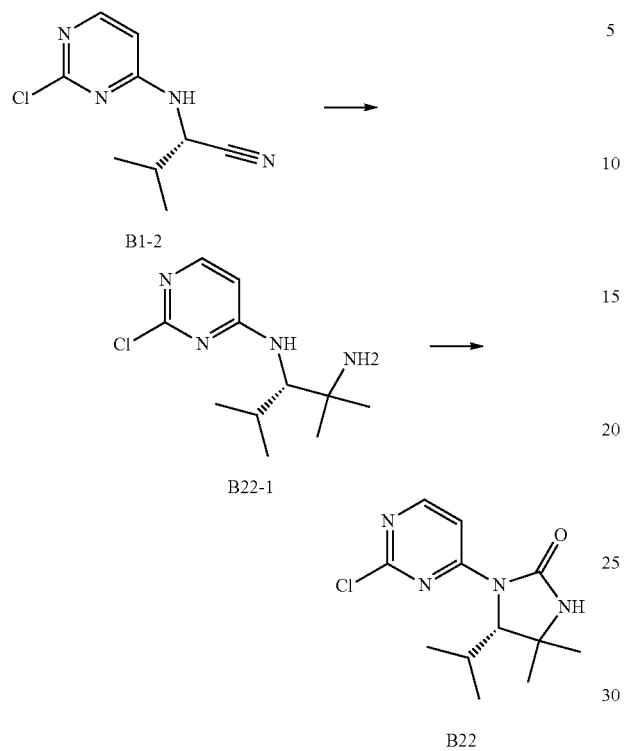

Step 1: Cerium trichloride (3.75 g, 15.2 mmol) was weighed in a dry 250 ml three-neck flask, nitrogen was used for replacement, and solvent tetrahydrofuran (50 mL) was added. A solution of methyl lithium (28.5 mmol, 1.6 M, 18 mL) was added dropwise in a dry ice acetone bath. After the addition was completed, the mixture was stirred at −78° C. for 45 minutes. B1-2 (1.0 g, 4.75 mmol) was added to the system, and after stirred at this temperature for 10 minutes, the mixture was returned to room temperature and stirred overnight. The reaction was quenched with 15 mL of methanol, and the reaction system was concentrated under reduced pressure. Dichloromethane was added and filtered, and the filtrate was evaporated to dryness. The crude product was purified through silica gel column chromatography and eluted with dichloromethane/methanol/ammonia at a ratio of 500/10/0.5 to give a crude product. The crude product was purified by prep-LC to afford B22-1 (200 mg, yield 17%, orange solid).

LCMS: m/z 243.4 [M+H]$^+$; RT=0.96 min.

Step 2: B22-1 (200 mg, 0.82 mmol) was added to a 25 ml round bottom flask, 10 ml of N,N-dimethylformamide was added, and N,N-diisopropylethylamine (423 mg, 3.28 mmol) was added. After stirred for 10 minutes, N,N'-carbonyldiimidazole (204 mg, 1.23 mmol) was added to the mixture and stirred at 35° C. overnight. The mixture was quenched with water, extracted with ethyl acetate, washed with saturated brine, dried over anhydrous sodium sulfate and concentrated under reduced pressure. The obtained crude product was purified through silica gel column chromatography, eluted with petroleum ether and ethyl acetate at a ratio of 5:1, concentrated to give intermediate B22 (114 mg, white solid), yield 52%.

LCMS: m/z 269.3 [M+H]$^+$; RT=1.64 min.

108

Synthesis of Intermediate B24: (S)-6-(2-chloropyrimidin-4-yl)-7-isopropyl-4,6-diazaspiro[2.4]hept-5-one

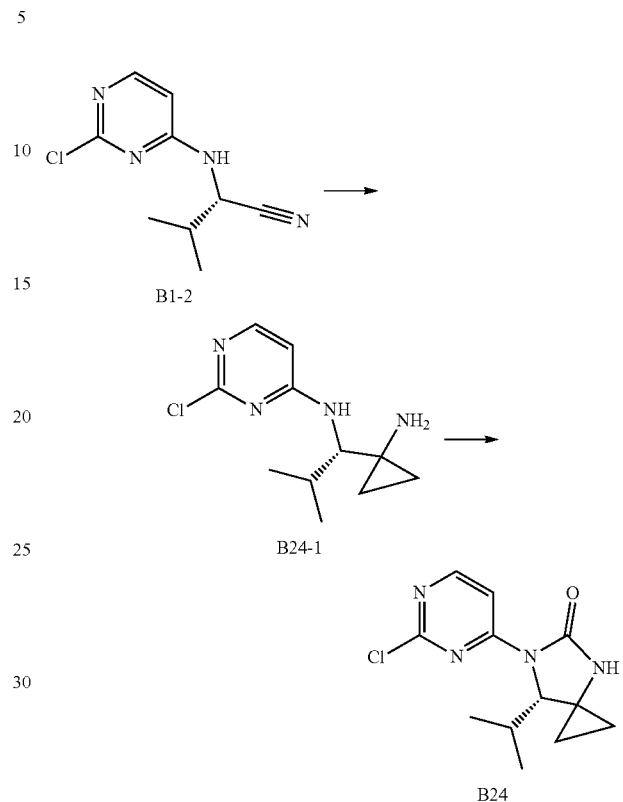

Step 1: In a 100 ml three-neck bottle containing 20 ml of a mixture of toluene and ethyl ether at a ratio of 1:1, B1-2 (1.4 g, 6.67 mmol) was added, after cooling to −78° C., then isopropyl titanate (2.34 ml) and ethyl magnesium bromide in ethyl ether (3.0 M, 7.7 mL) were sequentially added. After stirred for 20 min, the mixture was warmed to room temperature quickly and stirred for 1 hour, then boron trifluoride ethyl ether (3.3 ml) was added and stirred for 2 hours. After TLC detection showed that the reaction was completed, the pH value was adjusted to about 9 with 1N sodium hydroxide solution at room temperature, and extracted with ethyl acetate. The organic phase was washed successively with water and saturated brine, dried over anhydrous sodium sulfate, filtered, and the filtrate was concentrated and purified by column chromatography (dichloromethane/methanol=20/1) to afford B24-1 (440 mg, yield 28%) as yellow solid.

LCMS: m/z 241.4 [M+H]$^+$; RT=0.98 min.

Step 2: In a 50 ml round bottom flask containing 10 ml of N,N-dimethylformamide, B24-1 (230 mg, 0.96 mmol) and DIEA (371 mg, 2.88 mmol) were sequentially added and cooled to 0° C. CDI (230 mg, 1.44 mmol) was slowly added thereto, and the mixture was stirred at room temperature for 1 hour. After TLC detection showed that the reaction was completed, the system was diluted with water, extracted with ethyl acetate. The organic phase was washed with saturated sodium chloride, dried over anhydrous sodium sulfate, filtered, and the filtrate was concentrated and prep-TLC separated to give B24 (70 mg, yield 27%) as white solid.

¹H-NMR (CDCl₃, 400 MHz): 8.33 (d, J=6.0 Hz, 1H), 8.20 (d, J=5.6 Hz, 1H), 4.83 (s, 1H), 4.57 (s, 1H), 2.24-2.21 (m, 1H), 1.29-1.25 (m, 1H), 1.05-0.94 (m, 7H), 0.78-0.74 (m, 1H).

Synthesis of Intermediate B27: (S)-3-(2-chloropyrimidin-4-yl)-4-isopropyl-1-methylimidazolidine-2-one

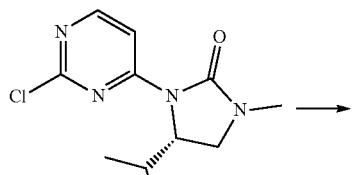

B8

(S)-3-(2-chloropyrimidin-4-yl)-4-isopropyl-1-methylimidazolidine-2-one (2.1 g, 8.1 mmol), potassium fluoride (18.9 g, 325.1 mmol) and 30 ml of dimethyl sulfoxide were sequentially added to a dry 50 mL round bottom flask, and the mixture was condensed and refluxed for 48 hours at 120° C. 100 ml of water was added, and the mixture was extracted with ethyl acetate for 5 times. The organic phase was dried over anhydrous sodium sulfate, and concentrated under reduced pressure. The residue was purified by silica gel column chromatography and eluted with petroleum ether and ethyl acetate at a ratio of 5:1. The product (S)-3-(2-fluoropyrimidin-4-yl)-4-isopropyl-1-methylimidazolidine-2-one (1.5 g, yellow solid) was obtained (yield: 77.7%).

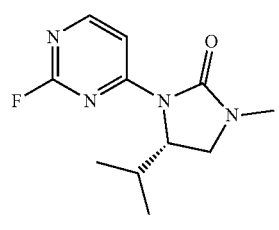

B27

¹H-NMR (CDCL3, 400 MHz): 8.32-8.30 (q, J=8.4 Hz, 1H), 8.22-8.20 (q, J=10.4 Hz, 1H), 4.61-4.57 (m, 1H), 3.48 (t, J=19.2 Hz, 1H), 3.28-3.25 (q, J=12.4 Hz, 1H), 2.91 (s, 3H), 2.64-2.60 (m, 1H), 0.96 (d, J=6.8 Hz, 3H), 0.78 (d, J=6.8 Hz, 3H).

Intermediates B28, B29 were obtained using similar starting materials and using the above method.

| Intermediate number | Name | Structural formula | analysis data |
|---|---|---|---|
| Intermediate B28 | (S)-3-(2-chloro-pyrimidin-4-yl)-4-isopropyl-1-hydro-imidazolidine-2-one | 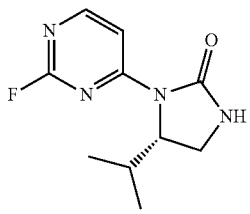 [SMILES: CC(C)[C@H]1CNC(=O)N1c1ccnc(F)n1] | LCMS: m/z 225.1 [M + H]⁺; RT = 1.1 min |
| Intermediate B29 | Synthesis of (S)-3-(2-fluoro-pyrimidin-4-yl)-4-cyclopropyl-1-ethylimidazolidine-2-one | 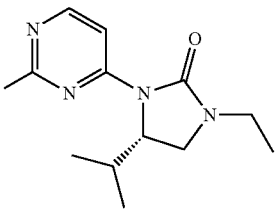 | LCMS: m/z 253.0 [M + H]⁺, RT = 1.15 min. |
| Intermediate B33 | (S)-3-(2-fluoro-pyrimidin-4-yl)-5,5-dideutero-4-isopropyl-1-methyl-imidazolidine-2-one | 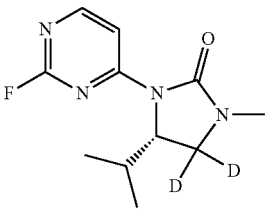 [SMILES: [2H]C1([2H])[C@H](C(C)C)N(c2ccnc(F)n2)C(=O)N1C] | LCMS: m/z 241.2 [M + H]⁺, RT = 1.2 min. |

Synthesis of Intermediate B30: (S)-3-(2-chloropyrimidin-4-yl)-4-isopropyl-1-methylimidazolidine-2-one

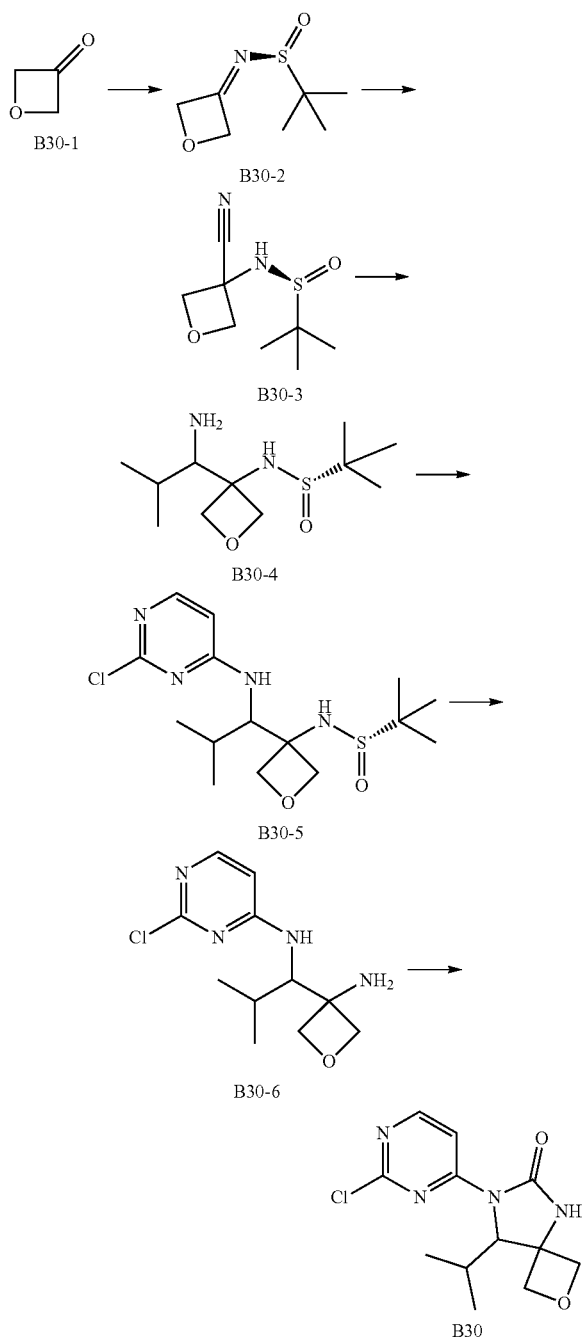

Step 1: In a 100 ml round bottom flask containing 50 ml of anhydrous dichloromethane, compound B30-1 (4.0 g, 55.51 mmol), (S)-2-methylpropane-2-sulfinamide (8.07 g, 66.61 mmol) and Ti(OiPr)4 (32.5 ml, 111.01 mmol) were sequentially added at room temperature, and stirred at 40° C. overnight. After TLC detection showed that the reaction was completed, the system was washed with saturated Na$_2$CO$_3$ solution, washed with water, and extracted with dichloromethane. The organic phase was washed with water and saturated sodium chloride in sequence, dried over anhydrous sodium sulfate, filtered, concentrated, and purified by column (petroleum ether/ethyl acetate=10/1) to give 2 (4.8 g, yield 50%) as yellow oil.

$^1$H-NMR (CDCl3, 400 MHz): 5.81-5.77 (m, 1H), 5.68-5.63 (m, 1H), 5.50-5.42 (m, 2H), 1.26 (s, 9H).

Step 2: Compound B30-2 (800 mg, 4.56 mmol) and Ti(OiPr)4 (647 mg, 2.28 mmol) were added to a 100 ml one-neck round bottom flask containing 20 ml of dry dichloromethane at room temperature. After stirred at room temperature for half an hour, the system was cooled to 0° C. and TMSCN (905 mg, 9.13 mmol) was added dropwise. After reacting at room temperature overnight, TLC detection showed that the reaction was almost completed. The system was washed with saturated brine, and the organic phase was dried over anhydrous sodium sulfate, filtered, and the filtrate was concentrated and then purified by column (petroleum ether/ethyl acetate=3/1) to give compound B30-3 (630 mg, yield 68%) as yellow solid.

$^1$H-NMR (CDCl$_3$, 400 MHz): 5.08-5.05 (m, 2H), 4.84 (d, J=7.2 Hz, 1H), 4.76 (d, J=7.2 Hz, 1H), 4.37-4.32 (m, 1H), 1.29 (s, 9H).

Step 3: B30-3 (500 mg, 2.47 mmol) was added to a 100 ml three-neck round bottom flask containing 20 ml of dry ethyl ether at room temperature. Isopropyl grignard reagent (6.4 ml, 12.36 mmol) was slowly added thereto at 0° C. under nitrogen. After reacting at room temperature overnight, the reaction was quenched with methanol. The concentrated solid was dissolved in methanol, and NaBH4 (187 mg, 4.94 mmol) was added thereto at 0° C., and reacted at room temperature for 2 hours. The system was concentrated and purified by column (DCM/MeOH=20/1) to give Compound B30-4 (390 mg, yield 63%) as yellow oil.

LCMS: m/z 249.4 [M+H]$^+$; RT=0.66 min.

Step 4: B30-4 (640 mg, 2.58 mmol), 2,4-dichloropyrimidine (420 mg, 2.83 mmol) and DIEA (998 mg, 7.74 mmol) were sequentially added to a 100 ml one-neck round bottom flask containing 20 ml of dimethyl sulfoxide, and stirred at 70° C. under nitrogen overnight. After TLC detection showed that the reaction was completed, the reaction mixture was diluted with water and extracted with ethyl acetate. The organic phase was washed successively with water and saturated brine, dried over anhydrous sodium sulfate, filtered, concentrated and purified by column (DCM/MeOH=20/1) to give B30-5 (270 mg, yield 30%) as yellow solid.

LCMS: m/z 361.3[M+H]$^+$; RT=1.003 min

Step 5: In a 50 ml round bottom flask containing 3 ml of methanol solution, B30-5 (200 mg, 0.56 mmol) was added, and hydrochloric acid (0.5 ml, 12.0 M) was added thereto at room temperature, and reacted at 10° C. for 3 hours. After LCMS detection showed that the reaction was completed, the reaction mixture was diluted with water, extracted with ethyl acetate, and the aqueous phase was kept. The aqueous phase was adjusted to basic with saturated Na$_2$CO$_3$ aqueous solution, and then extracted with ethyl acetate. The organic phase was washed with saturated brine, dried over anhydrous sodium sulfate, filtered and concentrated to give pure product B30-6 (100 mg, yield 70%) as yellow solid.

LCMS: m/z 257.4[M+H]$^+$; RT=0.443 min.

Step 6: B30-6 (80 mg, 0.312 mmol), DIEA (120 mg, 0.936 mmol) and CDI (75 mg, 0.468 mmol) were sequentially added to a 100 mL round bottom flask containing 8 mL of dry DMF, and the reaction was performed at 60° C. overnight. After TLC detection showed that the reaction was completed, the reaction mixture was diluted with water and extracted with ethyl acetate. The organic phase was washed with saturated sodium chloride, dried over anhydrous sodium sulfate, filtered, and the filtrate was concentrated and prep-TLC (petroleum ether/ethyl acetate=1/1) separated to give intermediate B30 (20 mg, yield 23%) as white solid.

$^1$H-NMR (CDCl$_3$, 400 MHz): 8.34 (d, J=6.4 Hz, 1H), 8.12 (d, J=6.0 Hz, 1H), 5.86-5.82 (m, 1H), 5.21-5.14 (m, 1H), 5.09-5.05 (m, 1H), 4.86-4.80 (m, 1H), 4.75-4.62 (m, 2H), 2.42-2.36 (m, 1H), 1.01-0.88 (m, 6H).

Example 1: Synthesis of Compound 1

2-chloro-N-cyclopentyl-4-(1-((4-((S)-5-isopropyl-2-oxoimidazolidine-1-yl)pyrimidin-2-yl)amino)ethyl)benzamide

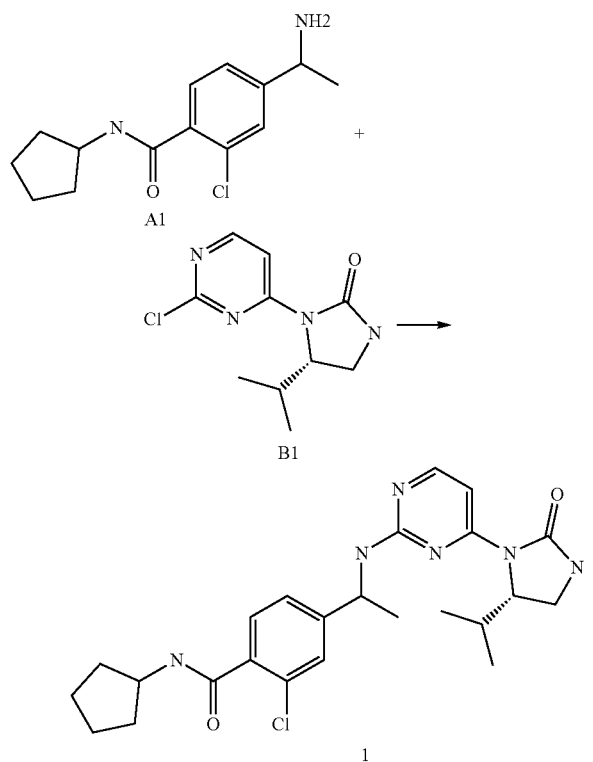

Intermediate A1 (40 mg, 0.14 mmoL) and intermediate B1 (24 mg, 0.1 mmoL) were dissolved in dichloromethane (2 mL) and homogeneously mixed, and dichloromethane was evaporated in vacuo (or slowly warmed to evaporate dichloromethane). Then, the reaction was performed without the solvent for 4 hours at 100° C. After the reaction was completed, the reaction system was dissolved in methanol (3 mL) and purified by high-performance liquid chromatography column to give the product 2-chloro-N-cyclopentyl-4-(1-((4-((S)-5-) isopropyl-2-oxoimidazolidine-1-yl)pyrimidin-2-yl)amino)ethyl)benzamide (9 mg, yellow solid), yield 19.1%

LCMS: m/z 471.5 [M+H]$^+$, RT=1.27 min.

$^1$H-NMR(D6-DMSO, 400 MHz) δ7.97-8.66 (t, 1H), 7.55-7.57 (d, J=8.0 Hz, 1H), 7.44-7.46 (dd, J1=1.6 Hz, J 2=5.6 Hz, 1H), 7.26-7.28 (m, 1H), 7.21 (s, 1H), 6.06-6.10 (m, 1H), 4.81 (s, 1H), 4.63 (s, 1H), 4.25-4.47 (m, 2H), 3.20-3.38 (m, 1H), 3.16-3.20 (m, 1H), 1.97-2.20 (m, 2H), 1.55-1.64 (m, 4H), 1.39-1.48 (m, 5H), 0.87-0.89 (d, J=8.0 Hz, 2H), 0.74-0.82 (m, 6H).

The following compounds can be obtained by using similar methods:

Example 2: Synthesis of Compound 2

(S)-3-(2-(((S)-1-(5-(3-chlorophenyl)pyridin-2-yl)ethyl)amino)pyrimidin-4-yl)-4-isopropyl-1-methyl-imidazolidine-2-one-5,5-dideutero

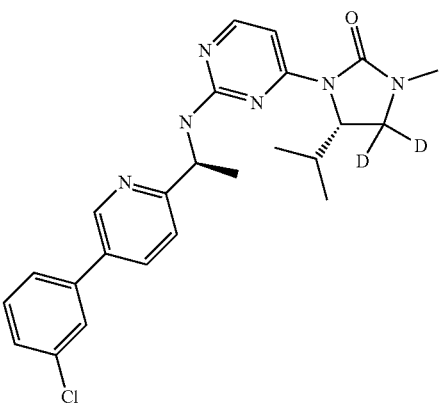 [SMILES: [2H]C1([2H])[C@H](C(C)C)N(c2ccnc(N[C@@H](C)c3ccc(-c4cccc(Cl)c4)cn3)n2)C(=O)N1C]

Compound 2 was obtained from Intermediate A66 and Intermediate B17 according to the method in Example 1.

LCMS: m/z 453.2 [M+H]$^+$; RT=1.12 min.

$^1$H NMR (400 MHz, CDCl$_3$) δ 8.75 (d, J=1.9 Hz, 1H), 8.09 (d, J=5.9 Hz, 1H), 7.78 (dd, J=8.1, 2.3 Hz, 1H), 7.57-7.49 (m, 2H), 7.40 (ddd, J=7.7, 7.0, 4.8 Hz, 4H), 5.71 (s, 1H), 5.16 (s, 1H), 4.46 (s, 1H), 2.84 (s, 3H), 1.69 (s, 1H), 1.61 (d, J=7.0 Hz, 3H), 0.62 (m, 6H).

Example 3: Synthesis of Compound 3

(R)-1-(2-(((S)-1-(1-(4-chlorophenyl)-1H-imidazol-4-yl)ethyl)amino)pyrimidin-4-yl)-5-isopropyl imidazolidine-2-one

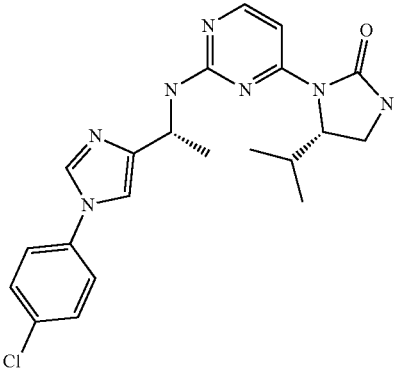 [SMILES: CC(C)[C@H]1CNC(=O)N1c1ccnc(N[C@H](C)c2cn(-c3ccc(Cl)cc3)cn2)n1]

Using the same manner as in Example 1, Compound 3 was obtained from Intermediate A3 and Intermediate B1.

LCMS: m/z 426.2[M+H]$^+$, RT=1.23 min;

$^1$H-NMR (D6-DMSO, 400 MHz) δ 8.02-8.04 (d, J=5.6 Hz, 1H), 7.70 (s, 1H), 7.42-7.44 (d, J=6.0 Hz, 1H), 7.35-7.38 (m, 2H), 7.22-7.26 (m, 2H), 7.06 (s, 1H), 5.33-5.35 (d, J=8.0 Hz, 1H), 5.12-5.16 (m, 1H), 4.78 (s, 1H), 4.58-4.62 (m, 1H), 3.37-3.42 (t, 1H), 3.22-3.25 (m, 1H), 2.54-2.57 (m, 1H), 1.52-1.54 (d, J=6.8 Hz, 3H), 0.85-0.87 (d, J=6.8 Hz, 3H), 0.77-0.79 (d, J=6.8 Hz, 3H).

Example 4: Synthesis of Compound 4

(S)-1-(2-(((S)-1-(1-(4-chlorophenyl)-1H-imidazol-4-yl)ethyl)amino)pyrimidin-4-yl)-5-isopropyl imidazolidine-2-one

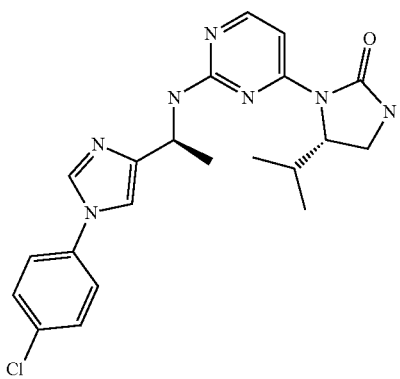 [SMILES: CC(C)[C@H]1CNC(=O)N1c1ccnc(N[C@@H](C)c2cn(-c3ccc(Cl)cc3)cn2)n1]

Using the same manner as in Example 1, Compound 4 was obtained from Intermediate A2 and Intermediate B1.

LCMS: m/z 426.2 [M+H]$^+$, RT=1.1 min.

$^1$H-NMR (CDCl3, 400 MHz) δ 10.62 (m, 1H), 8.35 (s, 1H), 7.90 (d, J=7.2, 1H), 7.78 (m, 1H), 7.52-7.54 (m, 3H), 7.39 (d, J=8.4, 2H) 5.48 (m, 1H), 5.08 (s, 2H), 4.75 (m, 1H), 3.36-3.62 (m, 2H), 2.31 (m, 1H), 1.91 (m, 3H), 0.78-0.89 (m, 6H).

Example 5: Synthesis of Compound 5

(S)-4-isopropyl-1-methyl-3-(2-(((S)-1-(5-(3-(trifluoromethyl)phenyl)pyridin-2-yl)ethyl)amino)pyrimidine-4-imidazolidine-2-one-5,5-d2

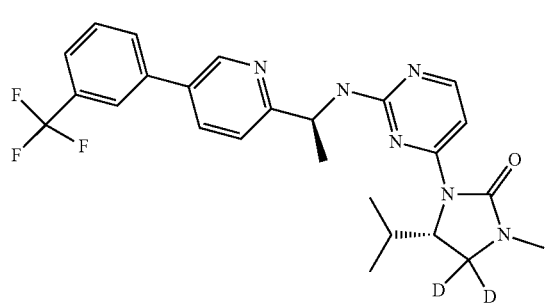 [SMILES: [2H]C1([2H])[C@H](C(C)C)N(c2ccnc(N[C@@H](C)c3ccc(-c4cccc(C(F)(F)F)c4)cn3)n2)C(=O)N1C]

Using the same manner as in Example 1, Compound 5 was obtained from Intermediate A65 and Intermediate B17.

LCMS: m/z 487.3 [M+H]$^+$; RT=1.09 min.

$^1$H NMR (400 MHz, CDCl$_3$) δ 8.78 (d, J=2.1 Hz, 1H), 8.10 (d, J=5.8 Hz, 1H), 7.84-7.76 (m, 2H), 7.73 (d, J=7.6 Hz, 1H), 7.66 (d, J=7.6 Hz, 1H), 7.63-7.57 (m, 1H), 7.55 (d, J=5.9 Hz, 1H), 7.41 (d, J=8.1 Hz, 1H), 5.66 (s, 1H), 5.17 (s, 1H), 4.47 (s, 1H), 2.84 (s, 3H), 2.17 (s, 1H), 1.60 (t, J=9.0 Hz, 3H), 0.64 (m, 6H).

Example 6: Synthesis of Compound 6

(S)-5-isopropyl-1-(2-(((S)-1-(6-methoxynaphthalen-2-yl)ethyl)amino)pyrimidin-4-yl)imidazolidine-2-one

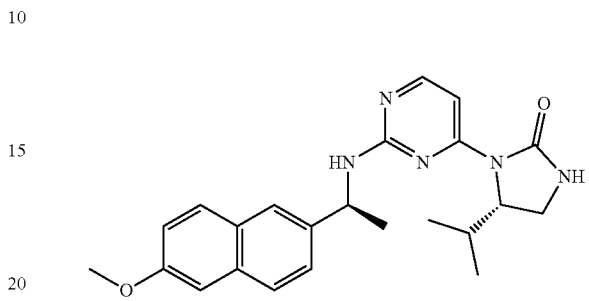

Using the same manner as in Example 1, Compound 6 was obtained from Intermediate A4 and Intermediate B1.

LCMS: m/z 406.2 [M+H]$^+$; RT=1.070 min.

$^1$H-NMR (CDCl3-d$_1$, 400 MHz): δ 10.49-10.51 (m, 1H), 7.63-7.80 (m, 5H), 7.45-7.50 (m, 1H), 7.41-7.43 (m, 1H), 7.11-7.15 (m, 2H), 5.34-5.40 (m, 1H), 5.16-5.20 (m, 1H), 4.58-4.60 (m, 1H) 3.91 (s, 3H), 3.27-3.52 (m, 2H), 1.78-1.79 (m, 3H), 0.45-1.09 (m, 6H).

Example 7: Synthesis of Compound 7

(5S)-1-(2-((1-([1,1'-biphenyl]-4-yl)ethyl)amino)pyrimidin-4-yl)-5-isopropylimidazolidine-2-one

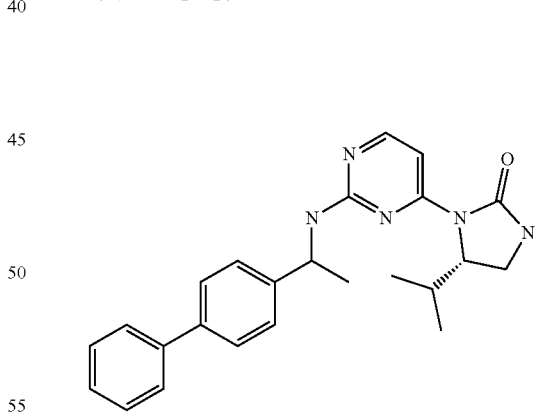

Using the same manner as in Example 1, Compound 7 was obtained from Intermediate A5 and Intermediate B1.

LCMS: m/z 402.0 [M+H]$^+$; RT=0.860 min.

$^1$H-NMR (MeOD-d$_4$, 400 MHz): δ 7.99-7.95 (m, 1H), 7.72-7.26 (m, 10H), 6.00 (s, 1H), 5.03 (d, J=36 Hz, 1H), 4.56-4.11 (m, 1H), 3.46-3.25 (m, 2H), 2.04-2.01 (m, 1H), 1.61-1.59 (m, 3H), 1.00-0.86 (m, 3H), 0.66-0.60 (m, 3H).

Example 8: Synthesis of Compound 8

(S)-1-(2-((1-(1-(4-chlorophenyl)-1H-imidazol-4-yl)cyclopropyl)amino)pyrimidin-4-yl)-5-isopropyl imidazolidine-2-one

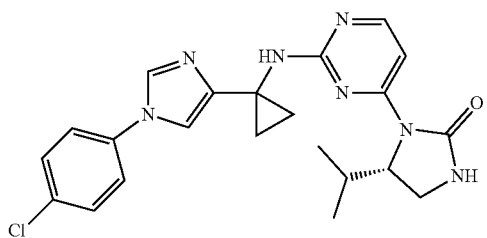 [SMILES: CC(C)[C@H]1CNC(=O)N1c1ccnc(NC2(c3cn(-c4ccc(Cl)cc4)cn3)CC2)n1]

Using the same manner as in Example 1, Compound 8 was obtained from Intermediate A6 and Intermediate B1.

LCMS: m/z 438.2 [M+H]$^+$; RT=1.12 min (2 min).

$^1$H-NMR (MEOD-d$_4$, 400 MHz): δ 8.01-8.03 (m, 2H), 7.48 (s, 5H), 7.22 (s, 1H), 4.52-4.58 (m, 1H), 2.30 (s, 1H), 1.38-1.50 (m, 3H), 1.22-1.35 (m, 4H), 0.65 (s, 6H).

Example 9: Synthesis of Compound 9

(5S)-5-isopropyl-1-(2-((1-(4-phenoxyphenyl)ethyl)amino)pyrimidin-4-yl)imidazolidine-2-one

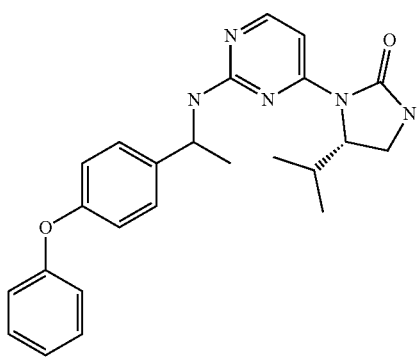 [SMILES: CC(Nc1nccc(N2C(=O)NC[C@@H]2C(C)C)n1)c1ccc(Oc2ccccc2)cc1]

Using the same manner as in Example 1, Compound 9 was obtained from Intermediate A7 and Intermediate B1.

$^1$H-NMR (CDCl3-d$_1$, 400 MHz): δ 8.04-8.07 (m, 1H), 7.47-7.50 (m, 1H), 7.27-7.33 (m, 4H), 7.00-7.08 (m, 1H), 6.93-6.98 (m, 4H), 5.49-5.52 (m, 1H), 4.95-5.06 (m, 2H), 4.43-4.61 (m, 1H), 3.33-3.47 (m, 1H), 3.26-3.28 (m, 1H), 2.09-2.66 (m, 1H), 1.25-1.64 (m, 3H), 0.88-0.94 (m, 2H), 0.80 (s, 4H).

LCMS: m/z 418.2 [M+H]$^+$; RT=1.158 min.

Example 10: Synthesis of Compound 10

(S)-1-(2-(((S)-1-(1-(4-chlorophenyl)-1H-imidazol-4-yl)ethyl)amino)pyrimidin-4-yl)-5-phenyl imidazolidine-2-one

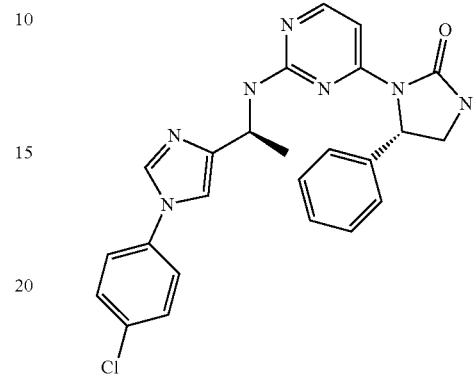

Using the same manner as in Example 1, Compound 10 was obtained from Intermediate A2 and Intermediate B4.

LCMS: m/z 460.1 [M+H]$^+$; RT=0.911 min.

$^1$H-NMR (CDCl3-d$_1$, 400 MHz): 8.95 (s, 1H), 8.00-8.06 (m, 2H), 7.63-7.65 (m, 2H), 7.57-7.59 (m, 2H), 7.48 (s, 1H), 7.18-7.20 (m, 2H), 7.11-7.14 (m, 2H), 6.96 (s, 1H), 5.70-5.73 (m, 1H), 5.14-5.16 (s, 1H), 3.98-4.02 (m, 1H), 3.17-3.30 (m, 1H), 1.64-1.66 (m, 3H).

Example 11: Synthesis of Compound 11

(S)-1-(2-((1-(1-(4-chlorophenyl)-1H-imidazol-4-yl)ethyl)amino)pyrimidin-4-yl)-1,3-diazaspiro[4.4]-2-one

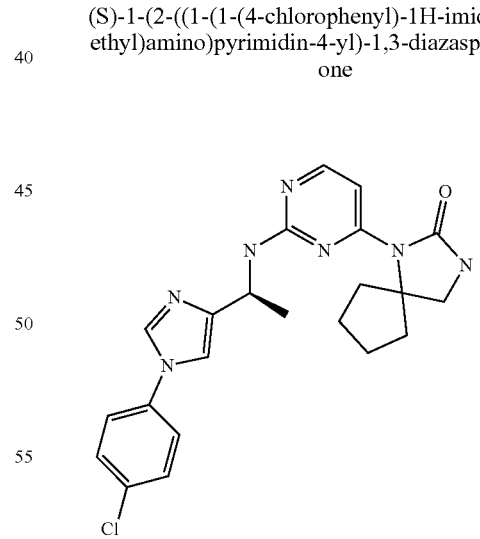

Using the same manner as in Example 1, Compound 11 was obtained from Intermediate A2 and Intermediate B5.

LCMS: m/z 438.2 [M+H]$^+$; RT=1.14 min.

$^1$H-NMR(MeOD-d$_4$, 400 MHz): δ 8.96 (brs, 1H), 7.99 (d, J=7.6 Hz, 1H), 7.89-7.91 (m, 2H), 7.59-7.66 (m, 4H), 5.35 (brs, 1H), 3.37 (s, 2H), 2.83-2.99 (m, 2H), 2.63 (brs, 1H), 1.91-1.92 (m, 1H), 1.60-1.74 (m, 8H).

Example 12: Synthesis of Compound 12

(S)-1-(2-((1-(1-(4-chlorophenyl)-1H-imidazol-4-yl)ethyl)amino)pyrimidin-4-y 1)-5,5-dimethyl imidazolidine-2-one

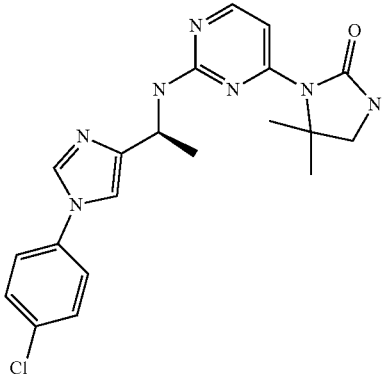 [SMILES: C[C@H](Nc1nccc(N2C(=O)NCC2(C)C)n1)c1cn(-c2ccc(Cl)cc2)cn1]

Using the same manner as in Example 1, Compound 12 was obtained from Intermediate A2 and Intermediate B6.

LCMS: m/z 412.3 [M+H]$^+$; RT=1.08 min.

$^1$H-NMR (MeOD-d$_4$, 400 MHz): δ 9.15 (brs, 1H), 8.00 (d, J=7.2 Hz, 2H), 7.87 (d, J=7.2 Hz, 1H), 7.60-7.68 (m, 4H), 5.39 (brs, 1H), 3.26 (s, 2H), 1.67-1.76 (m, 6H), 1.29 (s, 3H).

Example 13: Synthesis of Compound 13

(S)-1-(2-((1-(1-(4-chlorophenyl)-1H-imidazol-4-yl)cyclopropyl)amino)pyrimidin-4-yl)-5-phenylimidazolidine-2-one

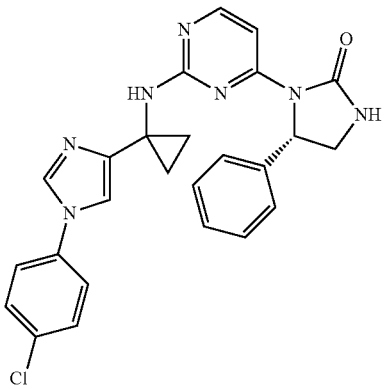 [SMILES: O=C1NC[C@H](c2ccccc2)N1c1ccnc(NC2(c3cn(-c4ccc(Cl)cc4)cn3)CC2)n1]

Using the same manner as in Example 1, Compound 13 was obtained from Intermediate A6 and Intermediate B4.

LCMS: m/z 472.2 [M+H]$^+$; RT=0.923 min.

$^1$H-NMR (MeOD-d$_4$, 400 MHz): δ 8.82-8.83 (m, 1H), 8.02-8.07 (m, 2H), 7.57-7.60 (m, 5H), 7.37-7.42 (m, 1H), 6.97-7.09 (m, 3H), 6.93-6.97 (m, 1H), 5.65-5.66 (m, 1H), 3.96-4.01 (m, 1H), 3.12 (s, 1H), 1.46-1.52 (m, 2H), 1.25-1.30 (m, 2H).

Example 14: Synthesis of Compound 14

(S)-1-(2-((S)-1-(1-(4-chlorophenyl)-1H-imidazol-4-yl)ethyl)amino)pyrimidin-4-yl)-5-cyclopropylimidazolidine-2-one

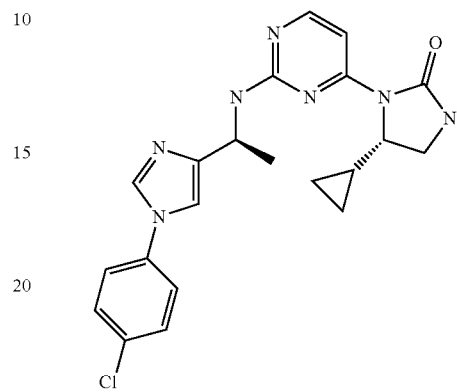

Using the same manner as in Example 1, Compound 14 was obtained from Intermediate A2 and Intermediate B7.

LCMS: m/z 424.4[M+H]$^+$; RT=0.96 min.

$^1$H-NMR(MeOD-d$_4$, 400 MHz): δ 9.11 (s, 1H), 7.97-8.03 (m, 2H), 7.90-7.92 (d, J=7.6 Hz, 1H), 7.60-7.70 (m, 4H), 5.44 (s, 1H), 4.69 (s, 1H), 3.54-3.60 (m, 1H), 3.13-3.19 (m, 1H), 1.72-1.76 (m, 3H), 1.15-1.19 (m, 1H), 0.26-0.65 (m, 4H).

Example 15: Synthesis of Compound 15

(S)-1-(2-((1-(1-(4-chlorophenyl)-1H-imidazol-4-yl)cyclopropyl)amino)pyrimidin-4-yl)-5-cyclopropyl imidazolidine-2-one

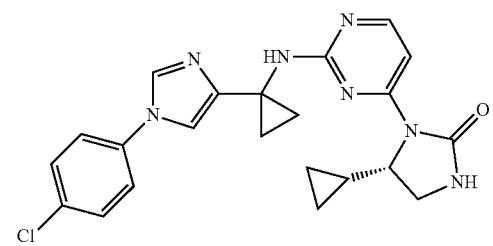 [SMILES: O=C1NC[C@H](C2CC2)N1c1ccnc(NC2(c3cn(-c4ccc(Cl)cc4)cn3)CC2)n1]

Using the same manner as in Example 1, Compound 15 was obtained from Intermediate A6 and Intermediate B7.

LCMS: m/z 436.4 [M+H]$^+$; RT=1.11 min.

$^1$H-NMR(MeOD-d$_4$, 400 MHz): δ 8.49-8.94 (m, 1H), 7.94-7.95 (m, 2H), 7.59 (s, 5H), 4.56 (s, 1H), 3.56 (s, 1H), 1.51-1.62 (m, 4H), 1.28-1.36 (m, 2H), 0.20-0.85 (m, 4H).

Example 16: Synthesis of Compound 16

(S)-1-(2-((1-(4'-chloro-[1,1'-biphenyl]-4-yl)cyclopropyl)amino)pyrimidin-4-yl)-5-isopropyl imidazolidine-2-one

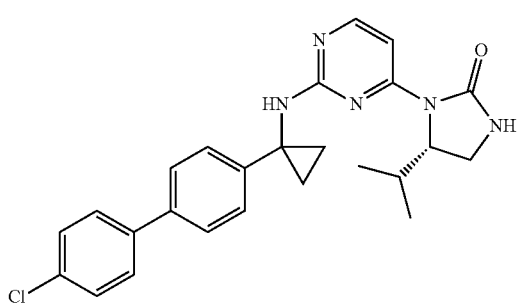 [SMILES: CC(C)[C@H]1CNC(=O)N1c1ccnc(NC2(c3ccc(-c4ccc(Cl)cc4)cc3)CC2)n1]

Using the same manner as in Example 1, Compound 16 was obtained from Intermediate A9 and Intermediate B1.

LCMS: m/z 448.3[M+H]+; RT=1.102 min.

1H-NMR (CDCl3-d1, 400 MHz): δ 8.10 (d, J=5.6 Hz, 1H), 7.55 (d, J=5.6 Hz, 1H), 7.48-7.37 (m, 6H), 7.18 (d, J=8.0 Hz, 2H), 6.10 (br, 1H), 4.89 (s, 1H), 4.46 (s, 1H), 3.73 (m, 1H), 3.20-3.18 (m, 1H), 2.15-2.12 (m, 1H), 1.39-1.23 (m, 6H), 0.63-0.51 (m, 4H).

Example 17: Synthesis of Compound 17

(S)-3-(2-(((S)-1-(1-(4-chlorophenyl)-1H-imidazol-4-yl)ethyl)amino)pyrimidin-4-yl)-4-isopropyl-1-methylimidazolidine-2-one

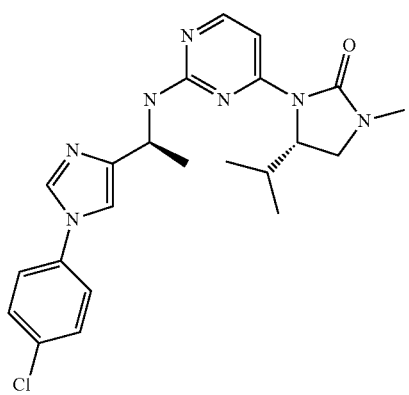 [SMILES: CC(C)[C@H]1CN(C)C(=O)N1c1ccnc(N[C@@H](C)c2cn(-c3ccc(Cl)cc3)cn2)n1]

Using the same manner as in Example 1, Compound 17 was obtained from Intermediate A2 and Intermediate B8.

LCMS: m/z 440.3 [M+H]+; RT=0.960 min.

1H-NMR (CDCl3-d1, 400 MHz): δ 8.01-7.99 (d, J=4.8 Hz, 1H), 7.69 (s, 1H), 7.47-7.46 (d, J=5.2 Hz, 1H), 7.37-7.35 (d, J=7.6 Hz, 2H), 7.00 (s, 1H), 5.45 (s, 1H), 5.09 (s, 1H), 4.47-4.45 (d, J=9.2 Hz, 1H), 3.30-3.28 (m, 1H), 3.10-3.08 (m, 1H), 2.79 (s, 3H), 2.34 (s, 1H), 1.55-1.54 (d, J=6.4 Hz, 3H), 0.87-0.85 (d, J=7.2 Hz, 3H), 0.62-0.60 (d, J=5.6 Hz, 3H).

Example 18: Synthesis of Compound 18

(S)-3-(2-(((R)-1-(1-(4-chlorophenyl)-1H-imidazol-4-yl)ethyl)amino)pyrimidin-4-yl)-4-isopropyl-1-methylimidazolidine-2-one

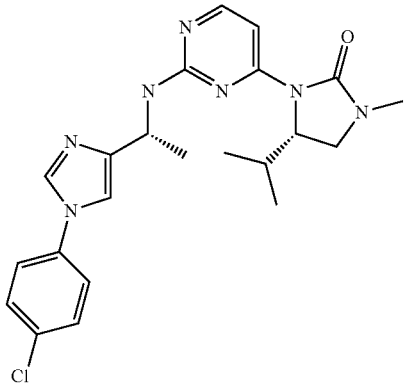 [SMILES: CC(C)[C@H]1CN(C)C(=O)N1c1ccnc(N[C@H](C)c2cn(-c3ccc(Cl)cc3)cn2)n1]

Using the same manner as in Example 1, Compound 18 was obtained from Intermediate A3 and Intermediate B8.

LCMS: m/z 440.3[M+H]+; RT=0.993 min.

1H-NMR (CDCl3-d1, 400 MHz): δ 8.94 (s, 1H), 7.96 (s, 1H), 7.85-7.83 (d, J=5.6 Hz, 1H), 7.66 (s, 1H), 7.58-7.56 (d, J=7.6 Hz, 1H), 7.49-7.47 (d, J=7.6 Hz, 2H), 5.53 (s, 1H), 4.63-4.62 (d, J=6.8 Hz, 1H), 3.56-3.52 (m, 1H), 3.26-3.24 (m, 1H), 2.94 (s, 3H), 2.22 (s, 1H), 1.74-1.73 (d, J=4.8 Hz, 3H), 0.85-0.84 (d, J=5.2 Hz, 3H), 0.72-0.71 (d, J=6.0 Hz, 3H).

Example 19: Synthesis of Compound 19

(S)-3-(2-((1-(1-(4-chlorophenyl)-1H-imidazol-4-yl)cyclopropyl)amino)pyrimidin-4-yl)-4-isopropyl-1-methylimidazolidine-2-one

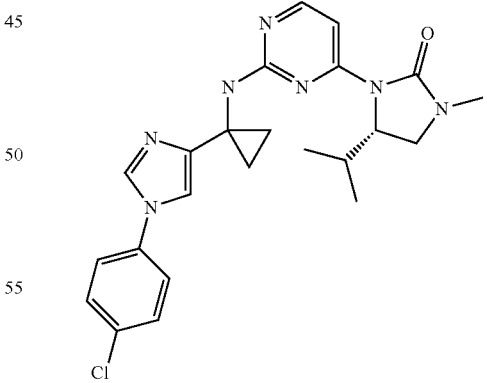

Using the same manner as in Example 1, Compound 19 was obtained from Intermediate A6 and Intermediate B8.

LCMS: m/z 452.2[M+H]+; RT=1.20 min.

1H-NMR (CDCl3-d1, 400 MHz): δ 8.03 (s, 1H), 7.58 (s, 1H), 7.52-7.51 (d, J=4.8 Hz, 1H), 7.34-7.24 (d, J=8.0 Hz, 2H), 7.18-7.16 (m, 1H), 6.91 (s, 1H), 5.71 (s, 1H), 4.34-4.33 (d, J=4.0 Hz, 1H), 3.29-3.25 (m, 1H), 3.06-3.05 (m, 1H), 2.77 (s, 3H), 2.31-2.26 (m, 1H), 1.47-1.45 (m, 3H), 0.82-0.77 (m, 2H), 0.62-0.56 (m, 6H).

Example 20: Synthesis of Compound 20

(S)-5-isopropyl-1-(2-((1-(1-(p-tolyl)-1H-imidazol-4-yl)cyclopropyl)amino)pyrimidin-4-yl)imidazolidine-2-one

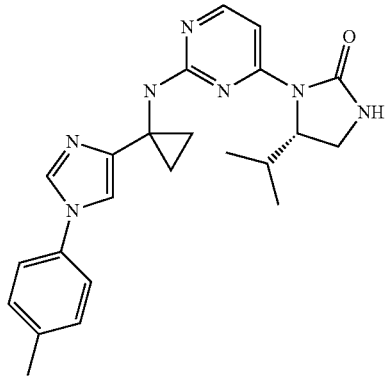 [SMILES: Cc1ccc(-n2cnc(C3(Nc4nccc(N5C(=O)NC[C@@H]5C(C)C)n4)CC3)c2)cc1]

Using the same manner as in Example 1, Compound 20 was obtained from Intermediate A12 and Intermediate B1.
LCMS: m/z 418.3 [M+H]$^+$; RT=0.349 and 0.873 min.
$^1$H-NMR (CDCl3-d$_1$, 400 MHz): δ 8.12 (s, 1H), 7.78-7.58 (m, 2H), 7.23-7.10 (m, 4H), 7.00 (s, 1H), 5.97 (s, 1H), 5.07 (s, 1H), 4.56 (s, 1H), 3.45-3.25 (m, 2H), 2.37 (s, 4H), 1.53-1.50 (m, 2H), 0.97-0.71 (m, 8H).

Example 21: Synthesis of Compound 21

(S)-1-(2-((1-(1-(4-ethylphenyl)-1H-imidazol-4-yl)cyclopropyl)amino)pyrimidin-4-yl)-5-isopropyl imidazolidine-2-one

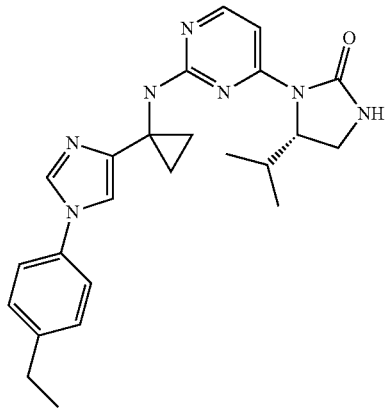 [SMILES: CCc1ccc(-n2cnc(C3(Nc4nccc(N5C(=O)NC[C@@H]5C(C)C)n4)CC3)c2)cc1]

Using the same manner as in Example 1, Compound 21 was obtained from Intermediate A13 and Intermediate B1.
LCMS: m/z 432.3[M+H]$^+$; RT=0.343 and 0.919 min.
$^1$H-NMR (CDCl3-d$_1$, 400 MHz): δ 8.15 (s, 1H), 7.86-7.71 (m, 2H), 7.28 (s, 2H), 7.23-7.21 (d, J=7.2 Hz, 2H), 7.05 (s, 1H), 6.27-6.22 (m, 1H), 5.35 (s, 1H), 4.54-4.53 (d, J=6.4 Hz, 1H), 3.46-3.41 (m, 1H), 3.26-3.24 (m, 1H), 2.71-2.66 (m 2H), 2.39 (s, 1H), 1.51 (s, 2H), 1.25 (s, 3H), 1.00-0.73 (m, 8H).

Example 22: Synthesis of Compound 22

(S)-5-isopropyl-1-(2-((1-(1-(3-(trifluoromethyl)phenyl)-1H-imidazol-4-yl)cyclopropyl)amino)pyrimidine-4-yl)imidazolidine-2-one

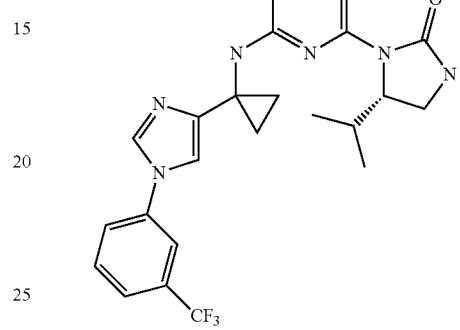

Using the same manner as in Example 1, Compound 22 was obtained from Intermediate A14 and Intermediate B1.
LCMS: m/z 472.1[M+H]$^+$; RT=0.935 min.
$^1$H-NMR (CDCl3-d$_1$, 400 MHz): δ 8.13 (s, 1H), 7.92 (s, 1H), 7.64 (s, 3H), 7.59 (s, 2H), 7.19 (s, 1H), 5.54 (s, 1H), 4.52 (s, 1H), 3.48-3.44 (m, 1H), 3.28-3.26 (m, 1H), 2.40 (s, 1H), 1.53 (s, 2H), 0.99-0.73 (m, 8H).

Example 23: Synthesis of Compound 23

(S)-5-isopropyl-1-(2-((1-(1-(m-tolyl)-1H-imidazol-4-yl)cyclopropyl)amino)pyrimidin-4-yl)imidazolidine-2-one

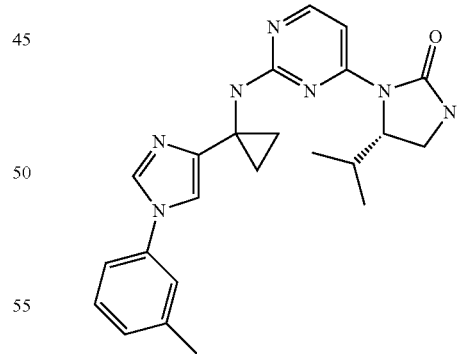

Using the same manner as in Example 1, Compound 23 was obtained from Intermediate A15 and Intermediate B1.
LCMS: m/z 418.3 [M+H]$^+$; RT=0.864 min.
$^1$H-NMR (CDCl3-d$_1$, 400 MHz): δ 8.08-8.00 (m, 1H), 7.75-7.65 (m, 1H), 7.53-7.42 (m, 1H), 7.25-7.22 (m, 1H), 7.07-6.95 (m, 4H), 6.13-6.05 (m, 1H), 5.24-5.17 (m, 1H), 4.48-4.46 (d, J=7.6 Hz, 1H), 3.38-3.33 (m, 1H), 3.18-3.16 (d, J=7.6 Hz, 1H), 2.33-2.32 (d, J=6.0 Hz, 4H), 1.46-1.43 (m, 2H), 0.88-0.63 (m, 8H).

Example 24: Synthesis of Compound 24

(S)-3-(2-((1-(1-(3-chloro-4-methylphenyl)-1H-imidazol-4-yl)cyclopropyl)amino)pyrimidin-4-yl)-4-isopropyl-1-methylimidazolidine-2-one

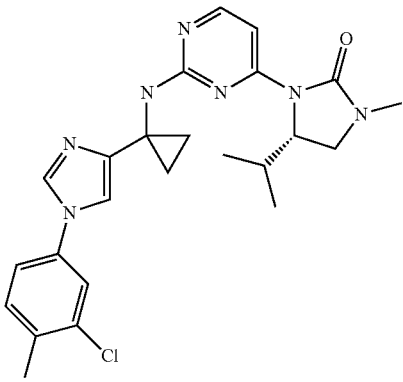 [SMILES: Cc1ccc(-n2cnc(C3(Nc4nccc(N5C(=O)N(C)C[C@@H]5C(C)C)n4)CC3)c2)cc1Cl]

Using the same manner as in Example 1, Compound 24 was obtained from Intermediate A16 and Intermediate B8.

LCMS: m/z 466.2 [M+H]$^+$; RT=1.036 min.

$^1$H-NMR (CDCl3-d$_1$, 400 MHz): δ 8.16 (s, 1H), 7.94-7.71 (m, 2H), 7.33-7.31 (m, 2H), 7.15-7.13 (d, J=7.2 Hz, 2H), 4.41-4.40 (d, J=6.0 Hz, H), 3.40-3.35 (m, 1H), 3.16-3.14 (d, J=8.0 Hz, 1H), 2.91 (s, 3H), 40 (s, 4H), 1.49 (s, 2H), 0.96-0.87 (m, 2H), 0.80-0.66 (m, 6H).

Example 25: Synthesis of Compound 25

(S)-5-isopropyl-1-(2-(1-(1-(5-methylpyridin-2-yl)-1H-imidazol-4-yl)cyclopropyl)amino)-2-one

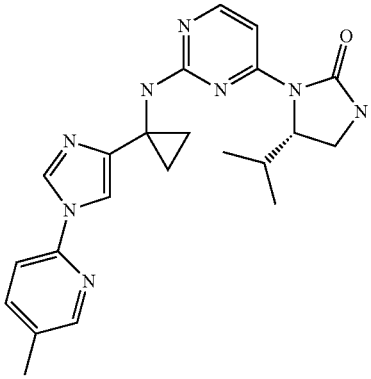 [SMILES: Cc1ccc(-n2cnc(C3(Nc4nccc(N5C(=O)NC[C@@H]5C(C)C)n4)CC3)c2)nc1]

Using the same manner as in Example 1, Compound 25 was obtained from Intermediate A17 and Intermediate B1.

LCMS: m/z 419.2 [M+H]$^+$; RT=0.350 and 0.830 min.

$^1$H-NMR (CDCl3-d$_1$, 400 MHz): δ 8.52 (s, 1H), 8.11 (s, 1H), 7.72-7.66 (m, 1H), 7.55-7.49 (m, 2H), 7.27-7.22 (m, 1H), 6.99 (s. 1H), 5.99 (d, J=2.4 Hz, 1H), 5.02 (s, 1H), 4.56 (s, 1H), 3.51-3.41 (m, 1H), 3.25 (s, 1H), 2.59 (s, 3H), 2.39 (s, 1H), 1.55-1.43 (m, 2H), 1.00-0.98 (m, 2H), 0.71 (s, 6H).

Example 26: Synthesis of Compound 26

(S)-3-(2-((1-(1-(3,5-dichlorophenyl)-1H-imidazol-4-yl)cyclopropyl)amino)pyrimidin-4-yl)-4-isopropyl-1-methylimidazolidine-2-one

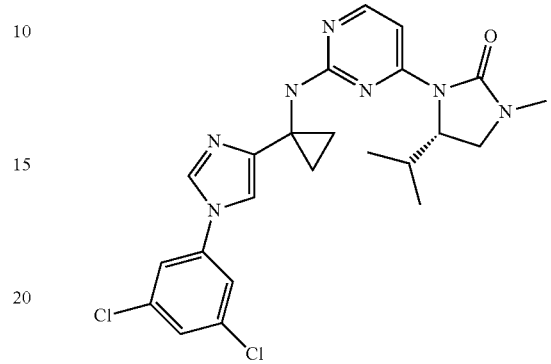

Using the same manner as in Example 1, Compound 26 was obtained from Intermediate A18 and Intermediate B8.

LCMS: m/z 486.3[M+H]$^+$; RT=1.31 min (2.00 min).

$^1$H-NMR (CDCl3-d$_1$, 400 MHz): δ 10.86 (s, 1H), 8.20 (s, 1H), 7.96 (d, J=6.8 Hz, 1H), 7.77 (d, J=7.2 Hz, 1H), 7.42 (s, 1H), 7.30 (s, 2H), 7.18 (s, 1H), 4.44-4.42 (m, 1H), 3.47-3.42 (m, 1H), 3.19 (d, J=10.0 Hz, 1H), 2.90 (s, 3H), 2.28-2.25 (m, 1H), 1.64-1.40 (m, 4H), 0.78-0.67 (m, 6H).

Example 27: Synthesis of Compound 27

(S)-4-isopropyl-1-methyl-3-(2-((1-(1-(3-(trifluoromethyl)phenyl)-1H-imidazol-4-yl)cyclopropyl)amino))imidazolidine-2-one

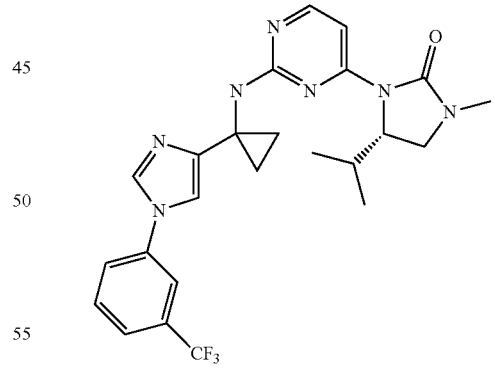

Using the same manner as in Example 1, Compound 27 was obtained from Intermediate A14 and Intermediate B8.

LCMS: m/z 486.3 [M+H]$^+$; RT=1.018 min.

$^1$H-NMR (CDCl3-d$_1$, 400 MHz): δ 9.40-9.27 (m, 1H), 8.45-8.35 (m, 1H), 7.97-7.95 (d, J=5.6 Hz, 1H), 7.79 (s, 1H), 7.76-7.74 (d, J=6.8 Hz, 1H), 7.65 (s, 1H), 7.55-7.52 (m, 3H), 3.27-3.14 (m, 1H), 2.97-2.95 (d, J=8.0 Hz, 1H), 2.58 (s, 3H), 1.83 (s, 1H), 1.03-0.99 (m, 2H), 0.69 (s, 1H), 0.50 (s, 1H), 0.23 (s, 6H).

Example 28: Synthesis of Compound 28

(S)-3-(2-((1-(1-(3-chloro-4-fluorophenyl)-1H-imidazol-4-yl)cyclopropyl)amino)pyrimidin-4-yl)-4-isopropyl-1-methylimidazolidine-2-one

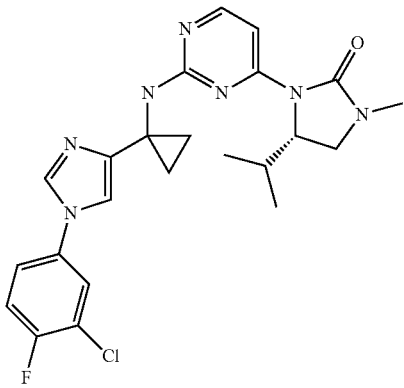 [SMILES: CC(C)[C@H]1CN(C)C(=O)N1c1ccnc(NC2(c3cn(-c4ccc(F)c(Cl)c4)cn3)CC2)n1]

Using the same manner as in Example 1, Compound 28 was obtained from Intermediate A19 and Intermediate B8.

LCMS: m/z 470.1[M+H]$^+$; RT=1.012 min.

$^1$H-NMR (CDCl3-d$_1$, 400 MHz): δ 8.00-7.95 (m, 1H), 7.82-7.77 (m, 1H), 7.58 (s, 1H), 7.38-7.23 (m, 4H), 4.49 (s, 1H), 3.46 (s, 1H), 3.21-3.18 (m, 1H), 2.90 (s, 3H), 2.28-2.26 (m, 1H), 1.72-1.54 (m, 4H), 0.95-0.69 (m, 6H).

Example 29: Synthesis of Compound 29

(S)-5-isopropyl-1-(2-((1-(1-(6-methylpyridin-3-yl)-1H-imidazol-4-yl)cyclopropyl)amino)pyrimidine-4-yl)-2-one

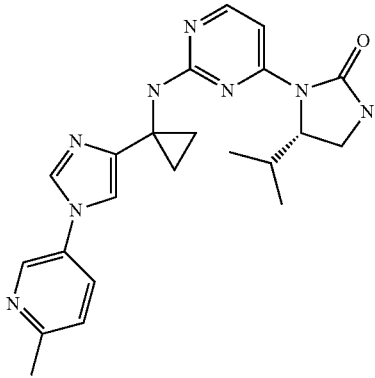 [SMILES: Cc1ccc(-n2cnc(C3(Nc4nccc(N5C(=O)NC[C@@H]5C(C)C)n4)CC3)c2)cn1]

Using the same manner as in Example 1, Compound 29 was obtained from Intermediate A20 and Intermediate B1.

LCMS: m/z 419.2 [M+H]$^+$; RT=0.830 min.

$^1$H-NMR (CDCl3-d$_1$, 400 MHz): δ 8.52 (s, 1H), 8.11 (s, 1H), 7.72-7.66 (m, 1H), 7.55-7.49 (m, 2H), 7.27-7.22 (m, 1H), 6.99 (s. 1H), 5.99 (d, J=2.4 Hz, 1H), 5.02 (s, 1H), 4.56 (s, 1H), 3.51-3.41 (m, 1H), 3.25 (s, 1H), 2.59 (s, 3H), 2.39 (s, 1H), 1.55-1.43 (m, 2H), 1.00-0.98 (m, 2H), 0.71 (s, 6H).

Example 30: Synthesis of Compound 30

(S)-3-(2-((1-(1-(3-isopropylphenyl)-1H-imidazol-4-yl)cyclopropyl)amino)pyrimidin-4-yl)-4-isopropyl-1-methylimidazolidne-2-one

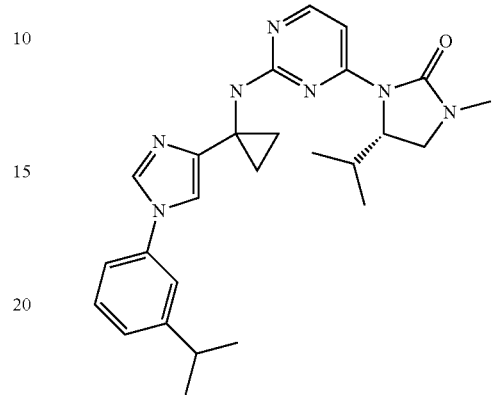

Using the same manner as in Example 1, Compound 30 was obtained from Intermediate A21 and Intermediate B8.

LCMS: m/z 460.4 [M+H]$^+$; RT=1.013 min.

$^1$H-NMR (CDCl3-d$_1$, 400 MHz): δ 11.0 (s, 1H), 8.61 (s, 1H), 7.97 (d, J=6.4 Hz, 1H), 7.76 (d, J=7.2 Hz, 1H), 7.46-7.18 (m, 5H), 4.56-4.55 (m, 1H), 3.49-3.45 (m, 1H), 3.21-3.17 (m, 1H), 3.02-2.90 (m, 1H), 2.85 (s, 3H), 2.24-2.21 (m, 1H), 1.72-1.47 (m, 4H), 1.29-1.25 (m, 6H), 0.88-0.61 (m, 6H).

Example 31: Synthesis of Compound 31

(S)-3-(2-((1-(1-(3-chlorophenyl)-1H-imidazol-4-yl)cyclopropyl)amino)pyrimidin-4-yl)-4-isopropyl-1-methylimidazolidine-2-one

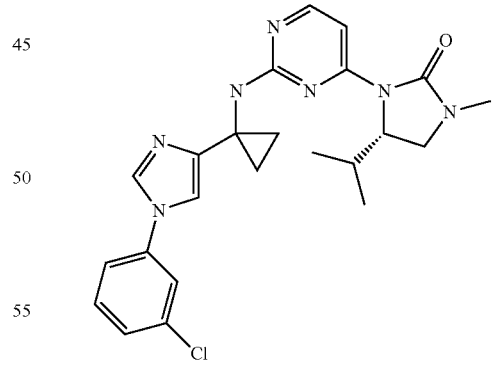

Using the same manner as in Example 1, Compound 31 was obtained from Intermediate A22 and Intermediate B8.

LCMS: m/z 452.2 [M+H]$^+$; RT=1.001 min.

$^1$H-NMR (CDCl3-d$_1$, 400 MHz): δ 8.49 (s, 1H), 7.98-7.97 (d, J=7.2 Hz, 1H), 7.79-7.77 (d, J=7.2 Hz, 1H), 7.53-7.30 (m, 5H), 4.51-4.48 (d, J=8.8 Hz, 1H), 3.49-3.44 (m, 1H), 3.21-3.19 (m, 1H), 2.91 (s, 3H), 2.27-2.26 (d, J=2.4 Hz, 1H), 1.68-1.45 (m, 4H), 0.82-0.80 (d, J=6.8 Hz, 3H), 0.70-0.68 (d, J=6.8 Hz, 3H).

Example 32: Synthesis of Compound 32

(S)-3-(2-((1-(1-(3,5-difluoro-4-methylphenyl)-1H-imidazol-4-yl)cyclopropyl)amino)pyrimidine-4-1-methylimidazolidine-2-one

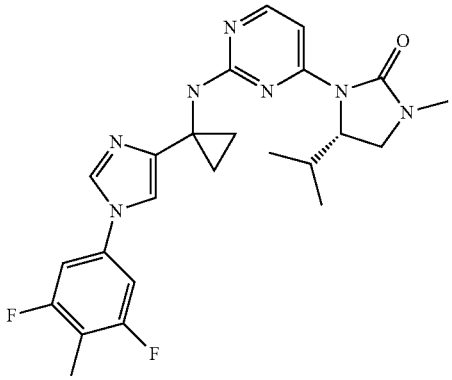 [SMILES: Cc1c(F)cc(-n2cnc(C3(Nc4nccc(N5C(=O)N(C)C[C@@H]5C(C)C)n4)CC3)c2)cc1F]

Using the same manner as in Example 1, Compound 32 was obtained from Intermediate A23 and Intermediate B8.

LCMS: m/z 468.3 [M+H]⁺; RT=1.015 min (2.5 min, Acid).

$^1$H NMR (MeOD-d$_4$, 400 MHz): δ 8.55-8.62 (m, 1H), 7.98-8.01 (m, 2H), 7.64-7.73 (m, 1H), 7.30-7.32 (m, 2H), 4.37-4.40 (m, 1H), 3.47-3.48 (m, 2H), 2.88 (s, 3H), 2.21 (m, 4H), 1.41-1.58 (m, 4H), 0.62-1.00 (m, 6H).

Example 33: Synthesis of Compound 33

(S)-3-(2-((1-(1-(cyclohexylmethyl)-1H-imidazol-4-yl)cyclopropyl)amino)pyrimidin-4-yl)-4-isopropyl-1-methylimidazolidine-2-one

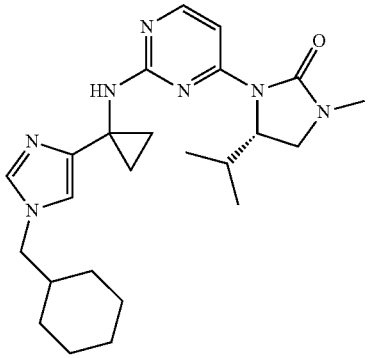 [SMILES: CC(C)[C@H]1CN(C)C(=O)N1c1ccnc(NC2(c3cn(CC4CCCCC4)cn3)CC2)n1]

Using the same manner as in Example 1, Compound 33 was obtained from Intermediate A25 and Intermediate B8.

LCMS: m/z 438.4[M+H]⁺; RT=0.848 min.

$^1$H NMR (CDCl3-d$_1$, 400 MHz): δ 8.07-8.08 (d, J=5.2 Hz, 1H), 7.54-7.55 (d, J=5.6 Hz, 1H), 7.22 (s, 1H), 6.58 (s, 1H), 5.72 (brs, 1H), 4.38 (m, 1H), 3.59-3.60 (d, J=6.8 Hz, 2H), 3.12-3.34 (m, 2H), 2.84 (s, 3H), 2.40 (m, 1H), 0.80-1.70 (m, 21H).

Example 34: Synthesis of Compound 34

(S)-3-(2-((1-(1-(3-cyclopropylphenyl)amino)pyrimidin-4-yl)-4-isopropyl-1-methyl imidazolidine-2-one

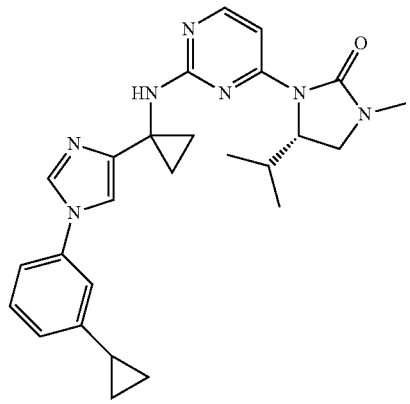 [SMILES: CC(C)[C@H]1CN(C)C(=O)N1c1ccnc(NC2(c3cn(-c4cccc(C5CC5)c4)cn3)CC2)n1]

Using the same manner as in Example 1, Compound 34 was obtained from Intermediate A26 and Intermediate B8.

LCMS: m/z 458.5 [M+H]⁺; RT=1.12 min (2.0 min).

$^1$H-NMR (CDCl3-d$_1$, 400 MHz): δ 10.97 (s, 1H), 8.72 (s, 1H), 7.99 (d, J=7.2 Hz, 1H), 7.78 (d, J=7.2 Hz, 1H), 7.40 (t, J=8.0 Hz, 1H), 7.31 (s, 1H), 7.18-7.11 (m, 3H), 4.55 (d, J=8.8 Hz, 1H), 3.48-3.45 (m, 1H), 3.20 (d, J=8.8 Hz, 1H), 2.91 (s, 3H), 2.25 (s, 1H), 1.96-1.95 (m, 1H), 1.72-1.49 (m, 4H), 1.08-1.05 (m, 2H), 0.84 (d, J=7.2 Hz, 2H), 0.75 (d, J=4.4 Hz, 2H), 0.70 (d, J=6.4 Hz, 2H).

Example 35: Synthesis of Compound 35

(S)-3-(2-((1-(1-(3-chloro-4-methylphenyl)-1H-imidazol-4-yl)cyclopropyl)amino)pyrimidin-4-yl)-4-isopropyl-1-methylimidazolidine-2-one

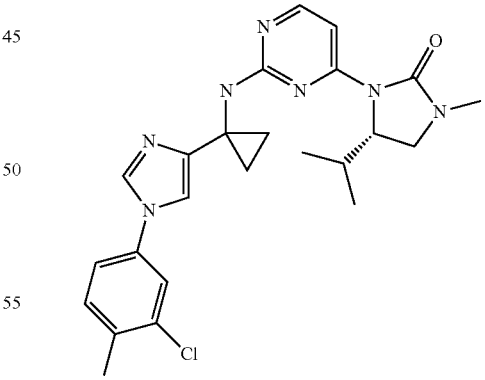

Using the same manner as in Example 1, Compound 35 was obtained from Intermediate A16 and Intermediate B8.

LCMS: m/z 466.2 [M+H]⁺; RT=1.036 min.

$^1$H-NMR (CDCl3-d$_1$, 400 MHz): δ 8.16 (s, 1H), 7.94-7.71 (m, 2H), 7.33-7.31 (m, 2H), 7.15-7.13 (d, J=7.2 Hz, 2H), 4.41-4.40 (d, J=6.0 Hz, 1H), 3.40-3.35 (m, 1H), 3.16-3.14 (d, J=8.0 Hz, 1H), 2.91 (s, 3H), 40 (s, 4H), 1.49 (s, 2H), 0.96-0.87 (m, 2H), 0.80-0.66 (m, 6H).

Example 36: Synthesis of Compound 36

(S)-3-(2-((1-(1-(4,4-difluorocyclohexyl)-1H-imidazol-4-yl)cyclopropyl)amino) pyrimidin-4-yl)-4-isopropyl-1-methylimidazolidine-2-one

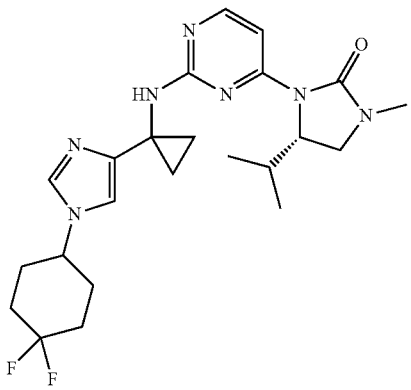 [SMILES: CC(C)[C@H]1CN(C)C(=O)N1c1ccnc(NC2(c3cn(C4CCC(F)(F)CC4)cn3)CC2)n1]

Using the same manner as in Example 1, Compound 36 was obtained from Intermediate A27 and Intermediate B8.
LCMS: m/z 460.2 [M+H]⁺; RT=0.878 min.
¹H NMR (MeOD-d$_4$, 400 MHz): δ 8.23 (s, 1H), 7.62 (m, 1H), 6.74-6.75 (m, 1H), 6.13 (m, 1H), 4.41 (m, 1H), 4.00-4.02 (m, 1H), 3.14-3.38 (m, 2H), 2.87 (s, 3H), 2.37 (m, 1H), 1.85-2.08 (m, 8H), 1.41-1.44 (m, 2H), 0.86-0.93 (m, 2H), 0.67-0.77 (m, 6H).

Example 37: Synthesis of Compound 37

(S)-4-isopropyl-1-methyl-3-(2-((1-(1-(4-methylcyclohexyl)-1H-imidazol-4-yl) cyclopropyl)amino)-2-one

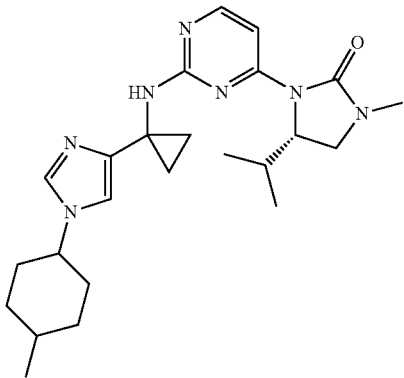 [SMILES: CC1CCC(n2cnc(C3(Nc4nccc(N5C(=O)N(C)C[C@@H]5C(C)C)n4)CC3)c2)CC1]

Using the same manner as in Example 1, Compound 37 was obtained from Intermediate A28 and Intermediate B8.
LCMS: m/z 438.4 [M+H]⁺; RT=0.833 min.
¹H-NMR (CDCl3-d$_1$, 400 MHz): δ 8.41 (s, 1H), 7.89-7.85 (m, 2H), 6.92 (s, 1H), 5.30 (s, 1H), 4.40 (d, J=8.8 Hz, 1H), 3.39-3.37 (m, 1H), 3.18-3.16 (m, 1H), 2.95 (s, 3H), 2.41-2.39 (m, 1H), 2.11-1.89 (m, 10H), 1.78-1.77 (m, 3H), 1.17-1.13 (m, 3H), 0.99-0.93 (m, 6H).

Example 38: Synthesis of Compound 38

(S)-3-(2-((1-(1-(3-chloro-5-methoxyphenyl)-1H-imidazol-4-yl)cyclopropyl)amino)pyrimidin-4-yl)-4-isopropyl-1-methylimidazolidine-2-one

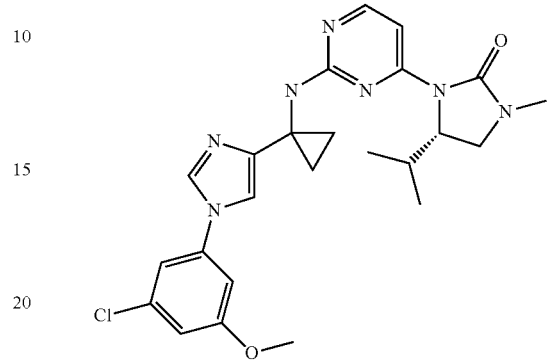

Using the same manner as in Example 1, Compound 38 was obtained from Intermediate A29 and Intermediate B8.
LCMS: m/z 482.2 [M+H]⁺; RT=1.058 min.
¹H-NMR (CDCl3-d$_1$, 400 MHz): δ 8.09-8.07 (d, J=5.6 Hz, 1H), 7.66 (s, 1H), 7.59-7.58 (d, J=5.6 Hz, 1H), 6.98 (s, 1H), 6.89 (s, 1H), 6.83 (s, 1H), 6.71 (s, 1H), 6.03 (s, 1H), 4.41-4.40 (d, J=6.4 Hz, 1H), 3.82 (s, 3H), 3.36-3.32 (m, 1H), 3.13-3.11 (d, J=6.8 Hz, 1H), 2.84 (s, 3H), 2.58-2.45 (m, 1H), 1.55-1.48 (m, 2H), 0.88-0.86 (m, 2H), 0.69-0.63 (m, 6H).

Example 39: Synthesis of Compound 39

(S)-3-(2-((1-(1-(4-cyclopropylphenyl)-1H-imidazol-4-yl)cyclopropyl)amino)pyrimidin-4-yl)-4-isopropyl-1-methylimidazolidine-2-one

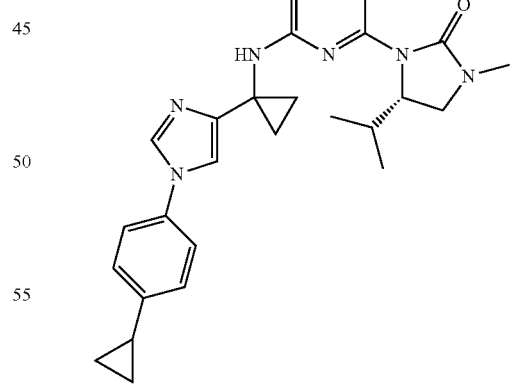

Using the same manner as in Example 1, Compound 39 was obtained from Intermediate A31 and Intermediate B8.
LCMS: m/z 458.2 [M+H]⁺; RT=0.967 min
¹H-NMR (CDCl3-d$_1$, 400 MHz): δ 10.93 (s, 1H), 8.71 (s, 1H), 7.98 (d, J=6.8 Hz, 1H), 7.78 (d, J=6.8 Hz, 1H), 7.29-7.26 (m, 2H), 7.20 (d, J=8.0 Hz, 3H), 4.54 (d, J=8.0 Hz, 1H), 3.47-3.45 (m, 1H), 3.19 (d, J=9.6 Hz, 1H), 2.91 (s, 3H), 2.25 (s, 1H), 1.96-1.95 (m, 1H), 1.53-1.50 (m, 4H), 1.07 (d, J=7.2 Hz, 2H), 0.82 (d, J=6.8 Hz, 2H), 0.74 (d, J=4.4 Hz, 3H), 0.69 (d, J=6.8 Hz, 3H).

Example 40: Synthesis of Compound 40

(S)-3-(2-((1-(1-(cyclopentylmethyl)-1H-imidazol-4-yl)cyclopropyl)amino)pyrimidin-4-yl)-4-isopropyl-1-methylimidazolidine-2-one

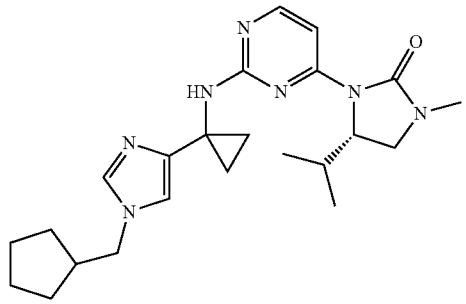 [SMILES: CC(C)[C@H]1CN(C)C(=O)N1c1ccnc(NC2(c3cn(CC4CCCC4)cn3)CC2)n1]

Using the same manner as in Example 1, Compound 40 was obtained from Intermediate A32 and Intermediate B8.

LCMS: m/z 424.4 [M+H]$^+$; RT=0.953 min.

$^1$H-NMR (CDCl3-d$_1$, 400 MHz): δ 10.86 (s, 1H), 8.63 (s, 1H), 7.97-7.99 (m, 1H), 7.77-7.79 (m, 1H), 7.05 (s, 1H), 4.50-4.52 (m, 1H), 3.94-3.96 (m, 2H), 3.45-3.47 (m, 1H), 3.19-3.21 (m, 1H), 2.91 (s, 3H), 2.22-2.32 (m, 2H), 1.61-1.74 (m, 8H), 1.21-1.25 (m, 4H), 0.82-0.84 (m, 3H), 0.70-0.71 (m, 3H).

Example 41: Synthesis of Compound 41

Using the same manner as in Example 1, Compound 41 was obtained from Intermediate A22 and Intermediate B29.

(S)-1-(2-(1-(1-(3-chlorophenyl)-1H-imidazol-4-yl)cyclopropyl)amino)pyrimidin-4-yl)-1-ethyl-4-isopropylimidazolidine-2-one

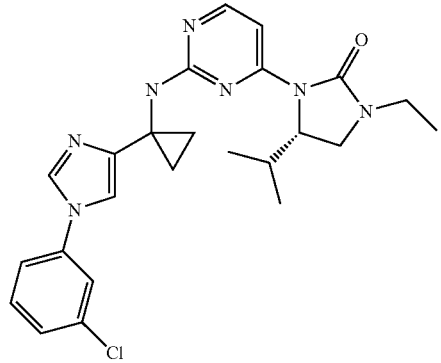 [SMILES: CCN1C[C@H](C(C)C)N(c2ccnc(NC3(c4cn(-c5cccc(Cl)c5)cn4)CC3)n2)C1=O]

$^1$H-NMR (CDCl$_3$, 400 MHz): 8.87 (s, 1H), 8.02-8.01 (d, J=6.0 Hz, 1H), 7.84-7.82 (d, J=6.8 Hz, 1H), 7.50 (s, 3H), 7.40 (s, 2H), 4.51-4.49 (d, J=8.4 Hz, 1H), 3.50-3.38 (m, 2H), 3.35-3.21 (m, 2H), 2.26 (s, 1H), 1.70-1.54 (m, 4H), 1.20-1.16 (m, 3H), 0.83-0.81 (d, J=6.8 Hz, 3H), 0.72-0.71 (d, J=6.8 Hz, 3H).

LCMS: m/z 466.1 [M+H]$^+$, RT=1.040 min.

Example 42: Synthesis of Compound 42 methyl (S)-methyl-3-(4-(1-((4-(5-isopropyl-3-methyl-2-oxoimidazoline-1-yl)pyrimidin-2-yl)amino)propyl-1H-imidazolin-1-yl)benzoate

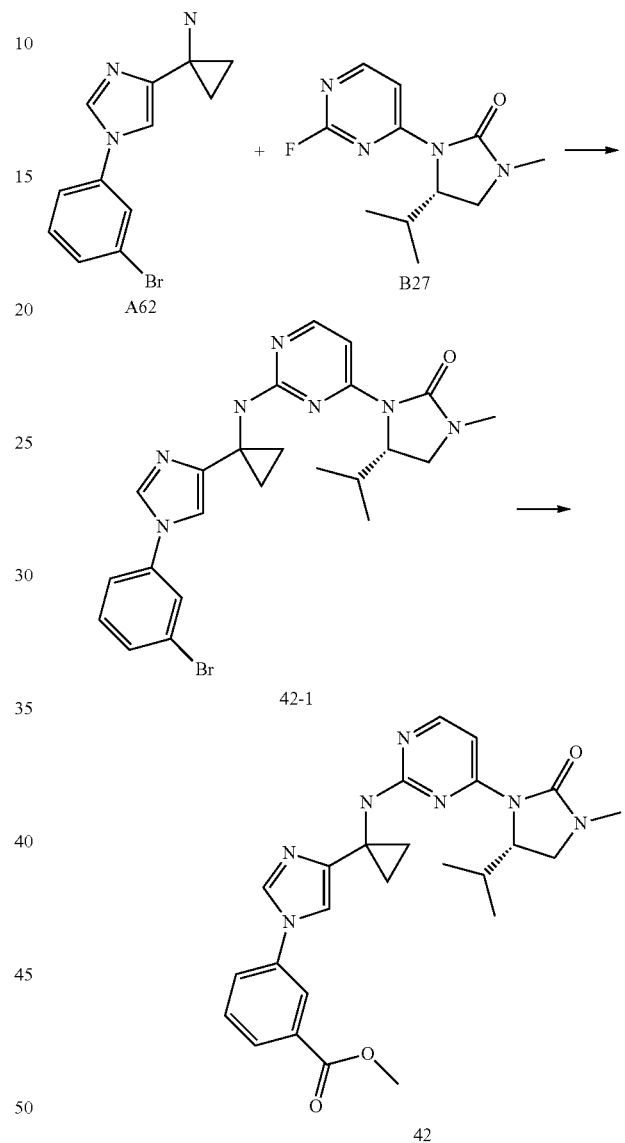

Step 1: Using the same manner as in Example 1, Intermediate 42-1: (S)-1-(2-(1-(1-(3-bromophenyl)-1H-imidazol-4-yl)cyclopropyl)amino)pyrimidin-4-yl)-1-methyl-4-isopropylimidazolidine-2-one was obtained from Intermediate A62 and Intermediate B27, LCMS: m/z 497.9 [M+H]$^+$, RT=0.983 min.

Step 2: Intermediate 42-1 (100 mg, 0.2 mmol), triethylamine (40 mg) and PdCl2 (dppf) 2 (20 mg) were sequentially added to a 100 ml one-neck bottle containing 20 ml of methanol solution. The mixture was stirred overnight at 70° C. After TLC detection showed that the reaction was completed, the system was concentrated and purified by chromatography separation (TFA) to afford compound 42 (80 mg, yield 84%) as white solid.

¹H-NMR (CDCl₃, 400 MHz): 10.94 (s, 1H), 8.63 (s, 1H), 8.16 (d, J=6.8 Hz, 1H), 8.07 (s, 1H), 7.99 (s, J=6.8 Hz, 1H), 7.79 (d, J=6.0 Hz, 1H), 7.63 (s, 2H), 7.34 (s, 1H), 4.52 (d, J=7.2 Hz, 1H), 3.97 (s, 3H), 3.50-3.45 (m, 1H), 3.20 (d, J=9.6 Hz, 1H), 2.91 (s, 3H), 2.27 (s, 1H), 1.71-1.50 (m, 4H), 0.81 (d, J=6.4 Hz, 3H), 0.69 (d, J=6.4 Hz, 3H).

LCMS: m/z 476.2 [M+H]⁺, RT=0.91 min

Example 43: Synthesis of Compound 43

Using the same manner as in Example 1, Compound 43 was obtained from Intermediate A34 and Intermediate B27.

(S)-3-(2-((1-(1-(benzo[d][1,3]dioxol-5-yl)-1H-imidazol-4-yl)cyclopropyl) amino)pyrimidin-4-ylthio)-4-isopropyl-1-methylimidazolidine-2-one

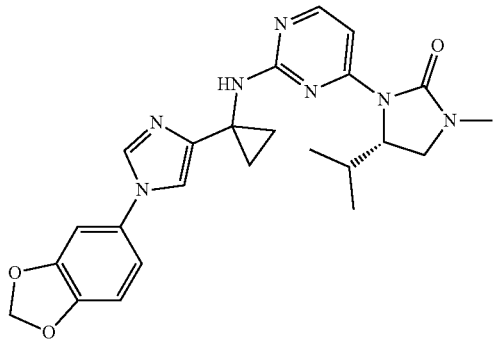 [SMILES: CC(C)[C@H]1CN(C)C(=O)N1c1ccnc(NC2(c3cn(-c4ccc5c(c4)OCO5)cn3)CC2)n1]

¹H-NMR (CDCl₃, 400 MHz): 8.09-8.07 (d, J=8.0 Hz, 1H), 7.57-7.55 (d, J=8.0 Hz, 2H), 6.90 (s, 1H), 6.82-6.80 (d, J=8.0 Hz, 1H), 6.75-6.71 (m, 2H), 6.01 (s, 2H), 5.69 (s, 1H), 4.43-4.41 (d, J=8.0 Hz, 1H), 3.36-3.31 (m, 1H) 3.13-3.11 (m, 1H), 4.34 (m, 1H), 2.84 (s, 3H), 2.37-2.35 (s, 1H), 1.25-1.21 (m, 2H), 1.19-1.14 (m, 2H), 0.69-0.56 (m, 3H), 0.06-0.00 (m, 3H).

LCMS: m/z 462.3 [M+H]⁺, RT=0.86 min

Example 44: Synthesis of Compound 44

Using the same manner as in Example 1, Compound 44 was obtained from Intermediate A35 and Intermediate B27.

(S)-3-(2-((1-(1-(3-bromo-5-chlorophenyl)-1H-imidazol-4-yl)cyclopropyl)amino)pyrimidin-4-yl)-4-isopropyl-1-methylimidazolidine-2-one

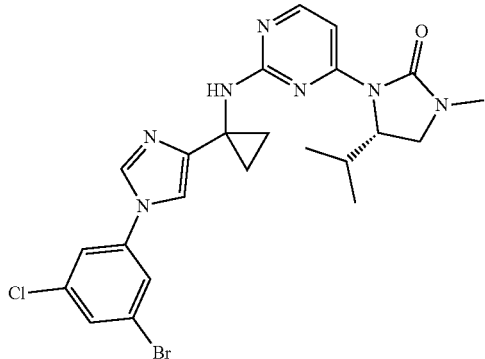 [SMILES: CC(C)[C@H]1CN(C)C(=O)N1c1ccnc(NC2(c3cn(-c4cc(Cl)cc(Br)c4)cn3)CC2)n1]

¹H-NMR (CDCl₃, 400 MHz): 8.09 (d, J=6.0 Hz, 1H), 7.66 (s, 1H), 7.58 (d, J=2.4 Hz, 1H), 7.45 (s, 1H), 7.35 (s, 1H), 7.24-7.26 (m, 1H), 6.98 (s, 1H), 5.70 (s, 1H), 4.39-4.41 (m, 1H), 3.32-3.36 (m, 1H), 3.11-3.13 (m, 1H), 2.84 (s, 3H), 2.38 (brs, 1H), 1.23-1.25 (m, 2H), 0.81-0.84 (m, 3H), 0.64-0.70 (m, 6H).

LCMS: m/z 532.1 [M+H]⁺, RT=1.3 min.

Example 45: Synthesis of Compound 45

(S)-3-chloro-5-(4-(1-((4-(5-isopropyl-3-methylimidazolidine-2-one-1-yl)pyrimidin-2-yl)amine)cyclopropyl)-1H-imidazolidine-1-yl) phenyl cyanide

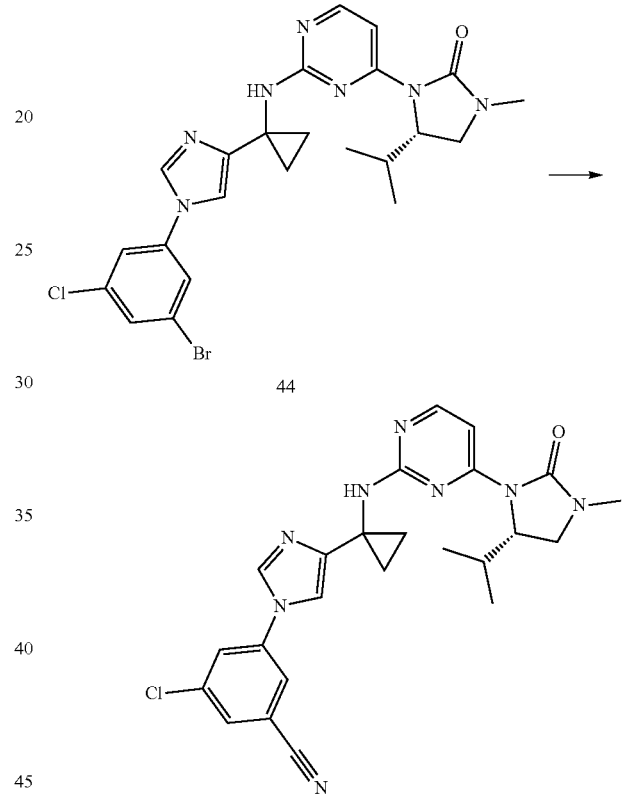

Compound 44 (80 mg, 0.15 mmol, 1.0 eq) and zinc cyanide (75 mg, 1.5 mmol, 10.0 eq) were sequentially added to a dry 25 mL one-neck flask and dissolved in N,N-dimethylformamide (5 mL). Under nitrogen atmosphere, tetratriphenylphosphine palladium (35 mg, 0.03 mmol) was added. The mixture was heated to 100° C. for 6 hours. The reaction solution was filtered and purified by preparative high performance liquid chromatography to give product (S)-3-chloro-5-(4-(1-((4-(5-isopropyl-3-methylimidazolidine-2)-one-1-yl)pyrimidin-2-yl)amino)cyclopropyl)-1H-imidazolidine-1-yl)benzonitrile (Compound 45) (10 mg, white solid), yield 14.1%.

¹H-NMR (CDCl₃, 400 MHz): 8.03 (d, J=6.0 Hz, 1H), 7.63 (s, 1H), 7.46-7.53 (m, 3H), 7.41 (s, 1H), 6.95 (s, 1H), 5.59 (s, 1H), 4.39-4.41 (m, 1H), 3.32-3.36 (m, 1H), 3.11-3.13 (m, 1H), 2.77 (s, 3H), 2.38 (brs, 1H), 1.23-1.25 (m, 1H), 0.81-0.84 (m, 4H), 0.64-0.70 (m, 6H).

LCMS: m/z 477.3 [M+H]⁺, RT=1.2 min.

Example 46: Synthesis of Compound 46

Using the same manner as in Example 1, Compound 46 was obtained from Intermediate A36 and Intermediate B27.

(S)-3-(2-((1-(1-(4,4-dimethylcyclohexyl)-1H-imidazol-4-yl)cyclopropyl)amino) pyrimidin-4-yl)-4-isopropyl-1-methylimidazolidine-2-one

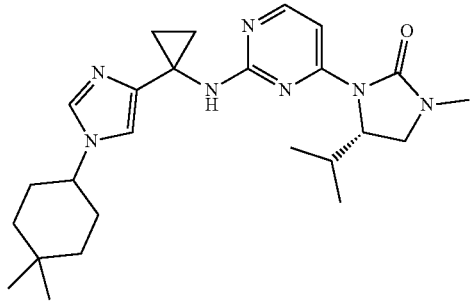

$^1$H NMR (CDCl3-d1, 400 MHz): δ 8.08 (d, J=6.0 Hz, 1H), 7.55 (d, J=6.0 Hz, 1H), 7.35 (s, 1H), 6.68 (s, 1H), 5.68 (s, 1H), 4.42-4.40 (m, 1H), 3.72-3.69 (m, 1H), 3.34 (t, J=9.6 Hz, 1H), 3.14-3.11 (m, 1H), 2.85 (s, 3H), 2.32 (m, 1H), 1.84-1.81 (m, 4H), 1.51-1.27 (m, 6H), 1.17 (m, 2H), 0.95 (s, 6H), 0.69-0.0.63 (m, 6H).

LCMS: m/z 454.2 [M+H]$^+$, RT=0.97 min.

Example 47: Synthesis of Compound 47

Using the same manner as in Example 1, Compound 47 was obtained from Intermediate A37 and Intermediate B27.

(S)-3-(2-((1-(1-(3-bromo-5-fluorophenyl)-imidazol-4-yl)cyclopropyl)amino)pyrimidin-4-yl)-4-isopropyl-1-methylimidazolidine-2-one

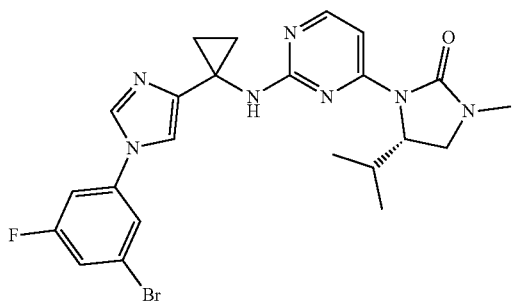 [SMILES: CC(C)[C@H]1CN(C)C(=O)N1c1ccnc(NC2(c3cn(-c4cc(F)cc(Br)c4)cn3)CC2)n1]

$^1$H-NMR (CDCl$_3$, 400 MHz): 8.09 (d, J=6.0 Hz, 1H), 7.67 (s, 1H), 7.59 (d, J=2.8 Hz, 1H), 7.19-7.26 (m, 2H), 6.97-6.99 (m, 2H), 5.77 (s, 1H), 4.30-4.40 (m, 1H), 3.32-3.36 (m, 1H), 3.12-3.13 (m, 1H), 2.84 (s, 3H), 2.36-2.38 (m, 1H), 1.51-1.59 (m, 2H), 1.21-1.23 (m, 3H), 0.57-0.65 (m, 6H).

LCMS: m/z 514.1 [M+H]$^+$, RT=1.2 min.

Example 48: Synthesis of Compound 48

((S)-3-(2-((1-(1-(3-chloro-5-cyclopropylphenyl)-1H-imidazol-4-yl)cyclopropyl)amino)pyrimidin-4-yl)-4-isopropyl-1-methylimidazolidine-2-one

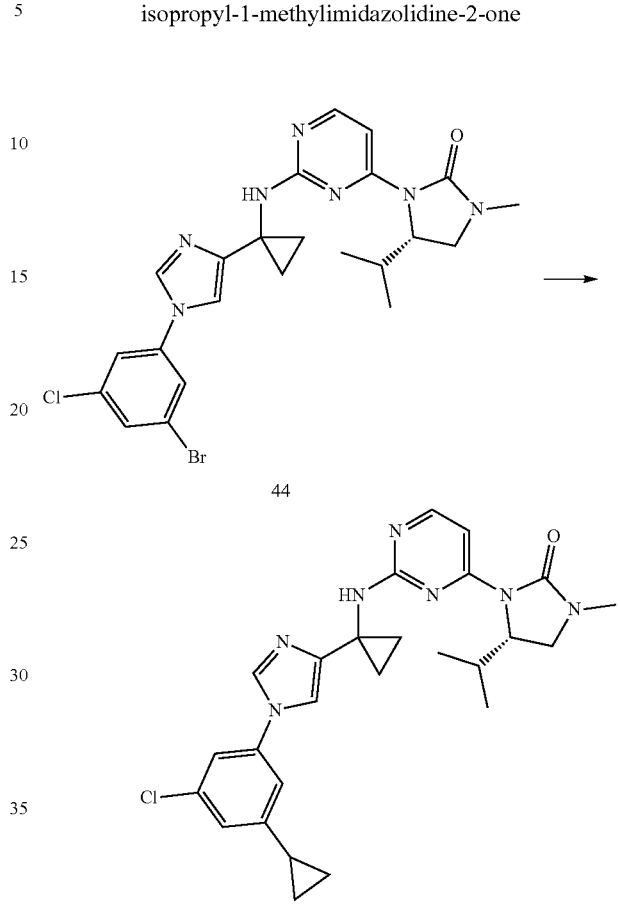

Under a nitrogen atmosphere, Compound 54 (100 mg, 0.189 mmol, 1.0 eq), cyclopropylboronic acid (16 mg, 0.189 mmol, 1.0 eq), 1,1'-bisdiphenylphosphinoferrocene palladium dichloride(14 mg, 0.0189 mmol), potassium carbonate (52 mg, 0.378 mmol) and 1,4 dioxane (5 ml) and water (5 ml) were sequentially added to a 25 mL one-neck flask. The reaction was heated to 100° C. for 8 hours. After cooled to room temperature, the reaction was extracted with ethyl acetate (2*10 mL). After concentrated, the organic phase was purified by preparative high performance liquid chromatography to give the product ((S)-3-(2-((1-(1-(3-chloro-5-cyclopropylphenyl)-1H-imidazol-4-yl)cyclopropyl)amino)pyrimidin-4-yl)-4-isopropyl-1-methylimidazolidine-2-one (Compound 48) (35 mg, white solid), yield 37.6%.

$^1$H-NMR (CDCl$_3$, 400 MHz): 10.92 (s, 1H), 8.44 (s, 1H), 7.96 (d, J=6.0 Hz 1H), 7.77 (d, J=6.8 Hz, 1H), 7.22 (s, 1H), 7.15 (s, 1H), 6.99 (s, 1H), 6.83 (s, 1H), 4.48-4.50 (m, 2H), 3.44-3.48 (m, 1H), 3.18-3.21 (m, 1H), 2.90 (s, 3H), 2.87-2.90 (m, 1H), 1.92-1.93 (m, 1H), 1.46-1.57 (m, 3H), 1.08-1.10 (m, 1H), 1.02-1.04 (m, 2H), 0.62-0.81 (m, 8H)

LCMS: m/z 492.2 [M+H]$^+$, RT=1.1 min.

Example 49: Synthesis of Compound 49

Using the same manner as in Example 1, Compound 49 was obtained from Intermediate A38 and Intermediate B8.

139

(S)-1-(2-(((S)-1-(1-(3-chlorophenyl)-1H-imidazol-4-yl)ethyl)amino)pyrimidin-4-yl)-5-isopropylimidazolidine-2-one

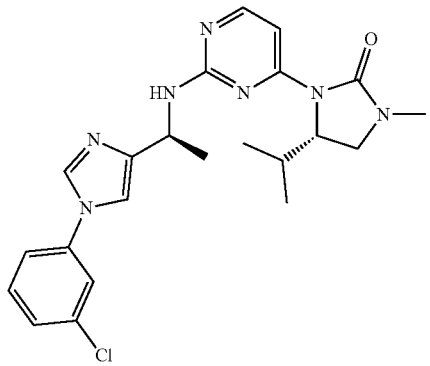 [SMILES: CC(C)[C@H]1CN(C)C(=O)N1c1ccnc(N[C@@H](C)c2cn(-c3cccc(Cl)c3)cn2)n1]

¹H-NMR (CDCl3,400 MHz): 1.08-8.07 (m, 1H), 7.77 (s, 1H), 7.55-7.54 (m, 1H), 7.39-7.31 (m, 3H), 7.23 (m, 1H) 7.09 (s, 1H), 5.48-5.45 (m, 1H) 5.14 (m, 1H), 4.52 (m, 1H), 3.38 (m, 1H), 3.17 (m, 1H), 2.85 (s, 3H) 2.40 (s, 1H), 1.62-1.59 (m, 3H), 0.81-0.79 (m, 3H), 0.70-0.68 (m, 3H).

LCMS: m/z 440.3 [M+H]⁺, RT=1.06 min.

Example 50: Synthesis of Compound 50

Using the same manner as in Example 1, Compound 50 was obtained from Intermediate A39 and Intermediate B27.

(S)-3-(2-((1-(1-(5-chloro-2-fluorophenyl)-1H-imidazol-4-yl)cyclopropyl)amino)pyrimidin-4-yl)-4-isopropyl-1-methylimidazolidine-2-one

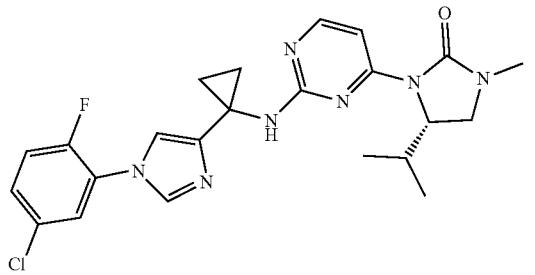 [SMILES: CC(C)[C@H]1CN(C)C(=O)N1c1ccnc(NC2(c3cn(-c4cc(Cl)ccc4F)cn3)CC2)n1]

¹H NMR (CDCl3-d1, 400 MHz): δ 10.30 (s, 1H), 8.80 (s, 1H), 7.99-7.87 (m, 2H), 7.52-7.49 (m, 2H), 7.30 (s, 1H), 4.48-4.47 (m, 1H), 3.52-3.48 (m, 1H), 3.23-3.21 (m, 1H) 2.92 (s, 3H), 2.25 (m, 1H), 1.64-1.56 (m, 4H), 0.82-0.71 (m, 6H).

LCMS: m/z 470.2 [M+H]⁺, RT=1.08 min.

Example 51: Synthesis of Compound 5

Using the same manner as in Example 1, Compound 51 was obtained from Intermediate A40 and Intermediate B27.

140

(S)-3-(2-((1-(1-(2-chlorophenyl)-1H-imidazol-4-yl)cyclopropyl)amino)pyrimidin-4-yl)-4-isopropyl-1-methylimidazolidine-2-one

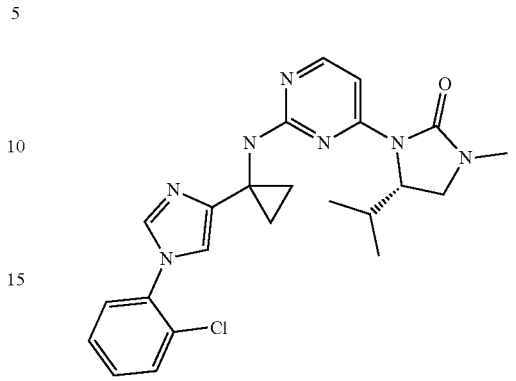

¹H-NMR (CDCl₃, 400 MHz): 8.02 (s, 1H), 7.57 (s, 2H), 7.46-7.44 (m, 1H), 7.30 (s, 2H), 7.20 (s, 1H), 6.89 (s, 1H), 4.35-4.33 (d, J=8.8 Hz, 1H), 3.31-3.26 (m, 1H), 3.09-3.07 (m, 1H), 2.78 (s, 3H), 2.36-2.30 (m, 1H), 1.46-1.43 (m, 2H), 1.18 (s, 2H), 0.73 (s, 3H), 0.62-0.60 (d, J=6.4 Hz, 3H).

LCMS: m/z 452.1 [M+H]⁺, RT=0.96 min.

Example 52: Synthesis of Compound 52

Using the same manner as in Example 1, Compound 52 was obtained from Intermediate A41 and Intermediate B8.

(S)-3-(2-((S)-1-(1-(3-cyclopropphenyl)-1-hydroimidazol-4-yl)ethyl)amino)pyrimidin-4-yl)-4-isopropyl-1-methylimidazolidine-2-one

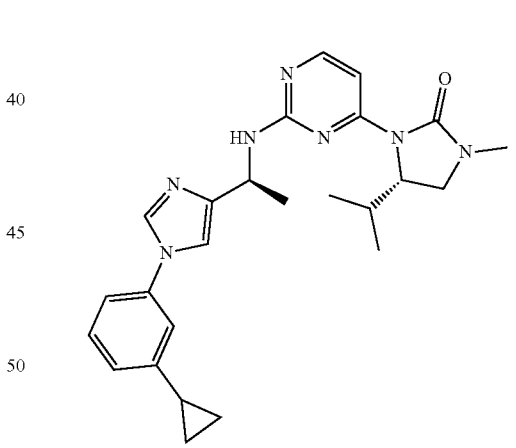

¹H NMR (CDCl₃-d₁, 400 MHz): δ 8.07 (d, J=6.0 Hz, 1H), 7.75 (s, 1H), 7.53 (d, J=6.0 Hz 1H), 7.32-7.26 (m, 1H), 7.08 (d, J=10 Hz, 2H), 7.02 (d, J=2.0 Hz, 1H), 5.42 (d, J=4.0 Hz, 1H), 5.15 (d, J=6.4 Hz, 1H) 4.55-4.53 (m, 1H), 3.40-3.35 (m, 1H), 3.17-3.14 (m, 1H), 3.28 (s, 3H), 2.44-2.43 (m, 1H), 1.95-1.90 (m, 1H), 1.51 (s, 3H), 1.05-0.89 (m, 3H), 0.88-0.76 (m, 3H), 0.75-0.70 (m, 2H), 0.69-0.60 (m, 3H).

LCMS: m/z 440.4 [M+H]⁺, RT=0.98 min.

Example 53: Synthesis of Compound 53

Using the same manner as in Example 48, Compound 53 was obtained from Compound 47.

(S)-3-((1-(1-(3-fluoro-5-cyclopropylphenyl)-1H-imidazol-4-yl)cyclopropyl) amino)pyrimidin-4-yl)-4-isopropyl-1-methylimidazolidine-2-one

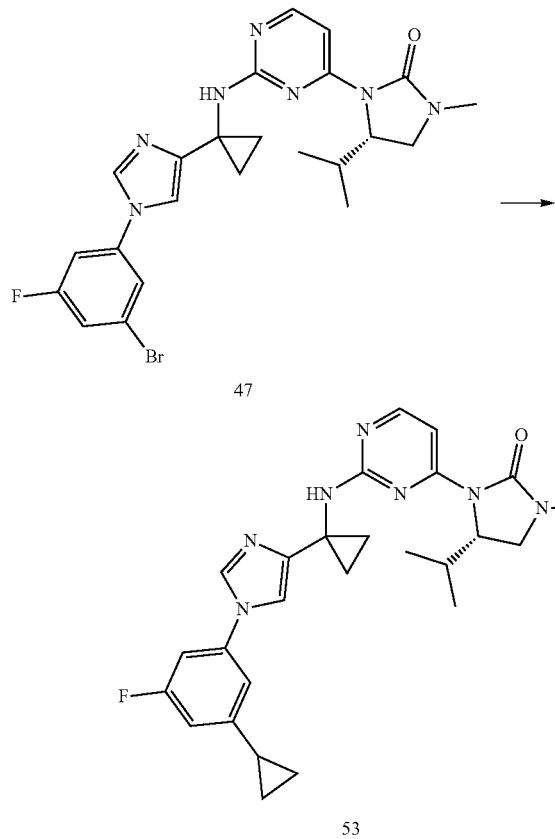

¹H-NMR (CDCl₃, 400 MHz): 8.06 (s, 1H), 7.59-7.66 (m, 2H), 7.00 (s, 1H), 6.68-6.79 (m, 2H), 6.66 (s, 1H), 5.88 (s, 1H), 4.39-4.41 (m, 1H), 3.32-3.37 (m, 1H), 3.12-3.14 (m, 1H), 2.84 (s, 3H), 2.45-2.48 (m, 1H), 1.92-1.97 (m, 1H), 1.45 (s, 3H), 1.08-1.10 (m, 1H), 1.04-1.06 (m, 2H), 0.76-0.93 (m, 8H).
LCMS: m/z 476.6 [M+H]⁺, RT=1.32 min.

Example 54: Synthesis of Compound 54

Using the same manner as in Example 1, Compound 54 was obtained from Intermediate A42 and Intermediate B8.

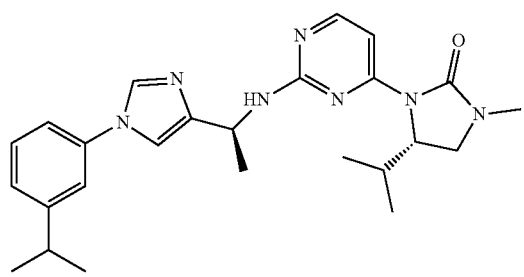 [SMILES: CC(C)c1cccc(-n2cnc([C@H](C)Nc3nccc(N4C(=O)N(C)C[C@@H]4C(C)C)n3)c2)c1]

¹H NMR (400 MHz, dmso) δ 9.32 (s, 1H), 9.19 (s, 1H), 8.17 (s, 1H), 8.00 (s, 1H), 7.69 (s, 1H), 7.54 (s, 1H), 7.48 (s, 1H), 7.34 (s, 1H), 5.16 (s, 1H), 4.40 (d, J=7.9 Hz, 1H), 3.41 (t, J=9.3 Hz, 1H), 3.23 (d, J=9.3 Hz, 1H), 3.00-2.84 (m, 1H), 2.76 (s, 3H), 1.95 (s, 1H), 1.59 (d, J=6.4 Hz, 3H), 1.21 (d, J=6.7 Hz, 6H), 0.86 (d, J=6.6 Hz, 1H), 0.61 (d, J=21.0 Hz, 6H).
LCMS: m/z 448.3 [M+H]⁺, RT=1.38 min.

Example 55: Synthesis of Compound 55

Using the same manner as in Example 1, Compound 55 was obtained from Intermediate A43 and Intermediate B8.

(S)-4-isopropyl-1-methyl-3-(2-(((S)-1-(1-(p-tolyl)-1H-imidazol-4-yl)methyl)amine)pyrimidin-4-yl) imidazolidine-2-one

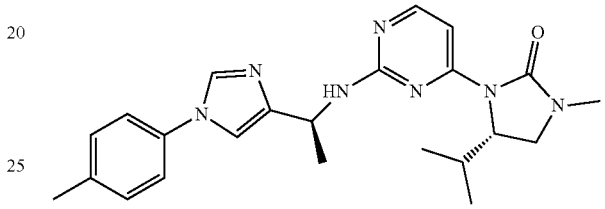

¹H-NMR (CDCl₃, 400 MHz): 8.09-8.07 (d, J=6.4 Hz, 1H), 7.74 (s, 1H), 7.54-7.53 (d, J=6.4 Hz, 1H), 7.24-7.20 (m, 4H), 7.06 (s, 1H), 5.48-5.40 (m, 1H), 5.17-5.15 (d, J=7.2 Hz, 1H), 4.55-4.53 (m, 1H), 3.40-3.35 (m, 1H), 3.18-3.14 (m, 1H), 2.86 (s, 3H), 2.39 (s, 4H), 1.63 (s, 3H), 0.81-0.79 (d, J=6.4 Hz, 3H), 0.69-0.68 (d, J=6.4 Hz, 3H).
LCMS: m/z 420.2 [M+H]⁺, RT=0.90 min.

Example 56: Synthesis of Compound 56

Using the same manner as in Example 1, Compound 56 was obtained from Intermediate A44 and Intermediate B8.

(S)-3-(2-(((S)-1-(1-(4,4-dimethylcyclohexyl)-1H-imidazol-4-yl)ethyl)amino)pyrimidin-4-yl)-4-isopropyl-1-methylimidazolidine-2-one

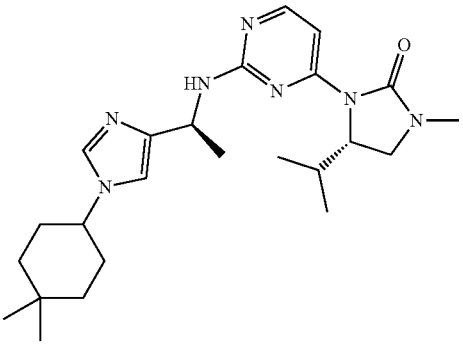

¹H NMR (CDCl3-d1, 400 MHz): δ 8.05 (d, J=5.6 Hz, 1H), 7.51 (d, J=5.6 Hz, 1H), 7.49 (s, 1H), 6.86 (s, 1H), 5.47 (br s, 1H), 5.16-5.12 (m, 1H), 4.56-4.54 (m, 1H), 3.83-3.77 (m, 1H) 3.38 (t, J=9.2 Hz, 1H), 3.20-3.17 (m, 1H), 2.86 (s, 3H), 2.63-2.60 (m, 1H), 1.93-1.73 (m, 6H), 1.54 (d, J=6.4 Hz, 3H), 1.38-1.32 (m, 2H), 0.99 (s, 3H), 0.98 (s, 3H), 0.92 (d, J=6.8 Hz, 3H), 0.77 (d, J=6.8 Hz, 3H)
LCMS: m/z 440.4 [M+H]⁺, RT=1.00 min.

Example 57: Synthesis of Compound 57

Using the same manner as in Example 1, Compound 57 was obtained from Intermediate A45 and Intermediate B8.

(S)-3-(2-(((S)-1-(1-(3-chloro-5-fluorophenyl)-1H-imidazol-4-yl)ethyl)amino)pyrimidin-4-yl)-4-isopropyl-1-methylimidazolidine-2-one

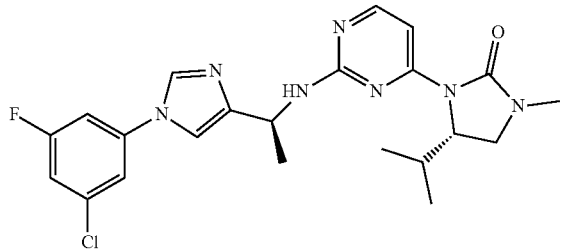 [SMILES: CC(C)[C@H]1CN(C)C(=O)N1c1ccnc(N[C@@H](C)c2cn(-c3cc(F)cc(Cl)c3)cn2)n1]

¹H-NMR (CDCl₃, 400 MHz): 8.09-8.08 (d, J=6.0 Hz, 1H), 7.78 (s, 1H), 7.55-7.54 (d, J=6.0 Hz, 1H), 7.17 (s, 1H), 7.08-7.07 (m, 2H), 7.00-6.98 (m, 1H), 5.37-5.35 (d, J=7.6 Hz, 1H), 5.17-5.14 (m, 1H), 4.56-4.52 (m, 1H), 3.40-3.38 (m, 1H), 3.18-3.15 (m, 1H), 2.86 (s, 3H), 2.41 (s, 1H), 1.62-1.60 (d, J=6.8 Hz, 1H), 0.81-0.80 (d, J=6.4 Hz, 3H), 0.70-0.68 (d, J=6.8 Hz, 3H).
LCMS: m/z 458.2 [M+H]⁺, RT=0.97 min.

Example 58: Synthesis of Compound 58

Using the same manner as in Example 1, Compound 58 was obtained from Intermediate A46 and Intermediate B8.

Synthesis of (S)-4-isopropyl-1-methyl-3-(2-(((S)-1-(1-(4-trifluoromethyl)phenyl)-1H-imidazole-4-yl)ethyl)amino)pyrimidin-4-yl)methylimidazolidine-2-one

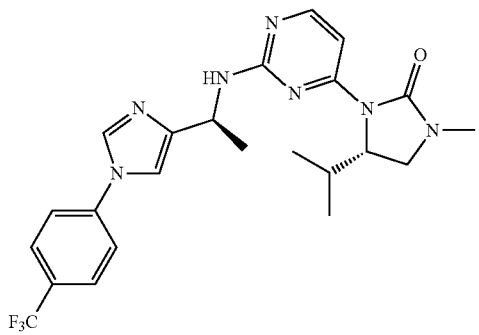 [SMILES: CC(C)[C@H]1CN(C)C(=O)N1c1ccnc(N[C@@H](C)c2cn(-c3ccc(C(F)(F)F)cc3)cn2)n1]

¹H NMR (CDCl₃-d₁, 400 MHz): δ 10.52 (s, 1H), 8.54 (s, 1H), 7.93 (d, J=6.4 Hz 1H), 7.82 (d, J=0.2 Hz, 2H), 7.76 (d, J=6.4 Hz, 1H), 7.61 (m, 3H), 5.45 (s, 1H), 4.62 (d, J=7.6 Hz, 1H) 3.53 (t, J=9.2 Hz, 1H), 3.24 (d, J=10.0 Hz, 1H), 2.93 (s, 3H), 3.30 (s, 1H), 1.71 (d, J=5.2 Hz, 3H), 0.87 (d, J=6.0 Hz, 3H), 0.71 (d, J=6.4 Hz, 3H).
LCMS: m/z 474.2 [M+H]⁺, RT=1.14 min.

Example 59: Synthesis of Compound 59

Using the same manner as in Example 1, Compound 59 was obtained from Intermediate A47 and Intermediate B8.

(S)-4-isopropyl-1-methyl-3-(2-((S)-1-(1-(3-trifluoromethylphenyl)-1H-imidazol-4-yl)ethyl)amino)pyrimidin-4-yl)-imidazolidine-2-one

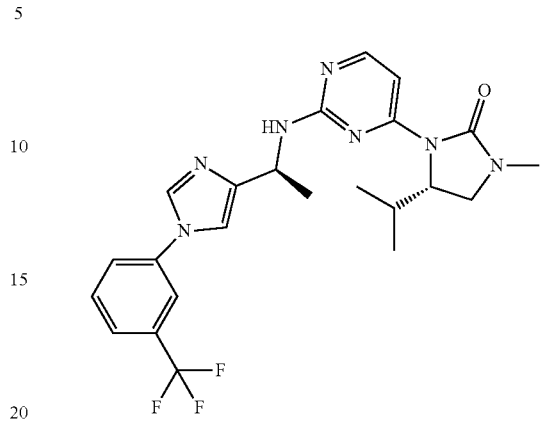

¹H NMR (CDCl₃-d₁, 400 MHz): δ 8.08 (d, J=5.6 Hz, 1H), 7.82 (s, 1H), 7.53-7.61 (m, 5H), 7.14 (s, 1H), 5.37-5.39 (m, 1H), 5.16-5.18 (m, 1H), 4.53-4.55 (m, 1H), 4.08-4.09 (m, 1H), 3.35-3.38 (m, 1H), 3.44 (s, 3H), 1.62 (d, J=6.8 Hz, 3H), 0.80 (d, J=6.8 Hz, 3H), 0.68 (d, J=6.8 Hz, 3H);
LCMS: m/z 474.2 [M+H]⁺, RT=1.154 min.

Example 60: Synthesis of Compound 60

Using the same manner as in Example 1, Compound 60 was obtained from Intermediate A48 and Intermediate B8.

(S)-3-(2-(((S)-1-(1-(3,5-dichlorophenyl)-1hydro-imidazol-4-yl)ethyl)amino)pyrimidin-4-yl)-4-isopropyl-1-methylimidazolidine-2-one

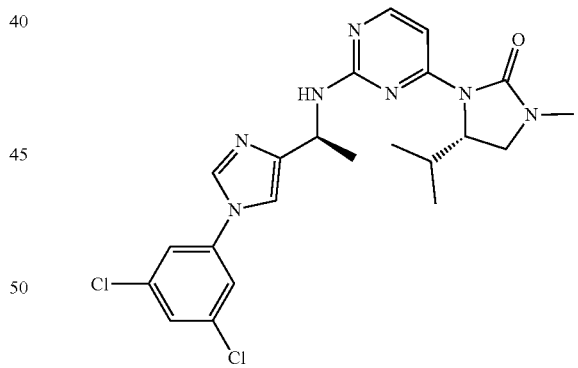

¹H NMR (CDCl3-d1, 400 MHz): δ 10.46 (t, J=1.2 Hz, 1H), 8.55 (s, 1H), 7.94 (d, J=6.8 Hz 1H), 7.78 (d, J=7.2 Hz, 1H), 7.61 (s, 1H), 7.50 (s, 1H), 7.42 (s, 1H), 7.26 (s 1H) 5.46 (t, J=6.4 Hz, 1H), 4.61 (d, J=8.8 Hz, 1H), 3.54 (t, J=9.6 Hz, 1H), 3.24 (d, J=9.6 Hz, 1H), 2.94 (s, 3H), 2.27 (s, 1H), 1.70 (d, J=6.4 Hz, 3H), 0.85 (d, J=6.4 Hz, 3H), 0.71 (d, J=6.8 Hz, 3H).
LCMS: m/z 474.2 [M+H]⁺, RT=1.2 min.

Example 61: Synthesis of Compound 61

Using the same manner as in Example 1, Compound 61 was obtained from Intermediate A49 and Intermediate B8.

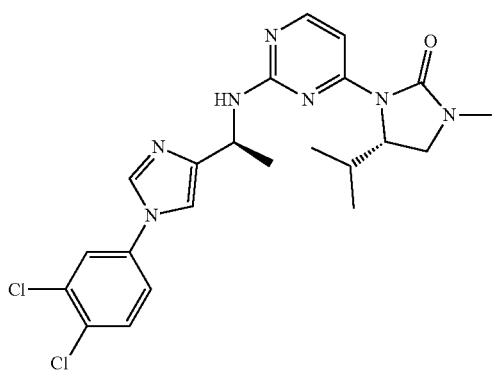 [SMILES: CC(C)[C@H]1CN(C)C(=O)N1c1ccnc(N[C@@H](C)c2cn(-c3ccc(Cl)c(Cl)c3)cn2)n1]

(S)-1-(2-(((S)-1-(1-(3,4-dichlorophenyl)-1H-imidazol-4-yl)ethyl)amino)pyrimidin-4-yl)-5-isopropylimidazolidine-2-one $^1$H-NMR (CDCl3, 400 MHz): 8.06 (d, J=6.0 Hz, 1H), 7.75 (s, 1H), 7.56-7.52 (m, 2H), 7.46 (s, 1H), 7.21-7.19 (m, 1H), 7.07 (s, 1H), 7.58-7.57 (m, 1H), 5.57-5.58 (brs, 1H), 5.13-5.17 (m, 1H), 4.51-4.55 (m, 1H), 3.38 (t, J=6.4 Hz, 1H), 3.15-3.18 (m, 1H), 2.86 (s, 3H), 2.37-2.41 (m, 1H), 1.60 (d, J=6.8 Hz, 3H), 0.79 (d, J=6.8 Hz, 3H), 0.68 (d, J=6.8 Hz, 3H).

LCMS: m/z 474.2 [M+H]$^+$, RT=1.14 min.

Example 62: Synthesis of Compound 62

Using the same manner as in Example 1, Compound 62 was obtained from Intermediate A50 and Intermediate B8.

(S)-3-(2-(((S)-1-(1-(4-cyclopropylphenyl)-1H-imidazol-4-yl)ethyl)amino)pyrimidin-4-yl) 1-methylimidazolidine-2-one

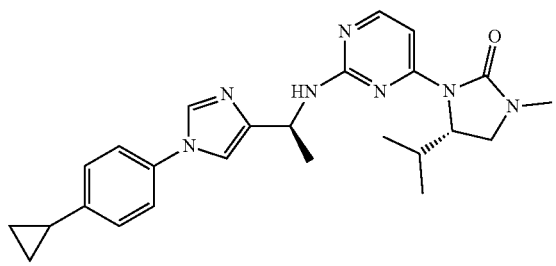 [SMILES: CC(C)[C@H]1CN(C)C(=O)N1c1ccnc(N[C@@H](C)c2cn(-c3ccc(C4CC4)cc3)cn2)n1]

$^1$H-NMR (CDCl$_3$, 400 MHz): 8.05 (d, J=6.0 Hz, 1H), 7.72 (s, 1H), 7.54 (d, J=6.0 Hz, 1H), 7.20 (d, J=8.4 Hz, 2H), 7.12 (d, J=8.4 Hz, 2H), 7.06 (s, 1H), 5.67 (s, 1H), 5.17-5.14 (m, 1H), 4.56-4.53 (m, 1H), 3.41-3.36 (m, 1H), 3.18-3.15 (m, 1H), 2.86 (s, 3H), 2.42 (brs, 1H), 1.95-1.89 (m, 1H), 1.62 (d, J=6.8 Hz, 3H), 1.03-0.99 (m, 2H), 0.81-0.80 (m, 3H), 0.73-0.68 (m, 5H).

LCMS: m/z 446.3 [M+H]$^+$, RT=0.9 min.

Example 63: Synthesis of Compound 63

Using the same manner as in Example 1, Compound 63 was obtained from Intermediate A51 and Intermediate B8.

(S)-1-(2-(((S)-1-(1-(3-fluoro-4-chlorophenyl)-1H-imidazol-4-yl)ethyl)amino)pyrimidin-4-yl)-5-isopropylimidazolidine-2-one

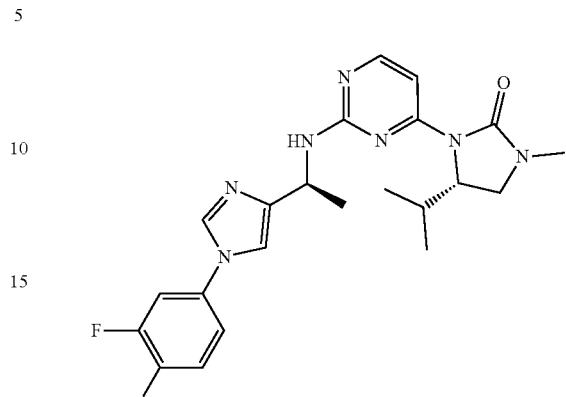

$^1$H-NMR (CDCl$_3$, 400 MHz): 8.07 (s, 1H), 7.77 (s, 1H), 7.53-7.49 (m, 2H), 7.16-7.08 (m, 3H), 5.42 (s, 1H) 5.15 (m, 1H), 4.54-4.53 (m, 1H), 3.38 (m, 1H), 3.17 (m, 1H), 2.85 (s, 3H), 2.38-2.40 (m, 1H), 2.02 (m, 3H), 0.80 (m, 3H), 0.68 (m, 3H).

LCMS: m/z 458.2 [M+H]$^+$, RT=1.1 min.

Example 64: Synthesis of Compound 64

Using the same manner as in Example 1, Compound 64 was obtained from Intermediate A60 and Intermediate B8.

(S)-3-(2-((1-(1-(3-cyclopropylphenyl)-1H-[1,2,4]-triazol-3-yl)cyclopropyl)amino)-1-isopropyl-1-methylimidazolidine-2-one

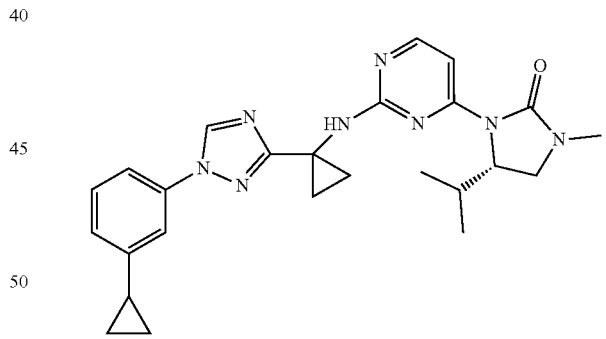

$^1$H-NMR (CDCl$_3$, 400 MHz): 8.32 (s, 1H), 8.13-8.11 (d, J=6.0 Hz, 1H), 7.59-7.57 (d, J=6.0 Hz, 1H), 7.30-7.29 (m, 2H), 7.26 (s, 1H), 7.02-7.00 (m, 1H), 5.83 (s, 1H), 4.41-4.39 (m, 1H), 3.33-3.28 (m, 1H), 3.12-3.09 (m, 1H), 2.82 (s, 3H), 2.37-2.33 (m, 1H), 1.97-1.90 (m, 1H), 1.62 (d, J=2.8 Hz, 2H), 1.38-1.31 (m, 2H), 1.03-0.99 (m, 2H), 0.74-0.70 (m, 5H), 0.61-0.60 (d, J=6.0 Hz, 3H).

LCMS: m/z 459.3 [M+H]$^+$, RT=1.0 min.

Example 65: Synthesis of Compound 65

Using the same manner as in Example 1, Compound 65 was obtained from Intermediate A52 and Intermediate B8.

(S)-3-(2-(((S)-1-(1-(4-chloro-3-methoxyphenyl)-1H-imidazol-4-yl)ethyl)amino)pyrimidine-4-yl)-4-isopropyl-1-methylimidazolidine-2-one

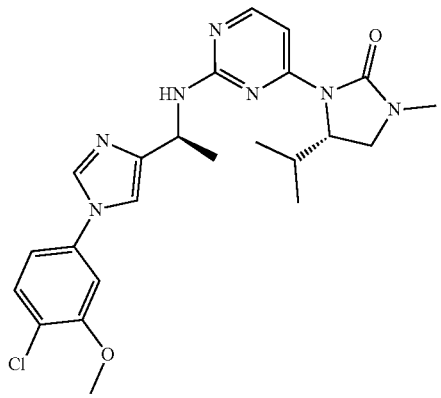 [SMILES: COc1cc(-n2cnc([C@H](C)Nc3nccc(N4C(=O)N(C)C[C@@H]4C(C)C)n3)c2)ccc1Cl]

¹H NMR (CDCl3-d₁, 400 MHz): δ 8.09 (d, J=6.0 Hz, 1H), 7.75 (s, 1H), 7.54-7.53 (m, 1H), 7.44-7.42 (m, 1H), 7.08 (s, 1H), 6.89-6.86 (m, 2H), 5.35-5.33 (m, 1H), 5.18-5.14 (m, 1H), 5.56-5.52 (m, 1H), 3.94 (s, 3H), 3.41-3.36 (m, 1H), 3.18-3.15 (m, 1H), 2.86 (s, 3H), 2.43 (s, 1H), 1.62 (d, J=6.8 Hz, 3H), 0.81 (d, J=6.8 Hz, 3H), 0.69 (d, J=6.8 Hz, 3H).

LCMS: m/z 470.2 [M+H]⁺, RT=0.93 min.

Example 66: Synthesis of Compound 66

Using the same manner as in Example 1, Compound 66 was obtained from Intermediate A53 and Intermediate B8.

(S)-3-(2-(((S)-1-(1-isopentyl-1H-imidazol-4-yl)yl)amino)pyrimidin-4-yl)-4-isopropyl-1-methylimidazolidine-2-one

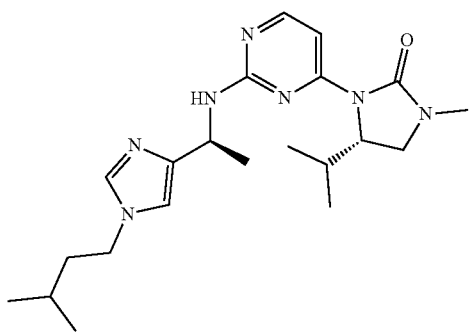 [SMILES: CC(C)CCn1cnc([C@H](C)Nc2nccc(N3C(=O)N(C)C[C@@H]3C(C)C)n2)c1]

¹H NMR (CDCl3-d₁, 400 MHz): δ 8.06 (s, 1H), 7.51-7.50 (m, 1H), 7.39-7.38 (m, 1H), 6.72-6.71 (m 1H), 5.38 (s, 1H), 5.08 (s, 1H), 4.53 (s, 1H), 3.86-3.84 (m, 2H), 3.40-3.36 (m, 1H), 3.18-3.16 (m, 1H), 2.85 (d, J=6.8 Hz, 3H), 2.46 (s, 1H), 1.57-1.55 (m, 3H), 0.94-0.91 (m, 6H), 0.83-0.70 (m, 9H).

LCMS: m/z 400.3 [M+H]⁺, RT=0.72 min.

Example 67: Synthesis of Compound 67

Using the same manner as in Example 1, Compound 67 was obtained from Intermediate A61 and Intermediate B8.

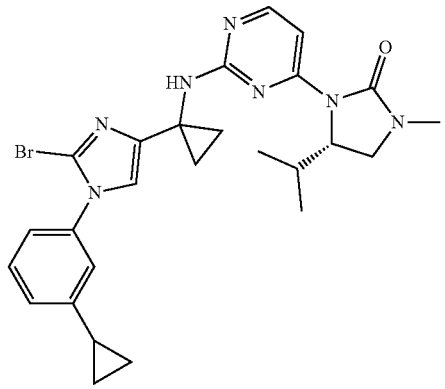 [SMILES: CC(C)[C@H]1CN(C)C(=O)N1c1ccnc(NC2(c3cn(-c4cccc(C5CC5)c4)c(Br)n3)CC2)n1]

¹HNMR (CDCl₃, 400 MHz): δ 8.05 (s, 1H), 7.55 (t, J=6.4 Hz, 2H), 7.24-7.32 (m, 1H), 7.00-7.11 (m, 2H), 6.84-6.93 (m, 2H), 5.79 (s, 1H), 4.44 (s, 1H), 3.32-3.39 (m, 2H), 3.14-3.16 (m, 1H), 2.82 (s, 3H), 2.32-2.37 (m, 1H), 1.57-1.60 (m, 2H), 1.18-1.20 (m, 3H), 0.99-1.01 (m, 2H), 0.67-0.85 (m, 8H);

LCMS: m/z 536.2 [M+H]⁺, RT=1.34 min.

Example 68: Synthesis of Compound 68

Using the same manner as in Example 1, Compound 68 was obtained from Intermediate A54 and Intermediate B8.

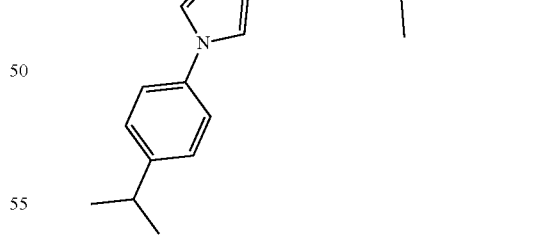

¹H NMR (400 MHz, DMSO): 8.08-8.02 (m, 1H), 7.98 (d, J=5.7 Hz, 1H), 7.44 (dd, J=14.7, 8.5 Hz, 2H), 7.30 (dd, J=6.9, 4.7 Hz, 4H), 6.90 (s, 1H), 4.96 (s, 1H), 4.40 (dd, J=6.4, 3.4 Hz, 1H), 3.36 (dd, J=11.7, 7.3 Hz, 1H), 3.15 (d, J=7.0 Hz, 1H), 2.88 (dd, J=13.7, 6.9 Hz, 1H), 2.70 (d, J=4.1 Hz, 3H), 2.02-1.90 (m, 1H), 1.43 (t, J=7.9 Hz, 3H), 1.17 (dd, J=6.9, 2.3 Hz, 6H), 0.67 (dd, J=54.0, 47.1 Hz, 6H).

LCMS: m/z 448.3/1 [M+H]⁺, RT=1.89 min.

Example 69: Synthesis of Compound 69

(S)-1-(3-cyclopropylphenyl)-4-(1-((4-(5-isopropyl-3-methyl-2-oxoimidazolidine-1-yl)pyrimidine-2-yl)amino)cyclopropyl)-1H-imidazole-5-carbonitrile

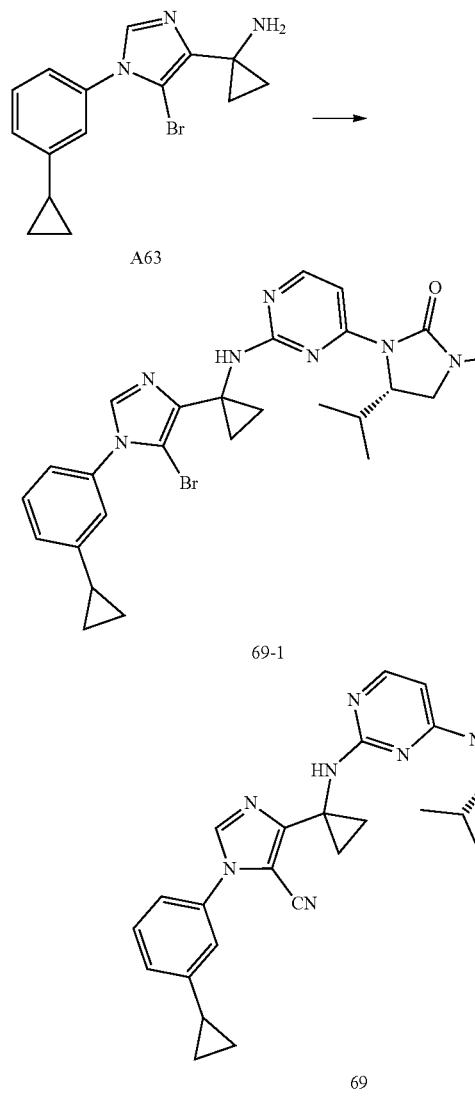

Step 1: Using the same manner as in Example 1, Intermediate 69-1 was obtained from Intermediate A63 and Intermediate B27.

LCMS: m/z 536.2 [M+H]$^+$, RT=1.11 min.

Step 2: Intermediate 69-1 (45 mg, 0.083 mmol), Zn(CN)$_2$ (98 mg, 0.838 mmol), Zn powder (10 mg) and catalytic amount of PdCl2dppf were sequentially added to a dry microwave tube containing 4 mL of N,N-dimethylformamide, ventilated with nitrogen for 3 times, heated to 140° C. and subjected to microwave reaction for 2 hours. After LCMS detection showed that the reaction was completed, filtered, and separated by high performance liquid phase preparation to obtain compound 69 (20 mg, yield 50%) as yellow solid.

$^1$H-NMR (CDCl$_3$, 400 MHz): 10.78 (s, 1H), 8.44 (s, 1H), 7.97 (d, J=5.2 Hz, 1H), 7.79-7.72 (m, 2H), 7.29-7.26 (m, 2H), 6.97 (s, 1H), 4.47 (d, J=7.2 Hz, 1H), 3.45 (t, J=9.2 Hz, 1H), 3.19 (d, J=9.2 Hz, 1H), 2.91 (s, 3H), 2.36-2.26 (m, 2H), 1.65-1.45 (m, 4H), 1.27 (d, J=7.6 Hz, 2H), 0.89 (d, J=4.4 Hz, 2H), 0.79 (d, J=6.8 Hz, 3H), 0.67 (d, J=6.4 Hz, 3H).

LCMS: m/z 483.2 [M+H]$^+$, RT=1.03 min.

Example 70: Synthesis of Compound 70

Using the same manner as in Example 1, Compound 70 was obtained from Intermediate A59 and Intermediate B8.

(S)-3-(2-(((S)-1-(1-(4-chlorophenyl)-1H-1,2,4-triazol-3-yl)ethyl)amino)-4-isopropyl-1-methylimidazolidine-2-one

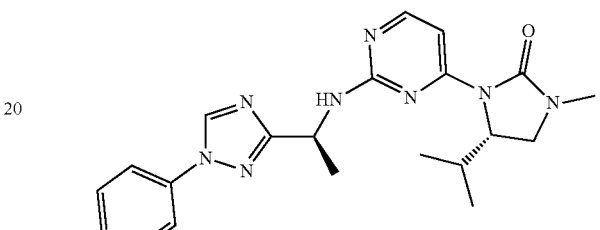

$^1$H-NMR (CDCl$_3$, 400 MHz): 8.44 (s, 1H), 8.10-8.08 (d, J=6.0 Hz, 1H), 7.61-7.55 (m, 3H), 7.47-7.45 (d, J=8.4 Hz, 2H), 5.69 (s, 1H), 5.36-5.33 (m, 1H), 4.60-4.56 (m, 1H), 3.42-3.38 (m, 1H), 3.20-3.17 (m, 1H), 2.86 (s, 3H), 2.49 (s, 1H), 1.68-1.66 (d, J=6.4 Hz, 3H), 0.86-0.85 (d, J=7.2 Hz, 3H), 0.61-0.60 (d, J=6.8 Hz, 3H).

LCMS: m/z 441.2 [M+H]$^+$, RT=1.0 min.

Example 71: Synthesis of Compound 71

(S)-3-(2-((1-(1-(3-cyclopropylphenyl)-1H-imidazol-4-yl)cyclobutyl)amino)pyrimidin-4-yl)-4-isopropyl-1-methylimidazolidine-2-one

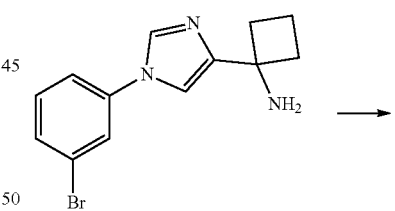

-continued

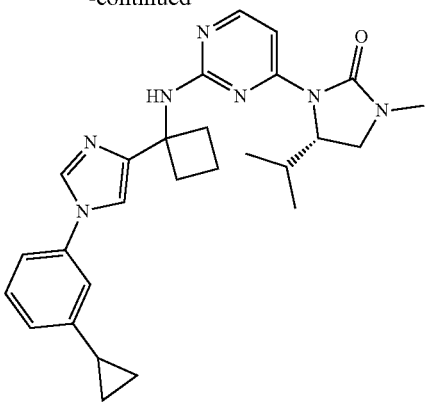

71

Step 1: Using the same manner as in Example 1, Intermediate 71-1 was obtained from Intermediate A64 and Intermediate B27.

LCMS: m/z 510.2 [M+H]⁺, RT=1.05 min.

Step 2: Intermediate 71-1 (60 mg, 0.117 mmol), cyclopropylboronic acid (25 mg, 0.294 mmol), cesium carbonate (95 mg, 0.294 mmol) and $PdCl_2$ (dppf) were added to a 50 ml round bottom flask containing 8 mL of toluene, and reacted overnight at 100° C. under nitrogen atmosphere. After LCMS detection showed that the reaction was completed, the system was concentrated and purified by prep-HPLC to afford compound 71 (35 mg, yield 64%) as white solid.

¹H-NMR ($CDCl_3$, 400 MHz): 10.87 (s, 1H), 8.87 (s, 1H), 7.93 (d, J=6.8 Hz, 1H), 7.77 (d, J=6.4 Hz, 1H), 7.42-7.38 (m, 1H), 7.25 (d, J=6.8 Hz, 1H), 7.19-7.12 (m, 3H), 4.37 (d, J=7.2 Hz, 1H), 3.43 (t, J=9.6 Hz, 1H), 3.16 (d, J=9.6 Hz, 1H), 2.88-2.78 (m, 7H), 2.25-2.23 (m, 2H), 1.97-1.95 (m, 2H), 1.07 (d, J=6.8 Hz, 2H), 0.82 (d, J=6.8 Hz, 3H), 0.76 (d, J=4.8 Hz, 2H), 0.64 (d, J=6.4 Hz, 3H).

LCMS: m/z 472.2 [M+H]⁺, RT=1.0 min.

Example 72: Synthesis of Compound 72

Using the same manner as in Example 1, Compound 72 was obtained from Intermediate A55 and Intermediate B8.

(S)-3-(2-((2-(1-(4-chlorophenyl)-1H-imidazol-4-yl)prop-2-yl)amino)pyrimidin-4-yl)-4-isopropyl-1-methylimidazolidine-2-one

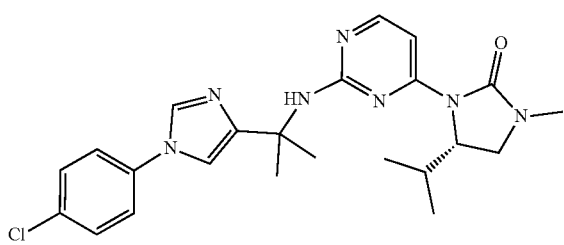 [SMILES: CC(C)[C@H]1CN(C)C(=O)N1c1ccnc(NC(C)(C)c2cn(-c3ccc(Cl)cc3)cn2)n1]

¹H-NMR ($CDCl_3$, 400 MHz): 8.06-8.04 (d, J=6.0 Hz, 1H), 7.72 (s, 1H), 7.52-7.51 (d, J=6.0 Hz, 1H), 7.43-7.41 (d, J=8.0 Hz, 2H), 7.28-7.26 (d, J=5.6 Hz, 2H), 7.01 (s, 1H), 5.59 (s, 1H), 4.38-4.35 (m, 1H), 3.34-3.29 (m, 1H), 3.13- 3.10 (m, 1H), 2.83 (s, 3H), 2.24 (s, 1H), 1.86 (s, 3H), 1.76 (s, 3H), 0.76-0.74 (d, J=6.8 Hz, 3H), 0.64-0.62 (d, J=7.2 Hz, 3H).

LCMS: m/z 441.2 [M+H]⁺, RT=1.00 min.

Example 73: Synthesis of Compound 73

Using the same manner as in Example 1, Compound 73 was obtained from Intermediate A2 and Intermediate B11.

(S)-3-(2-(((S)-1-(1-(4-chlorophenyl)-1H-imidazol-4-yl)ethyl)amino)pyrimidin-4-yl)-4-isopropyl-1-cyclopropylimidazolidine-2-one

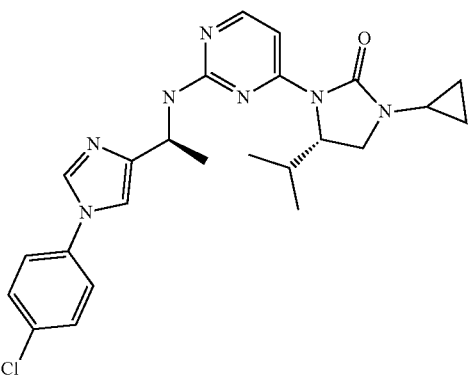 [SMILES: CC(C)[C@H]1CN(C2CC2)C(=O)N1c1ccnc(N[C@@H](C)c2cn(-c3ccc(Cl)cc3)cn2)n1]

¹H NMR (CDCl3-d1,400 MHz): δ 8.08 (d, J=6.0 Hz, 1H), 7.75 (s, 1H), 7.55-7.53 (m 1H), 7.44-7.42 (m, 2H), 7.29-7.27 (m, 1H), 7.06 (s, 1H), 5.36-5.34 (m, 1H), 5.16-5.15 (m, 1H), 4.51-4.47 (m, 1H), 3.39-3.35 (m, 1H), 3.15-3.12 (m, 1H), 2.55-2.50 (m, 1H), 2.38 (s, 1H), 1.62-1.61 (m, 3H), 0.87-0.83 (m, 7H), 0.80-0.64 (m, 4H).

LCMS: m/z 466.2 [M+H]⁺, RT=1.03 min.

Example 74: Synthesis of Compound 74

Using the same manner as in Example 1, Compound 74 was obtained from Intermediate A2 and Intermediate B9.

(S)-3-(2-(((S)-1-(1-(4-chlorophenyl) 1H-imidazol-4-yl)ethyl)amino) pyrimidin-4-yl)-1-ethyl-4-isopropylimidazolidine-2-one

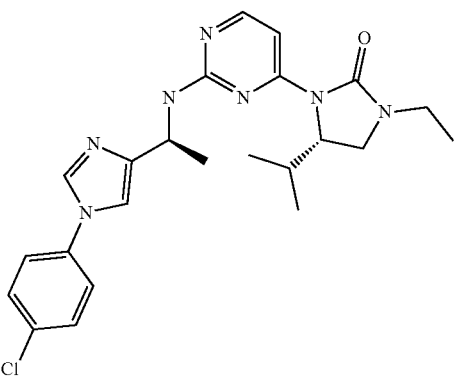 [SMILES: CCN1C[C@H](C(C)C)N(c2ccnc(N[C@@H](C)c3cn(-c4ccc(Cl)cc4)cn3)n2)C1=O]

¹H-NMR (CDCl₃, 400 MHz): 10.33 (s, 1H), 8.84 (s, 1H), 7.97 (d, J=5.6 Hz, 1H), 7.82 (s, 1H), 7.66 (s, 1H), 7.56 (s, J=8.0 Hz, 2H), 7.46 (d, J=8.0 Hz, 2H), 5.55 (s, 1H), 4.64 (d, J=7.2 Hz, 1H), 3.55-3.42 (m, 2H), 3.40-3.26 (m, 2H), 3.23 (s, 1H), 1.73 (d, J=5.2 Hz, 3H), 1.20 (t, J=14.4 Hz, 3H), 0.86 (d, J=6.0 Hz, 3H), 0.72 (d, J=6.4 Hz, 3H).

LCMS: m/z 454.2 [M+H]⁺, RT=0.95 min.

Example 75: Synthesis of Compound 75

Using the same manner as in Example 1, Compound 75 was obtained from Intermediate A56 and Intermediate B8.

(S)-3-(2-(((S)-1-(1-(4,4-difluorocyclohexyl)-1H-imidazol-4-yl)ethyl)amino)pyrimidin-4-yl)-4-isopropyl-1-methylimidazolidine-2-one

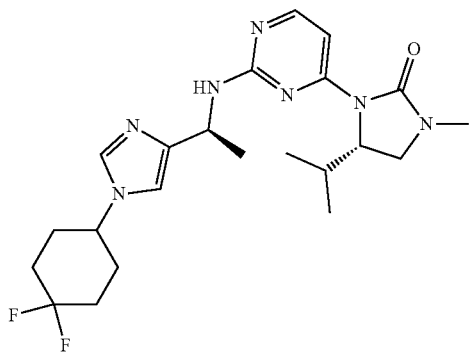 [SMILES: CC(C)[C@H]1CN(C)C(=O)N1c1ccnc(N[C@@H](C)c2cn(C3CCC(F)(F)CC3)cn2)n1]

¹H NMR (CDCl₃, 400 MHz): δ 7.88 (brs, 1H), 7.71-7.73 (m, 2H), 7.52-7.54 (m, 1H), 6.90 (brs, 1H), 5.29 (s, 1H), 4.48 (s, 1H), 4.07 (d, J=6.8 Hz, 1H), 3.40-3.44 (m, 1H), 3.19-3.22 (m, 1H), 2.87 (s, 3H), 2.46 (brs, 1H), 1.91-2.24 (m, 8H), 0.99 (d, J=6.4 Hz, 3H), 0.90-0.94 (m, 6H);

LCMS: m/z 448.2 [M+H]⁺, RT=0.76 min.

Example 76: Synthesis of Compound 76

Using the same manner as in Example 1, Compound 76 was obtained from Intermediate A57 and Intermediate B8.

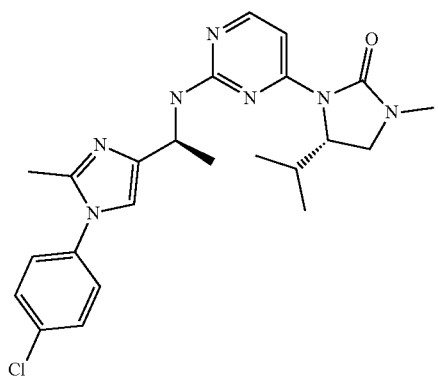 [SMILES: Cc1nc([C@H](C)Nc2nccc(N3C(=O)N(C)C[C@@H]3C(C)C)n2)cn1-c1ccc(Cl)cc1]

¹H-NMR (CDCL3, 400 MHz): 8.05 (d, J=6.0 Hz 1H), 7.52 (d, J=6.0 Hz 1H), 7.44-7.40 (m, 2H), 7.19-7.15 (m, 2H), 6.78 (d, J=5.2 Hz, 1H), 5.40 (t, J=5.6 Hz 1H), 5.07 (t, J=3.6 Hz 1H), 4.55 (t, J=6.0 Hz 1H), 3.38 (t, J=9.6 Hz 1H), 3.17 (t, J=6.0 Hz 1H), 2.86 (s, 3H), 2.45 (s, 1H), 2.30 (s, 3H), 1.70-1.35 (m, 3H), 0.83-0.70 (m, 3H), 0.05-0.10 (m, 3H).

LCMS: m/z 454.0 [M+H]⁺, RT=0.99 min.

Example 77: Synthesis of Compound 77

Using the same manner as in Example 1, Compound 77 was obtained from Intermediate A58 and Intermediate B10.

(S)-3-(6-chloro-2-(((S)-1-(1-(4-fluorophenyl)-1H-imidazol-4-yl)ethyl)amino)pyrimidin-4-yl)-4-cyclopropyl-1-methylimidazolidine-2-one

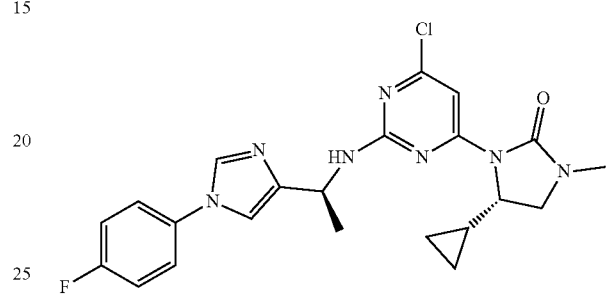

¹H-NMR (CDCl₃, 400 MHz): 7.71 (s, 1H), 7.60 (s, 1H), 7.33-7.30 (m, 2H), 7.18-7.14 (m, 2H), 7.08 (s, 1H), 5.44-5.42 (d, J=8.0 Hz, 1H), 5.8 (s, 1H), 4.37 (s, 1H), 3.48-3.43 (m, 1H), 3.10-3.07 (d, J=8.8 Hz, 1H), 2.87 (s, 3H), 1.60-1.58 (d, J=7.6 Hz, 3H), 1.15-1.13 (m, 1H), 0.35-00.31 (m, 2H), 0.16-0.15 (m, 2H).

LCMS: m/z 456.2 [M+H]⁺, RT=1.12 min.

Example 78: Synthesis of Compound 78

Using the same manner as in Example 1, Compound 78 was obtained from Intermediate A2 and Intermediate B12.

Synthesis of (S)-3-(2-(((S)-1-(1-(4-chlorophenyl)-1H-imidazol-4-yl)ethyl)amino)pyrimidin-4-yl)-4-isopropyl-1-trideuteromethyllimidazole-2-one

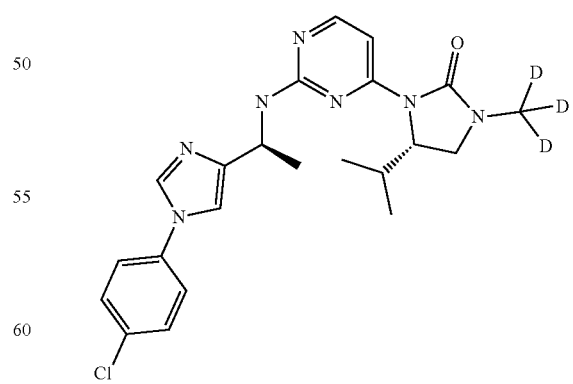

¹H NMR (CDCl3-d1, 400 MHz): δ 8.80 (d, J=5.6 Hz, 1H), 7.75 (s, 1H), 7.52 (d, J=5.6 Hz, 1H), 7.42 (d, J=8.4 Hz, 2H), 7.26 (d, J=9.2 Hz, 1H), 7.06 (s, 1H), 5.33 (d, J=7.6 Hz, 1H), 5.15 (s, 1H), 4.54-4.52 (m, 1H), 3.37 (t, J=9.2 Hz, 1H), 3.17-3.14 (m, 1H), 2.20 (s, 1H), 1.61 (d, J=6.8 Hz, 3H), 0.78 (d, J=6.0 Hz, 3H), 0.67 (d, J=6.4 Hz, 3H).
LCMS: m/z 443.2 [M+H]⁺, RT=0.88 min.

Example 79: Synthesis of Compound 79

Using the same manner as in Example 1, Compound 79 was obtained from Intermediate A2 and Intermediate B13.

(S)-3-(2-(((S)-1-(1-(4-chlorophenyl)-1H-imidazol-4-yl)ethyl)amino)-6-methylpyrimidin-4-yl) cyclopropyl-1-methylimidazolidine-2-one

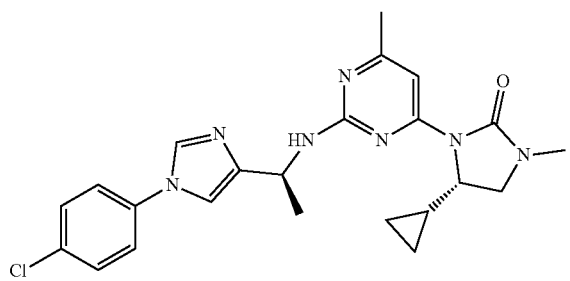 [SMILES: Cc1cc(N2C(=O)N(C)C[C@@H]2C2CC2)nc(N[C@@H](C)c2cn(-c3ccc(Cl)cc3)cn2)n1]

¹H-NMR (CDCl₃, 400 MHz): 10.63 (s, 1H), 8.59 (s, 1H), 7.72 (s, 1H), 7.62 (s, 1H), 7.54 (d, J=8.0 Hz, 2H), 7.42 (d, J=8.4 Hz, 2H), 5.57 (s, 1H), 34.61-4.58 (m, 1H), 3.62-3.58 (m, 1H), 3.17 (d, J=9.2 Hz, 1H), 2.94 (s, 3H), 2.45 (s, 3H), 1.69 (d, J=6.4 Hz, 3H), 1.08 (s, 1H), 0.30-0.19 (m, 4H).
LCMS: m/z 452.1 [M+H]⁺, RT=1.0 min.

Example 80: Synthesis of Compound 80

Using the same manner as in Example 1, Compound 80 was obtained from Intermediate A2 and Intermediate B14.

(S)-3-(2-(((S)-1-(1-(4-chlorophenyl)-1H-imidazol-4-yl)ethyl)amino)-5-fluoropyrimidin-4-yl)-1-isopropyl-1-methylimidazolidine-2-one

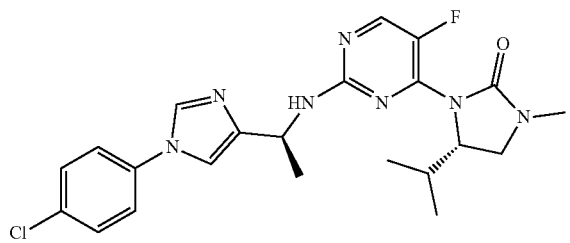 [SMILES: CC(C)[C@H]1CN(C)C(=O)N1c1nc(N[C@@H](C)c2cn(-c3ccc(Cl)cc3)cn2)ncc1F]

¹H-NMR (CDCl₃, 400 MHz): 8.13 (s, 1H), 7.75 (s, 1H), 7.45-7.43 (d, J=7.2 Hz, 2H), 7.30-7.28 (d, J=6.8 Hz, 2H), 7.08 (s, 1H), 5.42-5.35 (m, 1H), 5.15-5.05 (m, 1H), 4.54 (s, 1H), 3.40-3.6 (m, 1H), 3.26-3.22 (m, 1H), 2.87 (s, 3H), 2.11-2.02 (m, 1H), 1.58 (s, 3H), 0.79-0.77 (d, J=5.6 Hz, 3H), 0.74-0.73 (d, J=4.8 Hz, 3H).
LCMS: m/z 458.2 [M+H]⁺, RT=1.06 min.

Example 81: Synthesis of Compound 81

Using the same manner as in Example 1, Compound 81 was obtained from Intermediate A2 and Intermediate B15.

(R)-3-(2-((S)-1-(1-(4-chlorophenyl)-1H-imidazol-4-yl)ethyl)amino)pyrimidin-4-yl)-4-)-1-hydroxyethyl)-1-methyl-imidazolidine-2-one

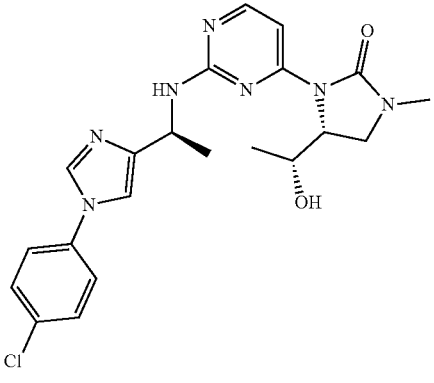 [SMILES: C[C@H](Nc1nccc(N2C(=O)N(C)C[C@@H]2[C@@H](C)O)n1)c1cn(-c2ccc(Cl)cc2)cn1]

¹H-NMR (CDCl₃, 400 MHz): 10.63 (s, 1H), 8.59 (s, 1H), 7.72 (s, 1H), 7.62 (s, 1H), 7.54 (d, J=8.0 Hz, 2H), 7.42 (d, J=8.4 Hz, 2H), 5.57 (s, 1H), 34.61-4.58 (m, 1H), 3.62-3.58 (m, 1H), 3.17 (d, J=9.2 Hz, 1H), 2.94 (s, 3H), 2.45 (s, 3H), 1.69 (d, J=6.4 Hz, 3H), 1.08 (s, 1H), 0.30-0.19 (m, 4H).
LCMS: m/z 442.2 [M+H]⁺, RT=0.82 min.

Example 82: Synthesis of Compound 82

(S)-1-(2-(((S)-1-(1-(4-chlorophenyl)-1H-imidazol-4-yl)ethyl)amino)pyrimidin-4-yl)-4, 4-dideutero-5-isopropylimidazolidine-2-one

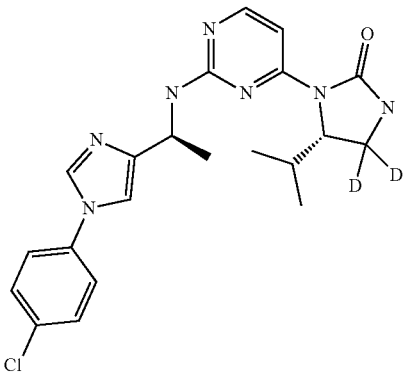 [SMILES: [2H]C1([2H])NC(=O)N(c2ccnc(N[C@@H](C)c3cn(-c4ccc(Cl)cc4)cn3)n2)[C@H]1C(C)C]

Using the same manner as in Example 1, Compound 82 was obtained from Intermediate A2 and Intermediate B16.
LCMS: m/z 428.2 [M+H]⁺; RT=0.838 min.
¹H-NMR (CDCl3-d1, 400 MHz): δ 8.08 (d, J=5.6 Hz, 1H), 7.76 (s, 1H), 7.48 (d, J=6.0 Hz, 1H), 7.42 (d, J=8.8 Hz, 2H), 7.27 (d, J=7.6 Hz, 2H), 7.08 (s, 1H), 5.51 (d, J=6.8 Hz, 1H), 5.41 (s, 1H), 5.18-5.14 (m, 1H), 4.65 (d, J=3.2 Hz, 1H), 2.43-2.42 (m, 1H), 1.62 (d, J=6.8 Hz, 3H), 0.79 (d, J=6.0 Hz, 3H), 0.75 (d, J=6.8 Hz, 3H).

Example 83: Synthesis of Compound 83

(S)-1-(2-(((S)-1-(1-(4-(trifluoromethyl)phenyl)-1H-imidazol-4-yl)ethyl)amino) pyrimidin-4-yl)-4,4-dideutero-5-isopropylimidazolidine-2-one

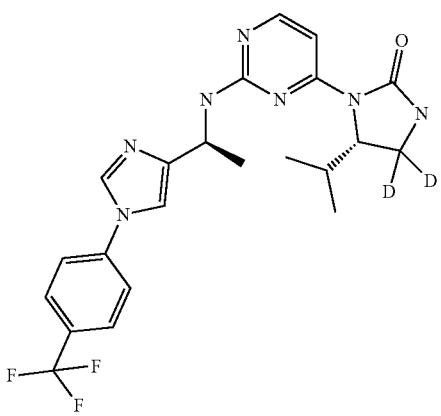 [SMILES: [2H]C1([2H])NC(=O)N(c2ccnc(N[C@@H](C)c3cn(-c4ccc(C(F)(F)F)cc4)cn3)n2)[C@H]1C(C)C]

Using the same manner as in Example 1, Compound 83 was obtained from Intermediate A46 and Intermediate B16.

LCMS: m/z 462.2 [M+H]$^+$; RT=0.922 min.

$^1$H-NMR (CDCl3-d1, 400 MHz): δ 8.10 (d, J=5.6 Hz, 1H), 7.85 (s, 1H), 7.72 (d, J=8.4 Hz, 2H), 7.50 (d, J=6.0 Hz, 1H), 7.46 (d, J=8.0 Hz, 2H), 7.16 (s, 1H), 5.43 (d, J=7.2 Hz, 1H), 5.19-5.16 (m, 1H), 5.08 (s, 1H), 4.65 (d, J=3.2 Hz, 1H), 2.43-2.42 (m, 1H), 1.63 (d, J=4.4 Hz, 3H), 0.79 (d, J=6.8 Hz, 3H), 0.75 (d, J=6.8 Hz, 3H).

Example 84: Synthesis of Compound 84

(S)-3-(2-(((S)-1-(1-(4-(trifluoromethyl)phenyl)-1H-imidazol-4-yl)ethyl)amino) pyrimidin-4-yl)-5,5-dideutero-4-isopropyl-1-methylimidazolidine-2-one

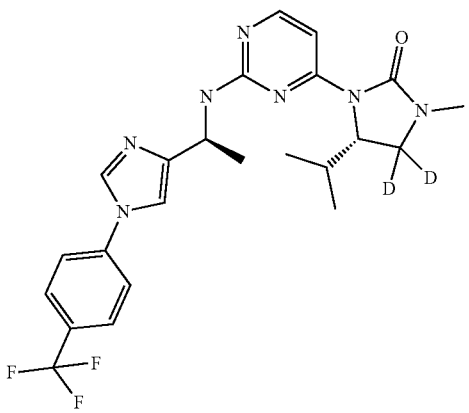 [SMILES: [2H]C1([2H])[C@H](C(C)C)N(c2ccnc(N[C@@H](C)c3cn(-c4ccc(C(F)(F)F)cc4)cn3)n2)C(=O)N1C]

Using the same manner as in Example 1, Compound 84 was obtained from Intermediate A46 and Intermediate B17.

LCMS: m/z 476.2 [M+H]$^+$; RT=0.969 min.

$^1$H-NMR (CDCl3-d1, 400 MHz): δ 8.07 (d, J=6.0 Hz, 1H), 7.85 (s, 1H), 7.72 (d, J=8.4 Hz, 2H), 7.54 (d, J=5.6 Hz, 1H), 7.46 (d, J=8.4 Hz, 2H), 7.15 (s, 1H), 5.48 (d, J=1.6 Hz, 1H), 5.19-5.16 (m, 1H), 4.52 (d, J=3.2 Hz, 1H), 2.86 (s, 3H), 2.43-2.42 (m, 1H), 1.62 (d, J=6.8 Hz, 3H), 0.79 (d, J=6.4 Hz, 3H), 0.67 (d, J=6.4 Hz, 3H).

Example 85: Synthesis of Compound 85

(S)-3-(2-(((S)-1-(1-(4-chlorophenyl)-1H-imidazol-4-yl)ethyl)amino)pyrimidin-4-yl)-5,5-dideutero-4-isopropyl-1-methylimidazolidine-2-one

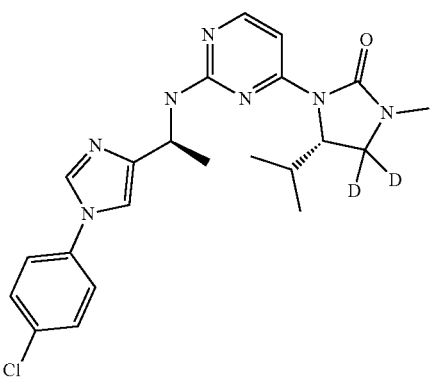 [SMILES: [2H]C1([2H])[C@H](C(C)C)N(c2ccnc(N[C@@H](C)c3cn(-c4ccc(Cl)cc4)cn3)n2)C(=O)N1C]

Using the same manner as in Example 1, Compound 85 was obtained from Intermediate A2 and Intermediate B17.

LCMS: m/z 442.2 [M+H]$^+$; RT=0.902 min.

$^1$H-NMR (CDCl3-d1, 400 MHz): δ 8.08 (d, J=6.0 Hz, 1H), 7.75 (s, 1H), 7.53 (d, J=6.0 Hz, 1H), 7.42 (d, J=8.8 Hz, 2H), 7.27 (d, J=8.8 Hz, 2H), 7.07 (s, 1H), 5.32 (d, J=6.8 Hz, 1H), 5.17-5.13 (m, 1H), 4.52 (d, J=3.6 Hz, 1H), 2.86 (s, 3H), 2.43-2.40 (m, 1H), 1.62 (d, J=3.2 Hz, 3H), 0.79 (d, J=6.8 Hz, 3H), 0.67 (d, J=6.8 Hz, 3H).

Example 86: Synthesis of Compound 86 and Compound 87

(5S)-1-(2-(((S)-1-(1-(4-chlorophenyl)-1H-imidazol-4-yl)ethyl)amino) pyrimidin-4-yl)-5-isopropyl-4-methylimidazolidine-2-one

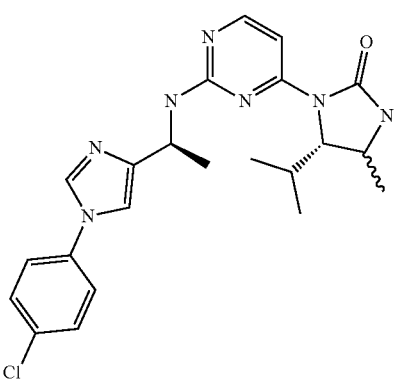 [SMILES: CC(C)[C@H]1C(C)NC(=O)N1c1ccnc(N[C@@H](C)c2cn(-c3ccc(Cl)cc3)cn2)n1]

Using the same manner as in Example 1, Compound 86 (single isomer) was obtained from Intermediate A2 and Intermediate B18.

¹H-NMR (CDCl₃, 400 MHz): 10.62 (s, 1H), 8.45 (s, 1H), 7.86 (d, J=7.2 Hz, 1H), 7.77 (d, J=7.2 Hz, 1H), 7.59-7.52 (m, 2H), 7.44-7.38 (m, 2H), 5.60-5.57 (m, 1H), 5.22 (s, 1H), 4.85 (s, 1H), 4.16-4.13 (m, 1H), 2.25-2.15 (m, 1H), 1.71 (d, J=6.8 Hz, 3H), 1.40 (d, J=6.8 Hz, 3H), 0.93-0.81 (m, 6H).

LCMS: m/z 440.2 [M+H]⁺; RT=0.97 min.

Using the same manner as in Example 1, Compound 87 (single isomer) was obtained from Intermediate A2 and Intermediate B19.

¹H NMR (CDCl₃, 400 MHz): δ 8.110-8.096 (m, 1H), 7.753-7.751 (m, 1H), 7.488-7.473 (m, 1H), 7.437-7.416 (m, 2H), 7.281-7.264 (m, 2H), 7.067 (s, 1H), 5.367-5.347 (m, 1H), 5.236-5.166 (m, 1H), 4.725-4.696 (m, 2H), 4.088-4.018 (m, 1H), 2.183-2.173 (m, 1H), 1.616 (d, J=7.2 Hz, 3H), 1.34 (d, J=6.8 Hz, 3H), 0.881-0.864 (m, 6H).

LCMS: m/z 440.2 [M+H]⁺; RT=0.89 min.

Example 87: Synthesis of Compound 88

(S)-5-isopropyl-1-(2-(((S)-1-(1-(4-(trifluoromethyl)phenyl)-1H-imidazol-4-yl) ethyl)amino))imidazolidine-2-one

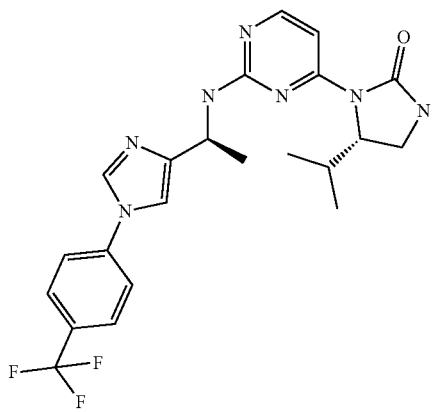 [SMILES: CC(C)[C@H]1CNC(=O)N1c1ccnc(N[C@@H](C)c2cn(-c3ccc(C(F)(F)F)cc3)cn2)n1]

Using the same manner as in Example 1, Compound 88 was obtained from Intermediate A46 and Intermediate B1.

¹H-NMR (CDCl₃, 400 MHz): 8.12-8.11 (d, J=5.6 Hz, 1H), 7.85 (s, 1H), 7.75-7.73 (d, J=8.4 Hz, 2H), 7.52-7.51 (d, J=5.6 Hz, 1H), 7.48-7.46 (d, J=8.4 Hz, 2H), 7.15 (s, 1H), 5.36-5.34 (d, J=6.8 Hz, 1H), 5.20-5.14 (m, 1H), 4.70-4.65 (m, 2H), 3.49-3.45 (m, 1H), 3.30-3.27 (m, 1H), 2.45-2.40 (m, 1H), 1.64-1.63 (d, J=6.8 Hz, 3H), 0.81-0.80 (d, J=5.2 Hz, 3H), 0.77-0.75 (d, J=7.2 Hz, 3H).

LCMS: m/z 460.3[M+H]⁺; RT=0.97 min.

Example 88: Synthesis of Compound 89

(S)-3-(2-(((S)-1-(1-(4-chlorophenyl)-1H-imidazol-4-yl)ethyl)amino)pyrimidin-4-yl)-5,5-dideutero-4-isopropyl-1-deuteromethylimidazolidine-2-one

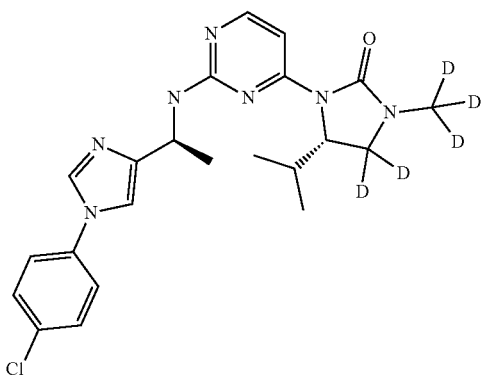 [SMILES: [2H]C([2H])([2H])N1C(=O)N(c2ccnc(N[C@@H](C)c3cn(-c4ccc(Cl)cc4)cn3)n2)[C@@H](C(C)C)C1([2H])[2H]]

Using the same manner as in Example 1, Compound 89 was obtained from Intermediate A2 and Intermediate B23.

LCMS: m/z 445.3 [M+H]⁺; RT=0.883 min.

¹H-NMR (CDCl3-d1, 400 MHz): δ 8.07 (d, J=6.0 Hz, 1H), 7.75 (s, 1H), 7.53 (d, J=5.60 Hz, 1H), 7.42 (d, J=8.4 Hz, 2H), 7.27 (d, J=8.4 Hz, 2H), 7.07 (s, 1H), 5.37 (d, J=7.2 Hz, 1H), 5.17-5.15 (m, 1H), 4.52 (d, J=3.6 Hz, 1H), 2.43-2.40 (m, 1H), 1.61 (d, J=6.8 Hz, 3H), 0.79 (d, J=6.4 Hz, 3H), 0.67 (d, J=6.8 Hz, 3H).

Example 89: Synthesis of Compound 90 and Compound 91

(5S)-1-(2-(((S)-1-(1-(4-chlorophenyl)-1H-imidazol-4-yl)ethyl)amino) pyrimidin-4-yl)-5-isopropyl-3,4-dimethylimidazolidine-2-one

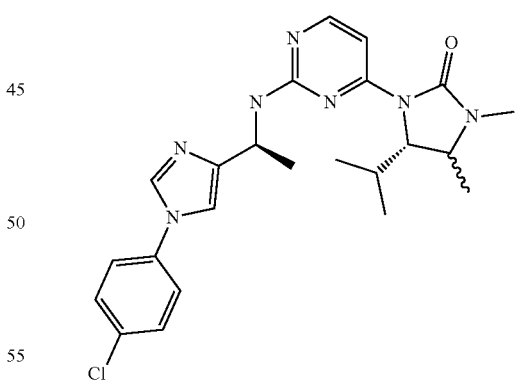

Using the same manner as in Example 1, Compound 90 (single isomer) was obtained from Intermediate A2 and Intermediate B20.

LCMS: m/z 454.2 [M+H]⁺; RT=1.02 min.

¹H-NMR (CDCl3-d1, 400 MHz): δ 10.57 (s, 1H), 8.64-8.62 (m, 1H), 7.94 (d, J=6.8 Hz, 1H), 7.76 (d, J=6.0 Hz, 1H), 7.63 (s, 1H), 7.55 (d, J=8.0 Hz, 2H), 7.43-7.38 (m, 2H), 5.66 (s, 1H), 4.87 (d, J=3.6 Hz, 1H), 3.89-3.85 (m, 1H), 2.85 (s, 3H), 2.15 (s, 1H), 1.72-1.66 (m, 3H), 1.41-1.34 (m, 3H), 0.82-0.69 (m, 3H).

Using the same manner as in Example 1, Compound 91 (single isomer) was obtained from Intermediate A2 and Intermediate B21.

LCMS: m/z 454.2 [M+H]$^+$; RT=0.94 min.

$^1$H-NMR (CDCl3-d1, 400 MHz): δ 8.101-8.087 (m, 1H), 7.749-7.747 (m, 1H), 7.532-7.518 (m, 1H), 7.436-7.414 (m, 2H), 7.279-7.263 (m, 2H), 7.059 (s, 1H), 5.296-5.276 (m, 1H), 5.240-5.170 (m, 1H), 4.713-4.686 (m, 1H), 3.727-3.657 (m, 1H), 2.756 (s, 3H), 2.126-2.118 (m, 1H), 1.612 (d, J=6.8 Hz, 3H), 1.34 (d, J=6.8 Hz, 3H), 0.835-0.818 (m, 6H).

Example 90: Synthesis of Compound 92 and Compound 93

(5S)-1-(2-(((S)-1-(1-(4-trifluoromethylphenyl)-1H-imidazol-4-yl)ethyl)amino) pyrimidin-4-yl)-5-isopropyl-4-methylimidazolidine-2-one

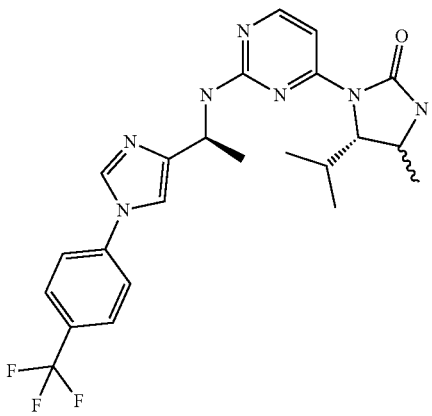 [SMILES: CC(C)[C@H]1C(C)NC(=O)N1c1ccnc(N[C@@H](C)c2cn(-c3ccc(C(F)(F)F)cc3)cn2)n1]

Using the same manner as in Example 1, Compound 92 (single isomer) was obtained from Intermediate A46 and Intermediate B18.

LCMS: m/z 474.3 [M+H]$^+$; RT=0.94 min.

$^1$H-NMR (CDCl3-d1, 400 MHz): δ 8.10 (d, J=5.6 Hz, 1H), 7.85 (s, 1H), 7.72 (d, J=8.4 Hz, 2H), 7.53 (d, J=6.0 Hz, 1H), 7.46 (d, J=8.4 Hz, 2H), 7.15 (s, 1H), 5.35 (d, J=8.0 Hz, 1H), 5.20-5.18 (m, 1H), 4.79 (s, 1H), 4.19 (s, 1H), 3.54-3.51 (m, 1H), 2.41-2.38 (m, 1H), 1.63 (d, J=7.2 Hz, 3H), 1.23 (d, J=6.4 Hz, 3H), 0.82 (d, J=6.4 Hz, 3H), 0.73 (d, J=6.8 Hz, 3H).

Using the same manner as in Example 1, Compound 93 (single isomer) was obtained from Intermediate A46 and Intermediate B19.

LCMS: m/z 474.3 [M+H]$^+$; RT=0.95 min.

$^1$H-NMR (CDCl3-d1, 400 MHz): δ 8.119-8.104 (m, 1H), 7.848 (s, 1H), 7.739-7.718 (m, 2H), 7.499-7.448 (m, 3H), 7.146 (s, 1H), 5.346-5.326 (m, 1H), 5.252-5.184 (m, 1H), 4.724-4.697 (m, 1H), 4.651 (s, 1H), 4.090-4.020 (m, 1H), 2.172 (s, 1H), 1.626 (d, J=6.8 Hz, 3H), 1.34 (d, J=6.8 Hz, 3H), 0.880-0.863 (m, 6H).

Example 91: Synthesis of Compound 94 and Compound 95

(4S)-4-isopropyl-1,5-methyl-3-(2-(((S)-1-(1-(4-trifluoromethylphenyl)-1H-imidazole-4-yl)ethyl)amino)pyrimidin-4-yl)imidazolidine-2-one

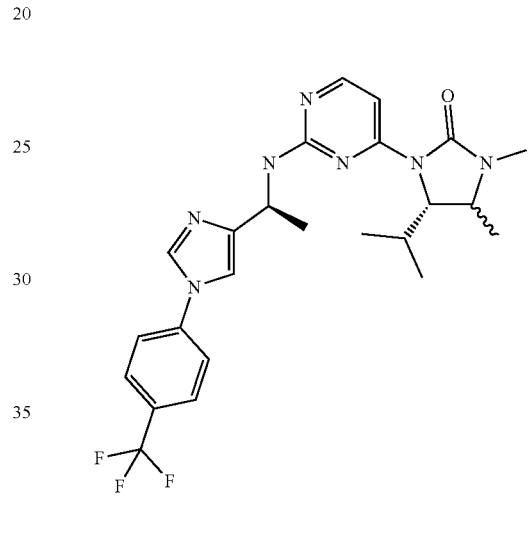

Using the same manner as in Example 1, Compound 94 (single isomer) was obtained from Intermediate A46 and Intermediate B20.

LCMS: m/z 488.3 [M+H]$^+$; RT=1.00 min.

$^1$H-NMR (CDCl3-d1, 400 MHz): δ 10.57 (s, 1H), 8.90 (s, 1H), 7.96 (s, 1H), 7.89-7.83 (m, 3H), 7.77 (s, 1H), 7.68 (d, J=8.0 Hz, 2H), 5.70-5.68 (m, 1H), 4.87 (d, J=6.0 Hz, 1H), 3.90-3.87 (m, 1H), 2.85 (s, 3H), 2.05 (s, 1H), 1.72 (d, J=5.6 Hz, 3H), 1.40 (d, J=6.8 Hz, 3H), 0.83-0.78 (m, 6H).

Using the same manner as in Example 1, Compound 95 (single isomer) was obtained from Intermediate A46 and Intermediate B21.

LCMS: m/z 488.3 [M+H]$^+$; RT=1.01 min.

$^1$H-NMR (CDCl3-d1, 400 MHz): δ 8.103-8.089 (m, 1H), 7.847-7.844 (m, 1H), 7.737-7.716 (m, 2H), 7.542-7.527 (m, 1H), 7.466-7.445 (m, 2H), 7.142 (s, 1H), 5.324-5.304 (m, 1H), 5.257-5.187 (m, 1H), 4.715-4.687 (m, 1H), 3.731-3.661 (m, 1H), 2.757 (s, 3H), 2.132-2.125 (m, 1H), 1.622 (d, J=6.8 Hz, 3H), 1.34 (d, J=7.2 Hz, 3H), 0.832-0.815 (m, 6H).

Example 92: Synthesis of Compound 96

(S)-3-(2-(((S)-1-(1-(4-trifluoromethylphenyl)-1H-imidazol-4-yl)ethyl)amino)pyrimidin-4-yl)-5,5-dideutero-4-isopropyl-1-trideuteromethylimidazolidine-2-one

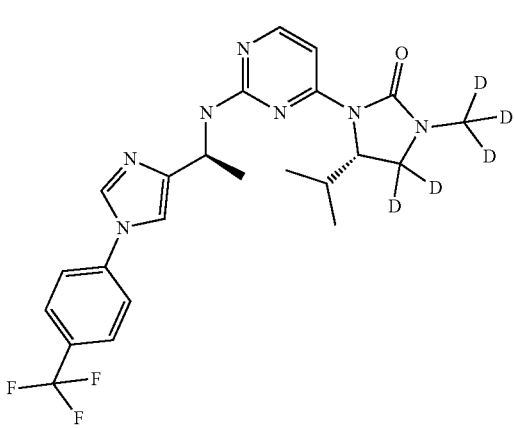 [SMILES: [2H]C([2H])([2H])N1C(=O)N(c2ccnc(N[C@@H](C)c3cn(-c4ccc(C(F)(F)F)cc4)cn3)n2)[C@@H](C(C)C)C1([2H])[2H]]

Using the same manner as in Example 1, Compound 96 was obtained from Intermediate A46 and Intermediate B23.
LCMS: m/z 479.3 [M+H]⁺; RT=1.04 min.
¹H-NMR (CDCl3-d1, 400 MHz): δ 8.07 (d, J=6.0 Hz, 1H), 7.85 (s, 1H), 7.72 (d, J=8.4 Hz, 2H), 7.54 (d, J=5.6 Hz, 1H), 7.46 (d, J=8.4 Hz, 2H), 7.15 (s, 1H), 5.32 (d, J=7.2 Hz, 1H), 5.17-5.15 (m, 1H), 4.52 (d, J=3.2 Hz, 1H), 2.42-2.40 (m, 1H), 1.62 (d, J=6.8 Hz, 3H), 0.79 (d, J=6.0 Hz, 3H), 0.67 (d, J=6.8 Hz, 3H).

Example 93: Synthesis of Compound 97

(S)-3-(2-((1-(1-(3-chloro-5-fluorophenyl)-1H-imidazol-4-yl)cyclopropyl)amino)pyrimidin-4-yl)-4-isopropyl-1-methylimidazolidine-2-one

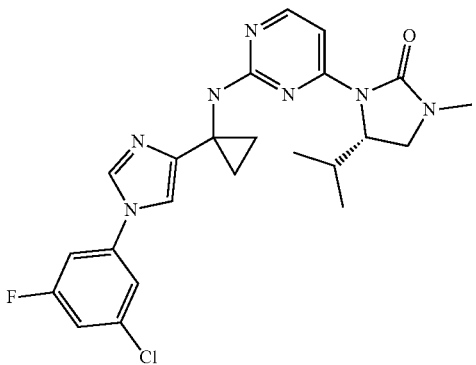 [SMILES: CC(C)[C@H]1CN(C)C(=O)N1c1ccnc(NC2(c3cn(-c4cc(F)cc(Cl)c4)cn3)CC2)n1]

Using the same manner as in Example 1, Compound 97 was obtained from Intermediate A33 and Intermediate B27.
LCMS: m/z 470.1 [M+H]⁺; RT=1.07 min.
¹H-NMR (CDCl3-d₁, 400 MHz): δ 8.39 (s, 1H), 7.98-7.97 (d, J=6.8 Hz, 1H), 7.81-7.79 (d, J=7.2 Hz, 1H), 7.25 (s, 2H), 7.21-7.19 (d, J=7.6 Hz, 1H), 7.09-7.07 (d, J=8.4 Hz, 1H), 4.47-4.44 (d, J=8.8 Hz, 1H), 3.48-3.44 (m, 1H), 3.21-3.18 (m, 1H), 2.91 (s, 3H), 2.27-2.26 (d, J=2.8 Hz, 1H), 1.65-1.43 (m, 4H), 0.80-0.78 (d, J=6.8 Hz, 3H), 0.69-0.68 (d, J=6.8 Hz, 3H).

Example 94: Synthesis of Compound 98

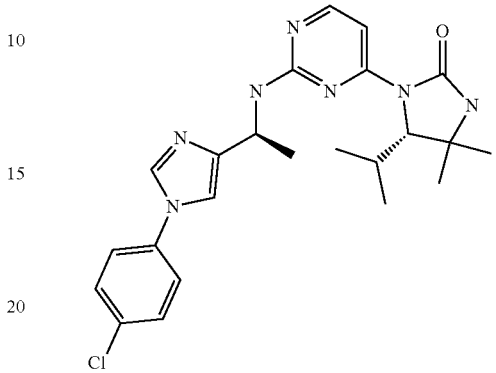

Using the same manner as in Example 1, Compound 98 was obtained from Intermediate A2 and Intermediate B22.
LCMS: m/z 454.3 [M+H]⁺; RT=0.98 min.
¹H-NMR (CDCl₃, 400 MHz): 8.110-8.096 (m, 1H), 7.759-7.756 (m, 1H), 7.490-7.475 (m, 1H), 7.439-7.417 (m, 2H), 7.285-7.266 (m, 2H), 7.076 (s, 1H), 5.393-5.374 (m, 1H), 5.220-5.186 (m, 1H), 4.718 (s, 1H), 4.424-4.416 (m, 1H), 2.150-2.125 (m, 1H), 1.618 (d, J=6.4 Hz, 3H), 1.351 (s, 3H), 1.270 (s, 3H), 0.875-0.829 (m, 6H).

Example 95: Synthesis of Compound 99

(S)-6-(2-(((S)-1-(1-(4-chlorophenyl)-1H-imidazol-4-yl)ethyl)amino) pyrimidin-4-yl)-7-isopropyl-4,6-diazaspiro[2.4] hept-5-one

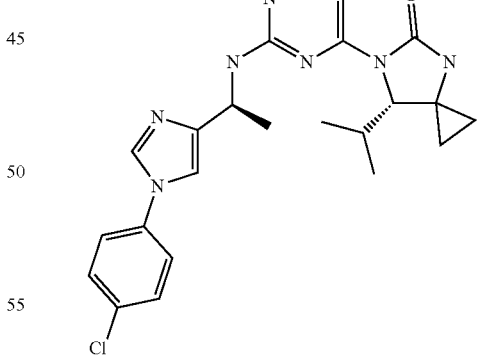

Using the same manner as in Example 1, Compound 99 was obtained from Intermediate A2 and Intermediate B24.
LCMS: m/z 452.2 [M+H]⁺; RT=0.967 min.
¹H-NMR (CDCl3-d1, 400 MHz): δ 10.68 (d, J=7.26 Hz, 1H), 8.48 (s, 1H), 7.90 (d, J=7.2 Hz, 1H), 7.79 (d, J=7.2 Hz, 1H), 7.58-7.53 (m, 3H), 7.40 (d, J=8.8 Hz, 2H), 5.61 (s, 1H), 4.89 (s, 1H), 4.63 (s, 1H), 4.36 (s, 1H), 2.12-2.08 (m, 1H), 1.71 (d, J=6.8 Hz, 3H), 1.29-1.25 (m, 1H), 0.98-0.78 (m, 9H).

Example 96: Synthesis of Compound 100

(S)-6-(2-(((S)-1-(1-(4-chlorophenyl)-1H-imidazol-4-yl)ethyl)amino) pyrimidin-4-yl)-7-isopropyl-4-methyl-4,6-diazaspiro[2.4]hept-5-one

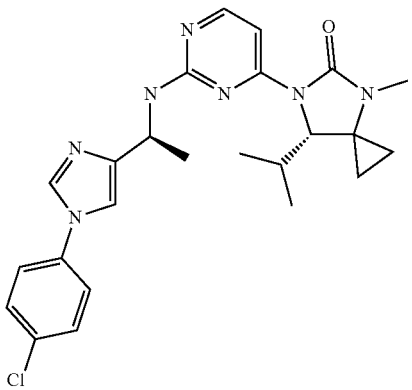 [SMILES: CC(C)[C@@H]1N(c2ccnc(N[C@@H](C)c3cn(-c4ccc(Cl)cc4)cn3)n2)C(=O)N(C)C12CC2]

Using the same manner as in Example 1, Compound 100 was obtained from Intermediate A2 and Intermediate B25.
LCMS: m/z 466.2 [M+H]$^+$; RT=1.003 min.
$^1$H-NMR (CDCl3-d1, 400 MHz): δ 10.61 (d, J=6.4 Hz, 1H), 8.43 (s, 1H), 7.94 (d, J=7.2 Hz, 1H), 7.75 (d, J=7.6 Hz, 1H), 7.56-7.52 (m, 3H), 7.39 (d, J=8.8 Hz, 2H), 5.60 (s, 1H), 4.59 (s, 1H), 2.62 (s, 3H), 1.70 (d, J=6.4 Hz, 3H), 1.20-1.16 (m, 2H), 1.04-1.01 (m, 1H), 0.92-0.86 (m, 4H), 0.78-0.73 (m, 3H).

Example 97: Synthesis of Compound 101

(S)-5-isopropyl-4,4-dimethyl-1-(2-(((S)-1-(1-(4-(trifluoromethyl)phenyl)-1H-imidazole)-4-yl)ethyl)amino)pyrimidin-4-yl)imidazolidine-2-one

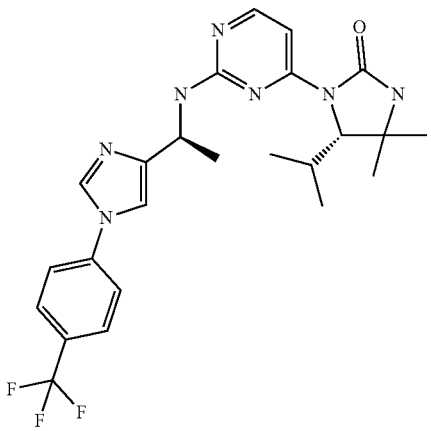 [SMILES: CC(C)[C@@H]1N(c2ccnc(N[C@@H](C)c3cn(-c4ccc(C(F)(F)F)cc4)cn3)n2)C(=O)NC1(C)C]

Using the same manner as in Example 1, Compound 101 was obtained from Intermediate A46 and Intermediate B22.
LCMS: m/z 488.3 [M+H]$^+$; RT=1.011 min.
$^1$H-NMR (CDCl3-d1, 400 MHz): δ 8.122-8.108 (m, 1H), 7.854-7.852 (m, 1H), 7.741-7.720 (m, 2H), 7.501-7.451 (m, 3H), 7.152 (s, 1H), 5.343-5.323 (m, 1H), 5.257-5.185 (m, 1H), 4.598 (s, 1H), 4.423-4.416 (m, 1H), 2.158-2.135 (m, 1H), 1.628 (d, J=6.4 Hz, 3H), 1.351 (s, 3H), 1.273 (s, 3H), 0.874-0.825 (m, 6H).

Example 98: Synthesis of Compound 102

(S)-7-isopropyl-6-(2-(((S)-1-(1-(4-(trifluoromethyl)phenyl)-1H-imidazol-4-yl) ethyl)amino))-4,6-diazaspiro[2.4]hept-5-one

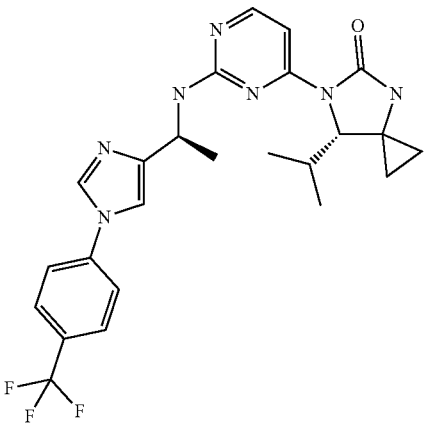 [SMILES: CC(C)[C@@H]1N(c2ccnc(N[C@@H](C)c3cn(-c4ccc(C(F)(F)F)cc4)cn3)n2)C(=O)NC12CC2]

Using the same manner as in Example 1, Compound 102 was obtained from Intermediate A46 and Intermediate B24.
LCMS: m/z 486.3 [M+H]$^+$; RT=0.97 min.
$^1$H-NMR (CDCl3-d1, 400 MHz): δ 10.59 (d, J=6.8 Hz, 1H), 8.38 (s, 1H), 7.89 (d, J=7.2 Hz, 1H), 7.83-7.78 (m, 3H), 7.62-7.58 (m, 2H), 5.52 (s, 1H), 5.04 (s, 1H), 4.59 (s, 1H), 2.12-2.10 (m, 1H), 1.69 (d, J=6.4 Hz, 3H), 1.32-1.29 (m, 1H), 1.02-0.99 (m, 1H), 0.94-0.78 (m, 8H).

Example 99: Synthesis of Compound 103

(S)-7-isopropyl-4-methyl-6-(2-(((S)-1-(1-(4-(trifluoromethyl)phenyl)-1H-imidazole-4-yl) Ethyl)amino)-4-yl)-4,6-diazaspiro[2.4]hept-5-one

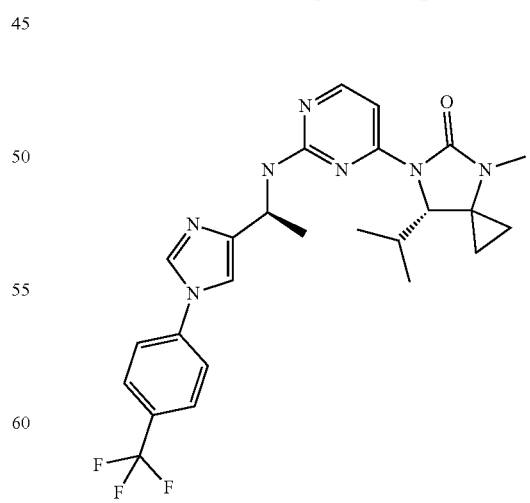

Using the same manner as in Example 1, Compound 103 was obtained from Intermediate A46 and Intermediate B25.
LCMS: m/z 500.2 [M+H]$^+$; RT=1.012 min.

¹H-NMR (CDCl3-d1, 400 MHz): δ 10.54 (s, 1H), 8.52 (s, 1H), 7.95 (d, J=6.8 Hz, 1H), 7.84 (d, J=8.0 Hz, 2H), 7.76 (d, J=6.8 Hz, 1H), 7.68 (s, 1H), 7.61 (d, J=4.0 Hz, 2H), 5.59 (s, 1H), 4.58 (s, 1H), 2.62 (s, 3H), 2.05-2.03 (m, 1H), 1.70 (d, J=6.0 Hz, 3H), 1.21-1.16 (m, 2H), 0.92-0.87 (m, 4H), 0.76 (d, J=6.0 Hz, 3H).

Example 100: Synthesis of Compound 104

(S)-8-isopropyl-7-(2-(((S)-1-(1-(4-chlorophenyl)-1H-imidazol-4-yl)ethyl)amino)pyrimidin-4-yl)-2-oxa-5,7-diazaspiro[3.4]oct-6-one Using the same manner as in Example 1, Compound 104 was obtained from Intermediate A2 and Intermediate B30.

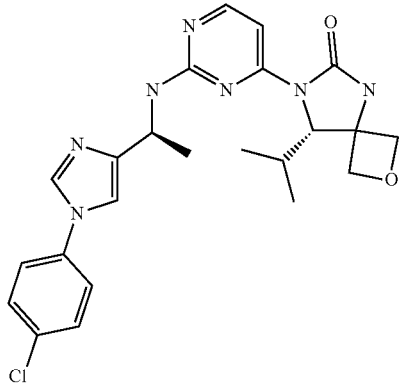 [SMILES: CC(C)[C@@H]1N(c2ccnc(N[C@@H](C)c3cn(-c4ccc(Cl)cc4)cn3)n2)C(=O)NC12COC2]

¹H-NMR (CDCl₃, 400 MHz): 8.13 (d, J=6.0 Hz, 1H), 7.78 (d, J=6.8 Hz, 1H), 7.44-7.41 (m, 3H), 7.32-7.27 (m, 2H), 7.09 (s, 1H), 5.88 (s, 1H), 5.47 (d, J=8.0 Hz, 1H), 5.23-5.17 (m, 2H), 4.98 (s, 1H), 4.79 (d, J=6.8 Hz, 1H), 4.72-4.69 (m, 1H), 4.63 (d, J=6.8 Hz, 1H), 2.29-2.27 (m, 1H), 1.63 (d, J=6.8 Hz, 3H), 0.93 (d, J=6.4 Hz, 3H), 0.78 (s, 3H).
LCMS: m/z 468.2 [M+H]⁺; RT=0.9 min.

Example 101: Synthesis of Compound 105

(S)-8-isopropyl-7-(2-(((S)-1-(1-(4-trifluoromethylphenyl)-1H-imidazol-4-yl)ethyl)amino)pyrimidin-4-yl)-2-oxa-5,7-diazaspiro[3.4]oct-6-one

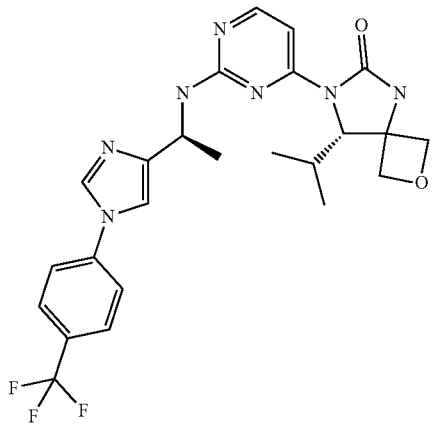 [SMILES: CC(C)[C@@H]1N(c2ccnc(N[C@@H](C)c3cn(-c4ccc(C(F)(F)F)cc4)cn3)n2)C(=O)NC12COC2]

Using the same manner as in Example 1, Compound 105 was obtained from Intermediate A46 and Intermediate B30.

¹H-NMR (CDCl₃, 400 MHz): 8.13 (d, J=6.0 Hz, 1H), 7.86 (s, 1H), 7.75-7.70 (m, 2H), 7.52-7.42 (m, 3H), 7.016 (s, 1H), 5.63 (s, 1H), 5.41-5.37 (m, 1H), 5.25-5.17 (m, 2H), 4.98 (s, 1H), 4.79 (d, J=7.2 Hz, 1H), 4.70 (d, J=7.6 Hz, 1H), 4.63 (d, J=7.2 Hz, 1H), 2.31-2.28 (m, 1H), 1.64 (d, J=6.8 Hz, 3H), 0.94-0.83 (m, 3H), 0.71 (d, J=6.4 Hz, 3H).
LCMS: m/z 502.2 [M+H]⁺; RT=1.0 min.

Example 102: Synthesis of Compound 106

(S)-8-isopropyl-5-methyl-7-(2-(((S)-1-(1-(4-trifluoromethylphenyl)-1H-imidazol-4-yl)ethyl)amino)pyrimidin-4-yl)-2-oxa-5,7-diazaspiro[3.4]oct-6-one

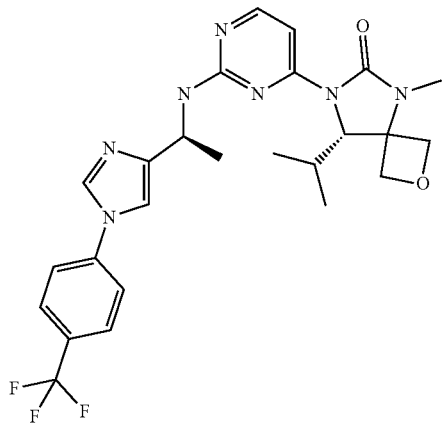 [SMILES: CC(C)[C@@H]1N(c2ccnc(N[C@@H](C)c3cn(-c4ccc(C(F)(F)F)cc4)cn3)n2)C(=O)N(C)C12COC2]

Using the same manner as in Example 1, Compound 106 was obtained from Intermediate A46 and Intermediate B31.

¹H-NMR (CDCl₃, 400 MHz): 8.11 (d, J=6.0 Hz, 1H), 7.86 (s, 1H), 7.73 (d, J=8.4 Hz, 2H), 7.47 (d, J=6.0 Hz, 3H), 7.15 (s, 1H), 5.34 (d, J=8.0 Hz, 1H), 5.25-5.16 (m, 2H), 4.95 (s, 1H), 4.88 (d, J=8.4 Hz, 1H), 4.78 (d, J=7.2 Hz, 1H), 4.67 (d, J=7.2 Hz, 1H), 3.13 (s, 3H), 2.25-2.22 (m, 1H), 1.63 (d, J=6.8 Hz, 3H), 0.85 (d, J=6.8 Hz, 3H), 0.73 (d, J=4.4 Hz, 3H).
LCMS: m/z 516.2 [M+H]⁺; RT=1.0 min.

Example 103: Synthesis of Compound 107

(S)-8-isopropyl-5-trideuteromethyl-7-(2-(((S)-1-(1-(4-trifluoromethylphenyl)-1H-imidazol-4-yl)ethyl)amino)pyrimidin-4-yl)-2-oxa-5,7-diazaspiro[3.4]oct-6-one

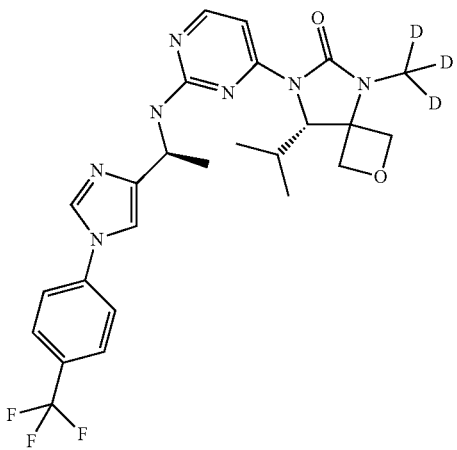 [SMILES: [2H]C([2H])([2H])N1C(=O)N(c2ccnc(N[C@@H](C)c3cn(-c4ccc(C(F)(F)F)cc4)cn3)n2)[C@@H](C(C)C)C12COC2]

Using the same manner as in Example 1, Compound 107 was obtained from Intermediate A46 and Intermediate B32.
$^{1}$H-NMR (CDCl$_3$, 400 MHz): 8.11 (d, J=6.0 Hz, 1H), 7.86 (s, 1H), 7.73 (d, J=8.4 Hz, 2H), 7.47 (d, J=6.0 Hz, 3H), 7.15 (s, 1H), 5.36 (d, J=8.0 Hz, 1H), 5.25-5.16 (m, 2H), 4.95 (s, 1H), 4.88 (d, J=8.0 Hz, 1H), 4.77 (d, J=7.2 Hz, 1H), 4.67 (d, J=7.2 Hz, 1H), 2.25-2.22 (m, 1H), 1.64 (d, J=6.8 Hz, 3H), 0.85 (d, J=6.8 Hz, 3H), 0.72 (br, 3H).
LCMS: m/z 519.2 [M+H]$^+$; RT=1.0 min.

Example 104: Synthesis of Compound 108

Compound (S)-4,4,-dideutero-5-isopropyl-1-(2-(((S)-1-(4-methyl-2'-(trifluoromethyl)-[3, 4'-bipyridyl]-6-yl)ethyl)amino)pyrimidin-4-yl)imidazolidine-2-one

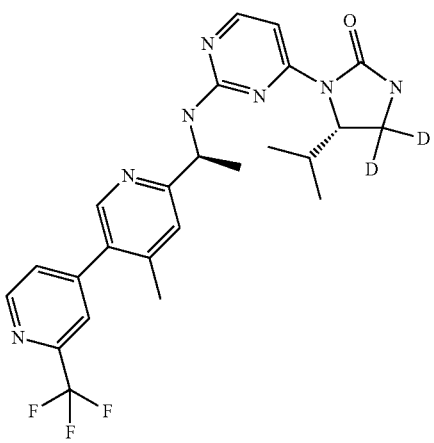 [SMILES: [2H]C1([2H])NC(=O)N(c2ccnc(N[C@@H](C)c3cc(C)c(-c4ccnc(C(F)(F)F)c4)cn3)n2)[C@H]1C(C)C]

Using the same manner as in Example 1, Compound 108 was obtained from Intermediate A8 and Intermediate B16.
$^{1}$H-NMR (CDCl$_3$, 400 MHz): 8.82 (d, J=5.2 Hz, 1H), 8.39 (s, 1H), 8.11 (d, J=6.0 Hz, 1H), 7.64 (s, 1H), 7.52 (d, J=6.0 Hz, 1H), 7.45 (d, J=4.8 Hz, 1H), 7.26 (s, 1H), 5.71 (d, J=6.8 Hz, 1H), 5.16-5.15 (m, 1H), 4.78 (s, 1H), 4.62 (s, 1H), 2.28 (s, 3H), 2.18-2.05 (m, 1H), 1.60 (d, J=6.8 Hz, 3H), 0.73-0.67 (m, 3H).
LCMS: m/z 488.2 [M+H]$^+$; RT=1.0 min.

Example 105: Synthesis of Compound 109

((S)-4-isopropyl-5,5-dideutero-1-methyl-3-(2-(((S)-1-(4-methyl-2'-(trifluoromethyl)-[3,4'-bipyridyl]-6-yl)ethyl)amino)pyrimidin-4-yl)imidazolidine-2-one

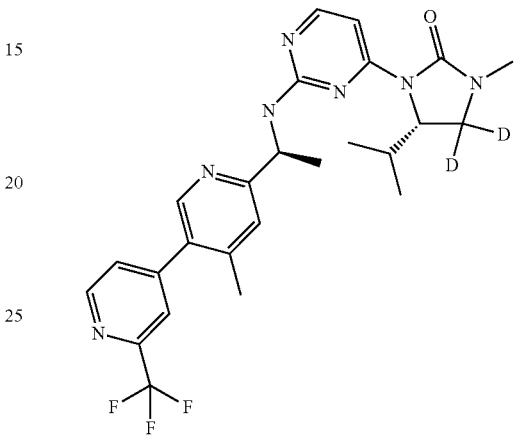

Using the same manner as in Example 1, Compound 109 was obtained from Intermediate A8 and Intermediate B17.
$^{1}$H-NMR (CDCl$_3$, 400 MHz): 8.82 (d, J=5.2 Hz, 1H), 8.38 (s, 1H), 8.09 (d, J=5.6 Hz, 1H), 7.64 (s, 1H), 7.55 (d, J=6.0 Hz, 1H), 7.45 (d, J=4.0 Hz, 1H), 7.27 (s, 1H), 5.69 (d, J=6.8 Hz, 1H), 5.16-5.15 (m, 1H), 4.48 (s, 1H), 2.85 (s, 3H), 2.28 (s, 3H), 2.18-2.05 (m, 1H), 1.59 (d, J=6.8 Hz, 3H), 0.73-0.64 (m, 3H).
LCMS: m/z 502.2 [M+H]$^+$; RT=0.98 min.

Example 106: Synthesis of Compound 110

(S)-3-(2-((1-(1-(3,5-dichlorophenyl)-1H-imidazol-4-yl)cyclopropyl)amino)pyrimidin-4-yl)-5,5-dideutero-4-isopropyl-1-methylimidazolidine-2-one

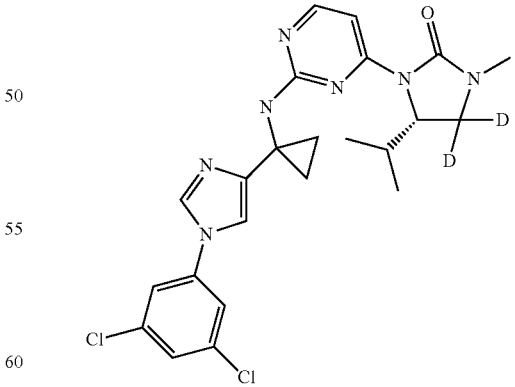

Using the same manner as in Example 1, Compound 110 was obtained from Intermediate A18 and Intermediate B33.
LCMS: m/z 488.2 [M+H]$^+$; RT=2.08 min.
1H NMR (400 MHz, cdcl3) δ 8.08 (d, J=5.9 Hz, 1H), 7.65 (d, J=1.6 Hz, 1H), 7.56 (dd, J=5.9, 1.8 Hz, 1H), 7.29-7.26

(m, 1H), 7.24 (s, 1H), 7.18 (d, J=1.8 Hz, 2H), 6.97 (s, 1H), 5.75 (s, 1H), 4.36 (s, 1H), 2.82 (s, 3H), 2.35 (s, 1H), 1.76 (s, 2H), 1.50 (dd, J=4.7, 2.5 Hz, 2H), 0.63 (s, 6H).

Example 107: Synthesis of Compound 111

(S)-3-(2-((1-(1-(3-chlorophenyl)-1H-imidazol-4-yl)cyclopropyl)amino)pyridin-4-yl)-5,5-dideutero-4-isopropyl-1-methylimidazolidine-2one

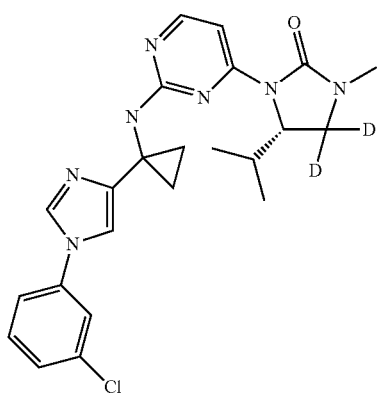 [SMILES: [2H]C1([2H])[C@H](C(C)C)N(c2ccnc(NC3(c4cn(-c5cccc(Cl)c5)cn4)CC3)n2)C(=O)N1C]

Using the same manner as in Example 1, Compound 111 was obtained from Intermediate A22 and Intermediate B33.
LCMS: m/z 488.2 [M+H]$^+$; RT=1.95 min.
1H NMR (400 MHz, cdcl3) δ 8.08 (d, J=5.9 Hz, 1H), 7.65 (s, 1H), 7.56 (d, J=5.9 Hz, 1H), 7.34 (d, J=8.7 Hz, 2H), 7.28 (s, 2H), 7.17 (d, J=6.6 Hz, 1H), 6.98 (s, 1H), 5.66 (s, 1H), 4.38 (s, 1H), 2.82 (s, 3H), 2.35 (s, 1H), 1.63 (s, 2H), 1.51 (d, J=9.2 Hz, 2H), 0.64 (d, J=21.4 Hz, 6H).

Example 108: Synthesis of Compound 112

Using the same manner as in Example 1, Compound 112 was obtained from Intermediate A46 and Intermediate B12.

(S)-3-(2-(((S)-1-(1-(4-trifluoromethylphenyl)-1H-imidazol-4-yl)ethyl)amino)pyrimidin-4-yl)-4-isopropyl-1-trideuteromethylimidazol-2-one

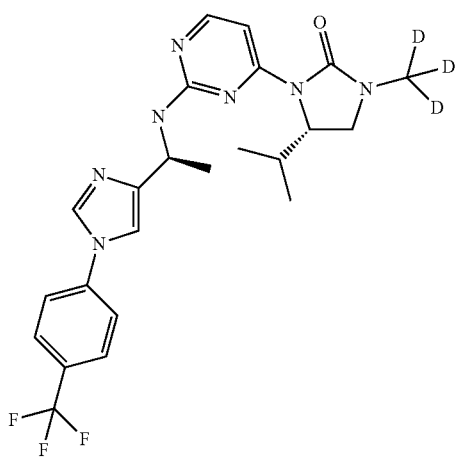 [SMILES: [2H]C([2H])([2H])N1C[C@H](C(C)C)N(c2ccnc(N[C@@H](C)c3cn(-c4ccc(C(F)(F)F)cc4)cn3)n2)C1=O]

LCMS: m/z 477.1 [M+H]$^+$; RT=2.01 min.

$^1$H NMR (400 MHz, DMSO) δ 8.30 (s, 1H), 7.99 (d, J=5.7 Hz, 1H), 7.82 (s, 4H), 7.49 (s, 1H), 7.30 (d, J=5.6 Hz, 1H), 7.01 (s, 1H), 4.94 (s, 1H), 4.37 (s, 1H), 3.35 (t, J=9.6 Hz, 1H), 3.16 (s, 1H), 2.25-2.08 (m, 1H), 1.44 (d, J=6.9 Hz, 3H), 0.85-0.36 (m, 6H).

Example 109: Synthesis of Compound 113

Using the same manner as in Example 1, Compound 113 was obtained from Intermediate A30 and Intermediate B28.

(S)-3-(2-(((S)-1-(1-(4-trifluoromethylphenyl)-1H-imidazol-4-yl)ethyl)amino)pyrimidin-4-yl)-4-isopropyl-1-trideuteromethylimidazol-2-one

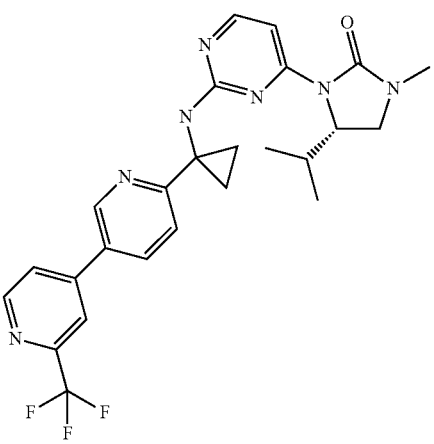 [SMILES: CC(C)[C@H]1CN(C)C(=O)N1c1ccnc(NC2(c3ccc(-c4ccnc(C(F)(F)F)c4)cn3)CC2)n1]

$^1$H NMR (CDCl$_3$-d$_1$, 400 MHz): 8.80 (d, J=4.8 Hz, 1H), 8.76 (s, 1H), 8.12 (d, J=6.0 Hz, 1H), 7.84 (s, 1H), 7.81-7.78 (m, 1H), 7.66-7.61 (m, 2H), 7.54 (d, J=8.0 Hz, 1H), 5.75 (s, 1H), 4.20-4.15 (m, 1H), 3.29-3.27 (m, 1H), 3.06-3.04 (m, 1H), 2.82 (s, 3H), 2.04-1.98 (m, 1H), 1.83-1.77 (m, 3H), 1.37-1.34 (m, 3H), 0.56-0.47 (m, 4H)
LCMS: m/z 498.2 [M+H]$^+$, RT=1.1 min.

Example 110: Synthesis of Compound 114

Using the same manner as in Example 1, Compound 114 was obtained from Intermediate A10 and Intermediate B16.

(S)-1-(2-(((S)-1-(2'-(trifluoromethyl)-[3,4'-bipyridyl]-6-yl)ethyl)amino)-5,5-dideutero-4-isopropyl-imidazolidine-2-one

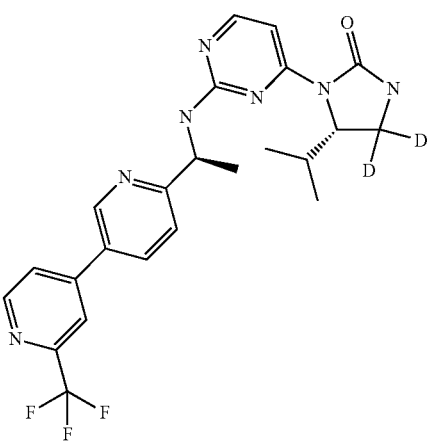 [SMILES: [2H]C1([2H])NC(=O)N(c2ccnc(N[C@@H](C)c3ccc(-c4ccnc(C(F)(F)F)c4)cn3)n2)[C@H]1C(C)C]

LCMS: m/z 474.2[M+H]$^+$; RT=1.77 min.

1H NMR (400 MHz, cdcl3): 8.85 (d, J=2.1 Hz, 1H), 8.81 (d, J=5.0 Hz, 1H), 8.09 (d, J=5.9 Hz, 1H), 7.90 (dd, J=8.2, 2.2 Hz, 1H), 7.86 (s, 1H), 7.68 (d, J=5.2 Hz, 1H), 7.52-7.49 (m, 1H), 7.47 (d, J=8.2 Hz, 1H), 5.77 (d, J=6.5 Hz, 1H), 5.13 (s, 1H), 4.65 (s, 1H), 4.37 (s, 1H), 2.69-2.57 (m, 1H), 1.58 (d, J=6.9 Hz, 3H), 0.93 (d, J=7.0 Hz, 3H), 0.83 (d, J=6.9 Hz, 3H).

Example 111: Synthesis of Compound 115

Using the same manner as in Example 1, Compound 115 was obtained from Intermediate A10 and Intermediate B1.

(S)-1-(2-(((S)-1-(2'-(trifluoromethyl)-[3,4'-bipyridyl]-6-yl)ethyl)amino)-4-isopropyl-imidazolidine-2-one

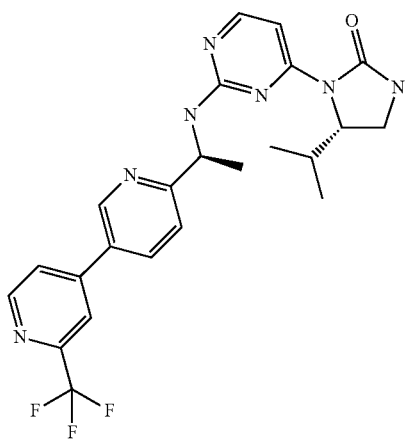 [SMILES: CC(C)[C@H]1CNC(=O)N1c1ccnc(N[C@@H](C)c2ccc(-c3ccnc(C(F)(F)F)c3)cn2)n1]

LCMS: m/z 472.2[M+H]$^+$; RT=1.77 min.

$^1$H NMR (400 MHz, cdcl3) δ 8.84 (d, J=2.2 Hz, 1H), 8.81 (d, J=5.1 Hz, 1H), 8.09 (d, J=5.8 Hz, 1H), 7.88 (dd, J=8.1, 2.4 Hz, 1H), 7.84 (s, 1H), 7.66 (dd, J=5.0, 1.5 Hz, 1H), 7.51 (d, J=6.0 Hz, 1H), 7.46 (d, J=8.1 Hz, 1H), 5.72 (d, J=6.5 Hz, 1H), 5.18 (s, 1H), 4.75 (s, 1H), 4.57 (s, 1H), 3.43 (t, J=9.4 Hz, 1H), 3.23 (d, J=7.6 Hz, 1H), 1.59 (s, 3H), 0.86 (t, J=6.9 Hz, 1H), 0.65 (s, 6H).

Example 112: Synthesis of Compound 116

Using the same manner as in Example 1, Compound 116 was obtained from Intermediate A65 and Intermediate B23.

(S)-4-isopropyl-1-trideuteromethyl-3-(2-(((S)-1-(5-(3-(trifluoromethyl)phenyl) pyridin-2-yl)ethyl) amino)pyrimidin-4-imidazolidine-2-one-5,5-dideutero

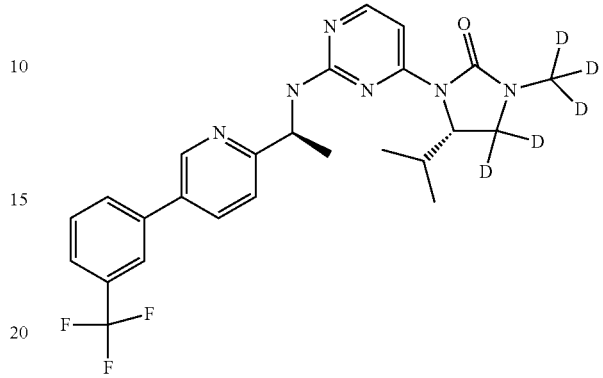

LCMS: m/z 490.3 [M+H]$^+$; RT=1.09 min.

$^1$H NMR (400 MHz, CDCl$_3$) δ 8.78 (d, J=2.1 Hz, 1H), 8.10 (d, J=5.8 Hz, 1H), 7.84-7.76 (m, 2H), 7.73 (d, J=7.6 Hz, 1H), 7.66 (d, J=7.6 Hz, 1H), 7.63-7.57 (m, 1H), 7.55 (d, J=5.9 Hz, 1H), 7.41 (d, J=8.1 Hz, 1H), 5.66 (s, 1H), 5.17 (s, 1H), 4.47 (s, 1H), 2.17 (s, 1H), 1.60 (t, J=9.0 Hz, 3H), 0.64 (m, 6H).

Control compound: AG120, CAS: 1448346-63-1, purchased from Shanghai Blue Wood Chemical Co., Ltd.

Test Example 1 Effect of the Compound of the Present Invention on the Enzyme Activity of IDH1 at the Molecular Level Reagents, consumables and instruments:

The enzyme used in the experiment was purchased from cayman Co.

The substrates α-KG, NADPH and Diaphorase were purchased from Sigma; Resazurin was purchased from J&K; and the remaining reagents were purchased from Sinopharm Chemical Reagent Co., Ltd.

The reaction microplate (6008260) was purchased from PerkinElmer Co.

The multi-function plate reader used for experiment was a product from PerkinElmer Co., model: EnVison.

The water used in the experiment was distilled water produced by Sinopharm Group.

Compound preparation: Compound 12000 g was centrifuged for 5 min, DMSO was added to prepare 10 mM, which was vortexed, then ultrasonic treatment for 10 minutes, and stored at −40° C. The stock solution was diluted firstly with DMSO to a 10 μM solution when tested and then gradient-diluted for 3 times to a different test concentration.

Test method: The enzyme activity of IDH1 to convert α-KG to 2HG was measured by the consumption of NADPH. After the enzymatic reaction was completed, a catalytic excess of diaphorase and reazurin were added, and the resulting fluorescent signal could reflect the amount of remaining NADPH. In a 384-well plate, 5 μL of enzyme system (150 mM NaCl, 20 mM Tris pH=7.5, 10 mM MgCl$_2$, 0.05% (w/v) bovine serum albumin, 0.012 μL enzyme), 2.5 μL of compound, 2.5 μL of mixture of substrate α-KG and NADPH (final concentration of substrate α-KG was 1 mM, final concentration of NADPH was 4 μM) were added, incubated at room temperature for 60 min in darkness. Detection reaction: 5 µL of 5 µM resazurin and 0.01 unit diaphrose diluted with 1× detection buffer were added to each well, and incubated at room temperature for 10 min in darkness. Reading plate: PerkinElmer EnVision® at Ex 544 Em 590. testing plate was used. $IC_{50}$ values were calculated using GraphPad Prism software.

Results

Table 1 shows the $IC_{50}$ values of some of the compounds of the present invention.

The letter A represents $IC_{50}$ of less than 100 nm;
The letter B represents $IC_{50}$ of from 100 nm to 1000 nm;
The letter C represents $IC_{50}$ of 1000 nM or more.

TABLE 1

| Compound Number | IDH1 R132H |
| --- | --- |
| 1 | B |
| 2 | B |
| 3 | A |
| 4 | A |
| 5 | A |
| 6 | B |
| 7 | B |
| 8 | B |
| 9 | B |
| 10 | A |
| 11 | B |
| 12 | B |
| 13 | B |
| 14 | B |
| 15 | B |
| 16 | B |
| 17 | A |
| 18 | A |
| 19 | B |
| 20 | A |
| 21 | A |
| 22 | A |
| 23 | A |
| 24 | A |
| 25 | B |
| 26 | A |
| 27 | A |
| 28 | A |
| 29 | B |
| 30 | A |
| 31 | A |
| 32 | A |
| 33 | A |
| 34 | A |
| 35 | A |
| 36 | B |
| 37 | A |
| 38 | A |
| 39 | B |
| 40 | B |
| 41 | B |
| 42 | A |
| 43 | A |
| 44 | B |
| 45 | A |
| 46 | A |
| 47 | A |
| 48 | A |
| 49 | A |
| 50 | A |
| 51 | B |
| 52 | A |
| 53 | A |
| 54 | B |
| 55 | A |
| 56 | B |
| 57 | A |
| 58 | A |
| 59 | B |
| 60 | B |
| 61 | A |
| 62 | A |
| 63 | A |
| 64 | B |
| 65 | A |
| 66 | B |
| 67 | B |
| 68 | A |
| 69 | B |
| 70 | B |
| 71 | B |
| 72 | B |
| 73 | B |
| 74 | B |
| 75 | B |
| 76 | A |
| 77 | A |
| 78 | A |
| 79 | B |
| 80 | A |
| 81 | B |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | B |
| 100 | A |
| 101 | A |
| 102 | A |
| 103 | B |
| 104 | A |
| 105 | A |
| 106 | A |
| 107 | A |
| 108 | B |
| 109 | B |
| 110 | A |
| 111 | A |
| 112 | A |
| 113 | B |
| 114 | B |
| 115 | A |
| 116 | A |
| Positive control AG120 | A |

The results show that the compounds of the present invention can effectively inhibit the activity of IDH1 at a very low concentration (<100 nm).

Test Example 2: 2HG Inhibition Assay of the Compounds of the Present Invention on Fibrosarcoma Cell Line HT1080

In this experiment, the inhibitory activity of the compounds of the present invention against the 2HG concentration level of fibrosarcoma cell line HT1080 was measured by the following method.

Cell sample preparation: Human fibrosarcoma cells HT-1080 in logarithmic growth phase were inoculated into 6-well culture plates at 2 ml per well, and incubated overnight. Different concentrations of compounds were added and incubated for 48 h. HT-1080 cells were trypsinized and collected, and centrifuged at 500 g for 5 min. The supernatant was discarded, and the cells were resuspended in 1 ml of PBS and the number of cells per sample was counting by a counter (Beckman coulter Z2, Beckman) and adjusted to be the same. After centrifuged at 500 g for 5 min, the supernatant was discarded, and the cell pellet was stored in a refrigerator at −80° C. for 2HG detection.

2Hg Detection:

Sample Treatment: an ice acetonitrile solution containing 200 μL of verapamil (internal standard) was added to sample tubes respectively, vortexed for 1 min, and placed in a refrigerator at 4° C. for 20 min to lyse the cells. 100 μL of sample was taken, another 100 μL of lysate was taken in a 96-well plate and dried with a nitrogen blower, and 100 μL of water was added and vortexed to be uniform.

1. Derivatization: 100 μL of o-benzylhydroxylamine hydrochloride derivatization reagent was added and shaken on a shaker for 1 h to complete the derivatization reaction.

2. Solution extraction: 300 μL of ethyl acetate was added separately, shaken for 20 min, centrifuged at 1900 rpm for 5 min, and placed in a refrigerator at −70° C. for 40 min. All the ethyl acetate was taken up to another sample plate, and dried with a nitrogen blower. 150 μL MEOH/H$_2$O (v/v, 1/1) was added for reconstitution.

3. Bioanalysis: All of the above samples were analyzed by LC-MS/MS (Waters ACQUITY H-Class System, Waters/AB6500, Sciex) after centrifuged at 4000 rpm for 10 min.

Calculation of Inhibition Rate and IC$_{50}$

The inhibition rate of the sample was obtained by the following formula:

$$\text{Inhibition rate (\%)} = \left(1 - \frac{2HG \text{ content of well with compound}}{2HG \text{ content of negative control}}\right) \times 100\%$$

IC$_{50}$ values were calculated using GraphPad Prism software. The 2HG level inhibitory activity of some compounds on HT1080 was shown in Table 2.

TABLE 2

| Compound number | HT1080 2HG Inhibitory IC$_{50}$(nM) |
|---|---|
| 17 | 12.9 |
| 26 | 27 |
| 30 | 15 |
| 34 | 16 |
| 38 | 14 |
| 83 | 10 |
| 86 | 66 |
| 87 | 29 |
| 89 | 39 |
| 90 | 24 |
| 91 | 12 |
| 92 | 33 |
| 93 | 34.5 |
| 94 | <10 |
| 95 | <10 |
| 101 | 20 |

Positive drug: AG120, IC$_{50}$ is 30 nM

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A compound of formula I, a stereoisomer, a racemate or a pharmaceutically acceptable salt thereof:

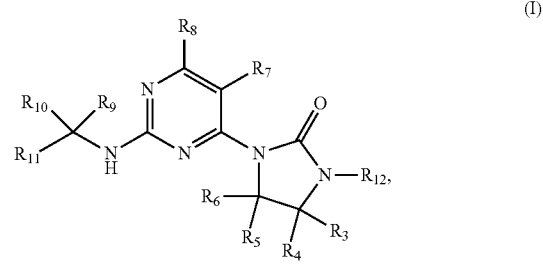

(I)

wherein,

R$_3$ and R$_4$ are each independently H, D, or substituted or unsubstituted C$_{1-4}$ alkyl;

or R$_3$ and R$_4$ together with the carbon atom connecting them form a substituted or unsubstituted C$_{3-6}$ cycloalkyl, or a substituted or unsubstituted C$_{3-6}$ epoxyalkyl;

R$_5$ and R$_6$ are each independently H, a substituted or unsubstituted C$_{1-4}$ alkyl, a substituted or unsubstituted C$_{6-10}$ aryl, or a substituted or unsubstituted C$_{3-6}$ cycloalkyl;

or R$_5$ and R$_6$ together with the carbon atom connecting them form a substituted or unsubstituted C$_{3-6}$ cycloalkyl;

R$_7$ and R$_8$ are each independently H, halogen, or a substituted or unsubstituted C$_{1-4}$ alkyl;

R$_9$ is H or a substituted or unsubstituted C$_{1-4}$ alkyl;

R$_{10}$ is a substituted or unsubstituted C$_{1-4}$ alkyl; or R$_9$ and R$_{10}$ together with the carbon atom connecting them form a substituted or unsubstituted C$_{3-6}$ cycloalkyl;

R$_{11}$ is a substituted or unsubstituted C$_{6-10}$ aryl, or a substituted or unsubstituted C$_{5-10}$ heteroaryl containing 1-4 heteroatoms selected from N, O or S, wherein the term "substituted" means having one or more substituents selected from Group A:

the group consisting of H, D, halogen, a substituted or unsubstituted C$_{1-6}$ alkyl, a substituted or unsubstituted C$_{3-8}$ cycloalkyl, a substituted or unsubstituted C$_{1-4}$ alkoxy, a substituted or unsubstituted C$_{6-10}$ aryl, a substituted or unsubstituted C$_{5-10}$ heteroaryl, a substituted or unsubstituted C$_{6-10}$ aryloxy, and —C(O)NHRa', wherein Ra' is a substituted or unsubstituted C$_{1-6}$ alkyl, or a substituted or unsubstituted C$_{3-8}$ cycloalkyl; and R$_{12}$ is H, D, a substituted or unsubstituted C$_{1-4}$ alkyl, or a substituted or unsubstituted C$_{3-6}$ cycloalkyl, wherein, for R$_3$-R$_{10}$ and R$_{12}$, the term "substituted" means having one or more substituents selected from Group B:

the group consisting of H, D, halogen, a substituted or unsubstituted C$_{1-6}$ alkyl, —OH, a substituted or unsubstituted C$_{1-4}$ alkoxy, C$_{3-8}$ cycloalkyl, amino, and nitro; and in Group A and Group B, the term "substituted" means having one or more substituents selected from the group consisting of D, halogen, C$_{1-4}$ alkyl, trifluoromethyl, amino, nitro, and —OH.

2. The compound, a stereoisomer, a racemate or a pharmaceutically acceptable salt thereof according to claim 1, wherein R$_3$ and R$_4$ are each independently H, D or methyl.

3. The compound, a stereoisomer, a racemate or a pharmaceutically acceptable salt thereof according to claim 1, wherein $R_5$ is H, $R_6$ is H, a substituted or unsubstituted $C_{1-4}$ alkyl, a substituted or unsubstituted $C_{6-10}$ aryl, or a substituted or unsubstituted $C_{3-6}$ cycloalkyl.

4. The compound, a stereoisomer, a racemate or a pharmaceutically acceptable salt thereof according to claim 1, wherein $R_{11}$ has the following structure:

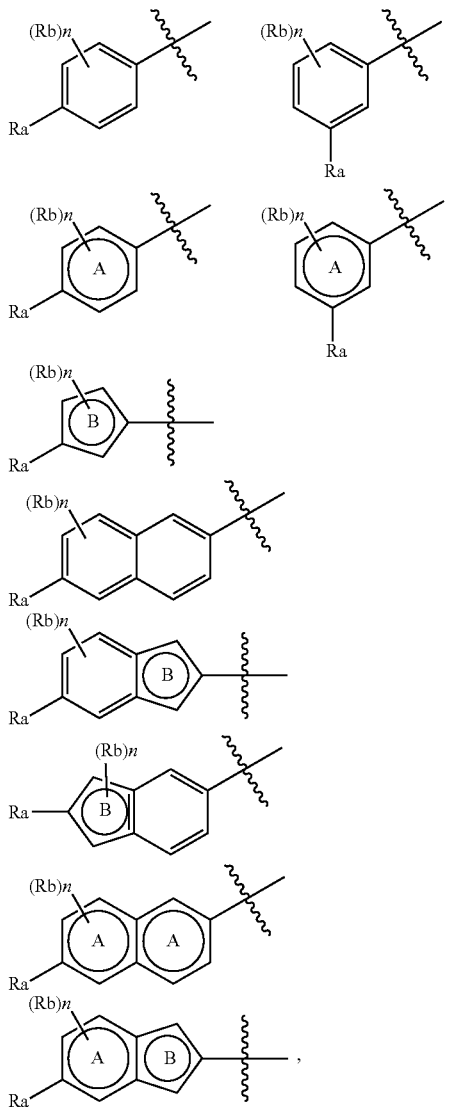

wherein ring A is a substituted or unsubstituted heteroaryl containing 1 to 3 heteroatoms;
ring B is a substituted or unsubstituted heteroaryl containing 1 to 4 heteroatoms selected from N, O or S;
Ra is H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, or —C(O)NHRa', wherein Ra' is a substituted or unsubstituted $C_{1-6}$ alkyl, or a substituted or unsubstituted $C_{3-8}$ cycloalkyl;
Rb is H, halogen, or a substituted or unsubstituted $C_{1-4}$ alkyl; and
n is 0, 1, 2 or 3.

5. The compound, a stereoisomer, a racemate or a pharmaceutically acceptable salt thereof according to claim 1, $R_{11}$ is

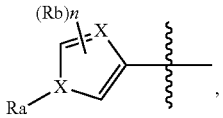

wherein X is N;
Ra is H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, or —C(O)NHRa', wherein Ra' is a substituted or unsubstituted $C_{1-6}$ alkyl, or a substituted or unsubstituted $C_{3-8}$ cycloalkyl;
Rb is selected from H, halogen, or a substituted or unsubstituted $C_{1-4}$ alkyl; and
n is 0, 1, 2 or 3.

6. The compound, a stereoisomer, a racemate or a pharmaceutically acceptable salt thereof according to claim 1, $R_{11}$ is

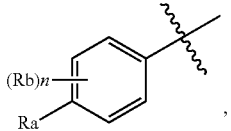

wherein Ra is H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, or —C(O)NHRa', wherein Ra' is a substituted or unsubstituted $C_{1-6}$ alkyl, or a substituted or unsubstituted $C_{3-8}$ cycloalkyl;
Rb is H, halogen, or a substituted or unsubstituted $C_{1-4}$ alkyl; and
n is 0, 1, 2 or 3.

7. The compound, a stereoisomer, a racemate or a pharmaceutically acceptable salt thereof according to claim 1, $R_{11}$ is

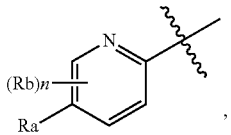

wherein Ra is H, halogen, a substituted or unsubstituted $C_{1-6}$ alkyl, a substituted or unsubstituted $C_{3-8}$ cycloalkyl, a substituted or unsubstituted $C_{1-4}$ alkoxy, a substituted or unsubstituted $C_{6-10}$ aryl, a substituted or unsubstituted $C_{5-10}$ heteroaryl, a substituted or unsubstituted $C_{6-10}$ aryloxy, or —C(O)NHRa', wherein Ra' is a substituted or unsubstituted $C_{1-6}$ alkyl, or a substituted or unsubstituted $C_{3-8}$ cycloalkyl;
Rb is H, halogen, or a substituted or unsubstituted $C_{1-4}$ alkyl; and
n is 0, 1, 2 or 3.
8. A compound, a stereoisomer, a racemate or a pharmaceutically acceptable salt thereof, selected from the group consisting of:
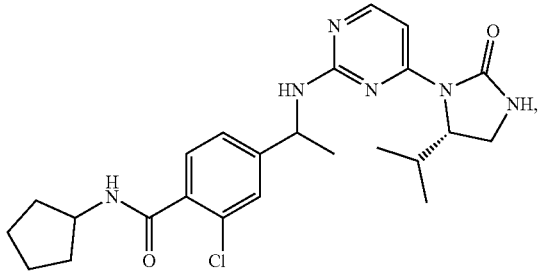
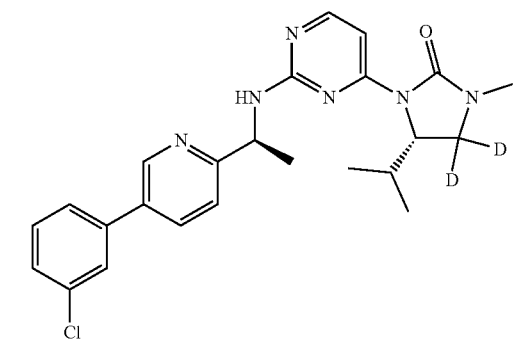
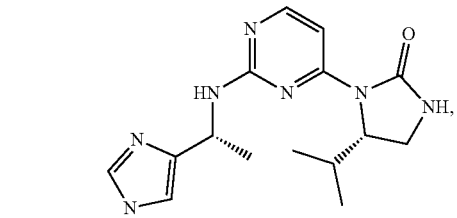
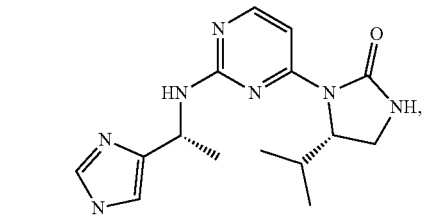
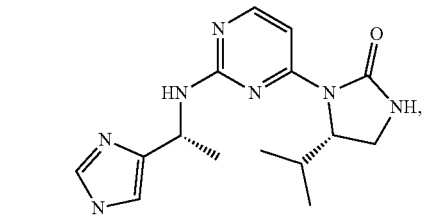
-continued
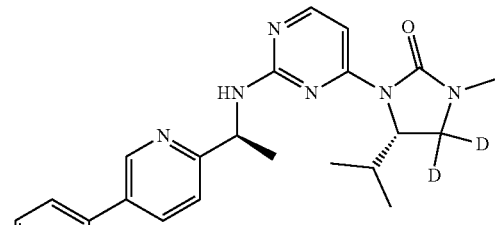
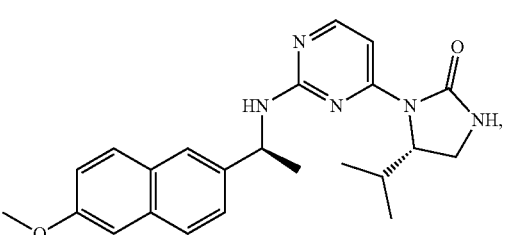
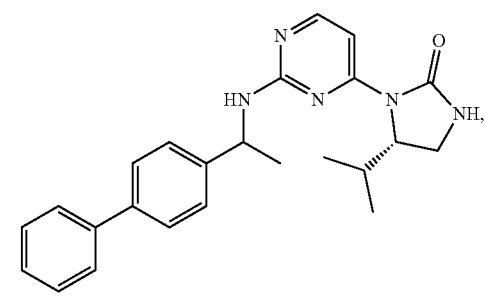
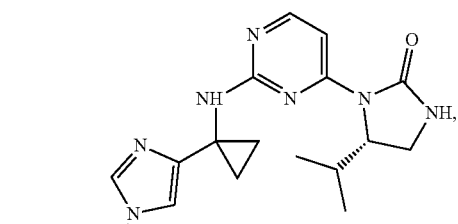
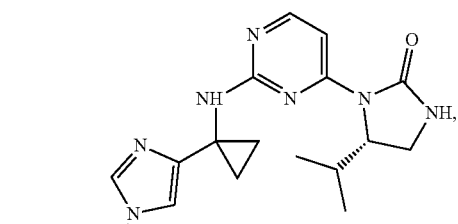

183
-continued
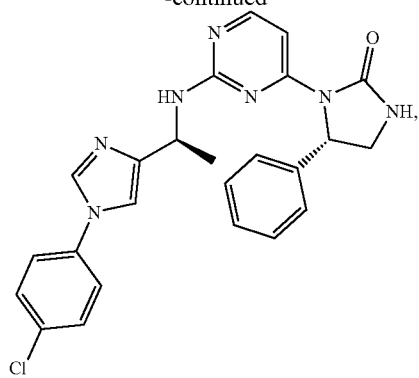
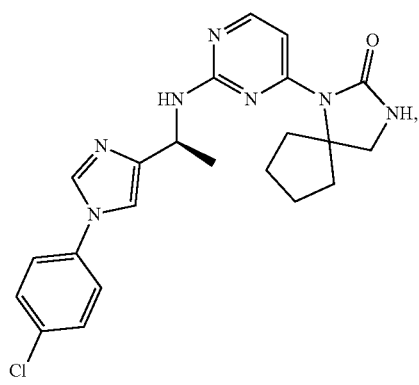
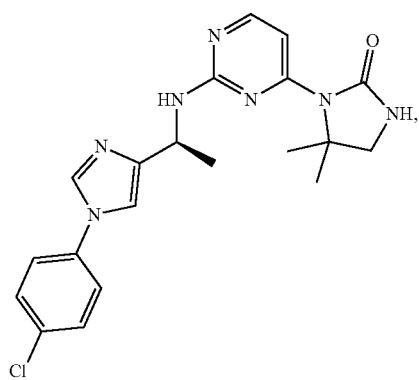
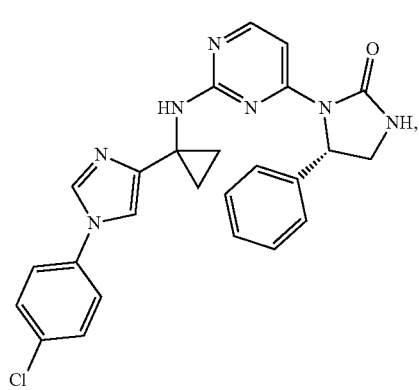
184
-continued
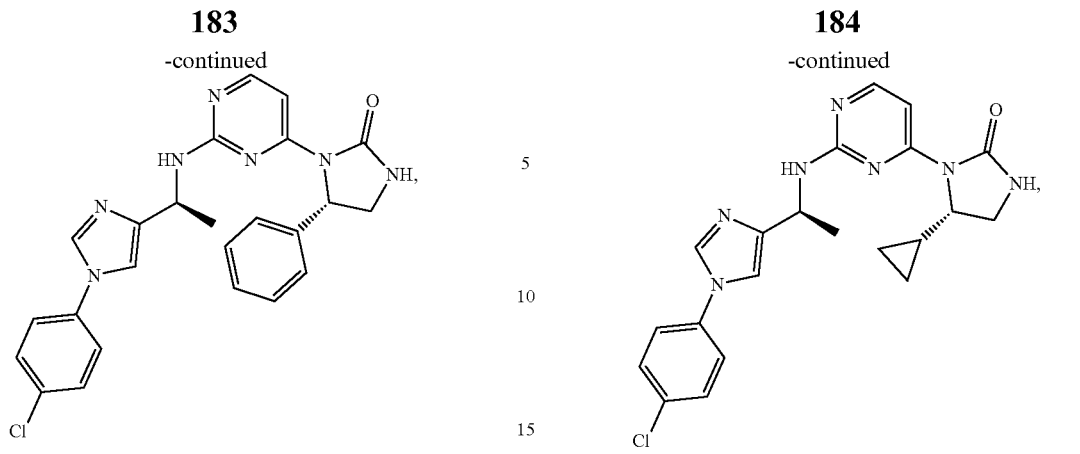
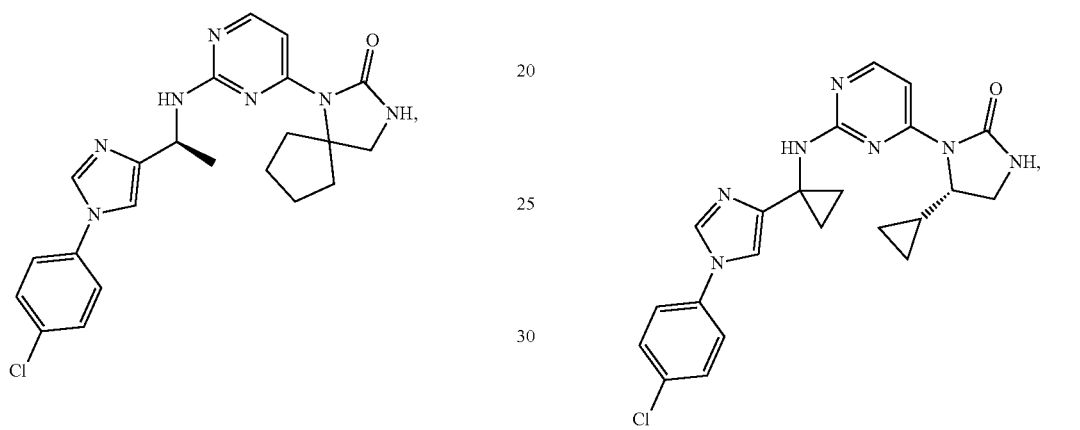
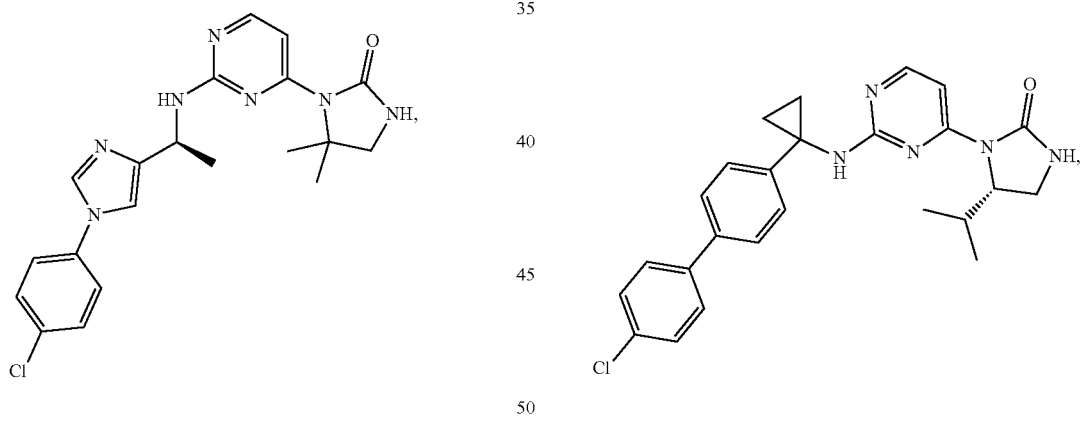
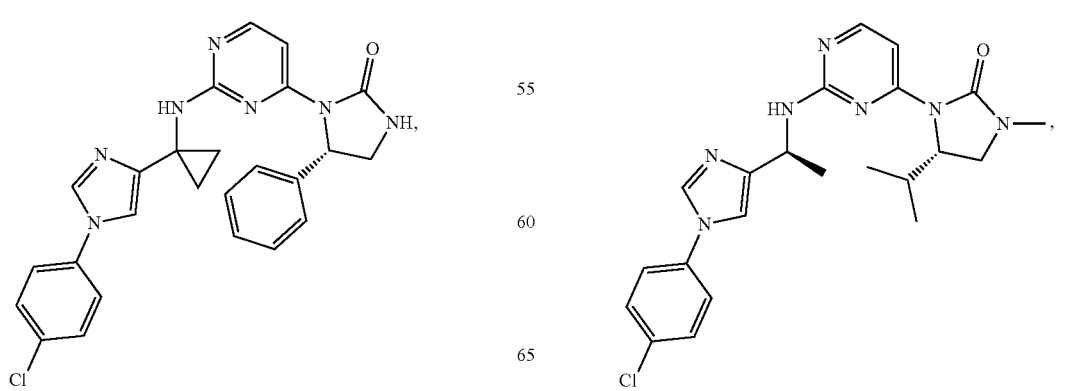

-continued
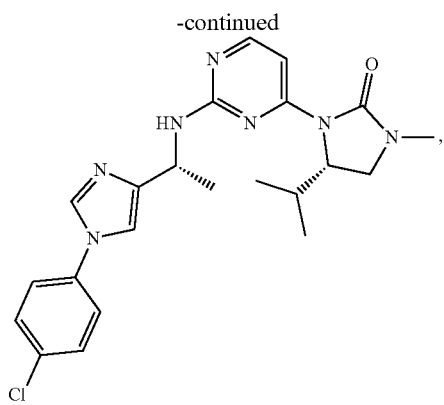
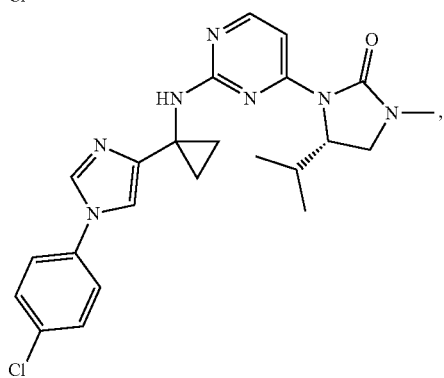
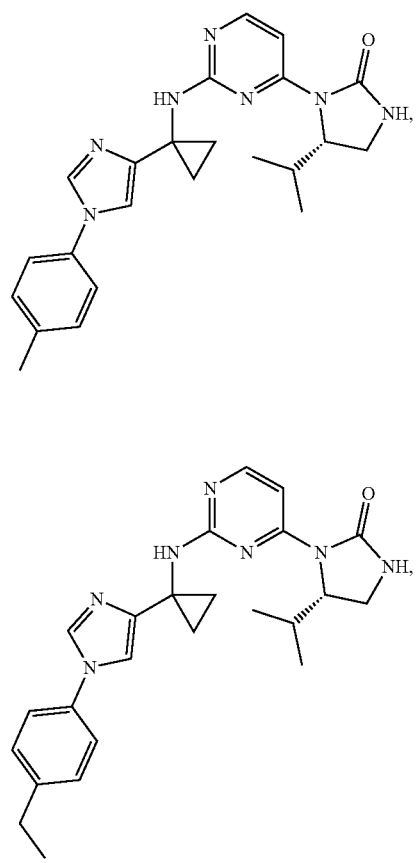
-continued
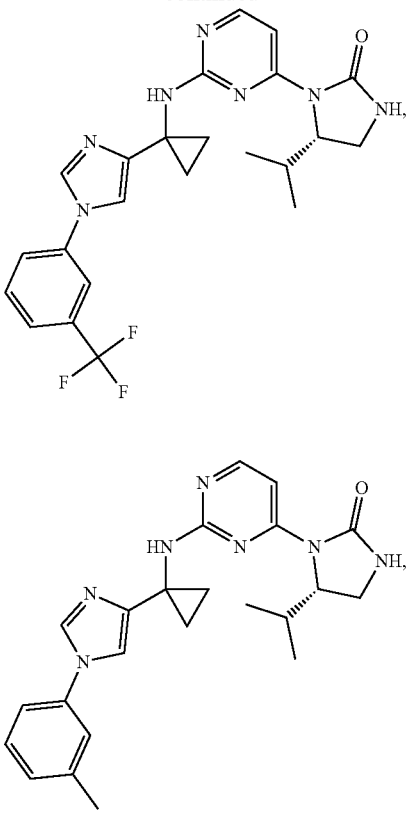
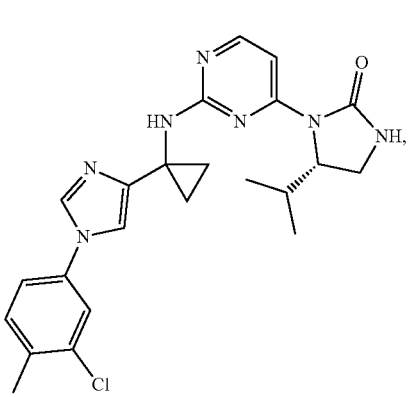
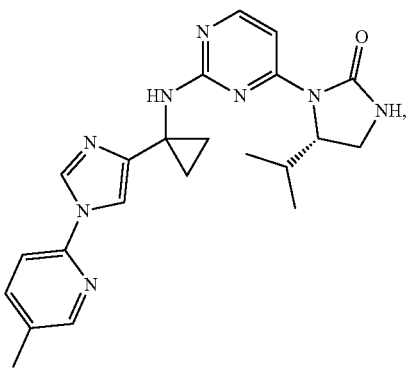

187                                188
-continued                         -continued
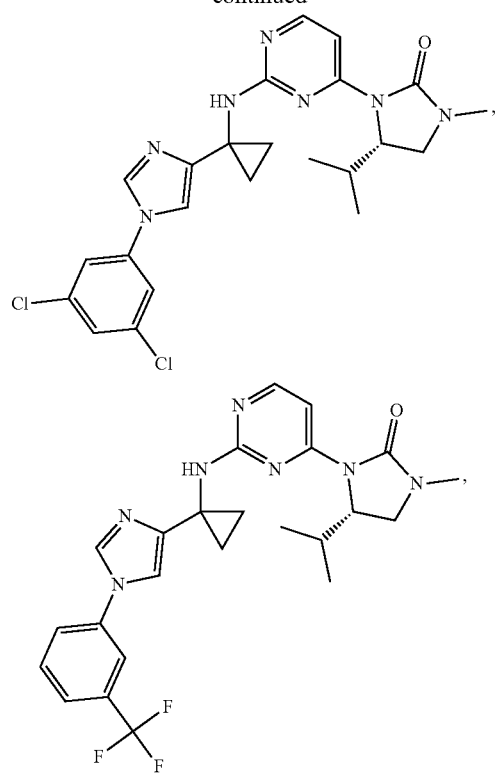
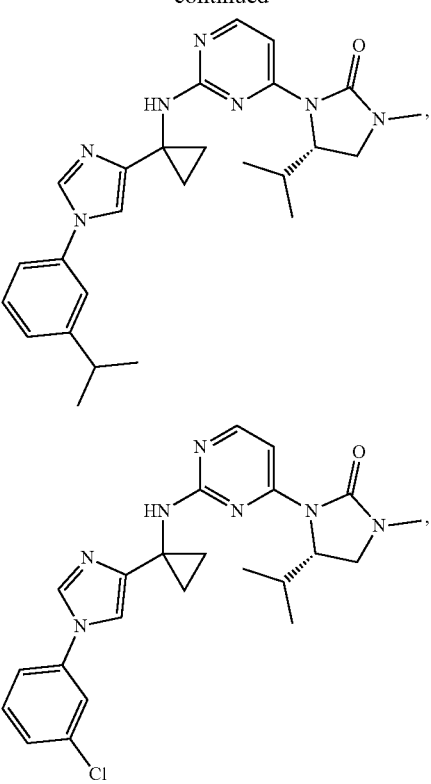
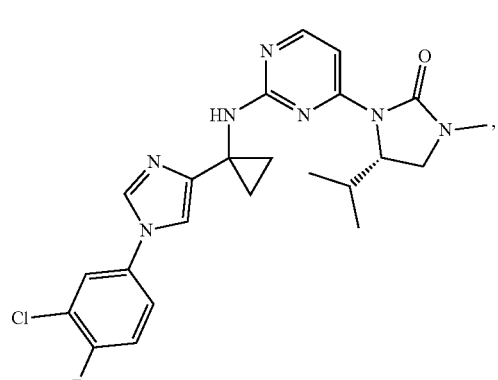
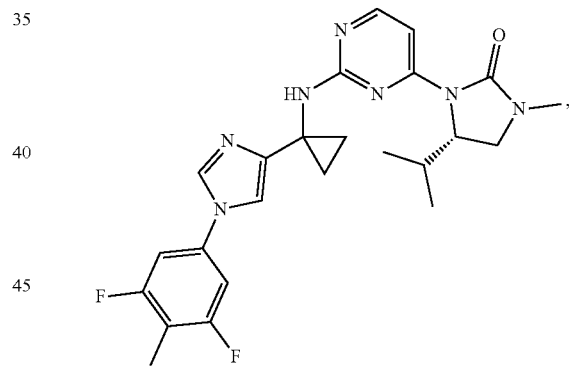
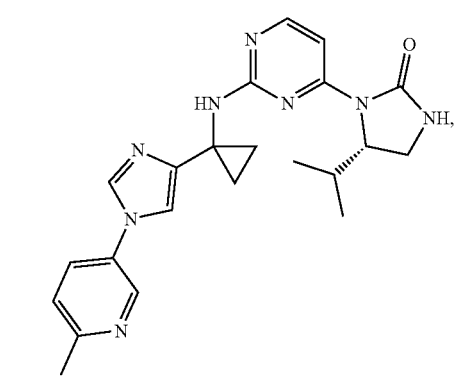
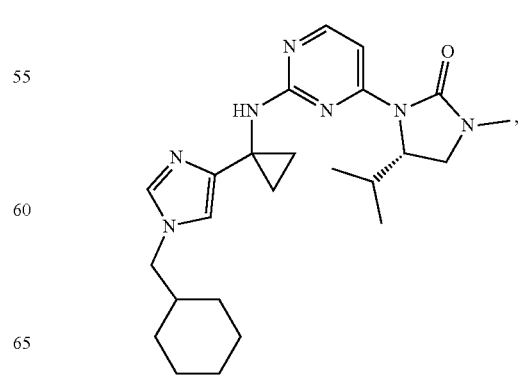

189
-continued
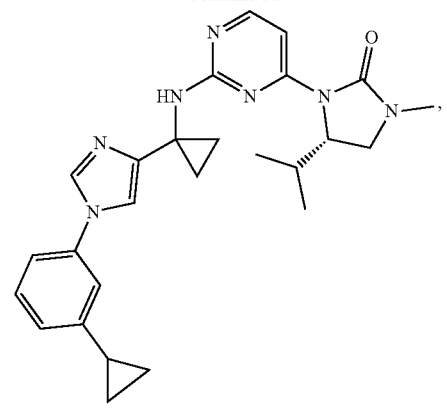
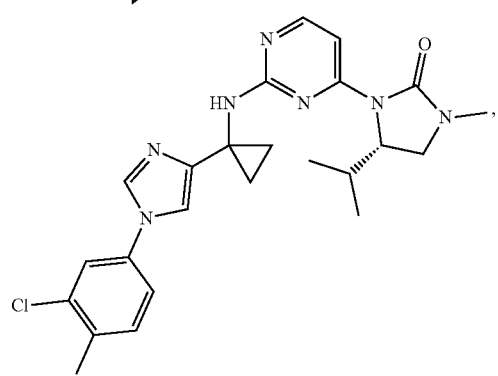
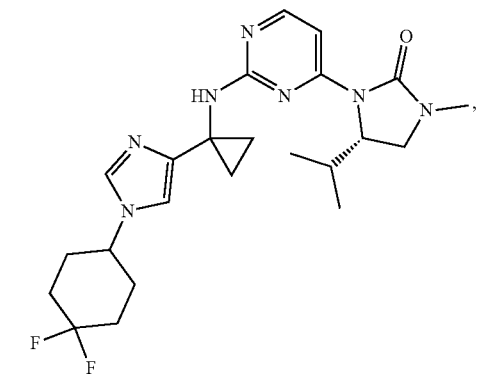
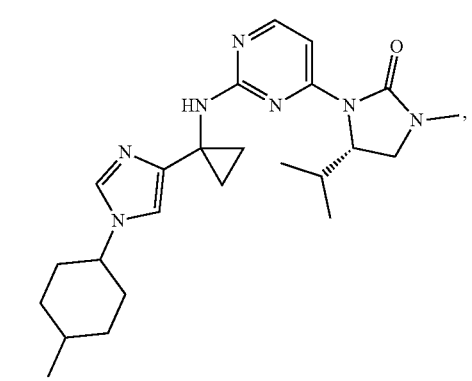
190
-continued
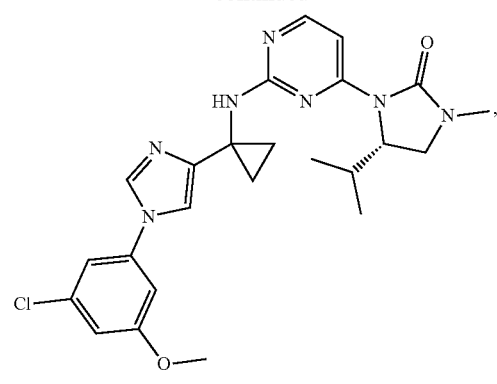
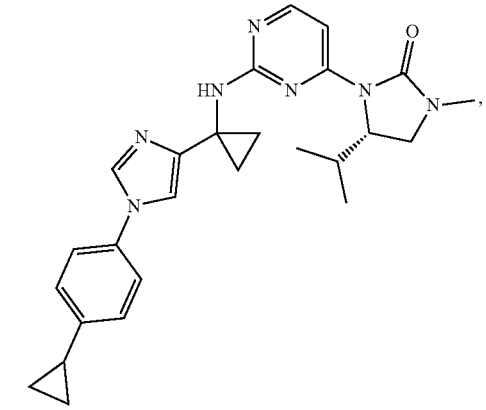
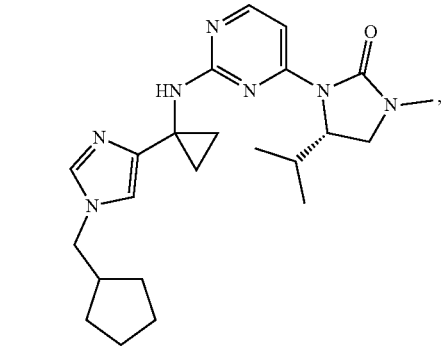
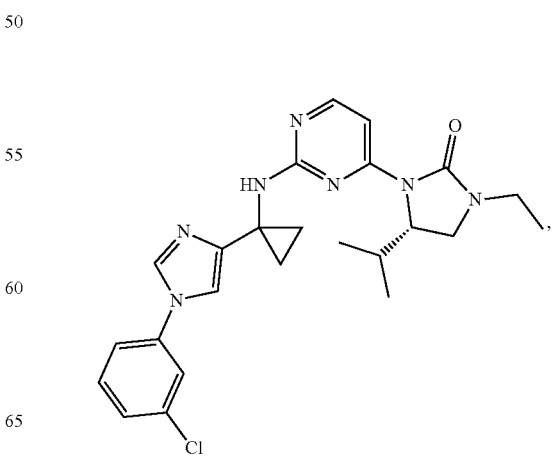

191
-continued
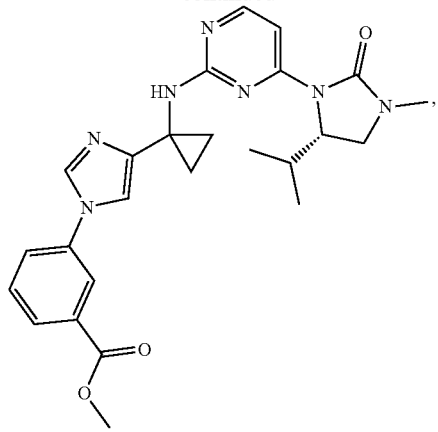
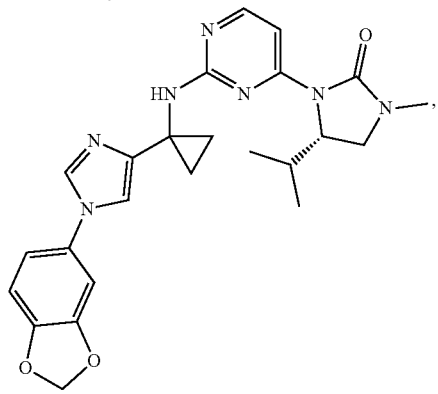
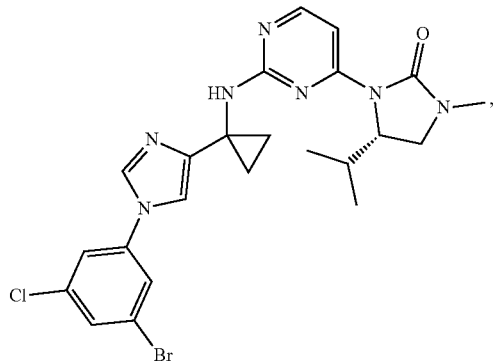
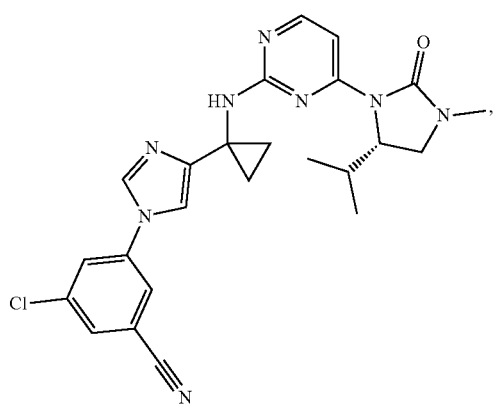
192
-continued
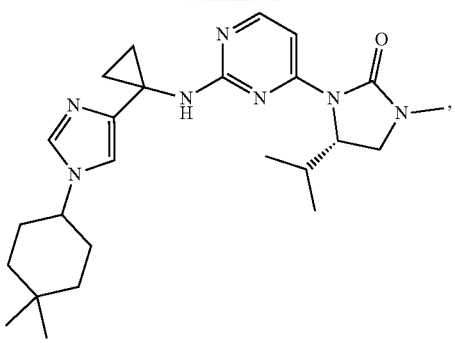
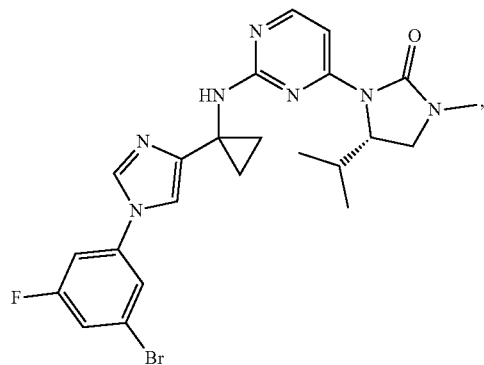
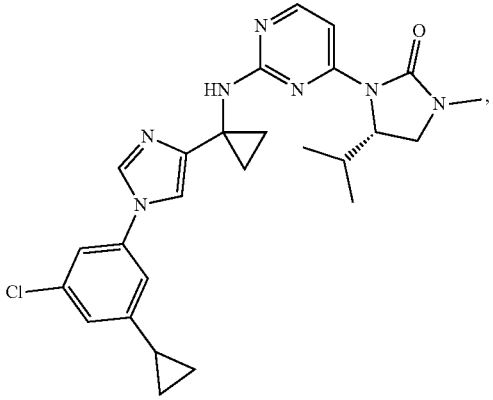
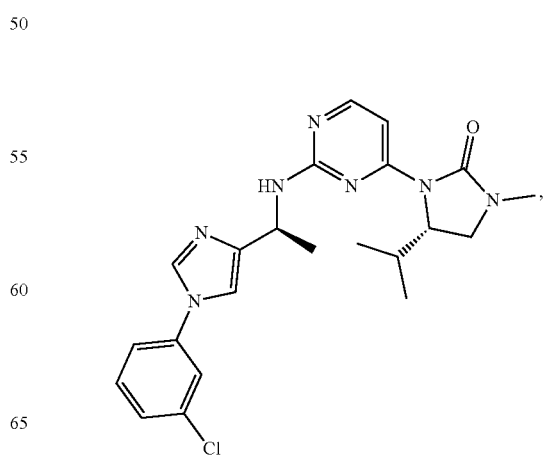

193
-continued
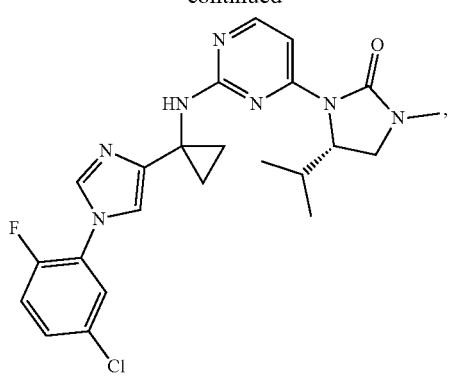
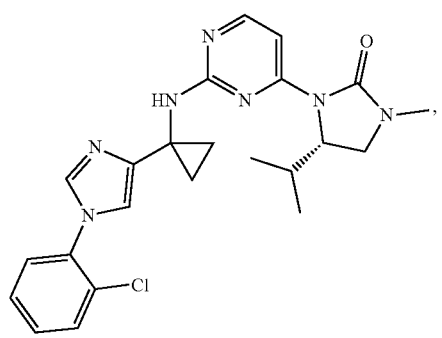
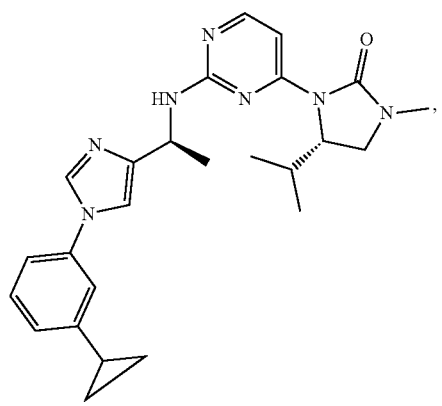
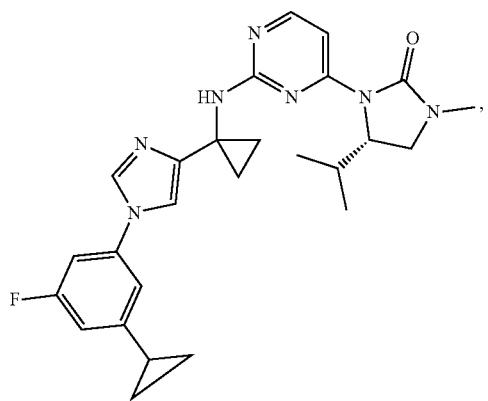
194
-continued
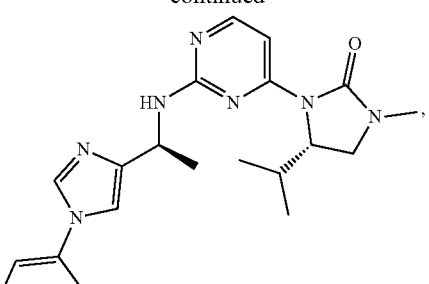
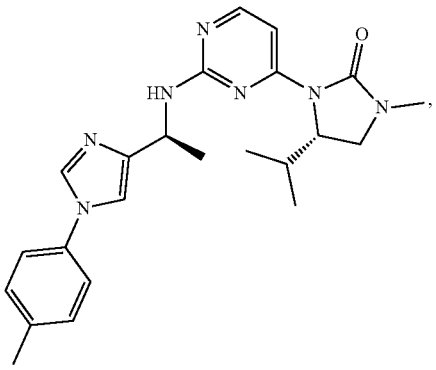
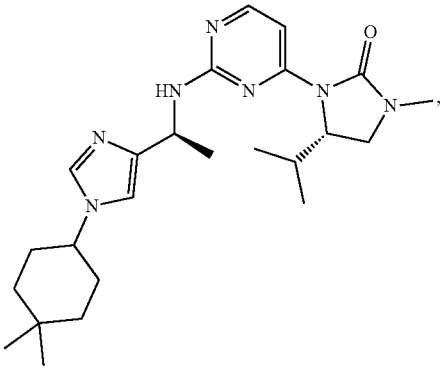

195
-continued
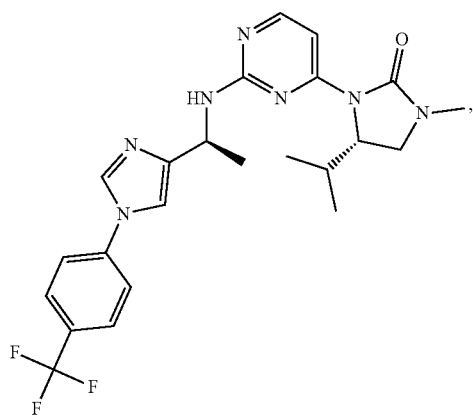
196
-continued
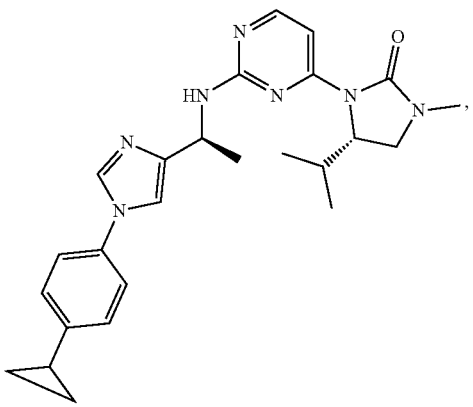
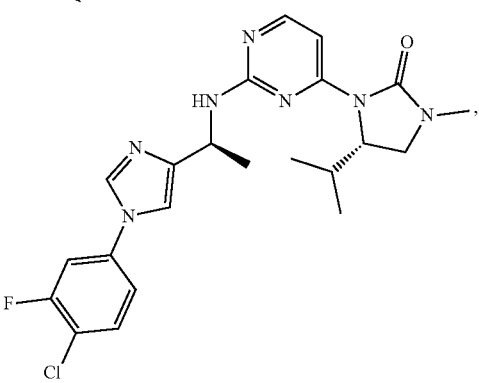
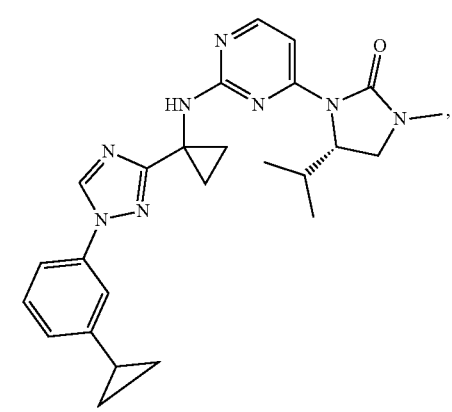
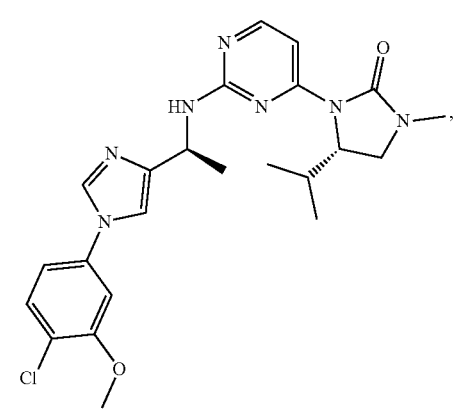

197
-continued
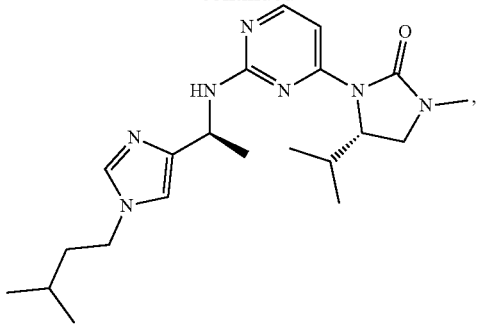
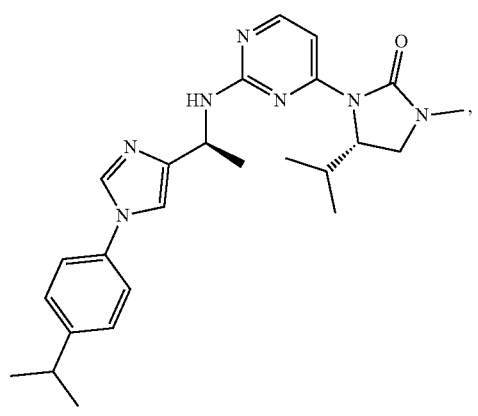
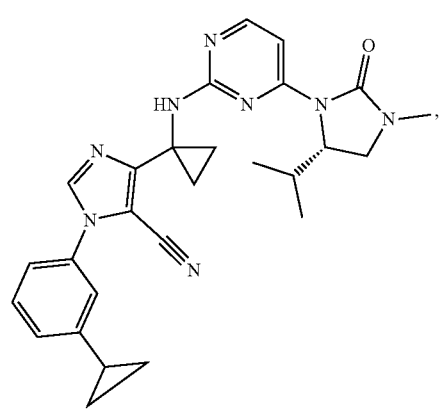
198
-continued
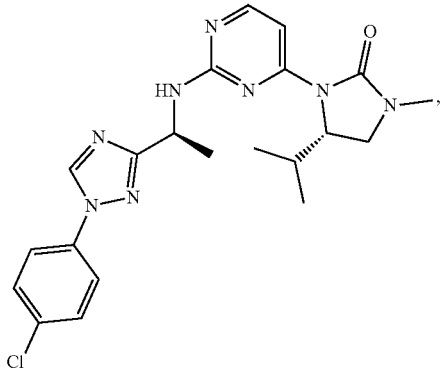
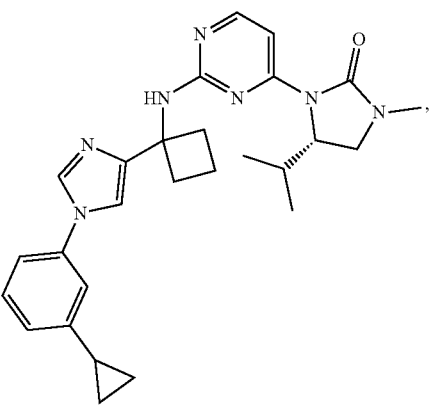
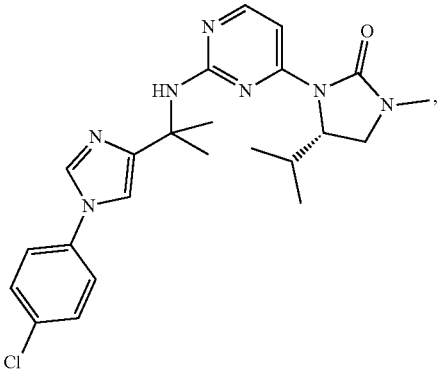
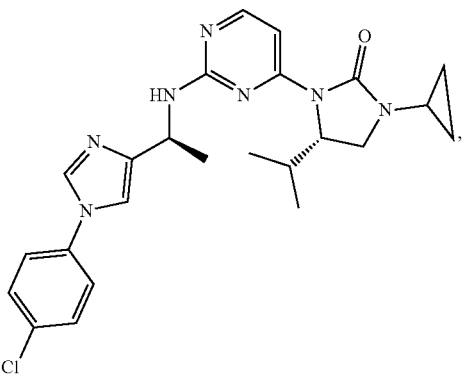

199
-continued
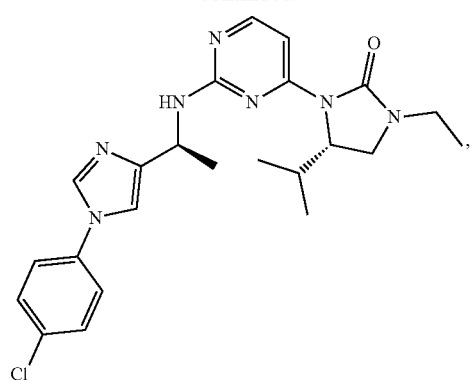
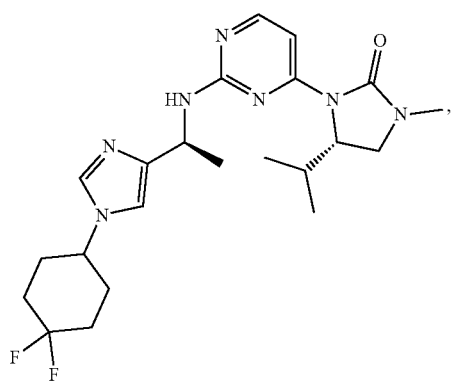
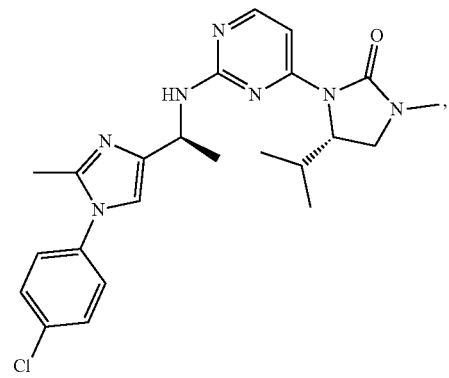
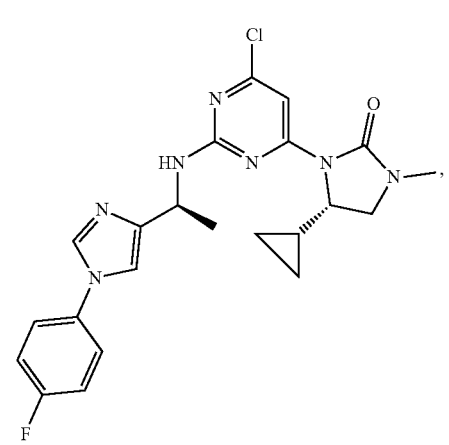
200
-continued
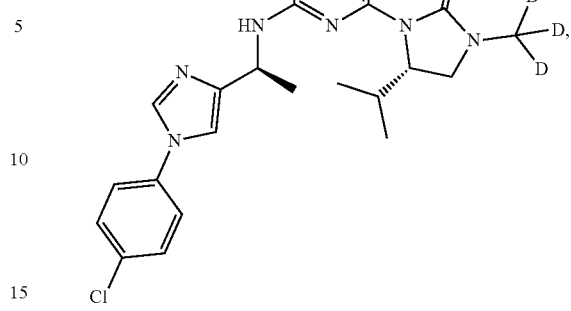
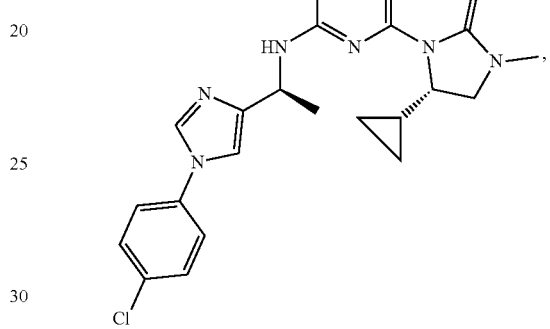
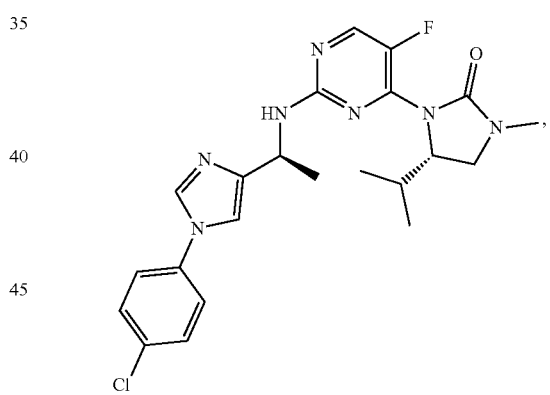
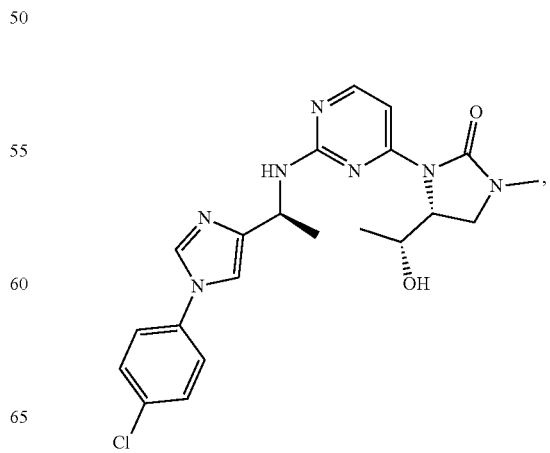

201
-continued
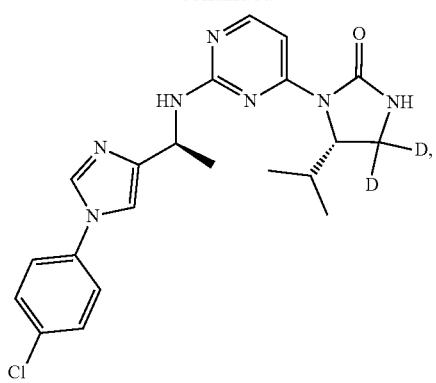
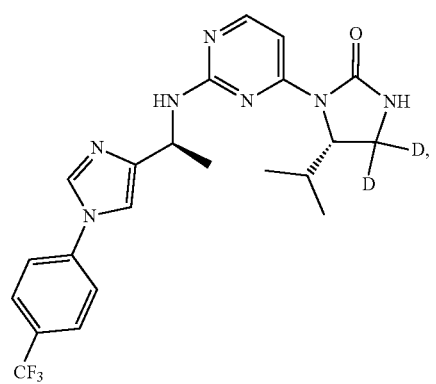
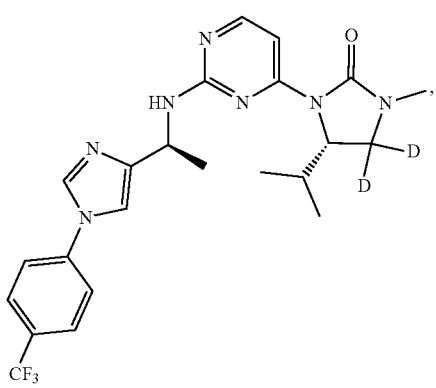
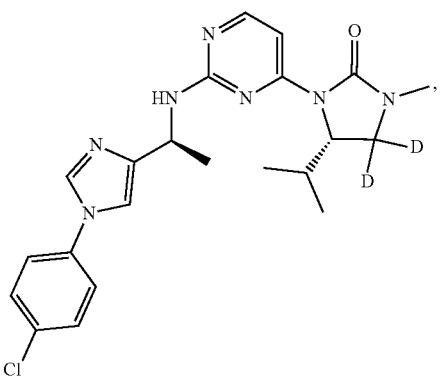
202
-continued
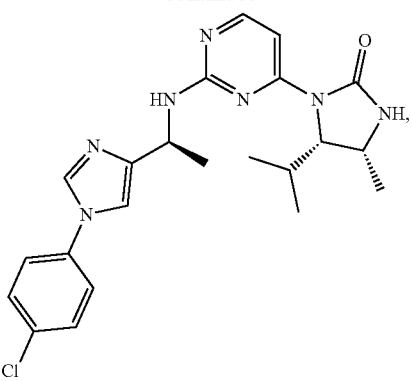
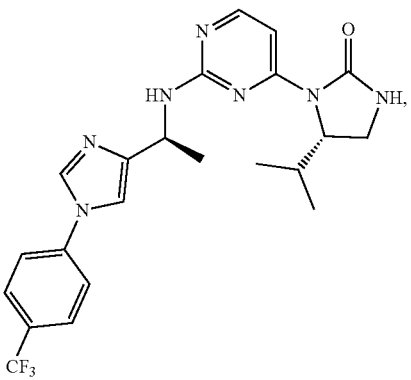
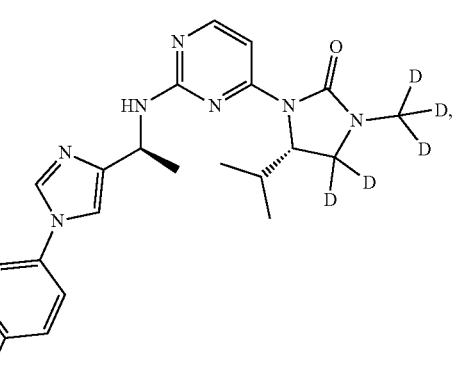

203
-continued
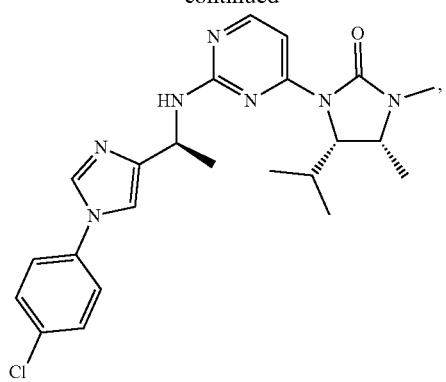
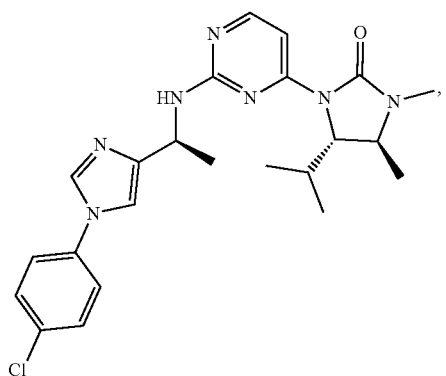
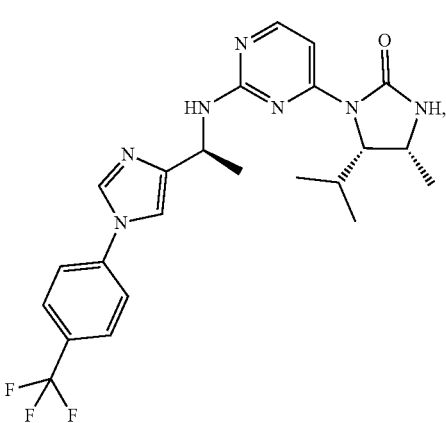
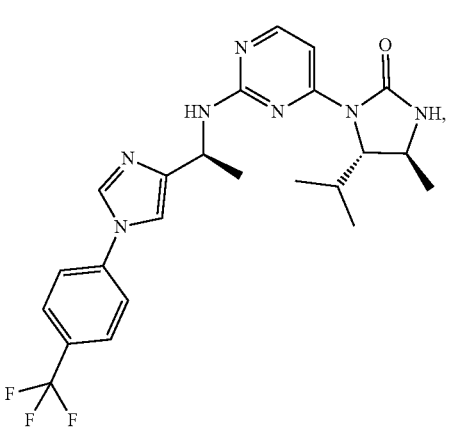
204
-continued
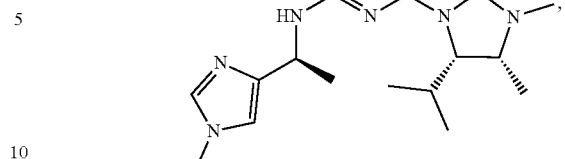
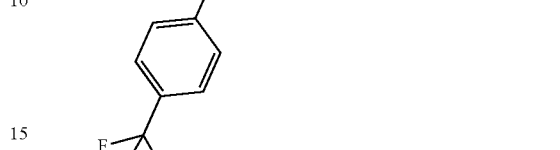
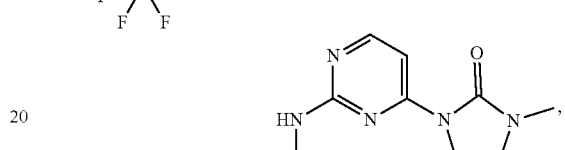
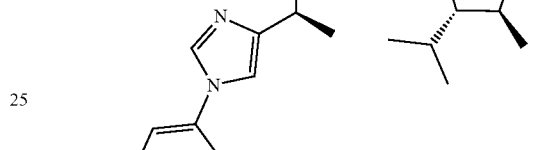
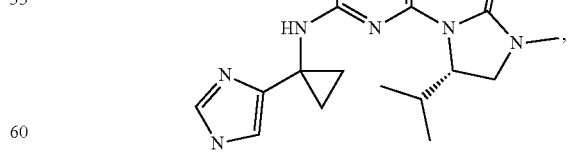

-continued
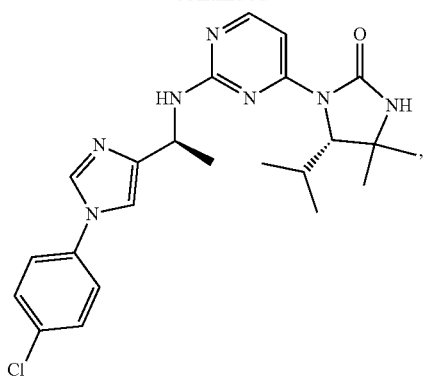
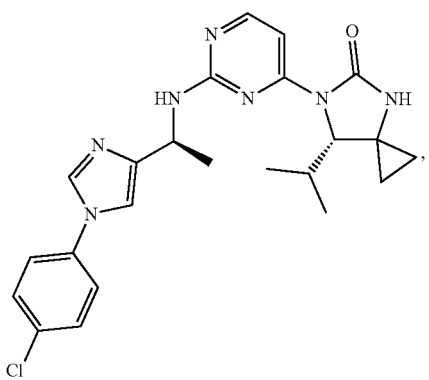
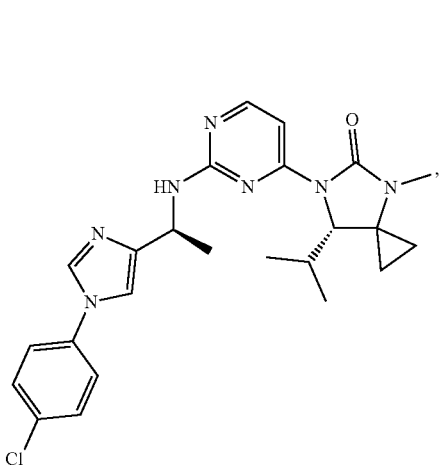
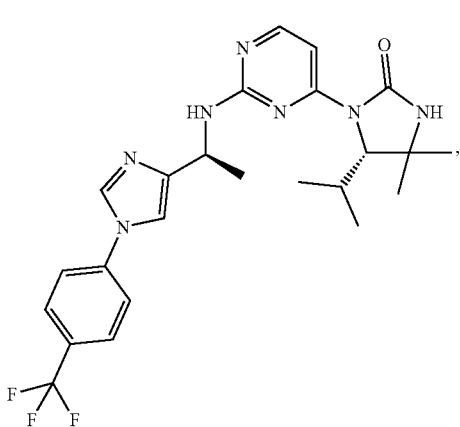
-continued
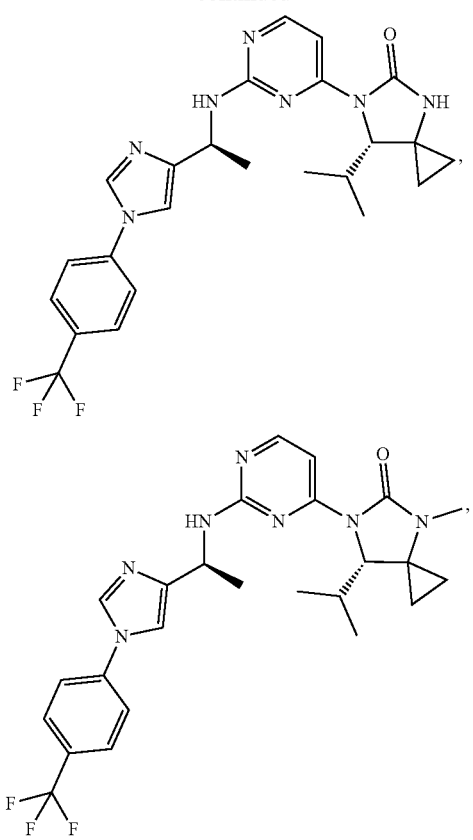
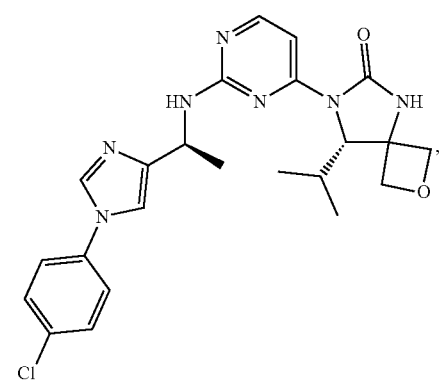
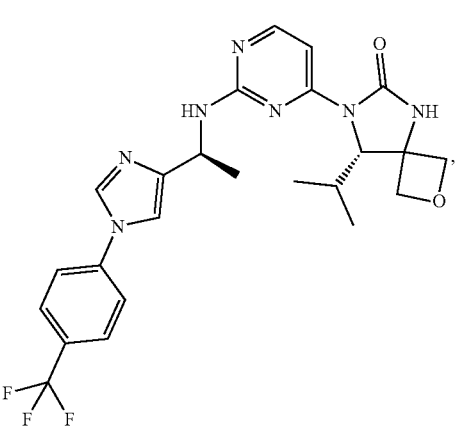

207
-continued
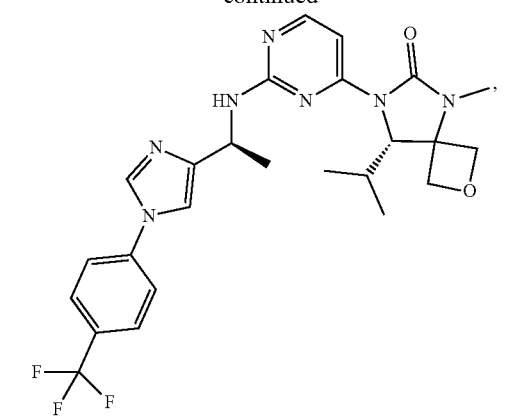
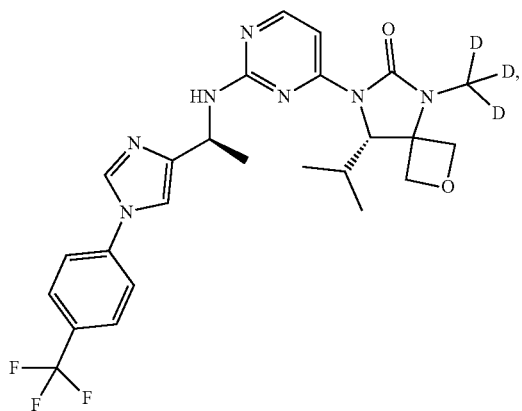
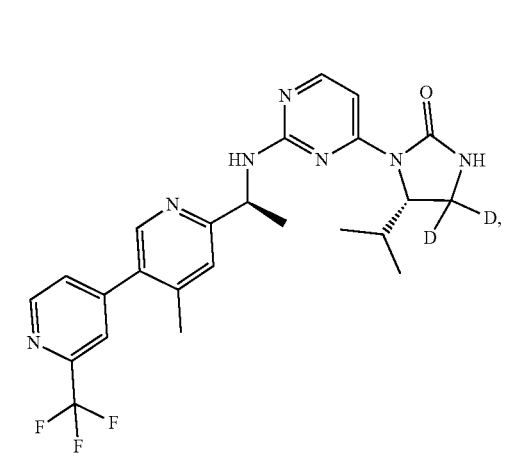
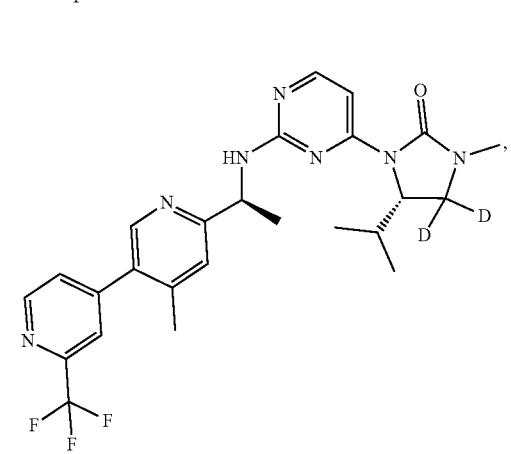
208
-continued
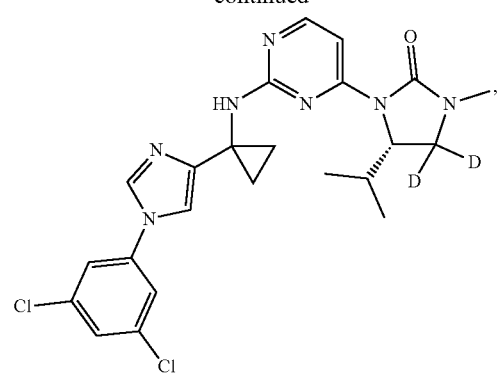
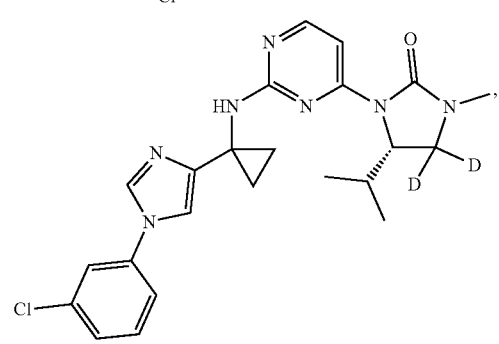
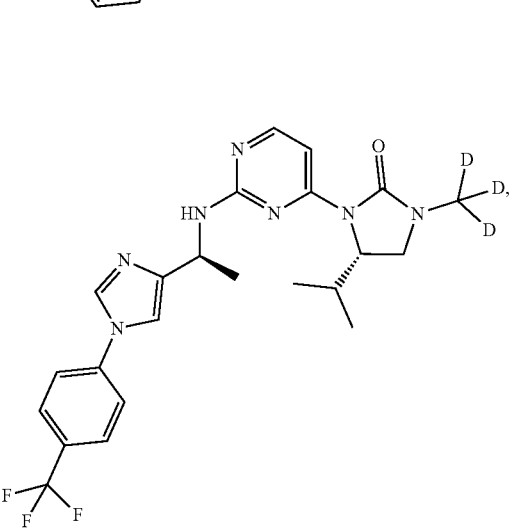
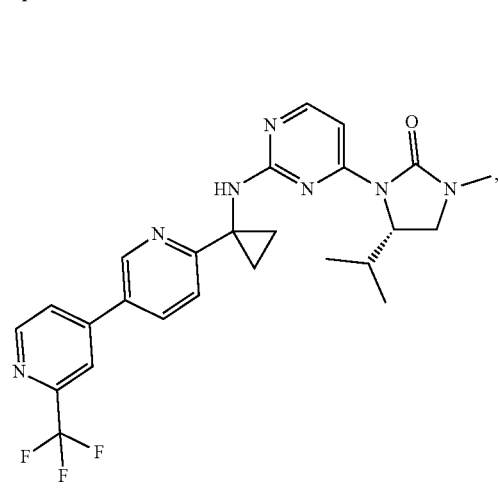

-continued

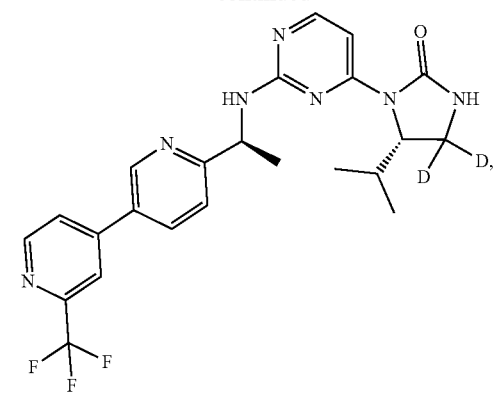

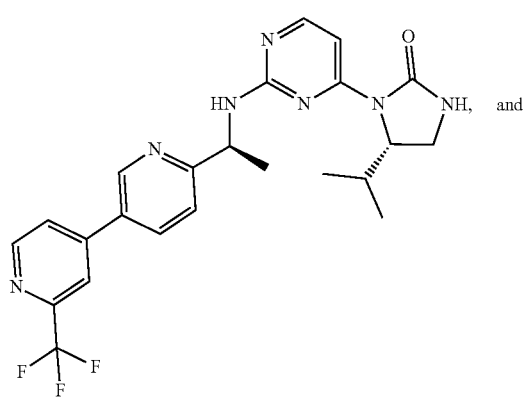

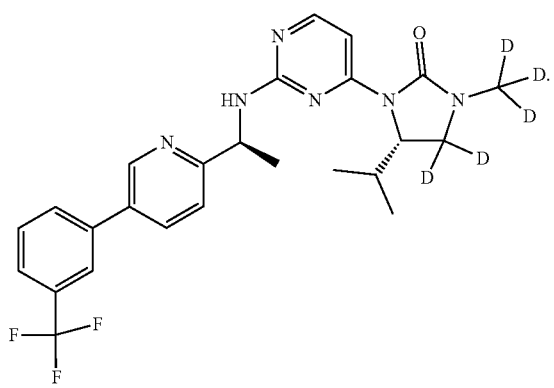

9. A pharmaceutical composition, comprising a therapeutically effective amount of the compound, a stereoisomer, a racemate or a pharmaceutically acceptable salt thereof of claim 1, and a pharmaceutically acceptable excipient.

10. A method for preparing the compound of claim 1, comprising the following steps:
   in the absence of a solvent, intermediate C and intermediate D are subjected to a substitution reaction by heating to give compound I,

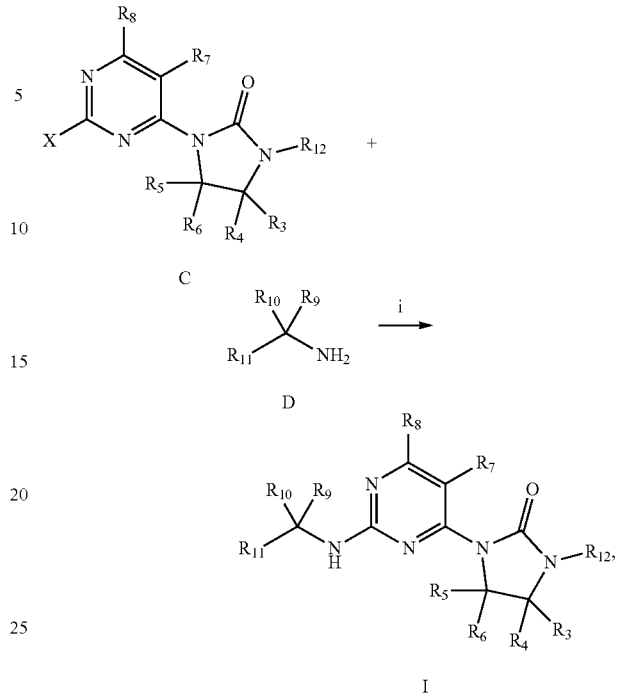

wherein X is halogen and $R_3$-$R_{12}$ are as defined in claim 1.

11. A method for treating an IDH mutation-related disease in a mammal, comprising administering to a mammal in need thereof a therapeutically effective amount of the compound of claim 1, a stereoisomer or a pharmaceutically acceptable salt thereof, wherein the IDH mutation-related disease is a tumor selected from the group consisting of glioma, acute myeloid leukemia, sarcoma, prostate cancer, melanoma, non-small cell lung cancer, articular chondrosarcoma, and cholangioma.

12. The compound, a stereoisomer, a racemate or a pharmaceutically acceptable salt thereof according to claim 1, wherein the term "substituted" in $R_{11}$ means having 1, 2, 3 or 4 substituents selected from Group A.

13. The compound, a stereoisomer, a racemate or a pharmaceutically acceptable salt thereof according to claim 1, wherein in Group A and Group B, the term "substituted" means having 1, 2, 3, 4 or 5 substituents selected from the group consisting of D, halogen, $C_{1-4}$ alkyl, trifluoromethyl, amino, nitro, and —OH.

14. A pharmaceutical composition, comprising a therapeutically effective amount of the compound, a stereoisomer, a racemate or a pharmaceutically acceptable salt thereof of claim 8, and a pharmaceutically acceptable excipient.

15. A method for treating an IDH mutation-related disease in a mammal, comprising administering to a mammal in need thereof a therapeutically effective amount of the compound of claim 8, a stereoisomer or a pharmaceutically acceptable salt thereof, wherein the IDH mutation-related disease is a tumor selected from the group consisting of glioma, acute myeloid leukemia, sarcoma, prostate cancer, melanoma, non-small cell lung cancer, articular chondrosarcoma, and cholangioma.

* * * * *